United States Patent
Hakonarson et al.

(10) Patent No.: US 11,779,577 B2
(45) Date of Patent: Oct. 10, 2023

(54) NONSELECTIVE METABOTROPIC GLUTAMATE RECEPTOR ACTIVATORS FOR TREATMENT OF ANOREXIA NERVOSA AND BINGE EATING DISORDER

(71) Applicant: The Children's Hospital of Philadelphia, Philadelphia, PA (US)

(72) Inventors: Hakon Hakonarson, Malvern, PA (US); Charily Kao, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 252 days.

(21) Appl. No.: 17/175,101

(22) Filed: Feb. 12, 2021

(65) Prior Publication Data
US 2021/0267958 A1    Sep. 2, 2021

Related U.S. Application Data

(63) Continuation of application No. 16/330,469, filed as application No. PCT/US2017/050228 on Sep. 6, 2017, now Pat. No. 10,918,632.

(60) Provisional application No. 62/384,686, filed on Sep. 7, 2016.

(51) Int. Cl.
*A61K 31/454* (2006.01)
*A61K 45/06* (2006.01)
*A61P 3/00* (2006.01)
*C12Q 1/6883* (2018.01)

(52) U.S. Cl.
CPC ............ *A61K 31/454* (2013.01); *A61K 45/06* (2013.01); *A61P 3/00* (2018.01); *C12Q 1/6883* (2013.01); *C12Q 2600/106* (2013.01); *C12Q 2600/156* (2013.01)

(58) Field of Classification Search
CPC ......... A61K 31/454; A61K 45/06; A61P 3/00; C12Q 1/6883; C12Q 2600/106; C12Q 2600/156
See application file for complete search history.

(56) References Cited

U.S. PATENT DOCUMENTS 10,918,632 B2 * 2/2021 Hakonarson ......... A61K 31/454

FOREIGN PATENT DOCUMENTS

| WO | 2006/048771 A1 | 5/2006 |
| WO | 2011/073347 A1 | 6/2011 |
| WO | 2015/032790 A1 | 3/2015 |

OTHER PUBLICATIONS

Wang, K. et al., "A genome-wide association study on common SNPs and rare CNVs in anorexia nervosa", Molecular Psychiatry, 16(9): 949-959 (2010).
Hinney, A. et al., "Evience for three genetic loci involved in both anorexia nervosa risk and variation of body mass index", Molecular Psychiatry, 22(2): 192-201 (2016).
Boraska, V. et al., "A genome-wide association study of anorexia nervosa". Molecular Psychiatry, 19(10): 1085-1094 (2014).
Shannon, P. et al., "Cytoscape: A Software Environment for Integrated Models of Biomolecular Interaction Networks", Genome Research, 13(11): 2498-2504 (2003).
Weiland, T.J. et al., "Metabotropic glutamate receptors mediate lipopolysaccharide-induced fever and sickness behavior". Brain, Behavior and Immunity, Academic Press, San Diego, CA, US, vol. 20, No. 3: 233-245 (2006).
International Search Report, dated Feb. 5, 2018, issued in corresponding International Application No. PCT/US2017/050228.
Written Opinion, dated Feb. 5, 2018, issued in corresponding International Application No. PCT/US2017/050228.
Henrichsen, Charlotte et al., "Copy number variants, diseases and gene expression", Human Molecular Genetics, 18: Review issue 1, doi:10.1093/hmg/ddp011 (2009).
Hirouchi, Masaaki et al., "Role of metabotropic glutamate receptor subclasses in modulation of adenylyl cyclase activity by a nootropic NS-105", European Journal of Pharmacology, 387: 9-17 (2009).
Malykh, Andrei et al., "Piracetam and Piracetam-Like Drugs", Drugs, 70(3): 287-312 (2010).
Oka, Michiko et al., "Involvement of metabotropic glutamate receptors in G1- and G8-dependent modulation of adenylate cyclase activity induced by a novel cognition enhancer NS-105 in rat brain", Brain Research, 754: 121-130 (1997).
Wang, Kai et al., "Penn CNV: An integrated hidden Markov model designed for high-resolution copy No. variation detection in whole-genome SNP genotyping data", Genome Research, 17: 1665-1674, Cold Spring Harbor Laboratory Press (2007).

* cited by examiner

*Primary Examiner* — John M Mauro
(74) *Attorney, Agent, or Firm* — Kathleen D. Rigaut; Howson & Howson LLP

(57) ABSTRACT

This application relates to methods of diagnosing and treating anorexia nervosa (AN) and binge eating disorder (BED) with a nonselective activator of metabotropic glutamate receptors (mGluRs).

19 Claims, 42 Drawing Sheets

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| ACAT1 | chr11:107992257-108018891 | chr11:107492257-108518891 | chr11:107497467-107523485 | rs7925970 | kgp3957860 |
| ACCN1 | chr17:31340105-32483825 | chr17:30840105-32983825 | chr17:28364218-29507938 | rs2519865 | kgp10854156 |
| ACTR2 | chr2:65454828-65498390 | chr2:64954828-65998390 | chr2:65308405-65351891 | rs1477043 | kgp4266233 |
| ADCY1 | chr7:45614124-45762714 | chr7:45114124-46262714 | chr7:45580649-45729239 | rs2289367 | kgp13398740 |
| ADRBK1 | chr11:67033904-67054029 | chr11:66533904-67554029 | chr11:66790480-66810605 | kgp7862175 | kgp2126040 |
| ALDOA | chr16:30064410-30081741 | chr16:29564410-30581741 | chr16:29971972-29989236 | kgp733881 | kgp6386467,rs33997546 |
| APP | chr21:27252860-27543446 | chr21:26752860-28043446 | chr21:26174731-26465003 | rs7281883 | kgp2004872 |
| ARL15 | chr5:53180613-53606403 | chr5:52680613-54106403 | chr5:53216370-53642160 | kgp10474479 | rs10058571 |
| ATXN7L3 | chr17:42269172-42275529 | chr17:41769172-42775529 | chr17:39624698-39631055 | rs11650560 | rs6503398 |
| BDKRB2 | chr14:96671134-96710666 | chr14:96171134-97210666 | chr14:95740887-95780419 | kgp19731302 | kgp1905230 |
| CA8 | chr8:61101422-61193954 | chr8:60601422-61693954 | chr8:61263976-61356508 | kgp9568230 | kgp1623935 |
| CACNA1B | chr9:140772240-141019076 | chr9:140272240-141519076 | chr9:139892061-140136452 | kgp18327422 | kgp12374930 |
| CACYBP | chr1:174968570-174981163 | chr1:174468570-175481163 | chr1:173235193-173247786 | rs1013769 | kgp15391194 |
| CALM1 | chr14:90863326-90874619 | chr14:90363326-91374619 | chr14:89933125-89944363 | kgp828819 | kgp22766175 |
| CHRM3 | chr1:239549864-240049896 | chr1:239049864-240549896 | chr1:237616487-238116519 | kgp1999037 | rs1537850 |
| CIC | chr19:42788816-42799949 | chr19:42288816-43299949 | chr19:47480656-47491789 | kgp21495548 | kgp22794755 |
| CNP | chr17:40118758-40129754 | chr17:39618758-40629754 | chr17:37372284-37383280 | kgp4988562 | kgp1573374 |

*Fig. 1-1*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| CNTN4 | chr3:2140549-3099645 | chr3:1640549-3599645 | chr3:2117246-3074645 | kgp7465125 | kgp11488181,rs9811783 |
| CRHR1 | chr17:954314-1170453 | chr17:454314-1670453 | chr17:41217448-41268973 | kgp12243700 | kgp2967880 |
| CTNNA2 | chr2:79412356-80875988 | chr2:78912356-81375988 | chr2:79265864-80729416 | kgp2692843 | kgp6161954 |
| DISC1 | chr1:231664398-232177019 | chr1:231164398-232677019 | chr1:229829183-230243641 | kgp15830047 | kgp10247084 |
| DPP6 | chr7:153584418-154685995 | chr7:153084418-155185995 | chr7:153215351-154316928 | rs1822707 | rs7781545 |
| DYNLL1 | chr12:120907659-120936298 | chr12:120407659-121436298 | chr12:119392042-119420681 | rs2393569 | rs1169303 |
| FPR1 | chr19:52249022-52255150 | chr19:51749022-52755150 | chr19:56940837-56946962 | rs11084062 | kgp21351572 |
| GAPDH | chr12:6643656-6647536 | chr12:6143656-7147536 | chr12:6513917-6517797 | kgp12277967 | kgp3951989 |
| GNA15 | chr19:3136190-3163766 | chr19:2636190-3663766 | chr19:3087190-3114766 | kgp9441497 | rs8109485 |
| GNAI2 | chr3:50263723-50296786 | chr3:49763723-50796786 | chr3:50238727-50271790 | rs1049256 | kgp1163947 |
| GNAO1 | chr16:56225250-56391356 | chr16:55725250-56891356 | chr16:54782751-54948857 | rs36013 | kgp16402238 |
| GNAQ | chr9:80335190-80646219 | chr9:79835190-81146219 | chr9:79525010-79836012 | rs3802497 | kgp478959 |
| GRIK1 | chr21:30909253-31312282 | chr21:30409253-31812282 | chr21:29831124-30234153 | kgp6759057 | kgp13183414 |
| GRIK3 | chr1:37261127-37499844 | chr1:36761127-37999844 | chr1:37033714-37272431 | kgp15160339 | kgp6185747 |
| GRM1 | chr6:146348781-146758731 | chr6:145848781-147258731 | chr6:146390474-146800424 | kgp17333275 | rs17076442 |
| GRM3 | chr7:86273229-86494192 | chr7:85773229-86994192 | chr7:86111165-86332128 | rs7809507 | rs6950721 |
| GRM5 | chr11:88237743-88796816 | chr11:87737743-89296816 | chr11:87881005-88436464 | kgp11022062 | rs7123374 |
| GRM7 | chr3:6902801-7783218 | chr3:6402801-8283218 | chr3:6877926-7758217 | rs17288121 | kgp10770379 |
| GRM8 | chr7:126078651-126893147 | chr7:125578651-127393147 | chr7:125865887-126680383 | rs11767202 | kgp13721602 |
| GSN | chr9:123963760-124095120 | chr9:123463760-124595120 | chr9:123003581-123134941 | rs10984984 | kgp10246924 |
| HOMER1 | chr5:78669785-78809700 | chr5:78169785-79309700 | chr5:78705541-78845456 | kgp22480767 | rs2438612 |

*Fig. 1-2*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| HTR2A | chr13:47407512-47471169 | chr13:46907512-47971169 | chr13:46305513-46368995 | rs4942513 | rs2185411 |
| LARP7 | chr4:113558119-113578742 | chr4:113058119-114078742 | chr4:113777568-113798191 | kgp20778198 | rs10516593 |
| MAPK1 | chr22:22113946-22221970 | chr22:21613946-22721970 | chr22:20443946-20551970 | rs2019503 | rs5758017 |
| MTHFD1 | chr14:64854758-64926725 | chr14:64354758-65426725 | chr14:63924845-63996474 | kgp8236539 | kgp19721535 |
| MX1 | chr21:42792519-42831141 | chr21:42292519-43331141 | chr21:41714311-41753008 | rs7280789 | kgp9356591 |
| NARG1 | chr4:140222675-140311935 | chr4:139722675-140811935 | chr4:140442125-140531385 | kgp951257 | kgp22761518 |
| NEGR1 | chr1:71868624-72748405 | chr1:71368624-73248405 | chr1:71641212-72520993 | kgp15840593 | kgp15187386 |
| NLN | chr5:65018022-65125111 | chr5:64518022-65625111 | chr5:65053840-65155145 | kgp8540617 | kgp6780911 |
| NMI | chr2:152126981-152146430 | chr2:151626981-152646430 | chr2:151835227-151854676 | rs9789673 | rs4303715 |
| PCBP3 | chr21:47063682-47355618 | chr21:46563682-47855618 | chr21:45888110-46180046 | rs13047590 | rs17371795 |
| PDE1C | chr7:31792631-32338383 | chr7:31292631-32838383 | chr7:31759156-32305466 | rs960434 | rs10264489 |
| PPP2R1A | chr19:52693054-52729678 | chr19:52193054-53229678 | chr19:57385045-57421483 | kgp3827878 | kgp21490256 |
| PRPSAP1 | chr17:74306867-74350279 | chr17:73806867-74850279 | chr17:71818609-71861526 | kgp13936725 | kgp5222426 |
| PSMD11 | chr17:30771501-30808042 | chr17:30271501-31308042 | chr17:27795614-27832155 | kgp12010810 | rs8065019 |
| PSMD13 | chr11:236807-252984 | chr11:1-752984 | chr11:226807-242984 | kgp9815230 | kgp7252222 |
| PXN | chr12:120648241-120703574 | chr12:120148241-121203574 | chr12:119132632-119187946 | kgp9790305 | kgp10851563 |
| QRICH2 | chr17:74270129-74303761 | chr17:73770129-74803761 | chr17:71781724-71815356 | kgp9494493 | kgp13978344 |
| RANBP1 | chr22:20105023-20114706 | chr22:19605023-20614706 | chr22:18485023-18494704 | kgp15081773 | kgp240898 |
| RAP2A | chr13:98086474-98120252 | chr13:97586474-98620252 | chr13:96884476-96918245 | kgp1964422 | kgp12456635 |
| RCC1 | chr1:28832454-28865708 | chr1:28332454-29365708 | chr1:28717331-28738194 | kgp4972332 | kgp10549261 |
| RGS12 | chr4:3315873-3441640 | chr4:2815873-3941640 | chr4:3285671-3411438 | kgp6603457 | kgp12100218 |

*Fig. 1-3*

| Tier 1 Gene | GeneRange (hg19) | GeneRange +500kb(hg19) | GeneRange (hg18) | StartSNP (GeneRange +500kb) | EndSNP (GeneRange +500kb) |
|---|---|---|---|---|---|
| RIF1 | chr2:152266396-152333860 | chr2:151766396-152833860 | chr2:151974645-152040665 | rs13010870 | kgp14366130 |
| RUVBL2 | chr19:49497155-49519182 | chr19:48997155-50019182 | chr19:54188967-54210994 | kgp2866116 | rs6509434 |
| RYR1 | chr19:38924339-39078204 | chr19:38424339-39578204 | chr19:43616179-43770044 | kgp21463042 | kgp10827233 |
| RYR2 | chr1:237205701-237997288 | chr1:236705701-238497288 | chr1:235272324-236063911 | kgp15265824 | kgp855991 |
| SDC3 | chr1:31342312-31381480 | chr1:30842312-31881480 | chr1:31114899-31154067 | kgp3545961 | rs1039630 |
| SELE | chr1:169691780-169703220 | chr1:169191780-170203220 | chr1:167958404-167969844 | kgp11738441 | kgp5736867 |
| SERPINB9 | chr6:2887503-2903545 | chr6:2387503-3403545 | chr6:2832502-2848506 | rs4959652 | kgp9198993 |
| SETD4 | chr21:37415981-37451687 | chr21:36915981-37951687 | chr21:36337851-36373557 | rs8131794 | kgp10193814 |
| SGTB | chr5:64961754-65017941 | chr5:64461754-65517941 | chr5:64997510-65053697 | rs2367239 | rs253229 |
| SHANK1 | chr19:51165083-51220195 | chr19:50665083-51720195 | chr19:55856895-55912007 | kgp8880890 | kgp5265049 |
| SLC7A10 | chr19:33699569-33716756 | chr19:33199569-34216756 | chr19:38391410-38408548 | kgp3880561 | kgp21532613 |
| SORD | chr15:45315301-45367287 | chr15:44815301-45867287 | chr15:43102632-43154331 | rs3752691 | rs17627219 |
| STRAP | chr12:16035287-16056410 | chr12:15535287-16556410 | chr12:15926554-15947677 | kgp9763258 | kgp18858589 |
| TK1 | chr17:76170159-76183285 | chr17:75670159-76683285 | chr17:73681754-73694880 | kgp13960604 | kgp4569268 |
| TNIK | chr3:170780291-171178197 | chr3:170280291-171678197 | chr3:172264363-172660546 | kgp17660929 | kgp3100328 |
| USP24 | chr1:55532031-55681039 | chr1:55032031-56181039 | chr1:55304619-55453350 | kgp3052862 | kgp5594096 |
| VHL | chr3:10183318-10195354 | chr3:9683318-10695354 | chr3:10158318-10168746 | kgp6652387 | rs9942062 |

*Fig. 1-4*

| Tier 2 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| ACAT2 | chr6:160182988-160200087 | chr6:159682988-160700087 | chr12:51783540-51804590 | kgp17016252 | rs3119312 |
| ACCN2 | chr12:50451486-50477394 | chr12:49951486-50977394 | chr12:48737753-48763661 | kgp6083801 | kgp2326833 |
| ACP1 | chr2:264868-278282 | chr2:1-778282 | chr2:254871-268282 | kgp14878812 | kgp6217001 |
| ACTB | chr7:5566778-5570232 | chr7:5066778-6070232 | chr7:5533304-5536758 | kgp10503129 | rs17136342 |
| ADA | chr20:43248162-43280376 | chr20:42748162-43780376 | chr20:42681576-42713790 | kgp505723 | rs2207199 |
| ADD1 | chr4:2845583-2931802 | chr4:2345583-3431802 | chr4:2815381-2901587 | kgp5601859 | kgp5383382 |
| ADD2 | chr2:70834749-70995375 | chr2:70334749-71495375 | chr2:70688257-70848837 | kgp14188216 | kgp4077094 |
| ADORA1 | chr1:203096835-203136533 | chr1:202596835-203636533 | chr1:201363458-201403156 | rs16850143 | rs12568960 |
| ADRA1B | chr5:159343739-159400017 | chr5:158843739-159900017 | chr5:159276317-159332595 | rs17056747 | kgp2774549 |
| ADRA2A | chr10:112836789-112840662 | chr10:112336789-113340662 | chr10:112826910-112830560 | kgp3219023 | rs10787379 |
| ADRA2C | chr4:3768295-3770253 | chr4:3268295-4270253 | chr4:3737872-3740016 | kgp21189210 | kgp21320659 |
| ADRB2 | chr5:148206155-148208197 | chr5:147706155-148708197 | chr5:148186348-148188381 | kgp6738042 | rs352336 |
| ANXA2 | chr15:60639349-60690185 | chr15:60139349-61190185 | chr15:58426641-58477477 | kgp19904124 | kgp1248561 |
| APTX | chr9:32972603-33001639 | chr9:32472603-33501639 | chr9:32962607-33015110 | kgp8123814 | kgp22778750 |
| AQP1 | chr7:30893009-30965131 | chr7:30393009-31465131 | chr7:30917992-30931656 | kgp13347683 | rs11983505 |
| ARHGAP24 | chr4:86396283-86923823 | chr4:85896283-87423823 | chr4:86615307-87142847 | kgp12192788 | kgp20991115 |
| ARRB1 | chr11:74971165-75062875 | chr11:74471165-75562875 | chr11:74654129-74740521 | kgp13077708 | kgp12867051 |
| ARRB2 | chr17:4613788-4624795 | chr17:4113788-5124795 | chr17:4560537-4571544 | kgp10630047 | rs2304905 |

*Fig. 2-1*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| BDKRB1 | chr14:96722546-96731100 | chr14:96222546-97231100 | chr14:95792311-95800853 | rs10146784 | kgp10194056 |
| BTBD2 | chr19:1985446-2015702 | chr19:1485446-2515702 | chr19:1936446-1966702 | kgp9698924 | rs12985186 |
| BTG2 | chr1:203274663-203278729 | chr1:202774663-203778729 | chr1:201541286-201545352 | kgp11073362 | kgp22834576 |
| C17orf44 | chr17:8123966-8127361 | chr17:7623966-8627361 | chr17:8064691-8068086 | kgp14083005 | kgp8066962 |
| C1orf116 | chr1:207191865-207206101 | chr1:206691865-207706101 | chr1:205258488-205272724 | kgp15208593 | rs12094477 |
| C7orf25 | chr7:42948871-42971805 | chr7:42448871-43471805 | chr7:42915396-42938330 | kgp13766903 | kgp8523923 |
| CALB2 | chr16:71392615-71424342 | chr16:70892615-71924342 | chr16:69950126-69981843 | rs1774414 | kgp16319275 |
| CALM2 | chr2:47387220-47403740 | chr2:46887220-47903740 | chr2:47146583-47257154 | kgp12094177 | kgp4237241 |
| CALM3 | chr14:90863326-90874619 | chr14:90363326-91374619 | chr19:51796351-51805879 | kgp828819 | kgp22766175 |
| CAMK1 | chr3:9799028-9811668 | chr3:9299028-10311668 | chr3:9774030-9786661 | kgp4340327 | kgp1318661 |
| CAMK2B | chr7:44256748-44365230 | chr7:43756748-44865230 | chr7:44223273-44331749 | rs10245456 | kgp10338229 |
| CAMK4 | chr5:110559946-110820748 | chr5:110059946-111320748 | chr5:110587980-110848647 | kgp11981357 | kgp22673631 |
| CCNB1 | chr5:68462836-68474070 | chr5:67962836-68974070 | chr5:68498668-68509826 | kgp5100830 | rs28529133 |
| CDC42 | chr1:22379119-22419436 | chr1:21879119-22919436 | chr1:22251706-22292023 | kgp15282552 | rs209696 |
| CENTG1 | chr12:58118076-58135944 | chr12:57618076-58635944 | chr12:56404343-56422211 | kgp22774357 | rs12825103 |
| CHGB | chr20:5891973-5906005 | chr20:5391973-6406005 | chr20:5840167-5854003 | kgp19217529 | kgp5406173 |
| CHP | chr15:41523436-41574083 | chr15:41023436-42074083 | chr15:39310728-39361375 | kgp9389002 | kgp10815429 |
| CHRM2 | chr7:136553398-136701771 | chr7:136053398-137201771 | chr7:136203938-136352311 | rs2882248 | kgp11051162 |
| CMPK | chr2:6988440-7005950 | chr2:6488440-7505950 | chr2:6905891-6923401 | rs16865056 | kgp6717309 |
| CNR1 | chr6:88849584-88875767 | chr6:88349584-89375767 | chr6:88910155-88932281 | kgp11366911 | kgp5424340 |

*Fig. 2-2*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| COPB2 | chr3:139076432-139108522 | chr3:138576432-139608522 | chr3:140559122-140591212 | kgp17652827 | rs2554152 |
| CYCS | chr7:25158269-25164980 | chr7:24658269-25664980 | chr7:25124799-25131480 | kgp22782658 | kgp9259047 |
| DCN | chr12:91539034-91576806 | chr12:91039034-92076806 | chr12:90063165-90100937 | rs11105720 | rs1602946 |
| DHCR7 | chr11:71145456-71159477 | chr11:70645456-71659477 | chr11:70823104-70837125 | rs2016495 | kgp4157665 |
| DLST | chr14:75348593-75370450 | chr14:74848593-75870450 | chr14:74418371-74440198 | kgp6099186 | rs11621369 |
| DRD2 | chr11:113280316-113346001 | chr11:112780316-113846001 | chr11:112785526-112851211 | kgp12732525 | rs1062613 |
| DRD3 | chr3:113847556-113918254 | chr3:113347556-114418254 | chr3:115330246-115400944 | kgp18078164 | kgp7361746 |
| DSTN | chr20:17550598-17588652 | chr20:17050598-18088652 | chr20:17498598-17536652 | kgp19350858 | rs1581925 |
| ECHS1 | chr10:135175986-135186908 | chr10:134675986-135686908 | chr10:135025979-135036898 | kgp21664075 | kgp22837031 |
| EGFR | chr7:55086724-55275031 | chr7:54586724-55775031 | chr7:55054218-55242525 | kgp12053718 | kgp3314724 |
| EIF3S3 | chr8:117657055-117768062 | chr8:117157055-118268062 | chr8:117726236-117837243 | kgp10576753 | rs1793723 |
| ERBB2 | chr17:37844392-37884915 | chr17:37344392-38384915 | chr17:35097918-35138441 | kgp11528115 | kgp670921 |
| F2R | chr5:76011867-76031595 | chr5:75511867-76531595 | chr5:76047623-76067351 | kgp22518836 | kgp1549629 |
| F2RL2 | chr5:75911306-75919240 | chr5:75411306-76419240 | chr5:75947062-75954996 | kgp10188048 | kgp8041699 |
| F2RL3 | chr19:16999825-17002830 | chr19:16499825-17502830 | chr19:16860825-16863830 | kgp9756004 | kgp12567834 |
| F3 | chr1:94994731-95007413 | chr1:94494731-95507413 | chr1:94767460-94779903 | kgp22732356 | kgp5203715 |
| FKBP3 | chr14:45584801-45604009 | chr14:45084801-46104009 | chr14:44654858-44674272 | kgp8973198 | kgp19724486 |
| FSCN1 | chr7:5632435-5646287 | chr7:5132435-6146287 | chr7:5598979-5612812 | kgp11535801 | kgp22733484 |
| FURIN | chr15:91411884-91426687 | chr15:90911884-91926687 | chr15:89212888-89227691 | kgp19755110 | kgp7570879 |
| FYN | chr6:111981534-112194655 | chr6:111481534-112694655 | chr6:112089177-112301320 | kgp9553033 | kgp10843976 |

Fig. 2-3

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| GLP1R | chr6:39016556-39055520 | chr6:38516556-39555520 | chr6:39124534-39163498 | kgp11427391 | kgp8067157 |
| GLP2R | chr17:9729380-9793022 | chr17:9229380-10293022 | chr17:9670105-9733747 | kgp13857921 | kgp14095302 |
| GNAI1 | chr7:79764139-79848725 | chr7:79264139-80348725 | chr7:79602075-79686661 | kgp3340161 | kgp96572 |
| GNAI3 | chr1:110091185-110138452 | chr1:109591185-110638452 | chr1:109892708-109939975 | rs28503409 | kgp2138201 |
| GNB2L1 | chr5:180663927-180670906 | chr5:180163927-181170906 | chr5:180596533-180603512 | kgp9825803 | kgp22785368 |
| GOT1 | chr10:101156626-101190530 | chr10:100656626-101690530 | chr10:101146617-101180336 | kgp21656902 | kgp21815940 |
| GP1BA | chr17:4835591-4838325 | chr17:4335591-5338325 | chr17:4776371-4779067 | kgp13949132 | kgp11186643 |
| GPR26 | chr10:125425870-125456913 | chr10:124925870-125956913 | chr10:125415860-125444113 | kgp7582662 | kgp21578542 |
| GRB2 | chr17:73314156-73401790 | chr17:72814156-73901790 | chr17:70825751-70913385 | kgp13841089 | kgp14035219 |
| GRB7 | chr17:37894161-37903538 | chr17:37394161-38403538 | chr17:35147712-35157064 | kgp14102913 | kgp13833584 |
| GRIA1 | chr5:152870083-153193429 | chr5:152370083-153693429 | chr5:152850276-153173622 | rs1438937 | rs10057369 |
| GRM2 | chr3:51741080-51752625 | chr3:51241080-52252625 | chr3:51716127-51727665 | rs4367100 | rs13060808 |
| GRM4 | chr6:33989627-34113869 | chr6:33489627-34613869 | chr6:34097605-34231377 | kgp17076142 | rs6909637 |
| GRM6 | chr5:178405329-178422124 | chr5:177905329-178922124 | chr5:178337935-178354730 | rs603852 | rs11249632 |
| HBXIP | chr1:110943876-110950546 | chr1:110443876-111450546 | chr1:110745399-110752069 | kgp8686658 | rs1936942 |
| HD | chr6:125596496-125623282 | chr6:125096496-126123282 | chr6:125638195-125664981 | rs11154263 | rs11967627 |
| HNRPA3 | chr2:178077422-178088685 | chr2:177577422-178588685 | chr2:177785668-177796931 | kgp14203861 | rs1344924 |
| HOMER3 | chr19:19017768-19045219 | chr19:18517768-19545219 | chr19:18901011-18912983 | rs13344313 | rs4808199 |
| HRPT2 | chr1:193091088-193223942 | chr1:192591088-193723942 | chr1:191357711-191490565 | kgp2473538 | kgp12065536 |
| HSP90AB1 | chr6:44214848-44221614 | chr6:43714848-44721614 | chr6:44322826-44329592 | kgp5836209 | kgp8706663 |

*Fig. 2-4*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| IL8RB | chr2:218989997-219001975 | chr2:218489997-219501975 | chr2:218698242-218710220 | kgp22730583 | rs1055816 |
| IMPDH2 | chr3:49061761-49066875 | chr3:48561761-49566875 | chr3:49036765-49041879 | kgp22731595 | kgp5626213 |
| IQGAP2 | chr5:75699148-76003957 | chr5:75199148-76503957 | chr5:75734904-76039713 | kgp22490664 | rs11739698 |
| ITGB1 | chr10:33189245-33247293 | chr10:32689245-33747293 | chr10:33229251-33287299 | kgp12034252 | rs11009395 |
| ITGB7 | chr12:53585106-53601000 | chr12:53085106-54101000 | chr12:51871373-51887267 | kgp19011413 | kgp3313746 |
| ITPR1 | chr3:4535031-4889524 | chr3:4035031-5389524 | chr3:4510033-4864286 | kgp17889944 | kgp1749057 |
| KIAA0090 | chr1:19544583-19578046 | chr1:19044583-20078046 | chr1:19417170-19450633 | rs624761 | rs1009631 |
| KIAA1683 | chr19:18367905-18385319 | chr19:17867905-18885319 | chr19:18228907-18246235 | kgp6435620 | rs10412356 |
| LAMA4 | chr6:112429133-112575828 | chr6:111929133-113075828 | chr6:112535826-112682521 | kgp16962466 | kgp17024247 |
| LRP2BP | chr4:186285031-186300172 | chr4:185785031-186800172 | chr4:186522026-186537166 | kgp7238414 | rs9994907 |
| LRRC59 | chr17:48458593-48474914 | chr17:47958593-48974914 | chr17:45813597-45829831 | kgp1609816 | kgp13856216 |
| LTA | chr6:2825414-2827639 | chr6:2825414-2827639 | chr6:2787675-2789683 | kgp11675228 | rs6912537 |
| LYAR | chr4:4269428-4291896 | chr4:3769428-4791896 | chr4:4320337-4342744 | kgp22780996 | kgp7317116 |
| LYN | chr8:56792385-56925006 | chr8:56292385-57425006 | chr8:56954939-57086494 | kgp8836202 | rs2670027 |
| MAP4 | chr3:47892179-48130769 | chr3:47392179-48630769 | chr3:47867188-48105715 | kgp17741397 | rs35623035 |
| MAPT | chr17:43971747-44105699 | chr17:43471747-44605699 | chr17:41327543-41461546 | kgp22730329 | kgp13941400 |
| MARK4 | chr19:45754515-45808541 | chr19:45254515-46308541 | chr19:50446681-50500381 | kgp10230030 | kgp21456098 |
| MC4R | chr18:58038563-58040001 | chr18:57538563-58540001 | chr18:56189543-56190981 | kgp7049183 | kgp1258536 |
| MGC11082 | chr18:3602998-3604385 | chr18:3102998-4104385 | chr18:3592998-3594385 | kgp15965827 | kgp12318627 |
| MRPL14 | chr6:44081372-44095191 | chr6:43581372-44595191 | chr6:44189349-44203169 | kgp17033193 | rs527322 |

*Fig. 2-5*

| Tier 2 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| MRPS16 | chr10:75006445-75012451 | chr10:74506445-75512451 | chr10:74678606-74682457 | kgp21628722 | rs12243089 |
| MTNR1A | chr4:187454808-187476537 | chr4:186954808-187976537 | chr4:187691802-187713531 | rs12648771 | rs4476657 |
| MTNR1B | chr11:92702788-92715948 | chr11:92202788-93215948 | chr11:92342436-92355596 | kgp10063029 | rs2658801 |
| MYC | chr8:128748314-128753680 | chr8:128248314-129253680 | chr8:128817497-128822855 | kgp3177285 | kgp1944877 |
| MYO6 | chr6:76458908-76629254 | chr6:75958908-77129254 | chr6:76515628-76685974 | kgp17262775 | kgp17183304 |
| NANS | chr9:100818958-100845365 | chr9:100318958-101345365 | chr9:99847709-99885178 | rs10817759 | rs2778908 |
| NCK1 | chr3:136581049-136667968 | chr3:136081049-137167968 | chr3:138063762-138150658 | kgp117446 | kgp10600232 |
| NFKBIA | chr14:35870715-35873960 | chr14:35370715-36373960 | chr14:34940466-34943711 | kgp19552677 | kgp19707730 |
| NPY2R | chr4:156129780-156138228 | chr4:155629780-156638228 | chr4:156349230-156357678 | kgp3956236 | kgp20850236 |
| NUDC | chr1:27248223-27272887 | chr1:26748223-27772887 | chr1:27120810-27145474 | rs11247955 | kgp15594139 |
| OPRD1 | chr1:29138653-29190208 | chr1:28638653-29690208 | chr1:29011240-29062795 | kgp9104521 | kgp15855740 |
| PAFAH1B3 | chr19:42801184-42806952 | chr19:42301184-43306952 | chr19:47493024-47498563 | kgp21540635 | kgp22735078 |
| PCBP1 | chr2:70314584-70316334 | chr2:69814584-70816334 | chr2:70168204-70169836 | kgp14596264 | kgp6568959 |
| PCDHA4 | chr5:140186671-140391929 | chr5:139686671-140891929 | chr5:140166855-140372115 | kgp6468526 | kgp10727572 |
| PCID1 | chr11:32605313-32624037 | chr11:32105313-33124037 | chr11:32561889-32580613 | kgp13035948 | rs10836023 |
| PCMT1 | chr6:150070830-150132557 | chr6:149570830-150632557 | chr6:150112657-150174249 | kgp17277449 | kgp10169289 |
| PDCD5 | chr19:33072093-33078358 | chr19:32572093-33578358 | chr19:37763943-37770169 | kgp21531284 | rs7259333 |
| PDE1B | chr12:54943176-54973023 | chr12:54443176-55473023 | chr12:53229670-53259290 | kgp18962385 | rs11171250 |
| PDE6G | chr17:79617488-79623607 | chr17:79117488-80123607 | chr17:77227893-77234038 | kgp317116 | kgp13898509 |
| PGM1 | chr1:64058946-64125916 | chr1:63558946-64625916 | chr1:63831534-63898505 | kgp175729 | kgp15416792 |

*Fig. 2-6*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| PHKB | chr16:47495209-47735434 | chr16:46995209-48235434 | chr16:46052710-46292935 | kgp8481371 | rs16945930 |
| PHKG2 | chr16:30759619-30772497 | chr16:30259619-31272497 | chr16:30667237-30676183 | kgp16316196 | kgp22773724 |
| PICK1 | chr22:38453261-38471708 | chr22:37953261-38971708 | chr22:36783207-36801654 | kgp5170623 | kgp1759680 |
| PIK3CA | chr3:178866310-178952497 | chr3:178366310-179452497 | chr3:180349004-180435191 | rs7615444 | rs1025864 |
| PIK3R1 | chr5:67511583-67597649 | chr5:67011583-68097649 | chr5:67547359-67633405 | kgp7844449 | rs7737296 |
| PLA2G7 | chr6:46672052-46703430 | chr6:46172052-47203430 | chr6:46780011-46811110 | kgp4678268 | kgp9155835 |
| PLCB1 | chr20:8113295-8865547 | chr20:7613295-9365547 | chr20:8061295-8813547 | kgp19226483 | rs2076234 |
| PLCB3 | chr11:64018994-64036924 | chr11:63518994-64536924 | chr11:63775697-63793195 | kgp9427286 | rs484886 |
| PLCG2 | chr16:81812898-81991899 | chr16:81312898-82491899 | chr16:80370430-80549400 | kgp4622733 | kgp3230988 |
| PPIH | chr1:43124047-43142429 | chr1:42624047-43642429 | chr1:42896634-42915016 | kgp1870818 | rs11210802 |
| PRDX1 | chr1:45976706-45988562 | chr1:45476706-46488562 | chr1:45749293-45760196 | rs3806405 | kgp15560310 |
| PRKCA | chr17:64298925-64806862 | chr17:63798925-65306862 | chr17:61729387-62237324 | kgp13847618 | kgp13994829 |
| PRLHR | chr10:120352915-120355160 | chr10:119852915-120855160 | chr10:120342905-120345150 | rs853584 | kgp21690663 |
| PRMT1 | chr19:50180408-50191707 | chr19:49680408-50691707 | chr19:54872307-54883516 | kgp1460116 | kgp5315133 |
| PSAT1 | chr9:80912058-80945009 | chr9:80412058-81445009 | chr9:80101878-80134829 | kgp2581728 | kgp9769053 |
| PSEN1 | chr14:73603142-73690399 | chr14:73103142-74190399 | chr14:72672931-72756862 | kgp8405661 | kgp19611371 |
| PSMA1 | chr11:14526421-14665180 | chr11:14026421-15165180 | chr11:14482997-14621739 | kgp12643195 | kgp13010596 |
| PSMC1 | chr14:90722893-90738966 | chr14:90222893-91238966 | chr14:89792646-89808719 | rs10140098 | kgp19595798 |
| PSMD1 | chr2:231921577-232037540 | chr2:231421577-232537540 | chr2:231629852-231745717 | rs1678155 | kgp11602861 |
| PSMD6 | chr3:63996230-64009658 | chr3:63496230-64509658 | chr3:63971270-63984698 | kgp9706776 | kgp17718198 |

*Fig. 2-7*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| PSME1 | chr14:24605377-24608176 | chr14:24105377-25108176 | chr14:23675217-23678016 | kgp11494860 | kgp2234181 |
| PTHR2 | chr2:209353736-209704818 | chr2:208853736-210204818 | chr2:209061981-209413063 | kgp14652386 | rs1020407 |
| PYGL | chr14:51371934-51411248 | chr14:50871934-51911248 | chr14:50441686-50480984 | kgp10991856 | rs7146882 |
| PYGM | chr11:64513860-64528187 | chr11:64013860-65028187 | chr11:64270436-64284763 | kgp12876954 | rs675671 |
| RAB2 | chr8:61429469-61536203 | chr8:60929469-62036203 | chr8:61592023-61698757 | kgp7067636 | rs3864667 |
| RALA | chr7:39663151-39747723 | chr7:39163151-40247723 | chr7:39629686-39714242 | kgp22733616 | rs11768838 |
| RCC2 | chr1:17733250-17766250 | chr1:17233250-18266250 | chr1:17605865-17638807 | kgp15535308 | kgp7647703 |
| RGS2 | chr1:192778168-192781407 | chr1:192278168-193281407 | chr1:191044793-191048026 | rs10921130 | kgp11065785 |
| RHOA | chr3:49396578-49449526 | chr3:48896578-49949526 | chr3:49371582-49424530 | kgp11466037 | rs868891 |
| RPA2 | chr1:28218048-28241236 | chr1:27718048-28741236 | chr1:28090635-28113823 | rs12033326 | kgp15705538 |
| RPLP2 | chr11:809935-812876 | chr11:309935-1312876 | chr11:799935-802876 | kgp11473410 | kgp7750669 |
| RPN2 | chr20:35807455-35870025 | chr20:35307455-36370025 | chr20:35240887-35303439 | kgp9846122 | kgp19260650 |
| RPS14 | chr5:149823791-149829319 | chr5:149323791-150329319 | chr5:149803984-149809512 | kgp22444746 | kgp22218062 |
| RRM1 | chr11:4137307-4223759 | chr11:3637307-4723759 | chr11:4072499-4116682 | rs6578398 | kgp4491491 |
| S100A6 | chr1:153507075-153508717 | chr1:153007075-154008717 | chr1:151773699-151775341 | kgp15193014 | rs10908627 |
| SACS | chr13:23902964-24007841 | chr13:23402964-24507841 | chr13:22800964-22905841 | kgp16818396 | rs2765089 |
| SARS | chr1:109756514-109780804 | chr1:109256514-110280804 | chr1:109558062-109582308 | kgp5910329 | rs1803687 |
| SCTR | chr2:120197418-120282028 | chr2:119697418-120782028 | chr2:119913888-119998498 | kgp12364473 | kgp22762988 |
| SET | chr9:131445933-131458675 | chr9:130945933-131958675 | chr9:130485754-130498496 | kgp11282765 | kgp18608937 |
| SF3B14 | chr2:24290453-24299314 | chr2:23790453-24799314 | chr2:24143957-24152818 | kgp14521970 | rs12474894 |

*Fig. 2-8*

| Tier 2 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| SHBG | chr17:7517381-7536700 | chr17:7017381-8036700 | chr17:7458106-7477395 | kgp7760759 | rs6503086 |
| SIAH1 | chr16:48390274-48482309 | chr16:47890274-48982309 | chr16:46947777-47039810 | kgp4639784 | kgp7644930 |
| SLC2A1 | chr1:43391045-43424847 | chr1:42891045-43924847 | chr1:43163632-43197434 | kgp2036523 | rs2782652 |
| SLC6A3 | chr5:1392904-1445543 | chr5:892904-1945543 | chr5:1445909-1498538 | kgp22585075 | kgp9690399 |
| SNCA | chr4:90645249-90759447 | chr4:90145249-91259447 | chr4:90865727-90978470 | kgp11552673 | kgp8195783 |
| SNRPB2 | chr20:16710608-16722417 | chr20:16210608-17222417 | chr20:16658628-16670037 | kgp19326624 | kgp19208923 |
| SOCS6 | chr18:67956136-67997434 | chr18:67456136-68497434 | chr18:66107116-66148414 | kgp10928836 | rs4243325 |
| SOCS7 | chr17:36508006-36561846 | chr17:36008006-37061846 | chr17:33761530-33809545 | rs12936144 | rs4794796 |
| SRC | chr20:35973087-36033821 | chr20:35473087-36533821 | chr20:35406501-35467235 | kgp19359278 | kgp9150551 |
| STAU1 | chr20:47729875-47805288 | chr20:47229875-48305288 | chr20:47163282-47238695 | rs11905650 | kgp19233876 |
| STX12 | chr1:28099693-28150963 | chr1:27599693-28650963 | chr1:27972280-28023550 | kgp22731625 | kgp15287949 |
| SYK | chr9:93564011-93660842 | chr9:93064011-94160842 | chr9:92603890-92698304 | kgp12394293 | rs894962 |
| TBCA | chr5:76986994-77072185 | chr5:76486994-77572185 | chr5:77022750-77107941 | rs2928164 | rs10059285 |
| TBXA2R | chr19:3594503-3606831 | chr19:3094503-4106831 | chr19:3545503-3557658 | kgp21472781 | kgp1760692 |
| TCP1 | chr6:160199529-160210735 | chr6:159699529-160710735 | chr6:160119519-160130725 | kgp16923201 | kgp10518192 |
| TEAD3 | chr6:35441373-35464861 | chr6:34941373-35964861 | chr6:35549351-35572839 | rs847861 | kgp3339 |
| TFAM | chr10:60145175-60155897 | chr10:59645175-60655897 | chr10:59815181-59825903 | kgp9406331 | kgp6514369 |
| TGM2 | chr20:36756863-36793700 | chr20:36256863-37293700 | chr20:36190277-36227114 | rs6067098 | kgp9992037 |
| TJP1 | chr15:29992356-30114706 | chr15:29492356-30614706 | chr15:27779648-27901998 | kgp19895791 | rs2604694 |
| TLR10 | chr4:38773859-38784611 | chr4:38273859-39284611 | chr4:38450646-38460984 | kgp9612652 | rs6531705 |

*Fig. 2-9*

| Tier 2 Gene | GeneRange(hg19) | GeneRange+500kb(hg19) | GeneRange(hg18) | StartSNP (GeneRange+ 500kb) | EndSNP (GeneRange+500kb) |
|---|---|---|---|---|---|
| TMEM4 | chr12:56704213-56710128 | chr12:56204213-57210128 | chr12:54990480-54996395 | kgp6718939 | kgp6565807 |
| TPI1 | chr12:6976583-6980110 | chr12:6476583-7480110 | chr12:6846966-6850253 | kgp3883976 | kgp18849054 |
| TRAF2 | chr9:139776384-139821067 | chr9:139276384-140321067 | chr9:138896205-138940888 | rs3812570 | kgp9465784 |
| TRMT112 | chr11:64084164-64085033 | chr11:63584164-64585033 | chr11:63840740-63841609 | kgp1242205 | rs2957154 |
| TUBA1 | chr12:49521565-49525304 | chr12:49021565-50025304 | chr12:47807832-47811571 | kgp4948752 | kgp18737983 |
| TUBA1A | chr12:49578582-49582861 | chr12:49078582-50082861 | chr12:47864849-47869128 | kgp5373125 | kgp1407179 |
| TUBA1B | chr12:49521566-49525304 | chr12:49021566-50025304 | chr12:47807832-47866883 | kgp4948752 | kgp18737983 |
| TUBA2 | chr12:49578793-49580616 | chr12:49078793-50080616 | chr12:47865060-47866883 | kgp18983720 | kgp75177 |
| TUBB | chr6:1981087-1986127 | chr6:1981087-1986127 | chr6:1935034-1940074 | kgp17000846 | kgp16908954 |
| TUBG1 | chr17:40761357-40767256 | chr17:40261357-41267256 | chr17:38015219-38020777 | rs12600570 | kgp3534380 |
| TXN | chr9:113006091-113018920 | chr9:112506091-113518920 | chr9:112046130-112058599 | kgp18601393 | kgp652846 |
| TXNDC4 | chr9:102741463-102861330 | chr9:102241463-103361330 | chr9:101781284-101901151 | kgp22740558 | rs10989168 |
| TXNL2 | chr10:131934639-131977932 | chr10:131434639-132477932 | chr10:131824629-131867922 | kgp21587397 | rs2921907 |
| TYMS | chr18:657603-673499 | chr18:157603-1173499 | chr18:647603-663499 | kgp1671520 | kgp5560925 |
| UBQLN4 | chr1:156005091-156023516 | chr1:155505091-156523516 | chr1:154271715-154290140 | rs12746592 | kgp204451 |
| UCHL1 | chr4:41258897-41270446 | chr4:40758897-41770446 | chr4:40953685-40965203 | rs10029833 | kgp21157719 |
| VIPR1 | chr3:42530790-42579065 | chr3:42030790-43079065 | chr3:42519120-42554064 | rs794894 | kgp10771397 |
| YWHAQ | chr2:9724105-9771106 | chr2:9224105-10271106 | chr2:9641556-9688557 | kgp7327726 | rs1138729 |
| ZAP70 | chr2:98330030-98356323 | chr2:97830030-98856323 | chr2:97696462-97722755 | kgp10723114 | kgp14308801 |

*Fig. 2-10*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| ABI3 | chr17:47287588-47300587 | chr17:46787588-47800587 | chr17:44642587-44655586 | rs7211412 | kgp13987803 |
| ACTA1 | chr1:229566992-229569843 | chr1:229066992-230069843 | chr1:227633615-227636466 | kgp706951 | kgp9594907 |
| ACTN2 | chr1:236849769-236927558 | chr1:236349769-237427558 | chr1:234916392-234994181 | kgp12139182 | kgp9945691 |
| ADCY5 | chr3:123001142-123167392 | chr3:122501142-123667392 | chr3:124486088-124650082 | kgp5729470 | kgp18234294 |
| ADCY8 | chr8:131792546-132052835 | chr8:131292546-132552835 | chr8:131861728-132122017 | rs11778881 | kgp4563992 |
| ADCYAP1R1 | chr7:31092075-31151093 | chr7:30592075-31651093 | chr7:31058666-31112836 | kgp6410265 | kgp5976045 |
| ADD3 | chr10:111756107-111895323 | chr10:111256107-112395323 | chr10:111746097-111885313 | kgp2922347 | kgp21705322 |
| AFAP1 | chr4:7760439-7941653 | chr4:7260439-8441653 | chr4:7811339-7992553 | kgp10066670 | kgp2565038 |
| AGTR1 | chr3:148415657-148460790 | chr3:147915657-148960790 | chr3:149898347-149943480 | kgp17969929 | rs9827666 |
| AHCYL1 | chr1:110527386-110566364 | chr1:110027386-111066364 | chr1:110328830-110367887 | kgp15280262 | kgp8467474 |
| AKAP12 | chr6:151561133-151679694 | chr6:151061133-152179694 | chr6:151603201-151719602 | kgp17415975 | kgp17180004 |
| AKAP13 | chr15:85923870-86292586 | chr15:85423870-86792586 | chr15:83724874-84093590 | rs11073778 | kgp10945265 |
| AKAP5 | chr14:64932216-64941221 | chr14:64432216-65441221 | chr14:64001969-64010974 | rs945029 | rs4499147 |
| AKAP9 | chr7:91570188-91739987 | chr7:91070188-92239987 | chr7:91408127-91577925 | kgp7513665 | kgp8102448 |
| AKR1C3 | chr10:5005453-5149878 | chr10:4505453-5649878 | chr10:4995453-5139878 | rs1679414 | kgp8379007 |
| AKT1 | chr14:105235686-105262080 | chr14:104735686-105762080 | chr14:104306731-104333125 | kgp10896929 | kgp7260890 |
| ANK2 | chr4:113739238-114304896 | chr4:113239238-114804896 | chr4:113958687-114524345 | kgp8454825 | kgp10144793 |
| ANKRD24 | chr19:4183350-4224811 | chr19:3683350-4724811 | chr19:4134350-4175811 | kgp3226366 | rs7255543 |

*Fig. 3-1*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| ANXA6 | chr5:150480266-150537443 | chr5:149980266-151037443 | chr5:150460460-150517560 | kgp22603058 | rs11747938 |
| ANXA7 | chr10:75135188-75173841 | chr10:74635188-75673841 | chr10:74805194-74843847 | kgp21588521 | kgp5026768,rs2227568 |
| APLP2 | chr11:129939715-130014706 | chr11:129439715-130514706 | chr11:129445010-129519910 | kgp22802171 | rs7116475 |
| AR | chrX:66763873-66950461 | chrX:66263873-67450461 | chrX:66680598-66860844 | rs478505 | kgp22776402 |
| ARF1 | chr1:228270360-228286913 | chr1:227770360-228786913 | chr1:226336983-226353536 | kgp7035482 | kgp5092378 |
| ARF3 | chr12:49329991-49351252 | chr12:48829991-49851252 | chr12:47616258-47637519 | kgp9963537 | kgp19162961 |
| ARHGAP1 | chr11:46698631-46722120 | chr11:46198631-47222120 | chr11:46655207-46678696 | rs11038804 | kgp12872953 |
| ARHGEF1 | chr19:42399421-42434296 | chr19:41899421-42934296 | chr19:47079106-47103444 | kgp21546138 | kgp9753873 |
| ARL3 | chr10:104433483-104474190 | chr10:103933483-104974190 | chr10:104423477-104464180 | rs4919614 | kgp2065500 |
| ARL8B | chr3:5163929-5222601 | chr3:4663929-5722601 | chr3:5138929-5197601 | kgp5083934 | kgp17728482 |
| ASCL2 | chr11:2289727-2292182 | chr11:1789727-2792182 | chr11:2246303-2248758 | kgp12845252 | kgp7129584 |
| ATF3 | chr1:212738675-212794119 | chr1:212238675-213294119 | chr1:210805319-210860739 | rs10863936 | kgp12569686 |
| ATN1 | chr12:7033625-7053815 | chr12:6533625-7553815 | chr12:6903886-6924076 | kgp18714644 | kgp19128481 |
| ATP1B1 | chr1:169075946-169101960 | chr1:168575946-169601960 | chr1:167342570-167368584 | rs10800363 | kgp305361 |
| ATP2B1 | chr12:89981825-90049844 | chr12:89481825-90549844 | chr12:88505956-88573975 | kgp4237218 | kgp19117315 |
| ATP2B2 | chr3:10365706-10749716 | chr3:9865706-11249716 | chr3:10342743-10724716 | kgp7774534 | rs7625756 |
| ATXN1 | chr6:16299342-16761721 | chr6:15799342-17261721 | chr6:16407321-16869700 | kgp2173519 | rs6921352 |
| ATXN3 | chr14:92524895-92572965 | chr14:92024895-93072965 | chr14:91594648-91642718 | kgp11986238 | rs2146498 |
| ATXN7 | chr3:63850232-63989136 | chr3:63350232-64489136 | chr3:63825272-63964176 | rs9311874 | kgp797614 |
| AVPR1A | chr12:63540215-63546590 | chr12:63040215-64046590 | chr12:61826482-61832857 | rs952865 | kgp3671976 |
| B4GALT1 | chr9:33110638-33167356 | chr9:32610638-33667356 | chr9:33100638-33157356 | kgp18539535 | kgp18370584 |
| BANK1 | chr4:102341117-102995969 | chr4:101841117-103495969 | chr4:102560140-103214992 | rs6851921 | kgp20796561 |

*Fig. 3-2*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| BCAP31 | chrX:152965946-152990201 | chrX:152465946-153490201 | chrX:152619145-152643081 | rs6627302 | kgp22764947 |
| BCAR1 | chr16:75262927-75301951 | chr16:74762927-75801951 | chr16:73820428-73859452 | kgp7158675 | kgp16367309 |
| BCL2 | chr18:60790578-60986657 | chr18:60290578-61486657 | chr18:58941558-59137637 | rs435439 | rs1720898 |
| BMI1 | chr10:22610138-22620414 | chr10:22110138-23120414 | chr10:22645304-22660192 | kgp3019331 | rs12775513 |
| BMPR2 | chr2:203241049-203432474 | chr2:202741049-203932474 | chr2:202949294-203140719 | rs2072504 | kgp3183288 |
| BOC | chr3:112930411-113006305 | chr3:112430411-113506305 | chr3:114413101-114488995 | kgp12164746 | kgp3299668 |
| BPGM | chr7:134331530-134364567 | chr7:133831530-134864567 | chr7:133982094-134015107 | kgp13720725 | kgp8542611 |
| BRCA1 | chr17:41196311-41322420 | chr17:40696311-41822420 | chr17:38449839-38530994 | kgp1014784 | kgp13921789 |
| BRCA2 | chr13:32889616-32973809 | chr13:32389616-33473809 | chr13:31787616-31871809 | rs2146284 | rs9596502 |
| BRD7 | chr16:50352928-50402845 | chr16:49852928-50902845 | chr16:48910441-48960330 | kgp3843480 | kgp6018549 |
| BRF2 | chr8:37701397-37707431 | chr8:37201397-38207431 | chr8:37820560-37826569 | rs7818467 | kgp22772561 |
| BRMS1 | chr11:66104803-66112582 | chr11:65604803-66612582 | chr11:65861379-65869158 | kgp22746103 | kgp12809093 |
| BTK | chrX:100604434-100645770 | chrX:100104434-101145770 | chrX:100491097-100532426 | kgp22759057 | kgp22747202 |
| C1orf128 | chr1:24104887-24114722 | chr1:23604887-24614722 | chr1:23977474-23987309 | kgp283495 | kgp2701674 |
| C1orf42 | chr1:152486978-152488481 | chr1:151986978-152988481 | chr1:150753602-150755105 | kgp15694971 | rs4363385 |
| C1QBP | chr17:5336098-5342471 | chr17:4836098-5842471 | chr17:5276822-5283195 | kgp14047547 | rs17825455 |
| C20orf20 | chr20:61427804-61431945 | chr20:60927804-61931945 | chr20:60898282-60902390 | kgp9228388 | kgp19363625 |
| C20orf24 | chr20:35234136-35240960 | chr20:34734136-35740960 | chr20:34636369-34674374 | rs6060820 | rs1744760 |
| C4orf14 | chr4:57829515-57843826 | chr4:57329515-58343826 | chr4:57524272-57538583 | kgp22756132 | kgp1831456 |
| C4orf17 | chr4:100432160-100463460 | chr4:99932160-100963460 | chr4:100651222-100682483 | kgp20878925 | kgp21204347 |
| C5orf25 | chr5:175665369-175772990 | chr5:175165369-176272990 | chr5:175598008-175705596 | kgp7679859 | rs480782 |
| C9orf25 | chr9:34398181-34458568 | chr9:33898181-34958568 | chr9:34388181-34448568 | kgp22772722 | rs7031962 |

*Fig. 3-3*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| CABIN1 | chr22:24407764-24574596 | chr22:23907764-25074596 | chr22:22737764-22904596 | kgp5637302 | kgp5793536 |
| CABP1 | chr12:121078421-121105127 | chr12:120578421-121605127 | chr12:119562804-119589510 | kgp18737891 | rs503720 |
| CACNA1C | chr12:2162415-2807115 | chr12:1662415-3307115 | chr12:2032676-2677376 | kgp9477564 | kgp1276729 |
| CALCR | chr7:93053798-93204042 | chr7:92553798-93704042 | chr7:92891734-93041978 | kgp3815436 | kgp10249142 |
| CALD1 | chr7:134464163-134655480 | chr7:133964163-135155480 | chr7:134114710-134306012 | rs16874469 | kgp22829820 |
| CAMK2A | chr5:149599053-149669403 | chr5:149099053-150169403 | chr5:149579247-149649529 | kgp9269229 | kgp22536863 |
| CAMK2G | chr10:75572258-75634349 | chr10:75072258-76134349 | chr10:75242264-75304349 | kgp5617603 | kgp4007437 |
| CAMKK1 | chr17:3763616-3796337 | chr17:3263616-4296337 | chr17:3710365-3743086 | kgp4927794 | kgp13998561 |
| CAMKK2 | chr12:121675494-121736111 | chr12:121175494-122236111 | chr12:120159877-120220494 | kgp3636283,rs1800556 | kgp3169612 |
| CAPN2 | chr1:223889294-223963720 | chr1:223389294-224463720 | chr1:221966741-222030343 | rs2430408 | kgp15138476 |
| CASP3 | chr4:185548849-185570629 | chr4:185048849-186070629 | chr4:185785843-185807623 | kgp8529169 | rs2046535 |
| CASP6 | chr4:110609784-110624629 | chr4:110109784-111124629 | chr4:110829233-110844078 | kgp20840443 | kgp20817413 |
| CASP7 | chr10:115438934-115490664 | chr10:114938934-115990664 | chr10:115428924-115480654 | kgp12503193 | rs12266538 |
| CASP8 | chr2:202098165-202152434 | chr2:201598165-202652434 | chr2:201806410-201860679 | kgp6115041 | rs12468196 |
| CASR | chr3:121902529-122005344 | chr3:121402529-122505344 | chr3:123385219-123488034 | kgp18115887 | rs13095775 |
| CAV1 | chr7:115929905-116201239 | chr7:115429905-116701239 | chr7:115717141-115988466 | kgp13705413 | kgp1550529,rs13222576 |
| CBL | chr11:119076989-119178859 | chr11:118576989-119678859 | chr11:118582199-118684069 | kgp4184476 | rs10892470 |
| CBX1 | chr17:46147413-46178883 | chr17:45647413-46678883 | chr17:43502412-43533882 | kgp4510682 | kgp14007862 |
| CCDC106 | chr19:56158953-56164526 | chr19:55658953-56664526 | chr19:60850765-60856338 | kgp2072564 | rs901476 |
| CCND1 | chr11:69455872-69469242 | chr11:68955872-69969242 | chr11:69165053-69178423 | kgp12357966 | rs1893085 |
| CCNE1 | chr19:30302900-30315215 | chr19:29802900-30815215 | chr19:34994740-35007059 | kgp21358604 | kgp21349680 |
| CCR4 | chr3:32993065-32996403 | chr3:32493065-33496403 | chr3:32968069-32971407 | rs4955290 | kgp3855989 |

*Fig. 3-4*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| CCR5 | chr3:46411632-46417697 | chr3:45911632-46917697 | chr3:46386636-46392701 | kgp17737690 | rs936173 |
| CD163 | chr12:7623411-7656414 | chr12:7123411-8156414 | chr12:7514676-7547681 | rs9668071 | kgp3219786 |
| CD5 | chr11:60869929-60895323 | chr11:60369929-61395323 | chr11:60626505-60651899 | rs7927817 | kgp13056421 |
| CD9 | chr12:6309481-6347437 | chr12:5809481-6847437 | chr12:6179133-6217688 | rs9669580 | kgp1124940 |
| CDC2 | chr10:62538235-62553924 | chr10:62038235-63053924 | chr10:62208241-62223930 | kgp21922934 | rs3125326 |
| CDKN2C | chr1:51433607-51440309 | chr1:50933607-51940309 | chr1:51206195-51212897 | rs17106219 | kgp15324656 |
| CENTA1 | chr7:937537-994306 | chr7:437537-1494306 | chr7:904063-960832 | kgp4856315,rs3924019 | kgp11391801 |
| CETN3 | chr5:89689528-89705603 | chr5:89189528-90205603 | chr5:89725284-89741359 | rs277054 | kgp22368793 |
| CFTR | chr7:117120016-117308718 | chr7:116620016-117808718 | chr7:116907252-117095954 | kgp13265715 | kgp13590397 |
| CHAT | chr10:50822349-50901939 | chr10:50322349-51401939 | chr10:50487146-50543156 | kgp8189482 | kgp8898453 |
| CHD3 | chr17:7788122-7816075 | chr17:7288122-8316075 | chr17:7728847-7756800 | rs7208523 | kgp11776706 |
| CHUK | chr10:101948123-101989344 | chr10:101448123-102489344 | chr10:101938113-101979334 | kgp6141810 | kgp9150190 |
| CISH | chr3:50643884-50649262 | chr3:50143884-51149262 | chr3:50618929-50624207 | kgp5610191 | rs6783700 |
| CKAP1 | chr19:36605888-36616849 | chr19:36105888-37116849 | chr19:41297728-41308689 | rs7249516 | rs3108171 |
| CKMT2 | chr5:80529138-80562217 | chr5:80029138-81062217 | chr5:80564894-80597973 | kgp9822295 | kgp7416171 |
| CLTB | chr5:175819455-175843540 | chr5:175319455-176343540 | chr5:175752061-175776146 | rs4867811 | kgp1551194 |
| CLU | chr8:27454433-27472328 | chr8:26954433-27972328 | chr8:27510367-27528244 | kgp886026 | rs4732823 |
| CMIP | chr16:81478774-81745367 | chr16:80978774-82245367 | chr16:80036394-80302866 | rs11150329 | kgp16425289 |
| CNGA2 | chrX:150903217-150914036 | chrX:150403217-151414036 | chrX:150653873-150664692 | rs1202896 | kgp22766776 |
| CNKSR2 | chrX:21392535-21672813 | chrX:20892535-22172813 | chrX:21302900-21580700 | kgp22768242 | kgp22744096 |
| CNN1 | chr19:11649578-11661138 | chr19:11149578-12161138 | chr19:11510578-11522138 | kgp11148982 | rs8100428 |
| CNR2 | chr1:24200459-24239817 | chr1:23700459-24739817 | chr1:24073046-24112404 | rs9887921 | kgp7256331 |

*Fig. 3-5*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| COIL | chr17:55015560-55038411 | chr17:54515560-55538411 | chr17:52370559-52393410 | rs7219528 | kgp13879956 |
| CORO1B | chr11:67205517-67211292 | chr11:66705517-67711292 | chr11:66962093-66967839 | kgp8733070 | kgp12910446 |
| COX17 | chr3:119388371-119396243 | chr3:118888371-119896243 | chr3:120871061-120878933 | rs2903301 | rs7634938 |
| CPE | chr4:166300096-166419482 | chr4:165800096-166919482 | chr4:166519546-166638932 | rs4541465 | kgp20841166 |
| CRADD | chr12:94071150-94288616 | chr12:93571150-94788616 | chr12:92595281-92768662 | kgp18995270 | rs10859694 |
| CREM | chr10:35415768-35501886 | chr10:34915768-36001886 | chr10:35455806-35541892 | kgp21684668 | rs654221 |
| CRIPT | chr2:46844324-46852881 | chr2:46344324-47352881 | chr2:46697811-46705687 | kgp11216746 | kgp5110136 |
| CSNK2A1 | chr20:463337-524482 | chr20:1-1024482 | chr20:411337-472482 | kgp19358001 | kgp2852236 |
| CSNK2A2 | chr16:58191811-58231782 | chr16:57691811-58731782 | chr16:56749312-56789283 | kgp3607479 | kgp9299300 |
| CSNK2B | chr6:2919235-2923423 | chr6:2919235-2923423 | chr6:31741635-31748206 | kgp7558035 | kgp17052091 |
| CTNNB1 | chr3:41236400-41280845 | chr3:40736400-41780845 | chr3:41211404-41255849 | kgp17791054 | kgp17873276 |
| DAPK3 | chr19:3958451-3971038 | chr19:3458451-4471038 | chr19:3909451-3922038 | kgp9392695 | kgp6448823 |
| DBN1 | chr5:176883613-176900694 | chr5:176383613-177400694 | chr5:176816219-176833300 | rs3733876 | kgp6700800 |
| DDIT4 | chr10:74033676-74035797 | chr10:73533676-74535797 | chr10:73703682-73705803 | kgp21593001 | kgp10561095 |
| DDX5 | chr17:62494373-62502484 | chr17:61994373-63002484 | chr17:59926199-59932869 | kgp14113893 | rs4239089 |
| DEFB1 | chr8:6728096-6735529 | chr8:6228096-7235529 | chr8:6715508-6722939 | kgp20078124 | rs12680482 |
| DGKD | chr2:234263152-234380743 | chr2:233763152-234880743 | chr2:233927891-234045482 | rs12477794 | rs28902188 |
| DGKZ | chr11:46354454-46402104 | chr11:45854454-46902104 | chr11:46311314-46358680 | rs2090602 | kgp22737291 |
| DIRAS2 | chr9:93372113-93405108 | chr9:92872113-93905108 | chr9:92411933-92444928 | rs7860989 | kgp10944799 |
| DLG1 | chr3:196769430-197026143 | chr3:196269430-197526143 | chr3:198253827-198510540 | kgp18074003 | rs841672 |
| DLG3 | chrX:69664704-69725339 | chrX:69164704-70225339 | chrX:69581448-69642062 | kgp22756738 | kgp22752290 |
| DLG4 | chr17:7093209-7123369 | chr17:6593209-7623369 | chr17:7033933-7063781 | kgp10999626 | rs3744258 |

*Fig. 3-6*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| DNM1 | chr9:130965662-131017527 | chr9:130465662-131517527 | chr9:130005483-130057348 | kgp1183767 | rs4836625 |
| DNM3 | chr1:171810620-172381857 | chr1:171310620-172881857 | chr1:170077260-170648480 | kgp15671556 | rs2213746 |
| DNMT2 | chr10:17184981-17243681 | chr10:16684981-17743681 | chr10:17224987-17283687 | kgp1566842 | kgp21855354 |
| DPYSL2 | chr8:26371708-26515693 | chr8:25871708-27015693 | chr8:26427707-26571610 | rs11998023 | rs12544814 |
| DRD1 | chr5:174867674-174871163 | chr5:174367674-175371163 | chr5:174800280-174803769 | kgp4432341 | kgp8293487 |
| DRD1IP | chr5:174867675-174871163 | chr5:174367675-175371163 | chr5:174800281-174803769 | kgp4432341 | kgp8293487 |
| DST | chr6:56479153-56716714 | chr6:55979153-57216714 | chr6:56430743-56816422 | kgp1980963 | rs12209200 |
| DVL1 | chr1:1270657-1284492 | chr1:770657-1784492 | chr1:1260520-1274355 | kgp4076808 | kgp15201879 |
| DVL2 | chr17:7128660-7137863 | chr17:6628660-7637863 | chr17:7069384-7078587 | kgp1788685 | kgp2456831,rs3744255 |
| DVL3 | chr3:183873283-183891314 | chr3:183373283-184391314 | chr3:185355977-185374008 | kgp10156744 | kgp4088221 |
| EDF1 | chr9:139756570-139760738 | chr9:139256570-140260738 | chr9:138876391-138880559 | rs3829109 | kgp4292076 |
| EDG3 | chr9:91606324-91620069 | chr9:91106324-92120069 | chr9:90796144-90809889 | kgp18366537 | kgp113389 |
| EDG5 | chr19:10332109-10341948 | chr19:9832109-10841948 | chr19:10193109-10202948 | kgp21505357 | kgp12277401 |
| EDG8 | chr19:10623418-10628668 | chr19:10123418-11128668 | chr19:10484418-10489668 | rs4804478 | kgp9055694 |
| EEF1D | chr8:144661866-144679845 | chr8:144161866-145179845 | chr8:144733040-144750726 | kgp20077380 | kgp4311396 |
| EEF2 | chr19:3976053-3985461 | chr19:3476053-4485461 | chr19:3927053-3936461 | kgp21334437 | rs10406730 |
| EFNB1 | chrX:68048839-68066029 | chrX:67548839-68566029 | chrX:67965564-67982754 | rs7879567 | kgp22774708 |
| EFNB2 | chr13:107142078-107187388 | chr13:106642078-107687388 | chr13:105940096-105985338 | rs9587049 | kgp1472981 |
| EIF1B | chr3:40351172-40353915 | chr3:39851172-40853915 | chr3:40326176-40328919 | kgp17543799 | kgp724180 |
| ENO2 | chr12:7023613-7032859 | chr12:6523613-7532859 | chr12:6893874-6903120 | kgp6644683 | kgp18788179 |
| EPB41 | chr1:29213602-29446558 | chr1:28713602-29946558 | chr1:29086214-29319545 | kgp15837735 | kgp8194212 |
| EPB41L1 | chr20:34679425-34820721 | chr20:34179425-35320721 | chr20:34142839-34284135 | rs1886695 | kgp10646202 |

*Fig. 3-7*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| EPB41L2 | chr6:131160487-131384462 | chr6:130660487-131884462 | chr6:131202180-131426058 | kgp3398782 | kgp16921144 |
| EPHB2 | chr1:23037330-23241823 | chr1:22537330-23741823 | chr1:22909917-23114410 | rs2473249 | kgp22776625 |
| ESR1 | chr6:152011630-152424408 | chr6:151511630-152924408 | chr6:152053323-152466101 | rs9478984 | rs818451 |
| ESR2 | chr14:64693750-64805268 | chr14:64193750-65305268 | chr14:63763503-63875021 | kgp3039416 | kgp8515773 |
| ESRRG | chr1:216676587-217311097 | chr1:216176587-217811097 | chr1:214743210-215377720 | kgp2104463 | kgp3054869 |
| ETHE1 | chr19:44010870-44031396 | chr19:43510870-44531396 | chr19:48702710-48723236 | rs11668932 | kgp561363 |
| EWSR1 | chr22:29663997-29696515 | chr22:29163997-30196515 | chr22:27994016-28026515 | rs6005868 | rs4823054 |
| F11R | chr1:160965000-161008774 | chr1:160465000-161508774 | chr1:159231624-159275404 | rs678456 | kgp10744728 |
| FADD | chr11:70049268-70053508 | chr11:69549268-70553508 | chr11:69726916-69731134 | kgp12619639 | kgp12640488 |
| FAS | chr10:90729552-90775542 | chr10:90229552-91275542 | chr10:90740267-90765522 | kgp6970830 | kgp1640747 |
| FBLIM1 | chr1:16083153-16113084 | chr1:15583153-16613084 | chr1:15955740-15985671 | rs16851480 | kgp15648830 |
| FER | chr5:108083522-108523373 | chr5:107583522-109023373 | chr5:108111421-108551272 | rs11958626 | rs845734 |
| FEZ1 | chr11:125315640-125366206 | chr11:124815640-125866206 | chr11:124820857-124871333 | rs10160591 | kgp12966369 |
| FEZ2 | chr2:36779403-36825332 | chr2:36279403-37325332 | chr2:36632904-36678836 | kgp10246319 | kgp9712350 |
| FFAR1 | chr19:35842444-35843367 | chr19:35342444-36343367 | chr19:40534294-40535197 | rs8106116 | kgp21511691 |
| FFAR2 | chr19:35939202-35941865 | chr19:35439202-36441865 | chr19:40631042-40633705 | rs2112502 | rs7247246 |
| FKBP1A | chr20:1349620-1373816 | chr20:849620-1873816 | chr20:1297621-1321745 | kgp4567229 | kgp10348674 |
| FLJ31945 | chr13:50699952-50702599 | chr13:50199952-51202599 | chr13:49597953-49600600 | kgp9786864 | kgp16621897 |
| FLJ41278 | chr12:65277553-65371302 | chr12:64777553-65871302 | chr12:63563820-63657569 | rs6581555 | kgp1662303 |
| FLNA | chrX:153576899-153603006 | chrX:153076899-154103006 | chrX:153230093-153256200 | rs7049293 | rs28412378 |
| FLNB | chr3:57994126-58157982 | chr3:57494126-58657982 | chr3:57969166-58133017 | rs7629743 | rs11130670 |
| FREQ | chr9:132934856-132999583 | chr9:132434856-133499583 | chr9:131974677-132039404 | kgp12208188 | kgp18380808 |

*Fig. 3-8*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| FRS2 | chr12:69864128-69973562 | chr12:69364128-70473562 | chr12:68150395-68259829 | kgp19095191 | kgp12534834 |
| FSHR | chr2:49189295-49381666 | chr2:48689295-49881666 | chr2:49043155-49235134 | kgp297164 | kgp11229604 |
| FXN | chr9:71650478-71715094 | chr9:71150478-72215094 | chr9:70840163-70878772 | rs265076 | kgp213209 |
| FXR1 | chr3:180630233-180700539 | chr3:180130233-181200539 | chr3:182113145-182177647 | kgp22773686 | kgp3235523 |
| G6PD | chrX:153759605-153775787 | chrX:153259605-154275787 | chrX:153412799-153428981 | rs2239471 | kgp22745531 |
| GABRR1 | chr6:89887222-89927496 | chr6:89387222-90427496 | chr6:89944690-89983779 | kgp3728710 | kgp17056993 |
| GABRR2 | chr6:89967238-90024967 | chr6:89467238-90524967 | chr6:90023957-90081686 | kgp16994883 | kgp9012178 |
| GALR2 | chr17:74070891-74073573 | chr17:73570891-74573573 | chr17:71582486-71585168 | rs1042861 | rs16967307 |
| GAP43 | chr3:115342150-115440334 | chr3:114842150-115940334 | chr3:116825141-116922842 | rs10511341 | kgp18168870 |
| GC | chr4:72607410-72671237 | chr4:72107410-73171237 | chr4:72826274-72888622 | rs10013437 | kgp12025264 |
| GFAP | chr17:42982993-42992920 | chr17:42482993-43492920 | chr17:40338518-40348394 | rs8066197 | rs12947718 |
| GFI1 | chr1:92940317-92952433 | chr1:92440317-93452433 | chr1:92712905-92725021 | kgp80379 | kgp15436210 |
| GFI1B | chr9:135853893-135867084 | chr9:135353893-136367084 | chr9:134843714-134856903 | kgp1227599 | kgp22817803 |
| GFPT1 | chr2:69546900-69614386 | chr2:69046900-70114386 | chr2:69405910-69467829 | kgp7360674 | kgp14824626 |
| GH1 | chr17:61994562-61996198 | chr17:61494562-62496198 | chr17:59348294-59349930 | kgp6455446 | kgp10132757 |
| GIT1 | chr17:27900486-27916610 | chr17:27400486-28416610 | chr17:24924612-24940736 | kgp14082001 | rs8065059 |
| GIT2 | chr12:110367606-110434194 | chr12:109867606-110934194 | chr12:108851991-108918483 | kgp8064273 | kgp556710 |
| GJA1 | chr6:121756744-121770873 | chr6:121256744-122270873 | chr6:121798443-121812572 | kgp5203283 | kgp1494786 |
| GJB1 | chrX:70435061-70445065 | chrX:69935061-70945065 | chrX:70351786-70361777 | kgp22820938 | rs35542412 |
| GMFB | chr14:54941208-54955744 | chr14:54441208-55455744 | chr14:54010958-54025494 | kgp5212952 | kgp7377769 |
| GNA12 | chr7:2767740-2883959 | chr7:2267740-3383959 | chr7:2734266-2850485 | kgp9177535 | kgp13694655 |
| GNAS | chr20:57414794-57486250 | chr20:56914794-57986250 | chr20:56848189-56919645 | rs471661 | rs729997 |

*Fig. 3-9*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| GNAZ | chr22:23412668-23467221 | chr22:22912668-23967221 | chr22:21742668-21797221 | kgp15075658 | rs9680742 |
| GPM6A | chr4:176554087-176923648 | chr4:176054087-177423648 | chr4:176791081-177160642 | rs6849435 | kgp8852764 |
| GPSM2 | chr1:109419602-109476957 | chr1:108919602-109976957 | chr1:109221125-109274567 | kgp15175401 | kgp15178378 |
| GRB14 | chr2:165349322-165478360 | chr2:164849322-165978360 | chr2:165057568-165186606 | kgp8982508 | kgp14153450 |
| GRIA2 | chr4:158141294-158287226 | chr4:157641294-158787226 | chr4:158361185-158506676 | kgp22818527 | rs6836401 |
| GRIA3 | chrX:122318095-122624766 | chrX:121818095-123124766 | chrX:122145776-122452447 | rs7057244 | rs12559968 |
| GRIA4 | chr11:105480799-105852819 | chr11:104980799-106352819 | chr11:104986009-105358029 | kgp12888967 | kgp2959570 |
| GRIN1 | chr9:140033608-140063214 | chr9:139533608-140563214 | chr9:139153429-139183029 | kgp18425565 | kgp18521447 |
| GRIN2A | chr16:9847264-10276611 | chr16:9347264-10776611 | chr16:9762922-10184112 | kgp16441783 | rs9932893 |
| GRIN2B | chr12:13714409-14133022 | chr12:13214409-14633022 | chr12:13605676-14024289 | rs3741818 | kgp7391296 |
| GRK1 | chr13:114321596-114438637 | chr13:113821596-114938637 | chr13:113369597-113373973 | kgp16671784 | rs11147317 |
| GRK4 | chr4:2965342-3042474 | chr4:2465342-3542474 | chr4:2935140-3012272 | rs846252 | rs6821202 |
| GSK3A | chr19:42734337-42746736 | chr19:42234337-43246736 | chr19:47426177-47438576 | kgp21481263 | kgp10870487 |
| GSK3B | chr3:119540801-119813264 | chr3:119040801-120313264 | chr3:121028235-121295203 | kgp17616951 | kgp4570827 |
| GSTM4 | chr1:110198697-110208123 | chr1:109698697-110708123 | chr1:110000225-110009648 | rs595635 | kgp15760598 |
| HABP4 | chr9:99212413-99253618 | chr9:98712413-99753618 | chr9:98252234-98293439 | kgp18578220 | kgp18630342 |
| HAND1 | chr5:153854531-153857824 | chr5:153354531-154357824 | chr5:153834724-153838017 | kgp7530958 | rs2431184 |
| HAND2 | chr4:174447651-174451378 | chr4:173947651-174951378 | chr4:174684226-174687953 | kgp20847640 | kgp20778226 |
| HARS | chr5:140053489-140070971 | chr5:139553489-140570971 | chr5:140033673-140051155 | rs6874491 | rs12654953 |
| HDAC6 | chrX:48660286-48683380 | chrX:48160286-49183380 | chrX:48545430-48568324 | kgp22835768 | rs2015487 |
| HES1 | chr3:193853930-193856401 | chr3:193353930-194356401 | chr3:195336627-195339090 | kgp11414670 | rs7649259 |
| HLA-A | chr6:1150035-1295564 | chr6:1150035-1295564 | chr6:30018304-30085130 | rs9392258 | rs9391920 |

*Fig. 3-10*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| HLA-C | chr6:2585738-2671188 | chr6:2585738-2671188 | chr6:2486041-2572197 | rs9392400 | kgp1905253 |
| HLA-DQA2 | chr6:4166320-4171833 | chr6:4166320-4171833 | chr6:3895192-3901275 | kgp17451336 | kgp17218419 |
| HMGB1 | chr13:31032878-31191510 | chr13:30532878-31691510 | chr13:29930878-30089510 | rs1557088 | kgp8054835 |
| HMGN1 | chr21:40714240-40721047 | chr21:40214240-41221047 | chr21:39636110-39643140 | kgp4524272 | kgp8317624 |
| HMGN2 | chr1:26798901-26803133 | chr1:26298901-27303133 | chr1:26671488-26675720 | rs1429936 | kgp8260087 |
| HMMR | chr5:162887516-162918953 | chr5:162387516-163418953 | chr5:162820240-162851525 | kgp9548441 | rs1363073 |
| HMOX2 | chr16:4524718-4560348 | chr16:4024718-5060348 | chr16:4464719-4500349 | kgp16414002 | kgp7117794 |
| HMP19 | chr5:173472723-173536182 | chr5:172972723-174036182 | chr5:173405329-173468788 | kgp22404239 | rs12186684 |
| HOMER2 | chr15:83517728-83621476 | chr15:83017728-84121476 | chr15:81314789-81412477 | rs1267659 | kgp4123064 |
| HRH4 | chr18:22040592-22059921 | chr18:21540592-22559921 | chr18:20294590-20313919 | rs7235445 | kgp7887799 |
| HSP90AA1 | chr14:102547074-102606086 | chr14:102047074-103106086 | chr14:101616827-101675839 | kgp3260354 | kgp19714004 |
| HSPA1A | chr6:31783290-31785719 | chr6:31283290-32285719 | chr6:31891315-31893698 | kgp4709627 | rs9296020 |
| HSPA1B | chr6:3089162-3091686 | chr6:3089162-3091686 | chr6:3043109-3045633 | kgp6503147 | kgp5869121 |
| HSPA4 | chr5:132387661-132440709 | chr5:131887661-132940709 | chr5:132415560-132468608 | kgp22352512 | kgp7658141 |
| HSPB1 | chr7:75931874-75933614 | chr7:75431874-76433614 | chr7:75769858-75771546 | kgp4195218 | kgp10852432 |
| HSPB3 | chr5:53751430-53752214 | chr5:53251430-54252214 | chr5:53787201-53787964 | rs16881895 | rs3815916 |
| HSPB8 | chr12:119616594-119632551 | chr12:119116594-120132551 | chr12:118100977-118116934 | kgp18981306 | kgp18823622 |
| HSPBP1 | chr19:55773590-55791751 | chr19:55273590-56291751 | chr19:60465518-60483540 | kgp3134010 | kgp21533588 |
| HSPE1 | chr2:198364720-198368187 | chr2:197864720-198868187 | chr2:198073364-198076416 | kgp9884304 | kgp12004769 |
| HSPH1 | chr13:31710762-31736502 | chr13:31210762-32236502 | chr13:30608762-30634502 | kgp16548529 | kgp16811501 |
| HTATIP | chr11:20385289-20405329 | chr11:19885289-20905329 | chr11:20341865-20361905 | rs2707094 | kgp309631 |
| HTR2B | chr2:231972949-231989824 | chr2:231472949-232489824 | chr2:231681198-231698068 | rs6761068 | rs4973459 |

*Fig. 3-11*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| HTR2C | chrX:113818550-114144624 | chrX:113318550-114644624 | chrX:113724806-114050880 | rs7055827 | kgp22830072 |
| HTR6 | chr1:19991779-20006055 | chr1:19491779-20506055 | chr1:19864366-19878642 | kgp15912015 | kgp10523409 |
| IGSF4 | chr11:115044345-115375241 | chr11:114544345-115875241 | chr11:114549555-114880451 | rs1607260 | rs7928212 |
| IKBKB | chr8:42128819-42190171 | chr8:41628819-42690171 | chr8:42247985-42309122 | kgp9748756 | kgp3164559 |
| IKBKE | chr1:206643585-206670223 | chr1:206143585-207170223 | chr1:204710418-204736845 | kgp15543770 | kgp6359437 |
| IKBKG | chrX:153770458-153793261 | chrX:153270458-154293261 | chrX:153423652-153446455 | rs633 | kgp22831959 |
| IL4R | chr16:27325250-27376099 | chr16:26825250-27876099 | chr16:27232751-27283600 | kgp11144142 | kgp16489203 |
| IL5RA | chr3:3108007-3152058 | chr3:2608007-3652058 | chr3:3086420-3127031 | kgp10211459 | kgp22835987 |
| IL8RA | chr2:219027567-219031716 | chr2:218527567-219531716 | chr2:218735812-218739961 | kgp14521358 | rs16859170 |
| INSR | chr19:7112265-7294011 | chr19:6612265-7794011 | chr19:7063265-7245011 | kgp5914741 | kgp21453659 |
| IQCB1 | chr3:121488609-121553926 | chr3:120988609-122053926 | chr3:122971299-123036616 | rs11921531 | rs6438722 |
| IQGAP1 | chr15:90931472-91045475 | chr15:90431472-91545475 | chr15:88732476-88846479 | kgp1876985 | kgp20028694 |
| IRAK1 | chrX:153275956-153285342 | chrX:152775956-153785342 | chrX:152929150-152938536 | kgp22756383 | rs6643680 |
| IRS1 | chr2:227596032-227663506 | chr2:227096032-228163506 | chr2:227304276-227371750 | kgp12414080 | kgp9391097 |
| IRS4 | chrX:107975726-107979607 | chrX:107475726-108479607 | chrX:107862367-107866295 | kgp22794644 | rs5985712 |
| ITGB2 | chr21:46305867-46348753 | chr21:45805867-46848753 | chr21:45130296-45173181 | kgp13225366 | rs11702782 |
| ITGB3BP | chr1:63906440-63988944 | chr1:63406440-64488944 | chr1:63679049-63761423 | rs1572109 | kgp5171315 |
| ITGB4 | chr17:73717515-73753899 | chr17:73217515-74253899 | chr17:71229110-71265494 | kgp2663142 | kgp4575494 |
| ITGB5 | chr3:124481794-124606144 | chr3:123981794-125106144 | chr3:125964484-126088834 | kgp5281659 | kgp17765518 |
| ITPKA | chr15:41786055-41795757 | chr15:41286055-42295757 | chr15:39573413-39583039 | kgp22747722 | kgp10507061 |
| ITPKB | chr1:226819390-226926876 | chr1:226319390-227426876 | chr1:224886013-224991987 | rs1219671 | rs7519099 |
| ITPR3 | chr6:33589155-33664348 | chr6:33089155-34164348 | chr6:33697138-33772326 | rs3117030 | kgp4515850 |

*Fig. 3-12*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| IXL | chr19:39881963-39891203 | chr19:39381963-40391203 | chr19:44573803-44583043 | kgp986483 | kgp6117029 |
| JAK1 | chr1:65298905-65432619 | chr1:64798905-65932619 | chr1:65071493-65205207 | kgp8976721 | kgp9745392 |
| KCNE1 | chr21:35818987-35884573 | chr21:35318987-36384573 | chr21:34740857-34806443 | kgp13187567 | kgp5041106 |
| KCNE4 | chr2:223916861-223920355 | chr2:223416861-224420355 | chr2:223625105-223628599 | kgp14948218 | kgp14631899 |
| KCNH2 | chr7:150642043-150675402 | chr7:150142043-151175402 | chr7:150272981-150305947 | kgp13542655 | kgp7948285 |
| KCNJ2 | chr17:68164813-68176183 | chr17:67664813-68676183 | chr17:65676408-65687778 | rs6501341 | kgp2814913 |
| KCNN2 | chr5:113698015-113832197 | chr5:113198015-114332197 | chr5:113725914-113860096 | kgp9619904 | rs10056549 |
| KCNN4 | chr19:44270684-44285409 | chr19:43770684-44785409 | chr19:48962524-48977249 | rs6509074 | kgp21388839 |
| KCNQ2 | chr20:62037541-62103993 | chr20:61537541-62603993 | chr20:61507985-61574437 | rs16983364 | kgp19265466 |
| KCNQ3 | chr8:133133104-133493004 | chr8:132633104-133993004 | chr8:133210437-133562186 | kgp20244043 | rs4074676 |
| KCNQ5 | chr6:73331570-73908573 | chr6:72831570-74408573 | chr6:73388555-73962301 | kgp7790415 | rs9446983 |
| KDR | chr4:55944425-55991762 | chr4:55444425-56491762 | chr4:55639405-55686519 | kgp11624145 | rs10022874 |
| KIAA1377 | chr11:101785745-101871793 | chr11:101285745-102371793 | chr11:101290955-101377003 | kgp12804311 | rs9667864 |
| KIAA1549 | chr7:138516126-138666064 | chr7:138016126-139166064 | chr7:138166666-138255110 | rs11769851 | kgp10209774 |
| KIF3A | chr5:132028322-132073265 | chr5:131528322-132573265 | chr5:132056221-132101164 | rs3805685 | rs4958109 |
| KIT | chr4:55524094-55606881 | chr4:55024094-56106881 | chr4:55218851-55301638 | kgp4467115 | kgp9403472 |
| KLHL20 | chr1:173684079-173755840 | chr1:173184079-174255840 | chr1:171950702-172022463 | rs13374515 | kgp5594942 |
| KLHL3 | chr5:136953188-137071779 | chr5:136453188-137571779 | chr5:136981087-137099678 | rs2966736 | rs10040989 |
| KLK10 | chr19:51515999-51523431 | chr19:51015999-52023431 | chr19:56207811-56215243 | kgp9495392 | kgp21503250 |
| KRAS | chr12:25358179-25403854 | chr12:24858179-25903854 | chr12:25249446-25295121 | kgp19038229 | kgp1316534 |
| KRT10 | chr17:38974368-38978863 | chr17:38474368-39478863 | chr17:36227894-36232373 | kgp7164026 | kgp6621387 |
| KRT18 | chr12:53342654-53346685 | chr12:52842654-53846685 | chr12:51628921-51632952 | rs406857 | rs11834179 |

*Fig. 3-13*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| LCK | chr1:32716839-32751766 | chr1:32216839-33251766 | chr1:32489426-32524353 | rs12037400 | kgp6229337 |
| LGALS2 | chr22:37966252-37976024 | chr22:37466252-38476024 | chr22:36296198-36305970 | kgp14999686 | rs8135665 |
| LMNA | chr1:156052368-156108548 | chr1:155552368-156608548 | chr1:154318992-154375172 | kgp11675488 | rs12408758 |
| LMNB1 | chr5:126112314-126172712 | chr5:125612314-126672712 | chr5:126140731-126200608 | kgp5014465 | kgp22418220 |
| LOC100133669 | chr8:144063447-144099807 | chr8:143563447-144599807 | chr8:144134822-144171182 | rs10875483 | kgp10850793 |
| LOC154092 | chr6:134758853-134825158 | chr6:134258853-135325158 | chr6:134800546-134866851 | kgp11630779 | kgp22793805 |
| LOC339290 | chr18:5238098-5246505 | chr18:4738098-5746505 | chr18:5222874-5228525 | kgp5290787 | kgp989326 |
| LOC340357 | chr8:12623570-12668910 | chr8:12123570-13168910 | chr8:12667941-12713281 | kgp22754906 | kgp20305069 |
| LOC400604 | chr17:48944039-48945732 | chr17:48444039-49445732 | chr17:46299038-46300731 | kgp11815481 | kgp10163248 |
| LOC613126 | chr7:91763906-91771854 | chr7:91263906-92271854 | chr7:91601842-91609790 | kgp13774218 | rs3731343 |
| LTB4R | chr14:24780704-24787242 | chr14:24280704-25287242 | chr14:23850544-23855992 | kgp19673807 | rs8007336 |
| LTF | chr3:46477495-46526724 | chr3:45977495-47026724 | chr3:46452499-46501728 | kgp17788490 | kgp1176589 |
| LXN | chr3:158384202-158390482 | chr3:157884202-158890482 | chr3:159866899-159873176 | rs6764092 | kgp7955381 |
| LYST | chr1:235824344-236030220 | chr1:235324344-236530220 | chr1:233890968-234096843 | rs2295815 | kgp9270301 |
| MAD2L1BP | chr6:43597278-43608688 | chr6:43097278-44108688 | chr6:43705256-43716666 | rs1537638 | kgp1522302 |
| MAGED1 | chrX:51546154-51645450 | chrX:51046154-52145450 | chrX:51562894-51662190 | kgp22779908 | kgp22784919 |
| MAP1A | chr15:43809805-43823818 | chr15:43309805-44323818 | chr15:41597097-41611110 | kgp12180163 | kgp10318377 |
| MAP1LC3A | chr20:33134691-33148149 | chr20:32634691-33648149 | chr20:32598352-32611810 | kgp19388199 | kgp5639543 |
| MAP2K1 | chr15:66679210-66783882 | chr15:66179210-67283882 | chr15:64466264-64570936 | kgp19795142 | kgp382480 |
| MAP2K4 | chr17:11924134-12047051 | chr17:11424134-12547051 | chr17:11864859-11987776 | rs16944942 | rs9915536 |
| MAP2K5 | chr15:67835020-68099455 | chr15:67335020-68599455 | chr15:65622074-65886506 | kgp19854650 | kgp20006731 |
| MAP3K10 | chr19:40697650-40721482 | chr19:40197650-41221482 | chr19:45389490-45413314 | kgp6290284 | rs2561531 |

*Fig. 3-14*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| MAP3K3 | chr17:61699774-61773670 | chr17:61199774-62273670 | chr17:59053506-59127402 | kgp14048701 | kgp5230870 |
| MAP3K7 | chr6:91225352-91296907 | chr6:90725352-91796907 | chr6:91282073-91353628 | rs9451316 | rs9451576 |
| MAP3K7IP1 | chr22:39745953-39827887 | chr22:39245953-40327887 | chr22:38075899-38157833 | kgp10431646 | rs137981 |
| MAP3K7IP2 | chr6:149639062-149732747 | chr6:149139062-150232747 | chr6:149680755-149774440 | kgp9485571 | kgp9110056 |
| MAP3K8 | chr10:30722949-30750762 | chr10:30222949-31250762 | chr10:30762871-30790767 | kgp22034763 | kgp11496819 |
| MAP6 | chr11:75297962-75379479 | chr11:74797962-75879479 | chr11:74975610-75057127 | rs11236323 | kgp695651 |
| MAPK14 | chr6:35995453-36079013 | chr6:35495453-36579013 | chr6:36103550-36186513 | rs4711420 | kgp10854130 |
| MAPK3 | chr16:30125425-30134630 | chr16:29625425-30634630 | chr16:30032926-30042131 | kgp11463254 | kgp2105557 |
| MARCKS | chr6:114178526-114184652 | chr6:113678526-114684652 | chr6:114285219-114291345 | kgp17187839 | kgp1113238 |
| MBP | chr18:74690788-74844774 | chr18:74190788-75344774 | chr18:72819776-72973762 | kgp5208536 | rs12960102 |
| MCC | chr5:112357795-112824527 | chr5:111857795-113324527 | chr5:112385694-112852426 | kgp22530369 | kgp22589538 |
| MGMT | chr10:131265453-131565783 | chr10:130765453-132065783 | chr10:131155455-131455358 | kgp11264334 | kgp1514587 |
| MIP | chr12:56843285-56848435 | chr12:56343285-57348435 | chr12:55130150-55134696 | kgp19052399,rs11834873 | kgp18750923 |
| MLF2 | chr12:6857935-6876641 | chr12:6357935-7376641 | chr12:6728196-6746902 | kgp18998724 | rs1001653 |
| MLLT3 | chr9:20344967-20622514 | chr9:19844967-21122514 | chr9:20334967-20612514 | kgp18504776 | rs1016129 |
| MNAT1 | chr14:61201458-61435398 | chr14:60701458-61935398 | chr14:60271222-60505151 | kgp5293246 | rs7142051 |
| MPHOSPH6 | chr16:82181766-82203829 | chr16:81681766-82703829 | chr16:80739267-80761330 | kgp406017 | rs3852734 |
| MRPS12 | chr19:39421347-39423659 | chr19:38921347-39923659 | chr19:44113187-44115499 | kgp21348524 | kgp21366907 |
| MRPS6 | chr21:35445822-35515334 | chr21:34945822-36015334 | chr21:34367692-34437204 | kgp11037760 | rs2834555 |
| MRVI1 | chr11:10594637-10715535 | chr11:10094637-11215535 | chr11:10551213-10672111 | rs7946995 | kgp11739225 |
| MSN | chrX:64887510-64961793 | chrX:64387510-65461793 | chrX:64804235-64878518 | rs7887705 | kgp22760405 |
| MYF5 | chr12:81110707-81113447 | chr12:80610707-81613447 | chr12:79634838-79637578 | rs12313692 | kgp5599463 |

*Fig. 3-15*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| MYF6 | chr12:81101407-81103256 | chr12:80601407-81603256 | chr12:79625576-79627382 | rs7954738 | rs7972054 |
| MYLK | chr3:123331142-123603149 | chr3:122831142-124103149 | chr3:124813832-125085839 | kgp9270532 | rs510324 |
| MYO10 | chr5:16662015-16936385 | chr5:16162015-17436385 | chr5:16715015-16989385 | kgp22359577 | kgp12241403 |
| MYO7A | chr11:76839309-76926286 | chr11:76339309-77426286 | chr11:76516957-76603934 | rs2186677 | kgp304899 |
| MYO9B | chr19:17186590-17324104 | chr19:16686590-17824104 | chr19:17047595-17185104 | kgp21430919 | kgp4164870 |
| MYOC | chr1:171604556-171621823 | chr1:171104556-172121823 | chr1:169871179-169888396 | rs1736563 | kgp1482992 |
| MYOD1 | chr11:17741109-17743678 | chr11:17241109-18243678 | chr11:17697685-17700254 | kgp10809253 | rs12285714 |
| MYOG | chr1:203052256-203055377 | chr1:202552256-203555377 | chr1:201318879-201322000 | rs4950858 | rs2798625 |
| MYOT | chr5:137022409-137223540 | chr5:136522409-137723540 | chr5:137231472-137251440 | kgp22294838 | kgp5559791 |
| MYT1L | chr2:1792884-2335045 | chr2:1292884-2835045 | chr2:1771891-2314052 | kgp356515 | kgp7720594 |
| NACA | chr12:57106210-57119326 | chr12:56606210-57619326 | chr12:55392477-55405593 | rs4759218 | kgp11483848 |
| NCALD | chr8:102698769-103137135 | chr8:102198769-103637135 | chr8:102767945-103206311 | kgp11277997 | rs16869664 |
| NCF1C | chr7:74572383-74587816 | chr7:74072383-75087816 | chr7:74210380-74225695 | kgp7635479 | kgp954065 |
| NCL | chr2:232319458-232329205 | chr2:231819458-232829205 | chr2:232027702-232037449 | rs13415867 | kgp12447433 |
| NCOR2 | chr12:124808956-125052010 | chr12:124308956-125552010 | chr12:123397062-123617963 | rs11057368 | kgp12274490 |
| NEUROD1 | chr2:182540832-182545392 | chr2:182040832-183045392 | chr2:182249438-182253626 | kgp7038037 | rs12612546 |
| NF2 | chr22:29999544-30094589 | chr22:29499544-30594589 | chr22:28329544-28424589 | kgp15024372 | kgp10478391 |
| NFASC | chr1:204797781-204991950 | chr1:204297781-205491950 | chr1:203064445-203258572 | rs12044614 | kgp11817505 |
| NFATC1 | chr18:77155771-77289323 | chr18:76655771-77789323 | chr18:75256759-75390311 | rs12150804 | kgp11226294 |
| NFATC2 | chr20:50007764-50179168 | chr20:49507764-50679168 | chr20:49441171-49612777 | rs761240 | kgp19325060 |
| NFKB2 | chr10:104154228-104162281 | chr10:103654228-104662281 | chr10:104144218-104152271 | kgp11777223 | rs7897654 |
| NFKBIB | chr19:39390339-39399534 | chr19:38890339-39899534 | chr19:44082454-44091374 | kgp21403480 | kgp4374047 |

*Fig. 3-16*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| NFKBIE | chr6:44225902-44233525 | chr6:43725902-44733525 | chr6:44333880-44341503 | rs866236 | kgp11221406 |
| NGB | chr14:77731833-77737655 | chr14:77231833-78237655 | chr14:76801586-76807408 | kgp4649405 | rs11622713 |
| NHP2L1 | chr22:42069936-42084913 | chr22:41569936-42584913 | chr22:40399882-40414859 | kgp22806642 | kgp282841 |
| NOS1 | chr12:117645946-117799607 | chr12:117145946-118299607 | chr12:116135361-116283965 | rs11068156 | kgp763518 |
| NP | chr14:20937541-20945248 | chr14:20437541-21445248 | chr14:20007381-20015088 | kgp8768601 | kgp19427360 |
| NPHP1 | chr2:110880913-110962639 | chr2:110380913-111462639 | chr2:110238202-110319928 | rs10496434 | kgp3845148 |
| NRBP1 | chr2:27650656-27665124 | chr2:27150656-28165124 | chr2:27504160-27518628 | kgp14600002 | kgp14258181 |
| NRGN | chr11:124609828-124617102 | chr11:124109828-125117102 | chr11:124115038-124122312 | kgp483624 | kgp5783287 |
| NUCB1 | chr19:49403306-49426540 | chr19:48903306-49926540 | chr19:54095380-54118339 | kgp282275 | kgp9015400 |
| OBSCN | chr1:228395860-228566575 | chr1:227895860-229066575 | chr1:226462483-226633198 | kgp22809391 | kgp706951 |
| OGG1 | chr3:9791627-9808353 | chr3:9291627-10308353 | chr3:9765704-9783342 | rs17744749 | rs1642974 |
| OPRK1 | chr8:54138275-54164194 | chr8:53638275-54664194 | chr8:54300828-54326747 | kgp11808605 | kgp7186378 |
| OPRM1 | chr6:154360442-154568001 | chr6:153860442-155068001 | chr6:154402135-154609693 | kgp22790919 | kgp7491549 |
| P2RY1 | chr3:152552735-152555843 | chr3:152052735-153055843 | chr3:154035425-154038533 | rs4472028 | kgp1812100 |
| PA2G4 | chr12:56498102-56507694 | chr12:55998102-57007694 | chr12:54784369-54793961 | kgp18842835 | rs12308290 |
| PABPC4 | chr1:40026484-40042521 | chr1:39526484-40542521 | chr1:39799074-39815003 | rs6692557 | rs6681804 |
| PAEP | chr9:138453603-138458622 | chr9:137953603-138958622 | chr9:137593424-137598443 | kgp4360258 | rs11103302 |
| PAFAH1B1 | chr17:2496922-2588909 | chr17:1996922-3088909 | chr17:2443672-2535659 | kgp13951566 | kgp4861640 |
| PAM | chr5:102201526-102366808 | chr5:101701526-102866808 | chr5:102229425-102393316 | rs10075318 | kgp4660412 |
| PARD6A | chr16:67694850-67696681 | chr16:67194850-68196681 | chr16:66252351-66254182 | kgp16268099,rs1106304 | kgp16328412 |
| PARD6B | chr20:49348080-49370278 | chr20:48848080-49870278 | chr20:48781487-48803685 | kgp19335956 | kgp19356310 |
| PARD6G | chr18:77915116-78005397 | chr18:77415116-78505397 | chr18:76016105-76106388 | kgp15973881 | rs12960632 |

*Fig. 3-17*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| PAWR | chr12:79985744-80084790 | chr12:79485744-80584790 | chr12:78509875-78608921 | rs2950386 | kgp19124809 |
| PCNT | chr21:47744035-47865682 | chr21:47244035-48365682 | chr21:46568463-46690110 | kgp13165624 | rs10483083 |
| PCP4 | chr21:41239346-41301322 | chr21:40739346-41801322 | chr21:40161216-40223192 | kgp5198475 | rs2837624 |
| PDC | chr1:186412697-186430239 | chr1:185912697-186930239 | chr1:184679337-184696862 | kgp15446019 | kgp15206197 |
| PDCD8 | chrX:129263338-129299861 | chrX:128763338-129799861 | chrX:129091019-129127542 | rs3131260 | kgp22747824 |
| PDCL | chr9:125580375-125590935 | chr9:125080375-126090935 | chr9:124620443-124630661 | kgp11050939 | rs7341862 |
| PDE1A | chr2:183007182-183387507 | chr2:182507182-183887507 | chr2:182715427-183095498 | kgp205462 | kgp14271078 |
| PDE4DIP | chr1:144676436-145076186 | chr1:144176436-145576186 | chr1:143388229-143787436 | rs7548928 | kgp15506281 |
| PDE6D | chr2:232597146-232645974 | chr2:232097146-233145974 | chr2:232305390-232354218 | kgp448503 | rs11686328 |
| PDIA2 | chr16:330605-337209 | chr16:1-837209 | chr16:270606-277210 | kgp4861413 | rs3817833 |
| PDLIM7 | chr5:176910394-176924602 | chr5:176410394-177424602 | chr5:176843000-176857208 | kgp10474318 | kgp9286031 |
| PDPK1 | chr16:2587969-2653189 | chr16:2087969-3153189 | chr16:2527970-2593190 | rs11876 | rs2741932 |
| PEA15 | chr1:160175124-160185162 | chr1:159675124-160685162 | chr1:158441750-158451786 | kgp15388960 | kgp4800109 |
| PELO | chr5:52083773-52098452 | chr5:51583773-52598452 | chr5:52119530-52134209 | kgp7417119 | kgp22419632 |
| PFDN1 | chr5:139624634-139682689 | chr5:139124634-140182689 | chr5:139604818-139662873 | kgp2976589 | rs3733707 |
| PFDN4 | chr20:52824501-52836492 | chr20:52324501-53336492 | chr20:52257908-52269899 | kgp2671049 | kgp19401284 |
| PFDN5 | chr12:53689234-53693234 | chr12:53189234-54193234 | chr12:51975501-51979501 | kgp9320945 | kgp18934893 |
| PFKFB2 | chr1:207207760-207254368 | chr1:206707760-207754368 | chr1:205293242-205320991 | rs6666087 | kgp15524399 |
| PFN1 | chr17:4848946-4851825 | chr17:4348946-5351825 | chr17:4789691-4792570 | kgp459103 | rs11869909 |
| PGK1 | chrX:77359665-77382324 | chrX:76859665-77882324 | chrX:77246321-77268980 | kgp22784498 | kgp22747606 |
| PHKA1 | chrX:71798663-71934029 | chrX:71298663-72434029 | chrX:71715388-71850754 | kgp22784635 | kgp22830838,rs5982097 |
| PHKA2 | chrX:18910415-19002480 | chrX:18410415-19502480 | chrX:18820336-18912401 | kgp22820040 | kgp22735291 |

*Fig. 3-18*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| PHKG1 | chr7:56148674-56160689 | chr7:55648674-56660689 | chr7:56116168-56128183 | rs4947514 | kgp13251786 |
| PIAS4 | chr19:4007748-4038067 | chr19:3507748-4538067 | chr19:3958748-3989067 | kgp21496330 | rs966384 |
| PIK3C3 | chr18:39535198-39661446 | chr18:39035198-40161446 | chr18:37789196-37915444 | kgp16093917 | kgp16001617 |
| PIK3CG | chr7:106505722-106547592 | chr7:106005722-107047592 | chr7:106292958-106334828 | kgp13830163 | kgp58259 |
| PLCB2 | chr15:40580097-40600174 | chr15:40080097-41100174 | chr15:38367389-38387466 | rs594863 | kgp19835274 |
| PLCD1 | chr3:38048986-38071154 | chr3:37548986-38571154 | chr3:38023990-38046137 | rs155528 | kgp8999289 |
| PLD1 | chr3:171318194-171528504 | chr3:170818194-172028504 | chr3:172801338-173011198 | kgp17613784 | kgp17918658 |
| PLD2 | chr17:4710395-4726727 | chr17:4210395-5226727 | chr17:4657377-4673694 | rs9915202 | kgp10024037 |
| PLEKHA4 | chr19:49340353-49371884 | chr19:48840353-49871884 | chr19:54032166-54063670 | kgp21466232 | kgp7036888 |
| PLK1 | chr16:23690200-23701688 | chr16:23190200-24201688 | chr16:23597701-23609189 | kgp6012631 | kgp22747639 |
| POLA2 | chr11:65029431-65065088 | chr11:64529431-65565088 | chr11:64786007-64821664 | rs637332 | rs12800057 |
| POLB | chr8:42195972-42229331 | chr8:41695972-42729331 | chr8:42315186-42348470 | kgp20057794 | kgp20541648 |
| POLR2C | chr16:57496550-57505921 | chr16:56996550-58005921 | chr16:56054051-56063422 | kgp12245826 | rs3888264 |
| POLR3F | chr20:18448032-18465286 | chr20:17948032-18965286 | chr20:18396032-18413286 | kgp4834782 | kgp4034265 |
| PPARA | chr22:46546498-46639653 | chr22:46046498-47139653 | chr22:44925162-45018317 | kgp1216941 | kgp15069036 |
| PPEF1 | chrX:18709044-18846034 | chrX:18209044-19346034 | chrX:18618965-18755955 | kgp22764965 | kgp22802655 |
| PPEF2 | chr4:76781025-76823681 | chr4:76281025-77323681 | chr4:77000049-77042705 | kgp3982074 | kgp4693685 |
| PPM1A | chr14:60712469-60765805 | chr14:60212469-61265805 | chr14:59782222-59835559 | kgp19716116 | kgp5849461 |
| PPP1R13B | chr14:104200087-104313927 | chr14:103700087-104813927 | chr14:103269840-103383680 | kgp19713395 | kgp19494408 |
| PPP1R14A | chr19:38741876-38747231 | chr19:38241876-39247231 | chr19:43433716-43439012 | kgp7541975 | kgp4659188 |
| PPP3CA | chr4:101944586-102268628 | chr4:101444586-102768628 | chr4:102163609-102487376 | kgp4575683 | kgp7268908 |
| PPYR1 | chr10:47083533-47088320 | chr10:46583533-47588320 | chr10:46503539-46508326 | kgp507194 | rs11259820 |

*Fig. 3-19*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| PQBP1 | chrX:48755194-48760422 | chrX:48255194-49260422 | chrX:48640138-48645364 | rs28833838 | rs2015487 |
| PREI3 | chr2:198364721-198418423 | chr2:197864721-198918423 | chr2:198072966-198126668 | kgp9884304 | kgp9480848 |
| PRG2 | chr11:57154833-57191532 | chr11:56654833-57691532 | chr19:763517-772952 | kgp13043879 | kgp12981403 |
| PRKACA | chr19:14202506-14228559 | chr19:13702506-14728559 | chr19:14063506-14089559 | kgp6577295 | kgp559477 |
| PRKCB1 | chr16:23847300-24231932 | chr16:23347300-24731932 | chr16:23754801-24139433 | rs7190829 | rs2343354 |
| PRKCD | chr3:53195222-53226733 | chr3:52695222-53726733 | chr3:53170262-53201773 | rs11715796 | kgp8788109 |
| PRKCG | chr19:54385466-54410901 | chr19:53885466-54910901 | chr19:59077278-59102713 | kgp1393848 | kgp11043930 |
| PRKCI | chr3:169940219-170023770 | chr3:169440219-170523770 | chr3:171422913-171506464 | kgp17942550 | rs12485248 |
| PRKCZ | chr1:1981908-2116834 | chr1:1481908-2616834 | chr1:1971768-2106694 | kgp15756715 | kgp907107 |
| PRKG1 | chr10:52750910-54058110 | chr10:52250910-54558110 | chr10:52420950-53725280 | kgp22035660 | rs7923443 |
| PSCD2 | chr19:48972465-48985571 | chr19:48472465-49485571 | chr19:53664277-53677383 | rs16981057 | rs5464 |
| PSEN2 | chr1:227058272-227083804 | chr1:226558272-227583804 | chr1:225124895-225150427 | rs3219110 | kgp1301981,rs3014274 |
| PSG9 | chr19:43757434-43773682 | chr19:43257434-44273682 | chr19:48449274-48465522 | kgp21418993 | kgp7929858 |
| PSMA2 | chr7:42956461-42971805 | chr7:42456461-43471805 | chr7:42922986-42938330 | kgp13636285 | kgp8523923 |
| PSMD2 | chr3:184017021-184026840 | chr3:183517021-184526840 | chr3:185499715-185509534 | kgp4284536 | rs11711955 |
| PSPC1 | chr13:20277008-20357159 | chr13:19777008-20857159 | chr13:19146895-19255083 | kgp249471 | kgp2992302 |
| PTGIR | chr19:47123724-47128354 | chr19:46623724-47628354 | chr19:51815564-51820194 | kgp21532737 | rs184290 |
| PTMAP7 | chr2:232573235-232578250 | chr2:232073235-233078250 | chr2:232281479-232286494 | kgp6878597 | kgp14464906 |
| PTP4A1 | chr6:64231650-64293489 | chr6:63731650-64793489 | chr6:64289609-64351448 | rs4710239 | kgp357802 |
| PTP4A3 | chr8:142432006-142441620 | chr8:141932006-142941620 | chr8:142501188-142510802 | rs12678285 | kgp3296894 |
| PTPN11 | chr12:112856535-112947717 | chr12:112356535-113447717 | chr12:111340918-111432100 | kgp22816522 | rs1293743 |
| PTPN12 | chr7:77166772-77269388 | chr7:76666772-77769388 | chr7:77004770-77107322 | kgp4690058 | rs3807707 |

*Fig. 3-20*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| PTPN6 | chr12:7055739-7070479 | chr12:6555739-7570479 | chr12:6926000-6940740 | kgp18831609 | kgp18845056 |
| PTPRA | chr20:2844824-3019315 | chr20:2344824-3519315 | chr20:2792824-2967315 | kgp725112 | rs2853218 |
| PTPRJ | chr11:48002109-48192394 | chr11:47502109-48692394 | chr11:47958685-48148970 | kgp11833163 | kgp12755942 |
| PTPRS | chr19:5158505-5340814 | chr19:4658505-5840814 | chr19:5109505-5291814 | kgp6271833 | kgp4407357 |
| PTPRU | chr1:29563027-29653325 | chr1:29063027-30153325 | chr1:29435633-29525903 | rs12068075 | kgp9719744 |
| RAB27A | chr15:55495163-55582013 | chr15:54995163-56082013 | chr15:53283091-53369293 | kgp19829554 | rs11631355 |
| RAB3B | chr1:52373627-52456436 | chr1:51873627-52956436 | chr1:52157422-52228936 | kgp22830492 | rs10493168 |
| RAB5A | chr3:19988571-20026667 | chr3:19488571-20526667 | chr3:19963762-20001647 | rs1348231 | kgp8738867 |
| RAB8B | chr15:63481727-63559973 | chr15:62981727-64059973 | chr15:61268780-61347026 | kgp20037308 | rs17773778 |
| RABAC1 | chr19:42460832-42463528 | chr19:41960832-42963528 | chr19:47152675-47155311 | kgp22776019 | kgp2186225 |
| RAC1 | chr7:6414125-6443598 | chr7:5914125-6943598 | chr7:6380650-6410123 | kgp13594313 | kgp2338008 |
| RACGAP1 | chr12:50382944-50419307 | chr12:49882944-50919307 | chr12:48669211-48705574 | rs12317050 | kgp2525417 |
| RAF1 | chr3:12625099-12705700 | chr3:12125099-13205700 | chr3:12600099-12680700 | kgp17997932 | kgp3531880 |
| RALB | chr2:120997639-121052286 | chr2:120497639-121552286 | chr2:120726883-120768756 | rs17661862 | kgp5177758 |
| RASSF1 | chr3:50367216-50378367 | chr3:49867216-50878367 | chr3:50342220-50353371 | kgp8151957 | kgp7341826 |
| RBM23 | chr14:23369853-23388396 | chr14:22869853-23888396 | chr14:22439693-22458236 | rs3811239 | kgp128686 |
| RBM5 | chr3:50126340-50156397 | chr3:49626340-50656397 | chr3:49952595-50112488 | kgp22823256 | rs375544 |
| RCVRN | chr17:9801026-9808684 | chr17:9301026-10308684 | chr17:9741751-9749409 | rs8082538 | kgp2141837 |
| REL | chr2:61108751-61150178 | chr2:60608751-61650178 | chr2:60962255-61003682 | kgp8245960 | kgp14294452 |
| RELA | chr11:65421066-65430443 | chr11:64921066-65930443 | chr11:65177647-65186951 | kgp6667058 | kgp4478491 |
| RELB | chr19:45504706-45541456 | chr19:45004706-46041456 | chr19:50196551-50233292 | kgp9280266 | kgp9663255 |
| RFC5 | chr12:118454505-118470042 | chr12:117954505-118970042 | chr12:116938892-116954422 | rs11068526 | kgp19024344 |

*Fig. 3-21*

| Tier 3 Gene | GeneRange(hg19) | GeneRange+500kb(hg19) | GeneRange(hg18) | StartSNP (GeneRange+ 500kb) | EndSNP (GeneRange+500 kb) |
| --- | --- | --- | --- | --- | --- |
| RGS10 | chr10:121259338-121302222 | chr10:120759338-121802222 | chr10:121249328-121292212 | kgp21619652 | kgp5105745 |
| RGS13 | chr1:192605267-192629440 | chr1:192105267-193129440 | chr1:190871904-190896012 | rs11806786 | kgp1816960 |
| RGS14 | chr5:176784843-176799599 | chr5:176284843-177299599 | chr5:176717449-176732205 | rs1000144 | kgp11311419 |
| RGS16 | chr1:182567757-182573548 | chr1:182067757-183073548 | chr1:180834380-180840171 | kgp15787070 | kgp4798391 |
| RGS18 | chr1:192127591-192154945 | chr1:191627591-192654945 | chr1:190394214-190421568 | rs1338034 | kgp6525246 |
| RGS19 | chr20:62704534-62711324 | chr20:62204534-63211324 | chr20:62174978-62181768 | rs1630157 | kgp19264714 |
| RGS4 | chr1:163038395-163046592 | chr1:162538395-163546592 | chr1:161305019-161313216 | kgp15623644 | kgp15384575 |
| RGS5 | chr1:163112088-163291581 | chr1:162612088-163791581 | chr1:161378720-161439496 | kgp15331781 | kgp2554099 |
| RGS7 | chr1:240938816-241520478 | chr1:240438816-242020478 | chr1:239005439-239587101 | rs16839692 | kgp15345284 |
| RHO | chr3:129247481-129254187 | chr3:128747481-129754187 | chr3:130730171-130736877 | kgp12236862 | kgp11280524 |
| RHOH | chr4:40198526-40246281 | chr4:39698526-40746281 | chr4:39874921-39922676 | rs3912392 | rs17513557 |
| RIC8A | chr11:208529-215110 | chr11:1-715110 | chr11:198529-205110 | kgp9815230 | rs11246286 |
| RIC8B | chr12:107168398-107283094 | chr12:106668398-107783094 | chr12:105692528-105807224 | kgp7665070 | kgp2084662 |
| RIOK3 | chr18:21032786-21063099 | chr18:20532786-21563099 | chr18:19286784-19317097 | kgp4053645 | kgp16177785 |
| RIPK1 | chr6:3064121-3115421 | chr6:2564121-3615421 | chr6:3009120-3060420 | rs17208835 | kgp17120238 |
| RIPK2 | chr8:90769974-90803292 | chr8:90269974-91303292 | chr8:90839109-90872433 | rs7813237 | rs2214416 |
| RIT1 | chr1:155867600-155881177 | chr1:155367600-156381177 | chr1:154134224-154147801 | kgp10974682 | rs12022607 |
| RIT2 | chr18:40323191-40695657 | chr18:39823191-41195657 | chr18:38577189-38949655 | rs6507465 | kgp3440940 |
| RNF10 | chr12:120972131-121015397 | chr12:120472131-121515397 | chr12:119456514-119499780 | kgp19140786 | kgp19017203 |
| RNF11 | chr1:51701944-51739119 | chr1:51201944-52239119 | chr1:51474532-51511707 | kgp4558813 | kgp7772065 |
| RPL10 | chrX:153627678-153632038 | chrX:153127678-154132038 | chrX:153279911-153283874 | rs2071127 | rs4074307 |
| RPL12 | chr9:130209952-130213711 | chr9:129709952-130713711 | chr9:129249775-129253505 | kgp11622632 | rs3802355 |

*Fig. 3-22*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| RPL37A | chr2:217363519-217366188 | chr2:216863519-217866188 | chr2:217071764-217074433 | kgp2247391 | kgp7636371 |
| RRAD | chr16:66955581-66959439 | chr16:66455581-67459439 | chr16:65513082-65516940 | kgp16522328 | kgp16305055 |
| RTN4 | chr2:55199326-55277734 | chr2:54699326-55777734 | chr2:55052830-55131238 | kgp3749465 | rs3748945 |
| S100A8 | chr1:153362507-153363664 | chr1:152862507-153863664 | chr1:151629131-151630173 | rs6587709 | kgp4686042 |
| SAT1 | chrX:23801274-23804327 | chrX:23301274-24304327 | chrX:23711224-23714248 | kgp22758306 | kgp22759648 |
| SCN8A | chr12:51985019-52202299 | chr12:51485019-52702299 | chr12:50271286-50488566 | rs7979705 | kgp7295633 |
| SDC1 | chr2:20400557-20425194 | chr2:19900557-20925194 | chr2:20264038-20288675 | kgp14253812 | kgp8380770 |
| SDC2 | chr8:97505881-97624037 | chr8:97005881-98124037 | chr8:97575057-97693213 | rs1421221 | kgp1305908 |
| SDC4 | chr20:43953928-43977064 | chr20:43453928-44477064 | chr20:43387342-43410478 | rs8116486 | kgp19276986 |
| SDCBP | chr8:59465727-59495419 | chr8:58965727-59995419 | chr8:59628281-59657973 | rs954172 | kgp20217944 |
| SDCBP2 | chr20:1290554-1373816 | chr20:790554-1873816 | chr20:1238620-1257838 | kgp9852208 | kgp10348674 |
| SDPR | chr2:192699031-192712006 | chr2:192199031-193212006 | chr2:192407280-192420226 | kgp6263901 | kgp14266860 |
| SELENBP1 | chr1:151336779-151345164 | chr1:150836779-151845164 | chr1:149603403-149611788 | rs12406660 | rs6684312 |
| SEMG1 | chr20:43835637-43838414 | chr20:43335637-44338414 | chr20:43269087-43271823 | rs6094023 | rs6094202 |
| SEMG2 | chr20:43835637-43853099 | chr20:43335637-44353099 | chr20:43269087-43286513 | rs6094023 | rs6017667 |
| SEPT4 | chr17:56597610-56618179 | chr17:56097610-57118179 | chr17:53952614-53964410 | kgp1250021 | rs34058624 |
| SETDB1 | chr1:150898814-150937220 | chr1:150398814-151437220 | chr1:149165511-149203837 | rs12759551 | kgp1978717 |
| SGOL1 | chr3:20202084-20227724 | chr3:19702084-20727724 | chr3:20177088-20202687 | kgp9539943 | kgp18040639 |
| SGOL2 | chr2:201390864-201448818 | chr2:200890864-201948818 | chr2:201099186-201156750 | kgp9074393 | kgp14634946 |
| SH2B3 | chr12:111843751-111889427 | chr12:111343751-112389427 | chr12:110328134-110373810 | kgp7682395 | kgp10017505 |
| SHC1 | chr1:154934773-154946959 | chr1:154434773-155446959 | chr1:153201397-153213464 | kgp11196367 | kgp15752431 |
| SIRT2 | chr19:39369194-39390502 | chr19:38869194-39890502 | chr19:44061039-44082201 | kgp21526327 | kgp9511717 |

*Fig. 3-23*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| SLC1A1 | chr9:4490426-4587469 | chr9:3990426-5087469 | chr9:4480443-4577469 | kgp7074545 | kgp9946842 |
| SLC6A9 | chr1:44457171-44497134 | chr1:43957171-44997134 | chr1:44234741-44269721 | rs6687571 | rs6672462 |
| SLC9A3R1 | chr17:72744762-72765499 | chr17:72244762-73265499 | chr17:70256378-70277089 | kgp14032523 | kgp14006779 |
| SMAD3 | chr15:67358194-67487533 | chr15:66858194-67987533 | chr15:65145248-65274587 | kgp1676807 | kgp19813377 |
| SMAD5 | chr5:135468535-135518422 | chr5:134968535-136018422 | chr5:135496434-135546321 | kgp5717445 | kgp8569495 |
| SMN2 | chr5:70220767-70248842 | chr5:69720767-70748842 | chr5:70256523-70284594 | rs28591114 | kgp22633148 |
| SMPD3 | chr16:68392229-68482409 | chr16:67892229-68982409 | chr16:66949730-67039905 | kgp2756941 | kgp16310484 |
| SNAP23 | chr15:42787503-42825259 | chr15:42287503-43325259 | chr15:40575126-40612548 | rs1668586 | kgp19741111 |
| SNAP25 | chr20:10199476-10288066 | chr20:9699476-10788066 | chr20:10147476-10236065 | kgp4923784 | kgp19370207 |
| SNAP91 | chr6:84262604-84419127 | chr6:83762604-84919127 | chr6:84319331-84475831 | kgp17413387 | kgp16958869 |
| SNTA1 | chr20:31995762-32031698 | chr20:31495762-32531698 | chr20:31459423-31495359 | kgp994844 | kgp22753335 |
| SNURF | chr15:25200069-25244225 | chr15:24700069-25744225 | chr15:22751162-22795318 | kgp20028287 | kgp5644000 |
| SOX4 | chr6:21593971-21598849 | chr6:21093971-22098849 | chr6:21701950-21706828 | kgp3609791 | rs9466264 |
| SPAG1 | chr8:101170262-101254132 | chr8:100670262-101754132 | chr8:101239438-101323306 | kgp5198147 | kgp20550876 |
| SPG7 | chr16:89574804-89624174 | chr16:89074804-90124174 | chr16:88102305-88151675 | kgp3688149 | rs3809643 |
| SPP1 | chr4:88896801-88904563 | chr4:88396801-89404563 | chr4:89115825-89123587 | kgp20744622 | kgp20764098 |
| SPTBN1 | chr2:54683453-54898583 | chr2:54183453-55398583 | chr2:54536957-54752087 | kgp14832324 | kgp12300457 |
| SQSTM1 | chr5:179233387-179265077 | chr5:178733387-179765077 | chr5:179170503-179197683 | kgp10101186 | kgp2553327 |
| SRGAP3 | chr3:9022277-9291311 | chr3:8522277-9791311 | chr3:8997277-9266311 | kgp5324812 | kgp18088153 |
| STARD13 | chr13:33677271-34250932 | chr13:33177271-34750932 | chr13:32575306-33148932 | kgp1217969 | kgp9105015 |
| STC2 | chr5:172741725-172756506 | chr5:172241725-173256506 | chr5:172674331-172689112 | kgp22378380 | kgp10706002 |
| STRN | chr2:37064840-37193615 | chr2:36564840-37693615 | chr2:36928975-37047119 | kgp3533593 | kgp9369923 |

*Fig. 3-24*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| STRN4 | chr19:47222767-47250251 | chr19:46722767-47750251 | chr19:51914607-51941560 | kgp21470253 | rs4804031 |
| STX4 | chr16:31044415-31051485 | chr16:30544415-31551485 | chr16:30951916-30958986 | kgp16259387 | kgp7678241 |
| STX5 | chr11:62574331-62599563 | chr11:62074331-63099563 | chr11:62330944-62356136 | kgp10937693 | kgp568990 |
| STXBP1 | chr9:130374485-130454995 | chr9:129874485-130954995 | chr9:129414388-129494816 | rs1768374 | kgp4399986 |
| STXBP3 | chr1:109289284-109352148 | chr1:108789284-109852148 | chr1:109090807-109153671 | rs6583070 | rs17036360 |
| SULT1E1 | chr4:70706929-70725870 | chr4:70206929-71225870 | chr4:70741518-70760459 | kgp22798798 | kgp5241292 |
| SUMO4 | chr6:149721494-149722182 | chr6:149221494-150222182 | chr6:149763187-149763875 | rs1871921 | kgp17155476 |
| SYT1 | chr12:79257772-79845788 | chr12:78757772-80345788 | chr12:77781903-78367834 | kgp11848377 | kgp18913198 |
| SYT9 | chr11:7273180-7490276 | chr11:6773180-7990276 | chr11:7229756-7446846 | rs7928685 | kgp8567849 |
| TANC1 | chr2:159825145-160089170 | chr2:159325145-160589170 | chr2:159533391-159797416 | rs4664962 | kgp22743229 |
| TANK | chr2:161993465-162092683 | chr2:161493465-162592683 | chr2:161701711-161800928 | kgp7233899 | rs1006427 |
| TAOK2 | chr16:29985187-30003582 | chr16:29485187-30503582 | chr16:29892722-29911082 | rs257868 | kgp2310172 |
| TBCD | chr17:80709939-80901062 | chr17:80209939-81401062 | chr17:78303228-78494351 | rs11653735 | kgp10867492 |
| TBCE | chr1:235530727-235612280 | chr1:235030727-236112280 | chr1:233597350-233678903 | rs2673969 | kgp15284682 |
| TBK1 | chr12:64845839-64895899 | chr12:64345839-65395899 | chr12:63132203-63182158 | kgp18934034 | kgp19122002 |
| TCF1 | chr5:134240810-134298336 | chr5:133740810-134798336 | chr5:134268709-134326235 | kgp22161149 | kgp4823163 |
| TCF3 | chr19:1609288-1652328 | chr19:1109288-2152328 | chr19:1560294-1603328 | rs2302109 | kgp2427498 |
| TCF4 | chr18:52889561-53303188 | chr18:52389561-53803188 | chr18:51040559-51454183 | kgp10409423 | rs1792746 |
| TDGF1 | chr3:46616044-46623952 | chr3:46116044-47123952 | chr3:46594216-46598956 | kgp980076 | kgp18003873 |
| TEP1 | chr14:20833825-20881579 | chr14:20333825-21381579 | chr14:19905765-19951420 | rs1780944 | rs12435821 |
| TERT | chr5:1253286-1295162 | chr5:753286-1795162 | chr5:1306286-1348162 | kgp22831882 | rs4975846 |
| TGFA | chr2:70674411-70781147 | chr2:70174411-71281147 | chr2:70527924-70634613 | kgp14279885 | kgp4236793 |

*Fig. 3-25*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| TIAM1 | chr21:32490735-32931290 | chr21:31990735-33431290 | chr21:31412606-31853161 | rs1702403 | rs1892577 |
| TM4SF1 | chr3:149086804-149095568 | chr3:148586804-149595568 | chr3:150569494-150578258 | kgp18120845 | kgp17746361 |
| TMSB4X | chrX:12993225-12995346 | chrX:12493225-13495346 | chrX:12903145-12905267 | kgp22760889 | kgp22772999 |
| TNFRSF14 | chr1:2487804-2495267 | chr1:1987804-2995267 | chr1:2479150-2486613 | rs2803309 | kgp11439882 |
| TNFRSF1A | chr12:6437922-6451283 | chr12:5937922-6951283 | chr12:6308183-6321522 | kgp6731378,rs4764519 | kgp19158534 |
| TNFRSF1B | chr1:12227059-12269277 | chr1:11727059-12769277 | chr1:12149646-12191864 | kgp15495881 | rs3010872 |
| TNIP2 | chr4:2743386-2758103 | chr4:2243386-3258103 | chr4:2713184-2727859 | kgp20948263 | kgp5432833 |
| TNNI2 | chr11:1860232-1862910 | chr11:1360232-2362910 | chr11:1817480-1819484 | kgp11231095 | rs800123 |
| TNNI3 | chr19:55663135-55669100 | chr19:55163135-56169100 | chr19:60354947-60360912 | rs13382124 | kgp21397937 |
| TNNT2 | chr1:201328141-201346805 | chr1:200828141-201846805 | chr1:199594764-199613428 | rs12733378 | rs10920269 |
| TOMM20 | chr1:235272657-235292256 | chr1:234772657-235792256 | chr1:233339282-233358754 | kgp8358331 | kgp15139309 |
| TOP2A | chr17:38544772-38574202 | chr17:38044772-39074202 | chr17:35798321-35827695 | kgp7375263 | kgp10420460 |
| TP53 | chr17:7571719-7590863 | chr17:7071719-8090863 | chr17:7512444-7531588 | kgp12029669 | kgp11286494 |
| TRADD | chr16:67188088-67193812 | chr16:66688088-67693812 | chr16:65745589-65751313 | kgp16482196 | kgp16510307,rs28521023 |
| TRAF1 | chr9:123664670-123691451 | chr9:123164670-124191451 | chr9:122704492-122731300 | kgp6551598 | rs306777 |
| TRAF6 | chr11:36505316-36531863 | chr11:36005316-37031863 | chr11:36467298-36488398 | kgp12764289 | rs333778 |
| TRBV21-1 | chr7:142344427-142344887 | chr7:141844427-142844887 | chr7:142025416-142025876 | kgp2155197 | kgp9570297 |
| TRIM2 | chr4:154074269-154260474 | chr4:153574269-154760474 | chr4:154293719-154479918 | rs6849505 | rs6843172 |
| TRIM29 | chr11:119981993-120008863 | chr11:119481993-120508863 | chr11:119487203-119514073 | kgp12998914 | rs7122702 |
| TRIO | chr5:14143828-14509458 | chr5:13643828-15009458 | chr5:14196828-14562458 | rs1445678 | kgp8041369 |
| TRPC1 | chr3:142443265-142526729 | chr3:141943265-143026729 | chr3:143925955-144009419 | rs9842771 | rs7641069 |
| TRPC3 | chr4:122800182-122872909 | chr4:122300182-123372909 | chr4:123019881-123092359 | kgp21231448 | kgp5789583 |

*Fig. 3-26*

| Tier 3 Gene | GeneRange(hg19) | GeneRange+500kb(hg19) | GeneRange(hg18) | StartSNP (GeneRange+500kb) | EndSNP (GeneRange+500kb) |
|---|---|---|---|---|---|
| TRPC4 | chr13:38210772-38443939 | chr13:37710772-38943939 | chr13:37108794-37341935 | kgp22792521 | rs7338958 |
| TRPV1 | chr17:3468739-3512705 | chr17:2968739-4012705 | chr17:3415489-3459454 | kgp8654960 | rs9890881 |
| TRPV4 | chr12:110220891-110271212 | chr12:109720891-110771212 | chr12:108705276-108755595 | kgp11365980 | kgp19139284 |
| TRPV6 | chr7:142568959-142583490 | chr7:142068959-143083490 | chr7:142279081-142293599 | kgp9647465 | kgp2837315 |
| TSC22D4 | chr7:100064141-100076902 | chr7:99564141-100576902 | chr7:99902077-99914838 | kgp5759639 | kgp10599319 |
| TSHR | chr14:81421868-81612646 | chr14:80921868-82112646 | chr14:80491621-80682399 | kgp19546597 | rs10134565 |
| TSPAN6 | chrX:99883794-99891794 | chrX:99383794-100391794 | chrX:99770450-99778450 | kgp22794008 | rs7059563 |
| TTBK1 | chr6:43211221-43255997 | chr6:42711221-43755997 | chr6:43319199-43363975 | kgp17369454 | kgp17498760 |
| TTC1 | chr5:159436179-159492550 | chr5:158936179-159992550 | chr5:159368757-159425128 | kgp5018309 | kgp22489460 |
| TTK | chr6:80714321-80752244 | chr6:80214321-81252244 | chr6:80771077-80808958 | kgp949561 | kgp12311980 |
| TTN | chr2:179390717-179672150 | chr2:178890717-180172150 | chr2:179098963-179380395 | rs959775 | rs6433773 |
| TUB | chr11:8040790-8127654 | chr11:7540790-8627654 | chr11:8016755-8084228 | kgp12365126 | kgp1066384 |
| TUBA8 | chr22:18593452-18614498 | chr22:18093452-19114498 | chr22:16940685-16994498 | rs1034470 | kgp9877961 |
| UBE2V2 | chr8:48920994-48974454 | chr8:48420994-49474454 | chr8:49083547-49137007 | kgp3293751 | kgp20374954 |
| ULK1 | chr12:132379278-132407707 | chr12:131879278-132907707 | chr12:130945231-130973649 | kgp7696078 | kgp11815104 |
| USP7 | chr16:8985950-9057341 | chr16:8485950-9557341 | chr16:8893451-8964842 | kgp79060 | rs1035944 |
| VAV1 | chr19:6772721-6857371 | chr19:6272721-7357371 | chr19:6723721-6808371 | kgp21410647 | kgp21471951 |
| VCL | chr10:75754950-75879914 | chr10:75254950-76379914 | chr10:75424956-75549920 | rs7099640 | kgp21840278 |
| VDAC1 | chr5:133307565-133340824 | chr5:132807565-133840824 | chr5:133335505-133368723 | kgp22321002 | kgp9499928 |
| VIL2 | chr6:159186773-159239340 | chr6:158686773-159739340 | chr6:159106761-159159328 | rs9366083 | kgp10633571 |
| VIM | chr10:17270257-17279592 | chr10:16770257-17779592 | chr10:17310475-17319598 | kgp1974218 | kgp8572563 |
| VTN | chr17:26694298-26697373 | chr17:26194298-27197373 | chr17:23718425-23721500 | rs12602762 | kgp2208161 |

*Fig. 3-27*

| Tier 3 Gene | GeneRange(hg19) | GeneRange+500kb(hg19) | GeneRange(hg18) | StartSNP (GeneRange+ 500kb) | EndSNP (GeneRange+500 kb) |
|---|---|---|---|---|---|
| WDR62 | chr19:36545782-36596012 | chr19:36045782-37096012 | chr19:41237622-41287852 | kgp5818871 | kgp7464156 |
| WDR91 | chr7:134868589-134896316 | chr7:134368589-135396316 | chr7:134520524-134546811 | kgp7394785 | kgp4752834 |
| WWC1 | chr5:167719064-167899308 | chr5:167219064-168399308 | chr5:167651669-167829342 | rs10454965 | rs7724207 |
| XK | chrX:37545132-37591383 | chrX:37045132-38091383 | chrX:37430051-37476322 | kgp22781551 | kgp22821350 |
| YWHAB | chr20:43514343-43537161 | chr20:43014343-44037161 | chr20:42947757-42970575 | rs4364072 | rs2247619 |
| YWHAE | chr17:1247833-1303556 | chr17:747833-1803556 | chr17:1194592-1250267 | rs4968122 | kgp1552188 |
| YWHAG | chr7:75956107-75988342 | chr7:75456107-76488342 | chr7:75794051-75826252 | kgp13357645 | kgp7952605 |
| YWHAZ | chr8:101930803-101965623 | chr8:101430803-102465623 | chr8:102000089-102034745 | rs4075553 | kgp4135753 |
| ZNF24 | chr18:32912177-32924426 | chr18:32412177-33424426 | chr18:31166175-31178424 | kgp5227729 | kgp15931312 |

*Fig. 3-28*

NONSELECTIVE METABOTROPIC GLUTAMATE RECEPTOR ACTIVATORS FOR TREATMENT OF ANOREXIA NERVOSA AND BINGE EATING DISORDER

CROSS-REFERENCE TO RELATED APPLICATIONS

This application is a continuation application of U.S. patent application Ser. No. 16/330,469, filed Mar. 5, 2019, which is a § 371 of International Application No. PCT/US2017/050228, filed Sep. 6, 2017, which claims benefit of U.S. Provisional Application No. 62/384,686, filed Sep. 7, 2016. The entire disclosure of each of the aforesaid applications is incorporated by reference in the present application.

FIELD

This application relates to diagnosing and treating anorexia nervosa (AN) and binge eating disorders (BED) with a nonselective activator of metabotropic glutamate receptors (mGluRs), for example, in subjects having a genetic alteration in at least one metabotropic glutamate receptor (mGluR) network gene.

BACKGROUND

Anorexia nervosa (AN) is a complex illness characterized by low body weight and persistent fear of weight gain during periods of growth, resulting in extreme emaciation. Patients with AN usually manifest with symptoms of depression, anxiety, and obsessive-compulsive behaviors that are common features in other neuropsychiatric disorders.

Multiple bodies of evidence now suggest the role of genetic influences to AN. Family studies have consistently demonstrated that AN occurs in families and twin studies have revealed the contribution of additive genetic factors to the observed familial aggregation. However, despite many studies, the genetic architecture underlying AN susceptibility remains largely unknown. Few genetic factors have been found to be specific to AN and no single factor has been shown to be necessary or sufficient to express the phenotype. Anorexia Nervosa (AN) has the highest mortality of any psychiatric disorder, and becomes intractable in around 20% of patients, resulting in huge individual cost.

Similarly, Binge Eating Disorder (BED) is characterized by recurrent episodes of eating large quantities of food (often very quickly and to the point of discomfort) without regularly purging. Subjects with BED usually have feelings of a loss of control during the binge, experience shame, distress or guilt afterwards, and often have functional impairment, suicide risk, and a high frequency of co-occurring psychiatric disorders. BED may be the most common eating disorder in the United States, with a reported 3.5% of women and 2% of men affected. Diagnostic and treatment strategies for AN and BED are urgently needed.

SUMMARY OF THE INVENTION

Provided herein are methods of treating anorexia nervosa (AN) and binge eating disorder (BED) in a subject comprising administering an effective amount of a nonselective metabotropic glutamate receptor (mGluR) activator to a subject with AN and/or BED, thereby treating AN and/or BED. In some embodiments, the subject has a genetic alteration, such as a copy number variation (CNV) in at least one gene in the mGluR network. In some embodiments, the subject has a genetic alteration in at least one Tier 1, Tier 2, or Tier 3 mGlurR network gene as disclosed herein in FIGS. 1-3.

In some embodiments, treating the subject may comprise treating the AN and/or BED, such as alleviating at least one AN and/or BED symptom in the subject. In some embodiments, the subject is a pediatric or adolescent subject, such as a subject between the ages of 5 and 17, 8 and 17, 5 and 12, 5 and 8, 8 and 12, 12 and 17, 13 and 17, or 13 and 18. In other embodiments, the subject is an adult. In some embodiments, the nonselective mGluR activator is fasoracetam, such as fasoracetam monohydrate.

In some embodiments where the activator is fasoracetam, the fasoracetam is administered at a dose of 50-400 mg, such as 100-400 mg, or 100-200 mg, or 200-400 mg, or 100 mg, or 200 mg, or 300 mg, or 400 mg, and is administered once, twice, or three times daily. In some embodiments, the fasoracetam is administered at a dose of 100 mg, 200 mg, 300 mg, or 400 mg twice daily, such as 100-200 mg twice daily.

In some embodiments, the activator is administered in combination with another pharmaceutical agent, such as an antidepressant, such as fluoxetine, escitalopram, bupropion, mirtazapine, amitriptyline, imipramine, venlafaxine, sertraline, paroxetine, tricyclic antidepressants, selective serotonin reuptake inhibitors, serotonin and norepinephrine reuptake inhibitors, norepinephrine and dopamine reuptake inhibitors, or monoamine oxidase inhibitors; and/or in combination with an anxiolytic, such as barbiturates, pregabalin, or benzodiazepines, including chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam; and/or in combination with an anti-psychotic, such as aripiprazole or risperidone.

In some embodiments, the activator is administered in combination with non-pharmaceutical therapy, such as brain stimulation, for example vagus nerve stimulation, repetitive transcranial magnetic stimulation, magnetic seizure therapy, and/or deep brain stimulation.

In some embodiments, the activator is administered in an amount or dosage regime shown to be effective to result in a clinical general impression—improvement (CGI-I) score of 1 or 2 after four weeks of treatment and/or an improvement of at least 25%, such as at least 30%, at least 35%, or at least 40%, in an AN rating scale score after four weeks of treatment in a majority of subjects of at least one clinical trial.

In any of the above embodiments, the AN may in some cases be deemed treated if at least one symptom of AN is improved in the subject. In any of the above embodiments, the BED may in some cases be deemed treated if at least one symptom of AN is improved in the subject.

Also provided herein are methods of treating anorexia nervosa (AN) in a subject comprising administering a therapeutically effective amount of a nonselective metabotropic glutamate receptor (mGluR) activator to a subject, thereby treating AN.

Further provided herein is a method of treating AN in a subject comprising administering fasoracetam to the subject at a dose of 50-400 mg, such as 100-400 mg, or 100-200 mg, or 200-400 mg, or 100 mg, or 200 mg, or 300 mg, or 400 mg, wherein the dose is administered once, twice, or three times daily, thereby treating AN. In some such embodiments, the fasoracetam is administered at a dose of 100 mg, 200 mg, 300 mg, or 400 mg twice daily, such as 100-200 mg twice daily.

In some embodiments of the above AN treatment methods, the subject has at least one genetic alteration in an mGluR network gene, such as a point mutation, insertion, deletion, or copy number variation (CNV). In some embodiments, the subject has a genetic alteration in two or more mGluR network genes. In some embodiments, the genetic alteration is detected by a process comprising a genetic test comprising obtaining a sample from the subject, optionally isolating nucleic acid from the sample, optionally amplifying the nucleic acid, and analyzing the nucleic acid for a genetic alteration in at least one mGluR network gene. In some embodiments, the treatment method further comprises obtaining results of the genetic test prior to initial administration of the activator. In some embodiments, the genetic test comprises analyzing the nucleic acid for a CNV or SNV in at least 5, 6, 7, 8, 9, 10, 15, 20, 30, 40, 50, 60, 70, or all Tier 1 mGluR network genes (FIG. 1 herein). In some embodiments, the genetic test comprises analyzing the nucleic acid for a CNV or SNV in at least 5, 10, 20, 30, 50, 100, 150, 175, or all Tier 2 mGluR network genes (FIG. 2). In some embodiments, the method comprises analyzing the nucleic acid for a CNV or SNV in at least 5, 10, 20, 50, 100, 200 300, 400, 500, or all Tier 3 mGluR network genes (FIG. 3). In some embodiments, the genetic test does not assess CNVs or SNVs in one or more of GRA/11, GRM2, GRM3, GRM4, GRM5, GRM6, GRM7 or GRM8. In some embodiments, the AN subject has a genetic alteration, such as a CNV, in a Tier 1 or Tier 2 mGluR network gene but does not have a genetic alteration, such as a CNV, in a Tier 3 mGluR network gene.

The invention comprises methods for diagnosing anorexia nervosa (AN) in a subject, comprising:
a) obtaining a biological sample from the patient;
b) assaying nucleic acid from the sample to determine whether a genetic alteration is present in one or more genes in the mGluR network; and
c) diagnosing the patient with AN if a genetic alteration is present in one or more genes in the mGluR network.

Also encompasses are methods for diagnosing binge eating disorder (BED) in a subject, comprising:
a) obtaining a biological sample from the patient;
b) assaying nucleic acid from the sample to determine whether a genetic alteration is present in one or more genes in the mGluR network; and
c) diagnosing the patient with AN if a genetic alteration is present in one or more genes in the mGluR network.

In some embodiments, the genetic alteration is a CNV, such as a deletion or a duplication. The genetic alteration may be in at least 2, 3, 4, 5, 6, 7, 8, 9, 10, 15, 20, 30, 40, 50, 60, 70, or all Tier 1 mGluR network genes. The genetic alteration may be in at least 2, 3, 4, 5, 10, 20, 30, 50, 100, 150, 175, or all Tier 2 mGluR network genes. In other instances, the genetic alteration may be in at least 2, 3, 4, 5, 10, 20, 50, 100, 200 300, 400, 500, or all Tier 3 mGluR network genes.

The subject may have a bingeing and/or purging subtype of AN. In other instances, the subject has the restricting subtype of AN.

The subject may be a pediatric or adolescent subject between the ages of 5 and 17, 8 and 17, 5 and 12, 5 and 8, 8 and 12, 12 and 17, 13 and 18 or 13 and 17. The subject may be an adult patient.

In some embodiments, the method further comprises providing a report comprising suggested treatment(s) for AN and/or BED based upon the genetic alteration(s) identified in the method. In some aspects, the method further comprises prescribing or administering an effective amount of an mGluR activator to the diagnosed patient.

In some embodiments, the diagnosed patient is prescribed, administered, or is already taking one or more antidepressant, anxiolytic or anti-psychotic.

In some instances, the antidepressant is fluoxetine, escitalopram, bupropion, mirtazapine, amitriptyline, imipramine, venlafaxine, sertraline, paroxetine, tricyclic antidepressants, selective serotonin reuptake inhibitors, serotonin and norepinephrine reuptake inhibitors, norepinephrine and dopamine reuptake inhibitors, or monoamine oxidase inhibitors.

In some embodiments, the anxiolytic is a barbiturate, pregabalin, or benzodiazepines, including chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam.

In some embodiments, the anti-psychotic is olanzapine, quetiapine, aripiprazole or risperidone.

In some embodiments, the invention comprises a method for determining whether a subject is susceptible to developing anorexia nervosa (AN) and/or binge eating disorder (BED), the method comprising:
a) obtaining a biological sample from the subject;
b) assaying nucleic acid from the sample to determine whether a genetic alteration in one or more genes in the mGluR network is present in the nucleic acid; and
c) determining that the subject is susceptible to developing AN and/or BED if a genetic alteration is present in one or more one or more genes in the mGluR network.

In some embodiments, the genetic alteration is a CNV. In some instances, the CNV is a deletion or a duplication.

A system for detecting a genetic alteration related to anorexia nervosa (AN) or binge eating disorder in a subject is provided, comprising probes specific for and capable of determining the presence of a genetic alteration in: i) at least 1, 2, 3, 4, 5, 6, 7, 8, 9, 10, 15, 20, 30, 40, 50, 60, 70, or all Tier 1 mGluR network genes; ii) at least 1, 2, 3, 4, 5, 10, 20, 30, 50, 100, 150, 175, or all Tier 2 mGluR network genes; and/or iii) at least 1, 2, 3, 4, 5, 10, 20, 50, 100, 200 300, 400, 500, or all Tier 3 mGluR network genes.

In some system embodiments, the genetic alteration is a point mutation, insertion, deletion, single nucleotide variation (SNV), single nucleotide polymorphism (SNP) or copy number variation (CNV). In some embodiments, the probes of the system are affixed to a solid support matrix, such as a chip.

BRIEF DESCRIPTION OF THE DRAWINGS

FIG. 1 shows the mGluR network genes included in the Tier 1 gene set. These genes have 2 degrees of protein-protein interaction with mGluR genes (GRM1-8) based on the Cytoscape Human Interactome, which is software for integrating biomolecular interaction networks with high-throughput data (as described in Shannon P (2003) *Genome Research* 13:2498-2504). The Tier 1 gene set includes 76 genes. The exact location for each gene in Tier 1 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The start single nucleotide polymorphism (StartSNP) (i.e., the SNP located 500 kilobases before the gene of interest) and the EndSNP (i.e., the SNP located 500 kilobases after the gene of interest) are also listed. Genes of the mGluRs themselves are noted as "GRIM." The expanded regions (i.e., 500 kg up and down stream) frequently harbor regulatory elements and if impacted by a CNV, can have the same impact on the gene expression and function as a CNV residing in the gene sequence itself.

FIG. 2 shows the mGluR network genes included in the Tier 2 gene set. These genes have 2 degrees of protein-protein interaction with mGluR genes (GRM1-8) based on the Cytoscape Human Interactome but exclude genes from Tier 1. The Tier 2 gene set includes 197 genes. The exact location for each gene in Tier 2 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The start single nucleotide polymorphism (StartSNP) (i.e., the SNP located 500 kilobases before the gene of interest) and the EndSNP (i.e., the SNP located 500 kilobases after the gene of interest) in hg19 are also listed.

FIG. 3 shows genes within the Tier 3 gene set. Genes with reciprocal gene querying with 2 degrees of protein-protein interaction with mGluR genes based on Cytoscape Human Interactome are included. Genes contained within Tiers 1 and 2 are excluded from Tier 3. The Tier 3 gene set includes 599 genes. The exact location for each gene in Tier 3 is listed in both the Human Genome version 18 (hg18) and Human Genome version 19 (hg19). In addition, the exact gene location plus 500 kilobase (i.e., the range from 500 kilobase before and 500 kilobase after the gene of interest) is listed for hg19. The StartSNP (i.e., the SNP located 500 kilobases before the gene of interest) and the EndSNP (i.e., the SNP located 500 kilobases after the gene of interest) in hg19 are also listed.

DESCRIPTION OF CERTAIN EMBODIMENTS

Definitions

In addition to definitions included in this sub-section, further definitions of terms are interspersed throughout the text.

In this invention, "a" or "an" means "at least one" or "one or more," etc., unless clearly indicated otherwise by context. The term "or" means "and/or" unless stated otherwise. In the case of a multiple-dependent claim, however, use of the term "or" refers back to more than one preceding claim in the alternative only.

A "mGluR" or metabotropic glutamate receptor refers to one of eight glutamate receptors expressed in neural tissue named mGluR1, mGluR2, mGluR3, mGluR4, mGluR5, mGluR6, mGluR7, and mGluR8. Their genes are abbreviated GRM1 to GRM8. The mGluR proteins are G-protein-coupled receptors. They are typically placed into three sub-groups, Group I receptors including mGluR1 and mGluR5 are classed as slow excitatory receptors. Group II includes mGluR2 and mGluR3. Group III includes mGluR4, mGluR6, mGluR7, and mGluR8. Groups II and III are classed as slow inhibitory receptors. The mGluRs are distinguished from the ionotropic GluRs or iGluRs, which are ion channel-associated glutamate receptors and are classed as fast excitatory receptors.

A "mGluR network gene," for purposes of this invention, comprises not only the mGluR genes GRM1, GRM2, GRM3, GRM4, GRM5, GRM6, GRM7, and GRM8, but also each of the other genes listed herein in FIGS. 1-3 as well as the regions of DNA that regulate the genes listed in FIGS. 1-3. In addition, "mGluR network proteins" are the proteins encoded by the mGluR network genes.

The mGluR network genes are grouped into three subsets: Tier 1, Tier 2, and Tier 3. (See FIGS. 1-3.) Tier 1 mGluR network genes, shown in FIG. 1, comprise 76 genes, including some GRM genes themselves as well as a number of other genes. The Tier 2 mGluR network genes, shown in FIG. 2, comprise 197 genes, and exclude the Tier 1 genes.

Tiers 1 and 2 together are included in the "primary mGluR network." The "primary network" of mGluR genes also includes the genes 4-Sep, LOC642393, and LOC653098, for a total of 276 genes. There are presently technical difficulties in assessing the 4-Sep, LOC642393, and LOC653098 genes. Thus, they are not included in Tiers 1 and 2, although they are included in the primary network of genes of the present invention. The genes of Tier 1 and Tier 2 differ in that alterations in Tier 1 genes had been documented in previous genotyping studies of subjects suffering from mental disorders.

Tier 3 mGluR network genes, shown in FIG. 3, comprise 599 genes that are in the distal part of the mGluR network based on the merged human interactome provided by the Cytoscape Software (Shannon P et al. (2003) Genome Research 13:2498-2504), and exclude the Tier 1 and Tier 2 genes. The Tier 3 genes are thus part of the "distal mGluR network." In addition to the Tier 3 genes, the genes LOC285147, LOC147004, and LOC93444 are included in the "distal mGluR network," although they were not assessed in the present study and are not included in Tier 3 due to technical difficulties.

A "genetic alteration" as used herein means any alteration in the DNA of a gene, or in the DNA regulating a gene, that, for example, may result in a gene product that is functionally changed as compared to a gene product produced from a non-altered DNA. A functional change may be differing expression levels (up-regulation or down-regulation) or loss or change in one or more biological activities, for example. A genetic alteration includes without limitation, copy number variations (CNVs), single nucleotide variations (SNVs) (also called single nucleotide polymorphisms (SNPs) herein, although a SNP differs from a SNV in that a SNP is found in greater than a certain percentage of the population and therefore is by definition more common than an SNV), frame shift mutations, or any other base pair substitutions, insertions, and deletions.

A "copy number variation" or "CNV" is a duplication or deletion of a DNA segment encompassing a gene, genes, segment of a gene, or DNA region regulating a gene, as compared to a reference genome. In some embodiments, a CNV is determined based on variation from a normal diploid state. In some embodiments, a CNV represents a copy number change involving a DNA fragment that is 1 kilobase (kb) or larger. CNVs described herein do not include those variants that arise from the insertion/deletion of transposable elements (e.g., 6-kb KpnI repeats). The term CNV therefore encompasses terms such as large-scale copy number variants (LCVs; Iafrate et al. 2004), copy number polymorphisms (CNPs; Sebat et al. 2004), and intermediate-sized variants (ISVs; Tuzun et al. 2005), but not retrotransposon insertions.

A "CNV deletion" or "deletion CNV" or similar terms refer to a CNV in which a gene or gene segment is deleted. A "CNV duplication" or "duplication CNV" or similar terms refer to a CNV in which a gene or gene segment is present in at least two, and possibly more than two, copies in comparison with the single copy found in a normal reference genome.

A "sample" refers to a sample from a subject that may be tested, for example, for presence of a CNV in one or more mGluR network proteins, as described herein. The sample may comprise cells, and it may comprise body fluids, such as blood, serum, plasma, cerebral spinal fluid, urine, saliva, tears, pleural fluid, and the like.

The terms "pediatric subject" or "pediatric patient" are used interchangeably to refer to a human less than 18 years of age. An "adult patient" or "adult subject" refers to a human 18 years of age or older. An "adolescent patient" or "adolescent subject" is typically about 12 to 18, such as 12 to 17 or 13 to 18, years old.

Anorexia Nervosa (AN)

The term "Anorexia Nervosa" (AN) refers to a psychiatric disorder that may be characterized at least in part by a pathological level of extreme weight loss. According to the *Diagnostic and Statistical Manual of Mental Disorders,* 5th Ed., (DSM-5), diagnostic criteria for AN include: 1) restricting food intake—eating less than needed to maintain a body weight that's at or above the minimum normal weight for your age and height; 2) fear of gaining weight: intense fear of gaining weight or becoming fat, or persistent behavior that interferes with weight gain, such as vomiting or using laxatives, even though you're underweight; and 3) problems with body image: denying the seriousness of having a low body weight, connecting your weight to your self-worth, or having a distorted image of your appearance or shape.

Physical signs and symptoms of AN can include: extreme weight loss; a thin appearance; abnormal blood counts; fatigue; insomnia; dizziness or fainting; bluish discoloration of the fingers; hair that thins, breaks or falls out; soft, downy hair covering the body; absence of menstruation; constipation; dry or yellowish skin; intolerance of cold; irregular heart rhythms; low blood pressure; dehydration; osteoporosis; and swelling of arms or legs.

Emotional and behavioral symptoms of AN can include severely restricting food intake through dieting or fasting and may include excessive exercise, and/or bingeing and self-induced vomiting to get rid of the food and may include use of laxatives, enemas, diet aids or herbal products. Other emotional and behavioral signs and symptoms related to anorexia may include: preoccupation with food; refusal to eat; denial of hunger; fear of gaining weight; lying about how much food has been eaten; flat mood (lack of emotion); social withdrawal; irritability; reduced interest in sex; depressed mood; and thoughts of suicide.

Additional signs and symptoms that can be indicative of AN can include: skipping meals; making excuses for not eating; eating only a few certain "safe" foods, usually those low in fat and calories; adopting rigid meal or eating rituals, such as spitting food out after chewing; cooking elaborate meals for others but refusing to eat; repeated weighing or measuring of themselves; frequent checking in the mirror for perceived flaws; complaining about being fat; not wanting to eat in public; calluses on the knuckles and eroded teeth if inducing vomiting; and covering up in layers of clothing.

There are two subtypes of AN. The restricting subtype refers to AN subjects in which in which weight loss is accomplished primarily through dieting, fasting, or excessive exercise. During the current episode of AN, these individuals have not regularly engaged in binge eating or purging. The other subtype of AN is the binge-eating/purging subtype. This subtype refers to AN subjects that have engaged in binge eating or purging (or both) during the current episode of AN. Most individuals with AN who binge eat also purge through self-induced vomiting or the misuse of laxatives, diuretics, or enemas. Some individuals included in this subtype do not binge eat, but do regularly purge after the consumption of small amounts of food.

The treatment methods of the invention may treat any of the above-mentioned AN symptoms. Improvement in any or all of the above-mentioned symptoms is indicative of successful treatment of AN.

Currently used therapeutics for AN include antidepressants, such as serotonin selective uptake inhibitors, e.g. fluoxetine, sertraline, and citalopram, as well as clonidine and guanfacine. These medications, however, may have a number of possible side effects and some also have short half-lives of activity.

Binge Eating Disorder

Binge Eating Disorder (BED) is characterized as recurring episodes of eating significantly more food in a short period of time than most people would eat under similar circumstances. These episodes typically are marked by feelings of lack of control. According to the *Diagnostic and Statistical Manual of Mental Disorders,* 5th Ed., (DSM-5), diagnostic criteria for BED include:

a. Recurrent episodes of binge eating, which is characterized by eating in a discrete period of time (for example, within any 2-hour period), and eating an amount of food that is larger than most people would eat in a similar period of time under similar circumstances; or b. a sense of lack of control over eating during the episode (for example, a feeling that one cannot stop eating or control what or how much one is eating).

A binge-eating episode is associated with three (or more) of the following: eating much more rapidly than normal, eating until feeling uncomfortably full, eating large amounts of food when not feeling physically hungry, eating alone because of feeling embarrassed by how much one is eating, and feeling disgusted with oneself, depressed, or very guilty afterwards.

The subject is typically distressed regarding binge eating being present. The binge eating occurs, on average, at least once a week for three months.

Binge Eating Disorder is not associated with the recurrent use of inappropriate compensatory behavior (for example, purging) and does not occur exclusively during the course Anorexia Nervosa, Bulimia Nervosa, or Avoidant/Restrictive Food Intake Disorder.

The treatment methods of the invention may treat any of the above-mentioned BED symptoms. Improvement in any or all of the above-mentioned BED symptoms is indicative of successful treatment.

The Binge Eating Scale (BES) is a 16-item questionnaire that assesses the presence of certain binge eating behaviors, and is used to diagnose BED, as well as to monitor progress throughout treatment.

The mGluR Network Genes

In some embodiments herein, AN and BED patients may be evaluated prior to treatment for a genetic alteration in one or more of the Tier 1, 2, and/or 3 mGluR network genes, such as single gene or a panel of such genes. In some embodiments, the genetic alteration is a copy number variation (CNV), resulting from a duplication or other multiplication of one or both copies of the gene or a deletion of one or both copies of the gene. A CNV deletion or duplication can alter the expression of a resulting gene product contained within the CNV because of the change in copy number of this gene, and may therefore contribute to a disease phenotype. However, a CNV deletion or duplication may also have no effect on relative expression of gene products in any tissue (see Henrichsen C N et al. (2009) *Human Molecular Genetics*, 2009, Vol 18 (1):R1-R8). A CNV deletion or duplication may also affect the expression of genes located in the vicinity of the CNV, such that expression of genes outside of the actual CNV may also be affected. A CNV can also influence gene expression through perturbation of transcript structure; for example, a duplication CNV may lead to an increase in copy number but may actually lead to a decrease in gene product due to interference with normal transcription.

In some embodiments, AN and BED patients who have at least one genetic alteration, such as at least one CNV in an mGluR network gene, such as in a Tier1, Tier2, and/or Tier3 gene as shown in FIGS. 1-3 are treated with an mGluR activator such as fasoracetam.

In some embodiments, gene sets or panels of mGluR network genes are used for analyzing samples from patients with suspected AN or BED. In some embodiments, the presence of genetic alterations such as CNV duplications or deletions within these gene sets or panels is determined. In some embodiments, genetic alterations such as CNVs in the Tier 1 genes shown in FIG. 1 are determined. In some embodiments a panel of at least 1, 2, 3, 4, 5, 6, 7, 8, 9, 10, 20, 30, 40, 50, 60, 70, or all of the Tier 1 genes is evaluated for the presence of genetic alterations such as CNVs. Within any such panel of genes, any individual, specific Tier 1 genes may also be excluded from the panel. For instance, in some embodiments, one or more of the GRM 1-8 genes are not included in the panel.

In some embodiments, the Tier 2 genes as shown in FIG. 2 are analyzed for the presence of genetic alterations such as CNVs, optionally in addition to evaluation of the above Tier 1 evaluations or in addition to evaluations of subsets of the Tier 1 genes as described above. In some embodiments, at least 50 Tier 2 genes are evaluated, while in some embodiments, at least 1, 2, 3, 4, 5, 10, 20, 30, 50, 100, 150, or all of the Tier 2 genes are evaluated. Individual, specific Tier 2 genes may be excluded from the gene set for evaluation in some embodiments.

In some embodiments, all of the Tier 3 genes shown in FIG. 3 are evaluated for genetic alterations such as CNVs, optionally in addition to evaluation of the above Tier 1 and/or Tier 2 evaluations or in addition to evaluations of subsets of the Tier 1 and/or Tier 2 genes as described above. Tier 3 genes are considered a wide range of potential interactors with the mGluR network, and genes contained within Tier 3 are not contained in Tier 1 and Tier 2. In some embodiments, at least 1, 2, 3, 4, 5, 10, 20, 50, 100, 200, 300, 400, 500 or all of the Tier 3 genes are included in a panel to evaluate genetic alterations.

Evaluation of Genetic Alterations in mGluR Network Genes

Any biological sample may be used to determine the presence or absence of mGluR network gene alterations, including, but not limited to, blood, urine, serum, gastric lavage, CNS fluid, any type of cell (such as brain cells, white blood cells, mononuclear cells) or body tissue. Any biological source material whereby DNA can be extracted may be used to determine the presence or absence of mGluR network gene alterations. Samples may be freshly collected, or samples may have been previously collected for any use/purpose and stored until the time of testing for genetic alterations. DNA that was previously purified for a different purpose may also be used.

Various methods for determining genetic alterations are known, including the following:

1. Single Nucleotide Variation (SNV)/Single Nucleotide Polymorphism (SNP) Genotyping Determining whether a patient has a genetic alteration, such as a CNV, in an mGluR network gene may be done by SNV/SNP Genotyping, using a SNV/SNP genotyping array such as those commercially available from Illumina or Affymetrix. A "single nucleotide variation (SNV)," also interchangeably referred to as a "single nucleotide polymorphism (SNP)" herein, refers to a change in which a single base in the DNA differs from the usual base at that position. Millions of SNVs have been cataloged in the human genome. Some SNVs are normal variations in the genome, while others are associated with disease. While specific SNVs may be associated with disease states or susceptibility, high-density SNV genotyping can also be undertaken, whereby sequencing information on SNVs is used to determine the unique genetic makeup of an individual.

In SNV genotyping, SNVs can be determined by hybridizing complementary DNA probes to the SNV site. A wide range of platforms can be used with SNV genotyping tools to accommodate varying sample throughputs, multiplexing capabilities, and chemistries. In high-density SNV arrays, hundreds of thousands of probes are arrayed on a small chip, such that many SNVs can be interrogated simultaneously when target DNA is processed on the chip. By determining the amount of hybridization of target DNA in a sample to a probe (or redundant probes) on the array, specific SNV alleles can be determined. Use of arrays for SNV genotyping allows the large-scale interrogation of SNVs.

When analyzing CNVs, after SNVs have been analyzed, a computer program can be used to manipulate the SNV data to arrive at CNV data. PennCNV or a similar program, can then be used to detect signal patterns across the genome and identify consecutive genetic markers with copy number changes. (See Wang K, et al. Uune 2008) Cold Spring Harb Protoc). PennCNV allows for kilobase-resolution detection of CNVs. (See Wang K, et al. (November 2007) *Genome Res.* 17(11):1665-74).

In CNV analysis, the SNV genotyping data is compared with the behavior of normal diploid DNA. The software uses SNV genotyping data to determine the signal intensity data and SNV allelic ratio distribution and to then use these data to determine when there is deviation from the normal diploid condition of DNA that indicates a CNV. This is done in part by using the log R Ratio (LRR), which is a normalized measure of the total signal intensity for the two alleles of the SNV (Wang 2008). If the software detects regions of contiguous SNVs with intensity (LRR) trending below 0, this indicates a CNV deletion. If the software instead detects regions of contiguous SNVs with intensity (LRR) trending above 0, this indicates a CNV duplication. If no change in LRR is observed compared to the behavior of diploid DNA, the sequence is in the normal diploid state with no CNV present. The software also uses B allele frequency (BAF), a normalized measure of the allelic intensity ratio of two alleles that changes when alleles are lost or gained as with a CNV deletion or duplication. For example, a CNV deletion is indicated by both a decrease in LRR values and a lack of heterozygotes in BAF values. In contrast, a CNV duplication is indicated by both an increase in LRR values and a splitting of the heterozygous genotype BAF clusters into two distinct clusters. The software automates the calculation of LRR and BAF to detect CNV deletions and duplications for whole-genome SNV data. The simultaneous analysis of intensity and genotype data accurately defines the normal diploid state and determines CNVs.

Array platforms such as those from Illumina, Affymetrix, and Agilent may be used in SNV Genotyping. Custom arrays may also be designed and used based on the data described herein.

2. Comparative Genomic Hybridization

Comparative genomic hybridization (CGH) is another method that may be used to evaluate genetic alterations such as CNVs. CGH is a molecular cytogenetic method for analyzing genetic alterations such as CNVs in comparison to a reference sample using competitive fluorescence in situ hybridization (FISH). DNA is isolated from a patient and a reference source and independently labeled with fluorescent molecules (i.e., fluorophores) after denaturation of the DNA. Hybridization of the fluorophores to the resultant samples are compared along the length of each chromosome to identify chromosomal differences between the two sources. A mismatch of colors indicates a gain or loss of material in the test sample in a specific region, while a match of the colors indicates no difference in genetic alterations such as copy number between the test and reference samples at a particular region.

3. Whole Genome Sequencing, Whole Exome Sequencing, and Targeted Sequencing

Whole genome sequencing, whole exome sequencing, or targeted sequencing may also be used to analyze genetic alterations such as CNVs. Whole genome sequencing (also known as full genome sequencing, complete genome sequencing, or entire genome sequencing) involves sequencing of the full genome of a species, including genes that do or do not code for proteins. Whole exome sequencing, in contrast, is sequencing of only the protein-coding genes in the genome (approximately 1% of the genome). Targeted sequencing involves sequencing of only selected parts of the genome.

A wide range of techniques would be known to those skilled in the art to perform whole genome, whole exome, or targeted sequencing with DNA purified from a subject. Similar techniques could be used for different types of sequencing. Techniques used for whole genome sequencing include nanopore technology, fluorophore technology, DNA nanoball technology, and pyrosequencing (i.e., sequencing by synthesis). In particular, next-generation sequencing (NGS) involves sequencing of millions of small fragments of DNA in parallel followed by use of bioinformatics analyses to piece together sequencing data from the fragments.

As whole exome sequencing does not need to sequence as large an amount of DNA as whole genome sequencing, a wider range of techniques are may be used. Methods for whole exome sequencing include polymerase chain reaction methods, NGS methods, molecular inversion probes, hybrid capture using microarrays, in-solution capture, and classical Sanger sequencing. Targeted sequencing allows for providing sequence data for specific genes rather than whole genomes and can use any of the techniques used for other types of sequencing, including specialized microarrays containing materials for sequencing genes of interest.

4. Other Methods for Determining Genetic Alterations

Proprietary methodologies, such as those from BioNano or OpGen, using genome mapping technology can also be used to evaluate genetic alterations such as CNVs.

Standard molecular biology methodologies such as quantitative polymerase chain reaction (PCR), droplet PCR, and TaqMan probes (i.e., hydrolysis probes designed to increase the specificity of quantitative PCR) can be used to assess genetic alterations such as CNVs. Fluorescent in situ hybridization (FISH) probes may also be used to evaluate genetic alterations such as CNVs. The analysis of genetic alterations such as CNVs present in patients is not limited by the precise methods whereby the genetic alterations such as CNVs are determined.

Treatment of AN and BED with Nonselective mGluR Activators

In some embodiments, a subject with AN is treated with a nonselective mGluR activator. In some embodiments, a subject with BED is treated with a nonselective mGluR activator. In some embodiments, a subject with AN and BED is treated with a nonselective mGluR activator. The terms "subject" and "patient" are used interchangeably to refer to a human. The terms "pediatric subject" or "pediatric patient" are used interchangeably to refer to a human less than 18 years of age. In some embodiments, the pediatric subject may be between 6 and 17 years old, such as between 12 and 17 years old or between 6 and 12 years old. The terms "adult subject" or "adult patient" refer to a human of at least 18 years of age. An "adolescent" subject, for example, may be between 12 and 18, such as 12-17, 12-18, 13-17, or 13-18 years old.

The term "treatment," as used herein, covers any administration or application of a therapeutic for disease in a subject, and includes inhibiting the disease, arresting its development, relieving one or more symptoms of the disease, or preventing reoccurrence of one or more symptoms of the disease. For example, treatment of AN subjects may comprise alleviating neurobehavioral, neuropsychiatric and neurodevelopmental symptoms associated with AN. Such symptoms include but are not limited to, improvements in increases in BMI, resumed menstruation, the resting energy expenditure (REE; measured in kilocalories per kilogram per day) returning to normal from heightened levels; improvements in eating attitudes, improvements in depression, and/or improvements in eating-related family conflict.

Treatment of BED subjects may, for example, comprise lessening of the frequency of recurrent episodes of binge eating, lessening of the frequency of episodes where the subject eats an amount of food that is larger than most people would eat in a similar period of time under similar circumstances, an improvement in the feeling of control when eating, slower eating, feeling less uncomfortable after eating, increase in the frequency of eating in public, and a lessening of a feeling of disgust with oneself, depression, or guilt after eating.

The mGluR proteins are typically placed into three subgroups, group I receptors including mGluR1 and mGluR5 are classed as slow excitatory receptors. Group II includes mGluR2 and mGluR3. Group III includes mGluR4, mGluR6, mGluR7, and mGluR8. Groups II and III are classed as slow inhibitory receptors. The mGluRs are distinguished from the ionotropic GluRs or iGluRs, which are ion channel-associated glutamate receptors and are classed as fast excitatory receptors.

A "nonselective activator of mGluRs" refers to a molecule that agonizes mGluRs from more than one of the group I, II, and III categories. Thus, a nonselective activator of mGluRs may provide for a general stimulation of the mGluR networks. This is in contrast to specific mGluR activators that may only significantly agonize a single mGluR, such as mGluR5, for example.

In some embodiments the nonselective mGluR activator is "fasoracetam." Fasoracetam is a nootropic (i.e., cognitive-enhancing) drug that can stimulate both group I and group II/III mGluRs in in vitro studies. (See Hirouchi M, et al. (2000) *European Journal of Pharmacology* 387:9-17.) Fasoracetam may stimulate adenylate cyclase activity through activation of group I mGluRs, while it may also inhibit adenylate cyclase activity by stimulating group II and III mGluRs. (Oka M, et al (1997) *Brain Research* 754:121-130.) Fasoracetam has been observed to be highly bioavailable (79%-97%) with a half-life of 5-6.5 hours in prior human studies (see Malykh A G, et al. (2010) *Drugs* 70(3:287-312). Fasoracetam is a member of the racetam family of chemicals that share a five-carbon oxopyrrolidone ring. The structure of fasoracetam is:

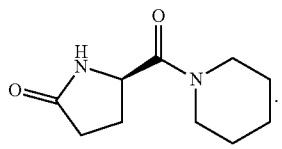 [SMILES: O=C1CC[C@H](C(=O)N2CCCCC2)N1]

The term "fasoracetam" as used herein encompasses pharmaceutically acceptable hydrates and any solid state, amorphous, or crystalline forms of the fasoracetam molecule. For example, the term fasoracetam herein includes forms such as fasoracetam: fasoracetam monohydrate. In addition to fasoracetam, fasoracetam is also known as C-NS-105, NS105, NS-105, and LAM-105.

Fasoracetam has been previously studied in Phase I-III clinical trials in dementia-related cognitive impairment but did not show sufficient efficacy in dementia in Phase III trials. These trials demonstrated that fasoracetam was generally safe and well tolerated for those indications. Phase III data indicated that fasoracetam showed beneficial effects on psychiatric symptoms in cerebral infarct patients and adult dementia patients with cerebrovascular diseases. Another racetam compound, piracetam, has been tested in pediatric ADHD subjects and found to actually increase ADHD symptoms in those subjects compared to a placebo control. (See Akhundian, J., *Iranian J. Pediatrics* 2001, 11(2): 32-36.)

Methods of Administration and Dosage

In some embodiments, fasoracetam may be administered as fasoracetam monohydrate (fasoracetam). In some embodiments, fasoracetam may be administered by mouth (i.e., per os). In some embodiments, fasoracetam may be administered as capsules, tablets, caplets, oral solutions, and oral suspensions. In some embodiments, fasoracetam capsules or tablets or the like may contain 50 mg, 100 mg, 150 mg, 200 mg, 250 mg, 300 mg, 350 mg, 400 mg, 600 mg, or 800 mg of fasoracetam, or any range bounded by two of the above numbers.

In some embodiments, fasoracetam at any of the 50 mg, 100 mg, 150 mg, 200 mg, 250 mg, 300 mg, 350 mg, or 400 mg dosages above may be administered once daily, twice, or three times daily. In some embodiments, the total daily dose of fasoracetam may be 50 mg, 100 mg, 150 mg, 200 mg, 250 mg, 300 mg, 350 mg, or 400 mg given once-daily or 50 mg, 100 mg, 150 mg, 200 mg, 250 mg, 300 mg, 350 mg, or 400 mg given twice-daily. In some embodiments, fasoracetam dosing may be adjusted using a series of dose escalations. In some embodiments, pharmacokinetic data on drug level or clinical response are used to determine changes in dosing. In some embodiments, dose escalation of fasoracetam is not used. In some embodiments, subjects are treated at a dose of fasoracetam expected to be clinically efficacious without a dose-escalation protocol.

Therapeutic Combinations

In some embodiments, the nonselective activator of mGluR network proteins, such as fasoracetam, is used in combination with other agents for the treatment of AN or BED. In some embodiments, it is used in combination with current AN and/or BED medications, such as antidepressants or antipsychotics.

In some embodiments, the activator may be used in combination with an anxiolytic (such as barbiturates, pregabalin, or benzodiazepines, including chlordiazepoxide, clorazepate, diazepam, flurazepam, halazepam, prazepam, lorazepam, lormetazepam, oxazepam, temazepam, clonazepam, flunitrazepam, nimetazepam, nitrazepam, adinazolam, alprazolam, estazolam, triazolam, climazolam, loprazolam, or midazolam). It may also be used in combination with antidepressents such as serotonin selective uptake inhibitors, e.g. fluoxetine, sertraline, and citalopram. Antidepressants include, for example, fluoxetine, escitalopram, bupropion, mirtazapine, amitriptyline, imipramine, venlafaxine, sertraline, paroxetine, or other compounds in the classes of tricyclic antidepressants, selective serotonin reuptake inhibitors, serotonin and norepinephrine reuptake inhibitors, norepinephrine and dopamine reuptake inhibitors, monoamine oxidase inhibitors, or other drugs approved for the use of depression. In some embodiments, the other agent may be an anti-psychotic drug, such as olanzapine, clozapine, quetiapine, haloperidol, aripiprazole or risperidone.

In some embodiments, fasoracetam may be used in combination with a non-pharmacologic treatment, such as psychotherapy or brain stimulation therapies. For example, in some embodiments the patient is further treated with brain stimulation, which may be vagus nerve stimulation, repetitive transcranial magnetic stimulation, magnetic seizure therapy, deep brain stimulation, or any other therapies involving modulation of brain function by electricity, magnets, or implants.

Efficacy Measures in Anorexia Nervosa and Binge Eating Disorder

A number of different outcome measures or rating scales are validated for determining the efficacy of a treatment for AN and BED. Each of the assessments recited in this section can be used to assess efficacy of treatment for AN and BED.

The Binge Eating Scale (BES) is a 16-item questionnaire that assesses the presence of certain binge eating behaviors, and is used to diagnose BED, as well as to monitor progress throughout treatment.

These can include increases in BMI, and global measures of the severity or improvement of patients. Rating scales currently used in AN include the Eating Disorder Examination (EDE) Global Score, the Yale-Brown-Cornell Eating Disorder Scale (YBS-EDS), and the Eating Disorder Inventory (EDI). Secondary efficacy measures include a Hamilton score on the Hamilton Depression Rating Scale and the Leeds-Oxford food preference task: "implicit wanting" of low versus high calorie foods, as indexed by reaction times to high versus low calorie food pictures.

The Eating Disorder Examination Interview (EDE) was devised in 1987 and is a semi-structured interview conducted by a clinical practioner in the assessment of an eating disorder. The EDE is rated through the use of four subscales and a global score. The four subscales are: 1) restraint; 2) eating concern; 3) shape concern; and 4) weight concern. The questions concern the frequency in which the patient engages in behaviors indicative of an eating disorder over a 28-day period. The test is scored on a 7-point scale from 0-6. With a zero score indicating not having engaged in the questioned behavior.

The Yale-Brown-Cornell Eating Disorder Scale (YBC-EDS) does not limit assessment to a particular set of eating-related concerns or behaviors. Rather, it assesses the severity of illness associated with an individual's unique symptomatology. In particular, the test is an interview which characterizes and quantifies preoccupations and rituals associated with eating disorders.

The Eating Disorder Inventory (EDI) test is a self-report measure of symptoms frequently related to anorexia nervosa and other eating disorders. The Eating disorder inventory (EDI) comprises 64 questions, divided into eight subscales. Each question is on a 6-point scale (ranging from "always" to "never"), rated 0-3. The score for each subscale is then summed. The 8 subscale scores on the original EDI are:
1. Drive for thinness an excessive concern with dieting, preoccupation with weight, and fear of weight gain;
2. Bulimia: episodes of binge eating and purging;
3. Body dissatisfaction: not being satisfied with one's physical appearance;
4. Ineffectiveness: assesses feelings of inadequacy, insecurity, worthlessness and having no control over their lives;
5. Perfectionism: not being satisfied with anything less than perfect;
6. Interpersonal distrust: reluctance to form close relationships;
7. Interoceptive awareness (IA): measures the ability of an individual to discriminate between sensations and feelings, and between the sensations of hunger and satiety; and
8. Maturity fears: the fear of facing the demands of adult life.

The first revision to the EDI was in 1991. The 1991 version, eating disorder inventory-two (EDI-2) is used for both males and females over age 12. The EDI-2 retains the original format of the EDI with the inclusion of 27 new items divided into three additional subscales:
1. Asceticism: reflects the avoidance of sexual relationships;
2. Impulse Regulation: shows the ability to regulate impulsive behavior, especially the binge behavior; and
3. Social Insecurity: estimates social fears and insecurity.

The latest revision to the Eating disorder inventory; eating disorder inventory-three (EDI-3) was released in 2004. It contains the original items of the first EDI as well as EDI-2, and it has been enhanced to reflect more modern theories related to the diagnosis of eating disorders. It was designed for use with females ages 13-53 years. It contains 91 items divided into twelve subscales rated on a 0-4 point scoring system. Three items are specific to eating disorders and 9 are general psychological scales that while not specific are relevant to eating disorders. It yields six composites: Eating Disorder Risk, Ineffectiveness, Interpersonal Problems, Affective Problems, Overcontrol, and General Psychological Maladjustment. It is also a self-report questionnaire administered in twenty minutes.

Other scoring systems used in AN assessment include the Ease of Eating Scale (EOES); the Color A Person Test (CAPT); Body Image Software (BIS) testing either Average Distortion, or Average Desired Thinness; a change in ratings of anxiety symptoms on the Multidimensional Anxiety Scale for Children (MASC); and changes in serum leptin or prolactin levels.

The Ease of Eating Scale (EOES) is a 14-item scale which measures Food avoidance behaviors (FABs). The scale is rated by staff observing a subject eating a meal or snack. A score of zero is normal eating behavior. The maximum score is 28. Higher scores indicate more food avoidance behaviors, such as taking small bites, taking >30 seconds between bites (slow eating), etc.

Color A Person Test (CAPT)—Subjects color an outlined image of a body to indicate body dissatisfaction (red (5): very dissatisfied, yellow: dissatisfied, black: neutral, green: satisfied, blue: very satisfied (1)). The outline is divided into 16 sections for scoring. Total CAPT scores are calculated by adding the total score and dividing by 16. Score range is 1-5. Lower scores indicate less body dissatisfaction.

Body Image Software (BIS): Average Distortion—The subject adjusts a digital image of themselves on the computer using the direction to "adjust their image to how they see themselves right now." This determines their perception of their current image. Accuracy is measured by a smaller score between desired image and actual image. There are no identifiable minimum/maximum values as there would be in a questionnaire scale. There are no subscales.

Body Image Software (BIS): Average Desired Thinness—The subject adjusts a digital image of themselves on the computer to "their desired image." The BIS program calculates the difference between their actual image, and how much they have adjusted the image to represent their "desired image." Accuracy is measured by a smaller score between desired image and actual image. There are no identifiable minimum/maximum values as there would be in a questionnaire scale. There are no subscales.

The Multidimensional Anxiety Scale for Children (MASC) is a self-report measure completed by the subject that measures anxiety symptoms. Higher scores indicate greater anxiety. A score of over 50 is significant for anxiety.

Change in Leptin Levels: Leptin is a protein hormone produced by adipocytes that provides information about body fat content. AN patients have decreased serum leptin levels compared to healthy control subjects, and a positive correlation has been found for body mass index and leptin levels in AN patients.

Change in Prolactin Levels: Men and non-pregnant women will normally have only small amounts of prolactin in their blood. A high level of prolactin (hyperprolactinemia) may be seen in AN patients.

A Clinical global impressions severity/improvement (CGI-S and CGI-I) score is also frequently used as a secondary efficacy measurement as it may correspond well to the judgments of global well-being that clinicians make in their normal clinical practice of treating AN patients.

Some embodiments of methods of treatment herein refer to administering to a subject an amount of a nonselective mGluR network activator effective to reduce an EDE Global Score, a YBC-EDS Scale Score, or an EDI Score by at least 25%, such as at least 30% or at least 40%, after a certain period of treatment, such as 4 weeks, in a majority of clinical trial subjects. In such embodiments, the amount for administration may, for example, be selected based on clinical results showing that the amount led to such a result in a majority of previously assessed clinical patients. For example, if a subject to be treated is a pediatric subject, the treatment amount may be selected on the basis of achieving such results in a majority of patients in a clinical trial of pediatric subjects.

The Clinical Global Impression Scale (CGI) is a widely-used assessment instrument in psychiatry and is a common secondary efficacy measure for AN clinical trials. The CGI scale generally asks the clinician to provide a global assessment of the patient's function, symptoms, and adverse events based on the clinician's experience with AN patients. The CGI scale has two component measurements, CGI-S (clinical global impression—severity; a measure of disease severity) and CGI-I (clinical global impression—improvement; a measure of improvement in symptoms). Both scales range from 1 to 7. The CGI-S scale ranges from 1 (normal) to 3 (mildly ill), 4 (moderately ill), 5 (markedly ill), 6 (severely ill) and 7 (among the most extremely impaired). The CGI-I scale ranges from 1 (very much improved), 2 (much improved), 3 (minimally improved), 4 (no change), 5 (minimally worse), 6 (much worse), to 7 (very much worse). In general, subjects with a CGI-I score of 1 or 2 compared to a base-line or placebo level are considered responders to a treatment regimen. For example, in some cases a responder to a drug regimen may show a reduction in EDE Global Score, a YBC-EDS Score, or an EDI Score of at least 25%, such as at least 30%, at least 35%, or at least 40%, as well as a CGI-I score of either 1 or 2 after a certain period of treatment, such as 4 weeks.

In some embodiments of the methods herein, the amount of nonselective mGluR activator administered to a subject is chosen based on that amount's ability to give a CGI-I score of 1 or 2 in a majority of subjects in a clinical trial, for example a clinical trial of similar subjects. Thus, for example, if a pediatric clinical trial shows that a particular amount of activator gives a CGI-I score of 1 or 2 in a majority of patients in the trial after a particular period of time, that amount may be chosen to give to another pediatric subject as a treatment dose.

Articles of Manufacture

In some embodiments, the invention comprises articles of manufacture that may be used in the methods and treatments described herein. In one embodiment, the manufacture is a solid support or microarray for use in detecting genetic alterations in some or all of the mGluR network genes listed in FIGS. 1-3 (i.e., Tiers 1-3). In some embodiments, genes contained in multiple Tiers are assessed within the same solid support or microarray. In some embodiments, certain mGluR network genes are excluded. In some embodiments, the GRM genes are excluded.

Thus, for example, in some embodiments in which mGluR network genes are assayed to determine if there is a genetic alteration in one or more of the genes, such as a CNV, a solid support or microarray, such as on a chip, is used that contains appropriate probes for determining the presence of genetic alterations in 10, 20, 30, 40, 50, 60, 70 or all of the Tier 1 genes. In some embodiments, the solid support or microarray may also include appropriate probes for determining the presence of genetic alterations in at least 10, 20, 30, 50, 100, 150, or all of the Tier 2 genes. In some embodiments, it may further include appropriate probes for determining the presence of genetic alterations in at least 10, 20, 50, 100, 200, 300, 400, 500 or all of the Tier 3 genes. For example, such a solid support, microarray, or chip may be used to determine the presence of genetic alterations such as CNVs or SNVs in the Tier 1, Tier 1+2, or Tier 1+2+3 mGluR gene networks as part of a method of treating an AN or BED patient.

In some embodiments, the manufacture is a set of probes for mGluR network genes of interest from Tiers 1, 2, and/or 3. In some embodiments the probes are labelled. The labels may be non-natural. Similarly, sets of probes may be manufactured for determining the presence of genetic alterations in 10, 20, 30, 40, 50, 60, 70 or all of the Tier 1 genes. In some embodiments, probes may be manufactured for determining the presence of genetic alterations in at least 10, 20, 30, 50, 100, 150, or all of the Tier 2 genes. In some embodiments, probes may further include those for determining the presence of genetic alterations in at least 10, 20, 50, 100, 200, 300, 400, 500 or all of the Tier 3 genes. These various probe sets may be used in methods of determining the presence of genetic alterations, such as CNVs and SNVs in the Tier 1, Tier 1+2, or Tier 1+2+3 mGluR gene networks as part of a method of treating an AN or BED patient

EXAMPLES

Example 1. Analysis of Genetic Alterations in the mGluR Network of Genes in Anorexia Nervosa and Binge Eating Disorder We analyzed 1,040 children, ages 12 to 20, with anorexia nervosa (AN) (See Table 1 below), and found that a total of 388 children (37.3%) had mutations in mGluR genes. Of these 388 children, 102 children (9.8%) had mutations in Tier 1 and Tier 2 genes (a total of 279 genes), and 80 children (6.6%) had mutations in Tier 1 genes (total of 79 genes).

TABLE 1

Total number of subjects among 1,040 children with AN who are mGluR mutation positive.

| Gene set | Number of AN mGluR mutation positive subjects | Percentage of AN mGluR mutation positive subjects |
|---|---|---|
| 79 (Tier-1) | 69 | 6.6% |
| 279 (primary mGluR network) | 102 | 9.8% |
| 868 (secondary mGluR network) | 388 | 37.3% |

Table 2 shows data of representative CNVs from subjects with AN wherein a Tier 1 mGluR network gene was located within, or in the vicinity of, a CNV in the patient's sample. CNVs can lead to structural changes that affect the transcription of genes located outside of, but in the vicinity of, the CNV. As such, mGluR network genes within one of the Tiers that were located within 500,000 base pairs of a CNV were included in the analysis. When an mGluR network gene is contained within the listed CNV, this is noted with a "distance from gene" value of 0. When an mGluR network gene is contained in close proximity to a CNV but not within it, this is presented with a "distance from gene" value of greater than 0.

Table 2 lists the chromosome wherein the CNV was located, with its start and stop location in relation to the Human Genome version 19 (hg19). The number of SNVs (SNPs) located within the CNV is noted as "Num SNP," and the length of the CNV is noted in base pairs. The StartSNP and EndSNP of the CNV are also provided.

The "State, CN" column indicates the copy number resulting from the CNV. As normal human DNA (i.e. with no CNV) should be diploid and would have a "State, CN" of 2. CNVs with a "State, CN" of 0 or 1 indicate a copy number deletion. In contrast, CNVs with a "State, CN" of three or greater indicate a copy number duplication.

The confidence value indicates the relative confidence that the call of the CNV is correct. All CNVs included in this analysis had a positive confidence value, indicating a high likelihood that the CNV call is correct. A value of 15 or greater was seen for most CNVs and is considered extremely high confidence in the CNV call based on qPCR and Taqman genotyping validation.

In Table 2, the "mGluR gene" column lists the specific mGluR network gene within Tier 1 contained within the listed CNV. Table 1 is sorted to show all of the CNVs that included a given Tier 1 mGluR network gene. Some Tier 1 genes may be represented in multiple CNVs from different patients in the study, leading to multiple rows for those particular mGluR network genes. Some Tier 1 genes may not have been represented in a CNV from this particular patient population.

Table 3 shows data from specific CNVs that contained a Tier 1 or Tier 2 mGluR network gene. The organization of Table 2 follows that of Table 1. The "mGluR gene" column lists the specific mGluR network gene within Tier 1 or Tier 2 contained within the listed CNV. Table 2 is sorted to show all of the CNVs that included a given Tier 1 or Tier 2 mGluR network gene. Some Tier 1 or Tier 2 genes may be represented in multiple CNVs from different patients in the study, leading to multiple rows for those particular genes. Some Tier 1 or Tier 2 genes may not have been represented in a CNV from this particular patient population.

Table 4 shows data from specific CNVs that contained a Tier 1, 2, or 3 mGluR network gene. The organization of Table 3 follows that of Tables 1 and 2. The "mGluR gene" column lists the specific mGluR network gene within Tier 1, Tier 2, or Tier 3 contained within the listed CNV. Table 3 is sorted to show all the CNVs that included a given Tier 1, 2, or 3 mGluR network gene. Some Tier 1, 2, or 3 genes may be represented in multiple CNVs from different patients in the study, leading to multiple rows for those particular mGluR network genes. Some Tier 1, 2, or 3 genes may not have been represented in a CNV from this particular patient population.

Together, the data in Tables 2-4 indicate that a wide variety of mGluR network genes contained within each Tier are present in CNVs from patients with AN. If a larger patient cohort with AN was genotyped, all the genes in Tier 1, Tier 2, and Tier 3 would show enrichment for CNVs in patients with AN.

Table 6 is a summary table that summarizes the information from Tables 2-4.

Fifty-two (52) of the AN subjects had symptoms of binge eating, consistent with a diagnosis of Binge Eating Disorder (BED). As shown in Table 5, seven (7) of these 52, or 13.5%, had mGluR mutations in a Tier 1 or Tier 2 mGluR network gene. The column headings are similar to Tables 2-4.

TABLE 5

CNVs impacting Tier 1 and Tier 2 mGluR network genes in seven patients with Binge Eating Disorder.

| Binge Eating Disorder | Chr: Start-Stop (hg19) | Length (bp) | CNState | MostRelevant GMR |
|---|---|---|---|---|
| 1 | Chr21: 36927793-37647438 | 719646 | cn = 3 | SETD4 |
| 2 | Chr21: 14601415-48084989 | 33483575 | cn = 3 | GRIK1, PCBP3, SETD4 |
| 3 | Chr8: 60997355-61005850 | 8496 | cn = 1 | CA8 |
| 4 | Chr22: 18877787-20306993 | 1429207 | cn = 1 | RANBP1 |
| 5 | Chr17: 64287309-64288738 | 1430 | cn = 1 | PRKCA |
| 6 | Chr1: 72549836-72659880 | 110045 | cn = 1 | NEGR1 |
| 7 | Chr18: 58267843-58310343 | 42501 | cn = 3 | MC4R |

Example 2. Treatment of Anorexia Nervosa and Binge Eating Disorder with CNVs in mGluR Network Genes with Fasoracetam (Fasoracetam Monohydrate)

Previously, an open-label Phase Ib clinical trial was conducted to study the safety, pharmacokinetics, and efficacy of fasoracetam (fasoracetam monohydrate) in adolescent subjects between the ages of 12 and 17 previously diagnosed with ADHD. Each of the study subjects in this clinical trial had one or more CNV in an mGluR network gene. Fasoracetam monohydrate successfully treated these ADHD patients. None of the patients in the ADHD clinical study had a formal diagnosis of AN. However, appetite was observed to be improved in the children tested, suggesting that fasoracetam may have beneficial effects in AN.

As such, a clinical trial will be initiated to investigate the safety, pharmacokinetics and efficacy of fasoracetam in subjects between the ages of 12 and 21 previously diagnosed with AN who also have at least one genetic alteration in an mGluR network gene.

The study will include at least 30 subjects who are between ages 12 and 21, of any ancestry or race, diagnosed with anorexia nervosa (AN) as defined by the Diagnostic and Statistical Manual of Mental Disorders, 5th Ed (DSM-5). Subjects will be genotyped and included in the trial if they possess at least one genetic alteration in the form of at least one copy number variation (deletion or duplication) in a mGluR network gene.

Exclusion criteria comprises subjects suffering from a clinically significant illness, either mental or physical, that, in the investigator's opinion, might confound the results of the study or that might prevent them from completing the study, subjects that are pregnant or nursing, subjects that test positive for illicit drugs of that have a history of drug abuse, subjects that consume alcoholic beverages, or subjects for which the investigator is otherwise concerned regarding their compliance or suitability.

Fasoracetam capsules of either 50 mg or 200 mg comprising fasoracetam monohydrate as active ingredient and placebo capsules comprising microcellulose will be used for the study. The design of the trial is a phone screening (1 day), enrollment phase (1 to 2 days), a wash-out phase for subjects currently on medications prescribed for AN (1-14 days), pharmacokinetic (PK) assessment (2 days), followed by a dose-escalation phase (35 days) and a follow-up phone visit approximately four weeks after the last dose, for a maximum of 127 days. All medications prescribed for AN will be discontinued during the wash-out phase prior to the study. No new AN medication will be started during the study.

The dose-escalation phase of the trial runs over a 5-week period. During week 1, all subjects are administered placebo capsules twice daily. After one week of placebo treatment, patients are started on 50 mg b.i.d. fasoracetam for 1 week. If safety and responsiveness data from prior dose level of fasoracetam indicates it was appropriate, subjects are then escalated to the next higher dose (100, 200, or 400 mg). Subjects who show tolerance to the 50 mg b.i.d. dose as well as response to the drug are to be maintained at that level for the remaining 3 weeks of the trial. Subjects who show tolerance but lack of response or partial response to the 50 mg b.i.d. dose are to be moved up to the next higher dose of 100 mg during the following week. Subjects who show tolerance at 100 mg but lack of response or partial response are to be moved up to the 200 mg dose the following week while those who show both tolerance and response at 100 mg are to be kept at 100 mg bid for the remainder of the trial. Similarly, subjects moved up to the 200 mg dose who showed both tolerance and response are to be kept at 200 mg for the final week of the trial while those showing tolerance but lack of response or partial response are moved to a 400 mg dose for the final week.

All efficacy assessments, will be made at study enrollment ("enrollment baseline") and again, once-per-week for the placebo week ("week 1" or "placebo baseline") and at each of the 4 weeks of fasoracetam treatment. These efficacy measures include measuring body mass index (BMI), an EDE Global Score, an EDI score, and assessment of leptin and prolactin serum levels. Prior to receiving the PK assessment dose, subjects return to the clinic to be administered the efficacy tests, and to be given a general physical examination including vital signs and weight, blood and urine sampling, and a pregnancy test for female subjects. During the 5-week placebo and dose-escalation phases of the study, subjects visit the clinic again at the end of each week to be administered the efficacy tests, and to be given a general physical examination including vital signs and weight, blood and urine sampling, and a pregnancy test for female subjects.

Efficacy for AN will be assessed by significant improvement in the various AN rating scales discussed herein and by documentation of steady weight gain. Efficacy for BED will be assessed by significant improvement in the BES and other applicable rating scales.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

TABLE 2

| Chr: Start-Stop(hg19) | Num SNP | Length | State, CN | ChipID | StartSNP |
|---|---|---|---|---|---|
| chr1: 169591373-169749154 | 40 | 157,782 | 1 | 4432273126_R01C02 | rs3917683 |
| chr11: 88376801-88379332 | 4 | 2,532 | 1 | 4432273141_R01C02 | rs1354411 |
| chr6: 1175965-29895228 | 39 | 28,719,264 | 0 | 4432273288_R02C02 | rs1611522 |
| chr2: 81235077-81241811 | 4 | 6,735 | 3 | 4432273335_R02C01 | rs13419182 |
| chr9: 140911199-140913833 | 4 | 2,635 | 3 | 4432273583_R01C02 | rs10780198 |
| chr9: 140911199-140913833 | 4 | 2,635 | 3 | 4432273583_R02C02 | rs10780198 |
| chr6: 2540921-31298743 | 9733 | 28,757,823 | 3 | 4432273639_R02C02 | rs9264651 |
| chr1: 73021243-73084221 | 7 | 62,979 | 1 | 4432273650_R02C01 | rs895281 |
| chr3: 11714521-90442925 | −97 | 78,728,405 | 1 | 4432273747_R02C02 | rs7627256 |
| chr9: 140911199-140913833 | 4 | 2,635 | 3 | 4432273758_R02C02 | rs10780198 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr11: 198510-257030 | 35 | 58,521 | 3 | 4457235015_R01C02 | rs3802985 |
| chr16: 29647342-30177807 | 51 | 530,466 | 3 | 4457235024_R02C02 | rs9926100 |
| chr11: 88376801-88379332 | 4 | 2,532 | 1 | 4457235045_R02C01 | rs1354411 |
| chr17: 76173423-76263906 | 28 | 90,484 | 3 | 4457235062_R01C02 | rs2854701 |
| chr21: 37410477-37415603 | 4 | 5,127 | 1 | 4457235072_R02C02 | rs2835239 |
| chr21: 37410477-37415603 | 4 | 5,127 | 1 | 4457235078_R02C02 | rs2835239 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr21: 37410477-37415603 | 4 | 5,127 | 1 | 4457235102_R01C02 | rs2835239 |
| chr11: 88376801-88379332 | 4 | 2,532 | 1 | 4457235153_R01C02 | rs1354411 |
| chr3: 1913371-1925851 | 7 | 12,481 | 1 | 4457235180_R01C02 | rs17193911 |
| chr21: 47091361-47145374 | 8 | 54,014 | 1 | 4457235209_R02C02 | rs2838973 |
| chr16: 29130999-35279083 | 745 | 6,148,085 | 3 | 4457235239_R01C01 | rs12922496 |
| chr7: 32211433-32399833 | 85 | 188,401 | 3 | 4457235243_R01C02 | rs9648380 |
| chr21: 27194869-27232198 | 13 | 37,330 | 1 | 4457235244_R01C02 | rs2829916 |
| chr11: 88376801-88379332 | 4 | 2,532 | 1 | 4457235345_R01C01 | rs1354411 |
| chr7: 32220497-32399833 | 80 | 179,337 | 3 | 4457235356_R01C02 | rs987069 |
| chr11: 88533414-88533632 | 3 | 219 | 3 | 4457235356_R02C02 | rs10501688 |
| chr11: 88376801-88379332 | 4 | 2,532 | 1 | 4457235366_R02C02 | rs1354411 |
| chr3: 2519703-2584376 | 29 | 64,674 | 1 | 4457235397_R01C02 | rs17014863 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr1: 73021243-73084221 | 7 | 62,979 | 1 | 4457235416_R01C01 | rs895281 |
| chr17: 32386209-32392346 | 3 | 6,138 | 3 | 4457235452_R02C02 | rs2214449 |
| chr1: 72549836-72659880 | 17 | 110,045 | 1 | 4457235470_R01C01 | rs988421 |
| chr11: 88533414-88533632 | 3 | 219 | 3 | 4457235487_R02C02 | rs10501688 |
| chr16: 56377045-56381277 | 6 | 4,233 | 1 | 4457235509_R02C01 | rs4783937 |
| chr3: 1819843-1981567 | 69 | 161,725 | 1 | 4457235609_R01C02 | rs9875417 |
| chr9: 141026318-141036645 | 4 | 10,328 | 3 | 4459273278_R01C01 | rs17583562 |
| chr11: 88376801-88379332 | 4 | 2,532 | 1 | 4459273422_R01C01 | rs1354411 |
| chr2: 80641365-80767037 | 39 | 125,673 | 1 | 4459273488_R01C02 | rs11902575 |
| chr7: 45620960-45626376 | 3 | 5,417 | 1 | 4459273491_R02C02 | rs4724420 |
| chr9: 139395473-140913833 | 210 | 1,518,361 | 1 | 4459273491_R02C02 | rs3124999 |
| chr9: 140911199-140913833 | 4 | 2,635 | 3 | 4459273550_R02C02 | rs10780198 |
| chr11: 88533414-88533632 | 3 | 219 | 3 | 4459273561_R02C01 | rs10501688 |
| chr1: 72621463-72657058 | 6 | 35,596 | 1 | 4459273573_R01C01 | rs12124523 |
| chr11: 88557991-88565086 | 4 | 7,096 | 1 | 4459273594_R02C01 | rs10831496 |
| chr16: 29130999-34607359 | 690 | 5,476,361 | 3 | 4459273628_R02C02 | rs12922496 |
| chr7: 85686982-85727083 | 6 | 40,102 | 1 | 4459273630_R02C02 | rs2107940 |
| chr11: 88533414-88533632 | 3 | 219 | 3 | 4459273634_R02C02 | rs10501688 |
| chr9: 141017240-141036645 | 6 | 19,406 | 3 | 4459273639_R01C01 | rs3750508 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |

TABLE 2-continued

| Chr: Start-Stop(hg19) | | | | Secondary ID | |
|---|---|---|---|---|---|
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr6: 1165092-29899147 | 56 | 28,734,056 | 0 | 4459273656_R02C01 | rs3128864 |
| chr11: 88533414-88533632 | 3 | 219 | 3 | 4459273718_R02C02 | rs10501688 |
| chr3: 7110195-7120529 | 6 | 10,335 | 1 | 4459273728_R01C01 | rs1353831 |
| chr16: 29130999-33908890 | 633 | 4,777,892 | 3 | 4459273747_R01C02 | rs12922496 |
| chr2: 80365294-80415634 | 19 | 50,341 | 1 | 4461875173_R02C02 | rs11685504 |
| chr1: 37532771-37538771 | 5 | 6,001 | 3 | 4461875174_R01C01 | rs12135742 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr21: 46746161-47590315 | 237 | 844,155 | 1 | 4461875351_R02C02 | rs4819063 |
| chr22: 19952561-21822059 | 391 | 1,869,499 | 1 | 4461875351_R02C02 | rs165774 |
| chr1: 239306319-239410745 | 34 | 104,427 | 3 | 4461875621_R01C02 | rs1858175 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr9: 140911199-140913833 | 4 | 2,635 | 3 | 4461875645_R01C02 | rs10780198 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr7: 153780244-153794636 | 4 | 14,393 | 3 | 4461875706_R01C01 | rs7357097 |
| chr7: 125687968-125707685 | 5 | 19,718 | 1 | 4461875714_R02C02 | rs6976605 |
| chr6: 1171596-29892436 | 39 | 28,720,841 | 1 | 4461875761_R02C02 | rs3128994 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr21: 46889666-47591770 | 194 | 702,105 | 1 | 4461875782_R02C01 | rs2282117 |
| chr11: 88533414-88533632 | 3 | 219 | 3 | 4461875788_R01C01 | rs10501688 |
| chr9: 139487092-140913833 | 197 | 1,426,742 | 1 | 4461875832_R02C02 | rs4880055 |
| chr3: 2568212-2573531 | 3 | 5,320 | 3 | 4461875832_R02C02 | rs17015749 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr21: 46944113-47591770 | 174 | 647,658 | 1 | 4461875832_R02C02 | cnvi0010857 |
| chr3: 2568212-2573531 | 3 | 5,320 | 3 | 4482537179_R02C02 | rs17015749 |
| chr1: 72621463-72657058 | 6 | 35,596 | 1 | 4482537383_R01C02 | rs12124523 |

| Chr: Start-Stop(hg19) | EndSNP | Confidence | Distance FromGene | Secondary ID | mGluR gene |
|---|---|---|---|---|---|
| chr1: 169591373-169749154 | rs12035144 | 102.668 | 0 | PF019974 203 | SELE |
| chr11: 88376801-88379332 | rs11020772 | 16.464 | 0 | PF004540 211 | GRM5 |
| chr6: 1175965-29895228 | rs9259831 | 50.146 | 0 | PF019135 202 | SERPINB9 |
| chr2: 81235077-81241811 | rs12465939 | 10.848 | 359089 | PF016482 203 | CTNNA2 |
| chr9: 140911199-140913833 | cnvi0002661 | 8.491 | 0 | PF018791 202 | CACNA1B |
| chr9: 140911199-140913833 | cnvi0002661 | 6.514 | 0 | PF018763 202 | CACNA1B |
| chr6: 2540921-31298743 | rs28752863 | 23.704 | 0 | PF019490 202 | SERPINB9 |
| chr1: 73021243-73084221 | rs12084200 | 27.453 | 272838 | PF003998 211 | NEGR1 |
| chr3: 11714521-90442925 | rs2316653 | 36.387 | 0 | PF016986 203 | GNAI2 |
| chr9: 140911199-140913833 | cnvi0002661 | 11.53 | 0 | PF004036 211 | CACNA1B |
| chr19: 43284120-55326739 | rs581623 | 43.93 | 0 | PF018678 202 | FPR1 |
| chr19: 43284120-55326739 | rs581623 | 43.93 | 0 | PF018678 202 | PPP2R1A |
| chr19: 43284120-55326739 | rs581623 | 43.93 | 0 | PF018678 202 | RUVBL2 |
| chr19: 43284120-55326739 | rs581623 | 43.93 | 0 | PF018678 202 | SHANK1 |
| chr11: 198510-257030 | rs532483 | 70.708 | 0 | PF019701 202 | PSMD13 |
| chr16: 29647342-30177807 | rs7202714 | 163.307 | 0 | PF018907 202 | ALDOA |

TABLE 2-continued

| | | | | | |
|---|---|---|---|---|---|
| chr11: 88376801-88379332 | rs11020772 | 14.102 | 0 | PF008070 204 | GRM5 |
| chr17: 76173423-76263906 | rs6501186 | 82.909 | 0 | PF004732 211 | TK1 |
| chr21: 37410477-37415603 | rs2835244 | 11.827 | 0 | PF019865 203 | SETD4 |
| chr21: 37410477-37415603 | rs2835244 | 13.457 | 0 | PF018476 212 | SETD4 |
| chr19: 43474699-55343606 | rs34177062 | 28.815 | 0 | PF004534 211 | FPR1 |
| chr19: 43474699-55343606 | rs34177062 | 28.815 | 0 | PF004534 211 | PPP2R1A |
| chr19: 43474699-55343606 | rs34177062 | 28.815 | 0 | PF004534 211 | RUVBL2 |
| chr19: 43474699-55343606 | rs34177062 | 28.815 | 0 | PF004534 211 | SHANK1 |
| chr21: 37410477-37415603 | rs2835244 | 10.902 | 0 | PF004534 211 | SETD4 |
| chr11: 88376801-88379332 | rs11020772 | 12.682 | 0 | PF016378 203 | GRM5 |
| chr3: 1913371-1925851 | rs6442701 | 23.613 | 214699 | PF020287 221 | CNTN4 |
| chr21: 47091361-47145374 | rs2838986 | 11.513 | 0 | PF008788 211 | PCBP3 |
| chr16: 29130999-35279083 | rs649602 | 21.915 | 0 | PF019089 202 | ALDOA |
| chr7: 32211433-32399833 | rs10486507 | 103.995 | 0 | PF018913 202 | PDE1C |
| chr21: 27194869-27232198 | rs2040273 | 43.862 | 20663 | PF018665 202 | APP |
| chr11: 88376801-88379332 | rs11020772 | 14.626 | 0 | PF018644 202 | GRM5 |
| chr7: 32220497-32399833 | rs10486507 | 78.211 | 0 | PF018870 202 | PDE1C |
| chr11: 88533414-88533632 | rs1903841 | 8.511 | 0 | PF018895 202 | GRM5 |
| chr11: 88376801-88379332 | rs11020772 | 15.254 | 0 | PF019037 202 | GRM5 |
| chr3: 2519703-2584376 | rs7649181 | 77.178 | 0 | PF019918 212 | CNTN4 |
| chr19: 43647130-55326739 | rs581623 | 37.188 | 0 | PF016050 203 | FPR1 |
| chr19: 43647130-55326739 | rs581623 | 37.188 | 0 | PF016050 203 | PPP2R1A |
| chr19: 43647130-55326739 | rs581623 | 37.188 | 0 | PF016050 203 | RUVBL2 |
| chr19: 43647130-55326739 | rs581623 | 37.188 | 0 | PF016050 203 | SHANK1 |
| chr1: 73021243-73084221 | rs12084200 | 17.235 | 272838 | PF008831 211 | NEGR1 |
| chr17: 32386209-32392346 | rs12602886 | 0 | 0 | PF005550 211 | ACCN1 |
| chr1: 72549836-72659880 | rs12070904 | 40.911 | 0 | PF020089 202 | NEGR1 |
| chr11: 88533414-88533632 | rs1903841 | 8.972 | 0 | PF020010 203 | GRM5 |
| chr16: 56377045-56381277 | rs7206796 | 14.386 | 0 | PF014850 211 | GNAO1 |
| chr3: 1819843-1981567 | rs1488757 | 209.132 | 158983 | PF018469 212 | CNTN4 |
| chr9: 141026318-141036645 | rs3855758 | 17.636 | 7242 | PF016670 203 | CACNA1B |
| chr11: 88376801-88379332 | rs11020772 | 16.775 | 0 | PF018897 202 | GRM5 |
| chr2: 80641365-80767037 | rs9309560 | 100.119 | 0 | PF008112 206 | CTNNA2 |
| chr7: 45620960-45626376 | rs4720512 | 13.58 | 0 | PF008299 204 | ADCY1 |
| chr9: 139395473-140913833 | cnvi0002661 | 25.969 | 0 | PF008299 204 | CACNA1B |
| chr9: 140911199-140913833 | cnvi0002661 | 13.206 | 0 | PF008323 204 | CACNA1B |
| chr11: 88533414-88533632 | rs1903841 | 12.69 | 0 | PF008588 204 | GRM5 |
| chr1: 72621463-72657058 | rs1342862 | 22.475 | 0 | PF016568 203 | NEGR1 |
| chr11: 88557991-88565086 | rs11021512 | 15.042 | 0 | PF008102 204 | GRM5 |
| chr16: 29130999-34607359 | rs2160315 | 36.497 | 0 | PF004547 211 | ALDOA |
| chr7: 85686982-85727083 | cnvi0001222 | 24.872 | 546147 | PF003677 211 | GRM3 |
| chr11: 88533414-88533632 | rs1903841 | 10.118 | 0 | PF018576 202 | GRM5 |
| chr9: 141017240-141036645 | rs3855758 | 22.906 | 0 | PF019326 203 | CACNA1B |
| chr19: 42012336-55294329 | rs2569676 | 25.419 | 0 | PF008486 204 | CIC |
| chr19: 42012336-55294329 | rs2569676 | 25.419 | 0 | PF008486 204 | FPR1 |
| chr19: 42012336-55294329 | rs2569676 | 25.419 | 0 | PF008486 204 | PPP2R1A |
| chr19: 42012336-55294329 | rs2569676 | 25.419 | 0 | PF008486 204 | RUVBL2 |
| chr19: 42012336-55294329 | rs2569676 | 25.419 | 0 | PF008486 204 | SHANK1 |
| chr6: 1165092-29899147 | rs2394704 | 58.313 | 0 | PF019474 202 | SERPINB9 |
| chr11: 88533414-88533632 | rs1903841 | 7.273 | 0 | PF008680 203 | GRM5 |
| chr3: 7110195-7120529 | rs9848973 | 21.088 | 0 | PF006741 211 | GRM7 |
| chr16: 29130999-33908890 | cnvi0022788 | 23.111 | 0 | PF020004 212 | ALDOA |
| chr2: 80365294-80415634 | rs1530397 | 45.412 | 0 | PF016682 203 | CTNNA2 |
| chr1: 37532771-37538771 | rs218419 | 17.253 | 32927 | PF016682 203 | GRIK3 |
| chr17: 17400972-81041077 | rs6502043 | 66.933 | 0 | PF008513 204 | ACCN1 |
| chr17: 17400972-81041077 | rs6502043 | 66.933 | 0 | PF008513 204 | ATXN7L3 |
| chr17: 17400972-81041077 | rs6502043 | 66.933 | 0 | PF008513 204 | CNP |
| chr17: 17400972-81041077 | rs6502043 | 66.933 | 0 | PF008513 204 | CRHR1 |
| chr17: 17400972-81041077 | rs6502043 | 66.933 | 0 | PF008513 204 | PRPSAP1 |
| chr17: 17400972-81041077 | rs6502043 | 66.933 | 0 | PF008513 204 | PSMD11 |
| chr17: 17400972-81041077 | rs6502043 | 66.933 | 0 | PF008513 204 | QRICH2 |
| chr17: 17400972-81041077 | rs6502043 | 66.933 | 0 | PF008513 204 | TK1 |
| chr19: 649825-55625944 | rs575144 | 37.792 | 0 | PF008513 204 | CIC |
| chr19: 649825-55625944 | rs575144 | 37.792 | 0 | PF008513 204 | FPR1 |
| chr19: 649825-55625944 | rs575144 | 37.792 | 0 | PF008513 204 | GNA15 |
| chr19: 649825-55625944 | rs575144 | 37.792 | 0 | PF008513 204 | PPP2R1A |
| chr19: 649825-55625944 | rs575144 | 37.792 | 0 | PF008513 204 | RUVBL2 |
| chr19: 649825-55625944 | rs575144 | 37.792 | 0 | PF008513 204 | RYR1 |
| chr19: 649825-55625944 | rs575144 | 37.792 | 0 | PF008513 204 | SHANK1 |
| chr19: 649825-55625944 | rs575144 | 37.792 | 0 | PF008513 204 | SLC7A10 |
| chr21: 46746161-47590315 | cnvi0010879 | 32.845 | 0 | PF008513 204 | PCBP3 |
| chr22: 19952561-21822059 | cnvi0020983 | 39.556 | 0 | PF008513 204 | RANBP1 |
| chr1: 239306319-239410745 | rs16838096 | 126.828 | 139120 | PF018384 221 | CHRM3 |
| chr19: 20612645-55326739 | rs581623 | 39.325 | 0 | PF018779 221 | CIC |
| chr19: 20612645-55326739 | rs581623 | 39.325 | 0 | PF018779 221 | FPR1 |
| chr19: 20612645-55326739 | rs581623 | 39.325 | 0 | PF018779 221 | PPP2R1A |
| chr19: 20612645-55326739 | rs581623 | 39.325 | 0 | PF018779 221 | RUVBL2 |
| chr19: 20612645-55326739 | rs581623 | 39.325 | 0 | PF018779 221 | RYR1 |
| chr19: 20612645-55326739 | rs581623 | 39.325 | 0 | PF018779 221 | SHANK1 |
| chr19: 20612645-55326739 | rs581623 | 39.325 | 0 | PF018779 221 | SLC7A10 |

TABLE 2-continued

| Chr: Start-Stop | SNP | Value | Value2 | PF | Num | Gene |
|---|---|---|---|---|---|---|
| chr9: 140911199-140913833 | cnvi0002661 | 0.412 | 0 | PF018857 | 202 | CACNA1B |
| chr19: 43474699-55343606 | rs34177062 | 33.082 | 0 | PF003933 | 211 | FPR1 |
| chr19: 43474699-55343606 | rs34177062 | 33.082 | 0 | PF003933 | 211 | PPP2R1A |
| chr19: 43474699-55343606 | rs34177062 | 33.082 | 0 | PF003933 | 211 | RUVBL2 |
| chr19: 43474699-55343606 | rs34177062 | 33.082 | 0 | PF003933 | 211 | SHANK1 |
| chr7: 153780244-153794636 | rs11762689 | 12.079 | 0 | PF019443 | 202 | DPP6 |
| chr7: 125687968-125707685 | rs2079055 | 14.334 | 370967 | PF019246 | 202 | GRM8 |
| chr6: 1171596-29892436 | rs9259806 | 57.331 | 0 | PF008278 | 204 | SERPINB9 |
| chr19: 411849-55606101 | rs34972456 | 27.671 | 0 | PF008280 | 206 | CIC |
| chr19: 411849-55606101 | rs34972456 | 27.671 | 0 | PF008280 | 206 | FPR1 |
| chr19: 411849-55606101 | rs34972456 | 27.671 | 0 | PF008280 | 206 | GNA15 |
| chr19: 411849-55606101 | rs34972456 | 27.671 | 0 | PF008280 | 206 | PPP2R1A |
| chr19: 411849-55606101 | rs34972456 | 27.671 | 0 | PF008280 | 206 | RUVBL2 |
| chr19: 411849-55606101 | rs34972456 | 27.671 | 0 | PF008280 | 206 | RYR1 |
| chr19: 411849-55606101 | rs34972456 | 27.671 | 0 | PF008280 | 206 | SHANK1 |
| chr19: 411849-55606101 | rs34972456 | 27.671 | 0 | PF008280 | 206 | SLC7A10 |
| chr21: 46889666-47591770 | rs2839133 | 44.285 | 0 | PF008280 | 206 | PCBP3 |
| chr11: 88533414-88583632 | rs1903841 | 11.703 | 0 | PF018588 | 202 | GRM5 |
| chr9: 139487092-140913833 | cnvi0002661 | 44.554 | 0 | PF008245 | 204 | CACNA1B |
| chr3: 2568212-2573531 | rs12636309 | 8.39 | 0 | PF019383 | 202 | CNTN4 |
| chr19: 730235-33902809 | rs754986 | 25.776 | 0 | PF008263 | 204 | GNA15 |
| chr19: 730235-33902809 | rs754986 | 25.776 | 0 | PF008263 | 204 | SLC7A10 |
| chr21: 46944113-47591770 | rs2839133 | 50.845 | 0 | PF008263 | 204 | PCBP3 |
| chr3: 2568212-2573531 | rs12636309 | 4.686 | 0 | PF018780 | 202 | CNTN4 |
| chr1: 72621463-72657058 | rs1342862 | 26.613 | 0 | PF020377 | 202 | NEGR1 |

TABLE 3

| Chr: Start-Stop(hg19) | Num SNP | Length | State, CN | ChipID | StartSNP |
|---|---|---|---|---|---|
| chr18: 58100799-58120972 | 11 | 20,174 | 1 | 4432273039_R01C02 | rs1539984 |
| chr1: 169591373-169749154 | 40 | 157,782 | 1 | 4432273126_R01C02 | rs3917683 |
| chr11: 88376801-88379332 | 4 | 2,532 | 1 | 4432273141_R01C02 | rs1354411 |
| chr6: 1175965-29895228 | 39 | 28,719,264 | 0 | 4432273288_R02C02 | rs1611522 |
| chr13: 23899627-24336981 | 113 | 437,355 | 3 | 4432273339_R01C02 | rs9510702 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr11: 75071783-75080920 | 4 | 9,138 | 1 | 4432273430_R01C02 | rs582477 |
| chr6: 2540921-31298743 | 9733 | 28,757,823 | 3 | 4432273639_R02C02 | rs9264651 |
| chr6: 2540921-31298743 | 9733 | 28,757,823 | 3 | 4432273639_R02C02 | rs9264651 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr11: 198510-257030 | 35 | 58,521 | 3 | 4457235015_R01C02 | rs3802985 |
| chr16: 29647342-30177807 | 51 | 530,466 | 3 | 4457235024_R02C02 | rs9926100 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |

TABLE 3-continued

| | | | | | |
|---|---|---|---|---|---|
| chr11: 88376801-88379332 | 4 | 2,532 | 1 | 4457235045_R02C01 | rs1354411 |
| chr2: 119984733-120833583 | 131 | 848,851 | 1 | 4457235057_R02C01 | rs838102 |
| chr2: 70880841-70953745 | 32 | 72,905 | 1 | 4457235058_R02C01 | rs17697969 |
| chr17: 76173423-76263906 | 28 | 90,484 | 3 | 4457235062_R01C02 | rs2854701 |
| chr21: 37410477-37415603 | 4 | 5,127 | 1 | 4457235078_R02C01 | rs2835239 |
| chr19: 43474699-55343606 | 2759 | 11,868,908 | 3 | 4457235102_R01C01 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr17: 64287309-64288738 | 4 | 1,430 | 1 | 4457235132_R02C01 | cnvi0008597 |
| chr5: 110756963-110759537 | 3 | 2,575 | 1 | 4457235134_R01C01 | rs307533 |
| chr6: 88843377-88861698 | 9 | 18,322 | 3 | 4457235134_R01C01 | rs9353525 |
| chr11: 88376801-88379332 | 4 | 2,532 | 1 | 4457235153_R01C02 | rs1354411 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 88842154-88861698 | 10 | 19,545 | 3 | 4457235211_R02C02 | rs11757832 |
| chr2: 179693712-237821589 | 11396 | 58,127,878 | 1 | 4457235234_R02C01 | rs2366912 |
| chr16: 29130999-35279083 | 745 | 6,148,085 | 3 | 4457235239_R01C01 | rs12922496 |
| chr16: 29130999-35279083 | 745 | 6,148,085 | 3 | 4457235239_R01C01 | rs12922496 |
| chr7: 32211433-32399833 | 85 | 188,401 | 3 | 4457235243_R01C02 | rs9648380 |
| chr18: 58267843-58304032 | 7 | 36,190 | 3 | 4457235243_R02C02 | rs7240781 |
| chr21: 27194869-27232198 | 13 | 37,330 | 1 | 4457235244_R01C02 | rs2829916 |
| chr6: 75923605-76473071 | 68 | 549,467 | 3 | 4457235337_R01C02 | rs1323070 |
| chr11: 88376801-88379332 | 4 | 2,532 | 1 | 4457235345_R01C01 | rs1354411 |
| chr7: 32220497-32399833 | 80 | 179,337 | 3 | 4457235356_R01C02 | rs987069 |
| chr4: 185621249-186622179 | 270 | 1,000,931 | 3 | 4457235366_R01C02 | rs877276 |
| chr11: 88376801-88379332 | 4 | 2,532 | 1 | 4457235366_R01C02 | rs1354411 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr6: 31281438-31795082 | −8770 | 513,645 | 1 | 4457235423_R02C02 | cnvi0006173 |
| chr6: 31289284-32514144 | 1747 | 1,224,861 | 3 | 4457235423_R02C02 | rs9265170 |
| chr17: 64287309-64288738 | 4 | 1,430 | 1 | 4457235441_R02C01 | cnvi0008597 |
| chr19: 18201757-18395537 | 42 | 193,781 | 1 | 4457235469_R02C01 | rs7250425 |
| chr9: 139607966-140266929 | 89 | 658,964 | 1 | 4457235469_R02C02 | rs11793385 |
| chr19: 1107035-2141209 | 166 | 1,034,175 | 1 | 4457235469_R02C02 | rs2074451 |
| chr6: 31289284-32499014 | 9991 | 1,209,731 | 3 | 4457235488_R02C01 | rs9265170 |
| chr20: 8096130-8575671 | 180 | 479,542 | 3 | 4457235488_R02C01 | rs6055550 |
| chr6: 3867382-32514144 | −112 | 28,646,763 | 3 | 4457235498_R01C02 | rs35779483 |
| chr6: 3867382-32514144 | −112 | 28,646,763 | 3 | 4457235498_R01C02 | rs35779483 |
| chr9: 93519280-93529807 | 3 | 10,528 | 3 | 4457235500_R02C01 | rs1172931 |
| chr17: 64287309-64288738 | 4 | 1,430 | 1 | 4457235506_R02C01 | cnvi0008597 |
| chr16: 56377045-56381277 | 6 | 4,233 | 1 | 4457235509_R02C01 | rs4783937 |
| chr10: 112846298-112859699 | 4 | 13,402 | 3 | 4457235530_R01C01 | rs745557 |
| chr9: 93557698-93577781 | 13 | 20,084 | 3 | 4457235609_R02C02 | rs10993693 |
| chr9: 141026318-141036645 | 4 | 10,328 | 3 | 4459273278_R01C01 | rs17583562 |
| chr17: 64287309-64288738 | 4 | 1,430 | 1 | 4459273278_R02C01 | cnvi0008597 |
| chr17: 64287309-64288738 | 4 | 1,430 | 1 | 4459273323_R01C02 | cnvi0008597 |
| chr11: 88376801-88379332 | 4 | 2,532 | 1 | 4459273422_R01C01 | rs1354411 |
| chr6: 19044000-31286381 | −6774 | 12,242,382 | 0 | 4459273423_R01C02 | rs6922929 |
| chr17: 64287309-64288738 | 4 | 1,430 | 1 | 4459273463_R02C01 | cnvi0008597 |
| chr7: 45620960-45626376 | 3 | 5,417 | 1 | 4459273491_R02C01 | rs4724420 |
| chr9: 139395473-140913833 | 210 | 1,518,361 | 1 | 4459273491_R02C01 | rs3124999 |
| chr9: 139395473-140913833 | 210 | 1,518,361 | 1 | 4459273491_R02C02 | rs3124999 |
| chr15: 60524025-60551926 | 5 | 27,902 | 3 | 4459273492_R01C02 | rs4775243 |
| chr11: 659906-1611018 | 179 | 951,113 | 3 | 4459273547_R02C02 | rs7940539 |
| chr9: 140911199-140913833 | 4 | 2,635 | 1 | 4459273550_R02C02 | rs10780198 |
| chr11: 88533414-88533632 | 3 | 219 | 3 | 4459273561_R02C01 | rs10501688 |
| chr18: 58267843-58310343 | 9 | 42,501 | 3 | 4459273573_R01C02 | rs7240781 |
| chr17: 64287309-64288738 | 4 | 1,430 | 1 | 4459273574_R02C02 | cnvi0008597 |
| chr11: 88557991-88565086 | 4 | 7,096 | 3 | 4459273594_R02C01 | rs10831496 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |

TABLE 3-continued

| | | | | | |
|---|---|---|---|---|---|
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr16: 29130999-34607359 | 690 | 5,476,361 | 3 | 4459273628_R02C01 | rs12922496 |
| chr16: 29130999-34607359 | 690 | 5,476,361 | 3 | 4459273628_R02C02 | rs12922496 |
| chr6: 31281438-32514144 | −7859 | 1,232,707 | 3 | 4459273629_R01C02 | cnvi0006173 |
| chr6: 10469826-32519005 | −2924 | 22,049,180 | 1 | 4459273629_R02C02 | rs645297 |
| chr6: 10469826-32519005 | −2924 | 22,049,180 | 1 | 4459273629_R02C02 | rs645297 |
| chr7: 85686982-85727083 | 6 | 40,102 | 1 | 4459273630_R02C01 | rs2107940 |
| chr6: 25533534-31286381 | −8651 | 5,752,848 | 1 | 4459273630_R02C02 | rs12526480 |
| chr9: 141017240-141036645 | 6 | 19,406 | 3 | 4459273639_R01C01 | rs3750508 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr6: 1165092-29899147 | 56 | 28,734,056 | 0 | 4459273656_R02C01 | rs3128864 |
| chr6: 31289284-32499014 | 9991 | 1,209,731 | 3 | 4459273692_R01C01 | rs9265170 |
| chr17: 64287309-64288738 | 4 | 1,430 | 1 | 4459273694_R01C01 | cnvi0008597 |
| chr6: 31275174-32499014 | 10017 | 1,223,841 | 3 | 4459273709_R01C01 | rs396243 |
| chr3: 7110195-7120529 | 6 | 10,335 | 1 | 4459273728_R01C01 | rs1353831 |
| chr16: 29130999-33908890 | 633 | 4,777,892 | 3 | 4459273747_R01C02 | rs12922496 |
| chr16: 29130999-33908890 | 633 | 4,777,892 | 3 | 4459273747_R01C02 | rs12922496 |
| chr18: 58267843-58310343 | 9 | 42,501 | 3 | 4459273788_R02C02 | rs7240781 |
| chr1: 37532771-37538771 | 5 | 6,001 | 3 | 4461875174_R01C01 | rs12135742 |
| chr17: 64287309-64288738 | 4 | 1,430 | 1 | 4461875174_R01C02 | cnvi0008597 |
| chr17: 64287309-64288738 | 4 | 1,430 | 1 | 4461875174_R01C02 | cnvi0008597 |
| chr6: 31285292-32499014 | 9998 | 1,213,723 | 3 | 4461875174_R02C02 | rs28367708 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R02C02 | rs28490179 |
| chr21: 46746161-47590315 | 237 | 844,155 | 1 | 4461875351_R02C02 | rs4819063 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr22: 19952561-21822059 | 391 | 1,869,499 | 1 | 4461875351_R02C02 | rs165774 |
| chr9: 139403770-140212642 | 119 | 808,873 | 1 | 4461875351_R02C02 | rs3124599 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr6: 32438542-39590788 | 9928 | 7,152,247 | 1 | 4461875352_R02C02 | rs9368726 |
| chr6: 32438542-39590788 | 9928 | 7,152,247 | 1 | 4461875352_R02C02 | rs9368726 |

TABLE 3-continued

| | | | | | |
|---|---|---|---|---|---|
| chr6: 32438542-39590788 | 9928 | 7,152,247 | 1 | 4461875352_R02C02 | rs9368726 |
| chr8: 56757808-56876219 | 38 | 118,412 | 3 | 4461875449_R01C02 | rs12155521 |
| chr17: 44424726-66163795 | 3995 | 21,739,070 | 1 | 4461875494_R02C01 | cnvi0022894 |
| chr17: 44424726-66163795 | 3995 | 21,739,070 | 1 | 4461875494_R02C01 | cnvi0022894 |
| chr15: 30007573-30011918 | 3 | 4,346 | 1 | 4461875581_R01C01 | rs767514 |
| chr17: 44458950-66154676 | 3987 | 21,695,727 | 1 | 4461875604_R02C01 | cnvi0016818 |
| chr17: 44458950-66154676 | 3987 | 21,695,727 | 1 | 4461875604_R02C01 | cnvi0016818 |
| chr1: 239306319-239410745 | 34 | 104,427 | 3 | 4461875621_R01C02 | rs1858175 |
| chr17: 64287309-64288738 | 4 | 1,430 | 1 | 4461875621_R02C01 | cnvi0008597 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 1238899-2080051 | 138 | 841,153 | 1 | 4461875659_R01C01 | rs2301759 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr18: 58267843-58294706 | 6 | 26,864 | 3 | 4461875707_R01C01 | rs7240781 |
| chr6: 31277740-32525688 | 10024 | 1,247,949 | 3 | 4461875711_R02C02 | rs9264967 |
| chr7: 125687968-125707685 | 5 | 19,718 | 1 | 4461875714_R02C02 | rs6976605 |
| chr6: 1171596-29892436 | 39 | 28,720,841 | 1 | 4461875761_R02C01 | rs3128994 |
| chr17: 64287309-64295688 | 6 | 8,380 | 1 | 4461875763_R01C02 | cnvi0008597 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr17: 79132759-80758198 | 237 | 1,625,440 | 1 | 4461875782_R02C01 | rs7209950 |
| chr21: 46889666-47591770 | 194 | 702,105 | 1 | 4461875782_R02C01 | rs2282117 |
| chr9: 138603740-140382705 | 265 | 1,778,966 | 1 | 4461875782_R02C01 | rs487750 |
| chr17: 64287309-64288738 | 4 | 1,430 | 1 | 4461875785_R01C02 | cnvi0008597 |
| chr18: 58267843-58294706 | 6 | 26,864 | 3 | 4461875786_R01C02 | rs7240781 |
| chr18: 58117429-58120972 | 4 | 3,544 | 1 | 4461875801_R02C01 | rs1943242 |
| chr17: 64287309-64288738 | 4 | 1,430 | 1 | 4461875802_R02C01 | cnvi0008597 |
| chr9: 139487092-140913833 | 197 | 1,426,742 | 1 | 4461875832_R01C01 | rs4880055 |
| chr9: 139487092-140913833 | 197 | 1,426,742 | 1 | 4461875832_R01C01 | rs4880055 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr11: 406483-2050558 | 368 | 1,644,076 | 1 | 4461875832_R02C02 | rs3210908 |
| chr21: 46944113-47591770 | 174 | 647,658 | 1 | 4461875832_R02C02 | cnvi0010857 |
| chr9: 139492789-140222311 | 111 | 729,523 | 1 | 4461875832_R02C02 | rs28485548 |
| chr17: 79375997-81031768 | 273 | 1,655,772 | 1 | 4475687205_R01C01 | rs1701 |
| chr9: 139395473-140671147 | 176 | 1,275,675 | 1 | 4475687205_R02C01 | rs3124999 |
| chr19: 581070-2050823 | 291 | 1,469,754 | 1 | 4475687205_R02C01 | rs10422066 |
| chr17: 79065650-80758198 | 246 | 1,692,549 | 1 | 4475687205_R02C01 | rs4969384 |
| chr13: 23528685-24897901 | 510 | 1,369,217 | 1 | 4482537037_R01C01 | rs9580476 |
| chr17: 64287309-64288738 | 4 | 1,430 | 1 | 4482537381_R02C01 | cnvi0008597 |
| chr5: 152821589-152847022 | 5 | 25,434 | 3 | 4482537383_R02C02 | rs4958655 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 162204206-179888268 | 4398 | 17,684,063 | 3 | 4482537383_R02C02 | rs2422269 |

TABLE 3-continued

| Chr: Start-Stop(hg19) | EndSNP | Confidence | Distance FromGene | SecondaryID | mGluR gene |
|---|---|---|---|---|---|
| chr17: 64287309-64288738 | 4 | 1,430 | 1 | 4482537427_R02C02 | cnvi0008597 |
| chr13: 23528685-24897901 | 510 | 1,369,217 | 1 | 4482537640_R02C02 | rs9580476 |
| chr18: 58100799-58120972 | rs2000778 | 51.574 | 60798 | PF018457 212 | MC4R |
| chr1: 169591373-169749154 | rs12035144 | 102.668 | 0 | PF019974 203 | SELE |
| chr11: 88376801-88379332 | rs11020772 | 16.464 | 0 | PF004540 211 | GRM5 |
| chr6: 1175965-29895228 | rs9259831 | 50.146 | 0 | PF019135 202 | SERPINB9 |
| chr13: 23899627-24336981 | rs1359426 | 233.119 | 0 | PF018955 202 | SACS |
| chr6: 31277740-44419336 | rs532492 | 35.835 | 0 | PF018793 202 | GLP1R |
| chr6: 31277740-44419336 | rs532492 | 35.835 | 0 | PF018793 202 | GRM4 |
| chr6: 31277740-44419336 | rs532492 | 35.835 | 0 | PF018793 202 | HSP90AB1 |
| chr6: 31277740-44419336 | rs532492 | 35.835 | 0 | PF018793 202 | LTA |
| chr6: 31277740-44419336 | rs532492 | 35.835 | 0 | PF018793 202 | MRPL14 |
| chr6: 31277740-44419336 | rs532492 | 35.835 | 0 | PF018793 202 | TEAD3 |
| chr11: 75071783-75080920 | rs11236410 | 15.24 | 8908 | PF016165 203 | ARRB1 |
| chr6: 2540921-31298743 | rs28752863 | 23.704 | 0 | PF019490 202 | SERPINB9 |
| chr6: 2540921-31298743 | rs28752863 | 23.704 | 0 | PF019490 202 | TUBB |
| chr3: 11714521-90442925 | rs2316653 | 36.387 | 0 | PF016986 203 | GNAI2 |
| chr3: 11714521-90442925 | rs2316653 | 36.387 | 0 | PF016986 203 | GRM2 |
| chr3: 11714521-90442925 | rs2316653 | 36.387 | 0 | PF016986 203 | IMPDH2 |
| chr3: 11714521-90442925 | rs2316653 | 36.387 | 0 | PF016986 203 | MAP4 |
| chr3: 11714521-90442925 | rs2316653 | 36.387 | 0 | PF016986 203 | PSMD6 |
| chr3: 11714521-90442925 | rs2316653 | 36.387 | 0 | PF016986 203 | RHOA |
| chr3: 11714521-90442925 | rs2316653 | 36.387 | 0 | PF016986 203 | VIPR1 |
| chr19: 43284120-55326739 | rs581623 | 43.93 | 0 | PF018678 202 | CALM3 |
| chr19: 43284120-55326739 | rs581623 | 43.93 | 0 | PF018678 202 | FPR1 |
| chr19: 43284120-55326739 | rs581623 | 43.93 | 0 | PF018678 202 | MARK4 |
| chr19: 43284120-55326739 | rs581623 | 43.93 | 0 | PF018678 202 | PPP2R1A |
| chr19: 43284120-55326739 | rs581623 | 43.93 | 0 | PF018678 202 | PRMT1 |
| chr19: 43284120-55326739 | rs581623 | 43.93 | 0 | PF018678 202 | RUVBL2 |
| chr19: 43284120-55326739 | rs581623 | 43.93 | 0 | PF018678 202 | SHANK1 |
| chr11: 198510-257030 | rs532483 | 70.708 | 0 | PF019701 202 | PSMD13 |
| chr16: 29647342-30177807 | rs7202714 | 163.307 | 0 | PF018907 202 | ALDOA |
| chr6: 32519005-69913177 | rs3799055 | 55.338 | 0 | PF003738 211 | GLP1R |
| chr6: 32519005-69913177 | rs3799055 | 55.338 | 0 | PF003738 211 | GRM4 |
| chr6: 32519005-69913177 | rs3799055 | 55.338 | 0 | PF003738 211 | HSP90AB1 |
| chr6: 32519005-69913177 | rs3799055 | 55.338 | 0 | PF003738 211 | MRPL14 |
| chr6: 32519005-69913177 | rs3799055 | 55.338 | 0 | PF003738 211 | PLA2G7 |
| chr6: 32519005-69913177 | rs3799055 | 55.338 | 0 | PF003738 211 | TEAD3 |
| chr6: 31289284-141041329 | rs12211936 | 26.611 | 0 | PF019439 202 | CNR1 |
| chr6: 31289284-141041329 | rs12211936 | 26.611 | 0 | PF019439 202 | FYN |
| chr6: 31289284-141041329 | rs12211936 | 26.611 | 0 | PF019439 202 | GLP1R |
| chr6: 31289284-141041329 | rs12211936 | 26.611 | 0 | PF019439 202 | GRM4 |
| chr6: 31289284-141041329 | rs12211936 | 26.611 | 0 | PF019439 202 | HSP90AB1 |
| chr6: 31289284-141041329 | rs12211936 | 26.611 | 0 | PF019439 202 | LAMA4 |
| chr6: 31289284-141041329 | rs12211936 | 26.611 | 0 | PF019439 202 | LTA |
| chr6: 31289284-141041329 | rs12211936 | 26.611 | 0 | PF019439 202 | MRPL14 |
| chr6: 31289284-141041329 | rs12211936 | 26.611 | 0 | PF019439 202 | MYO6 |
| chr6: 31289284-141041329 | rs12211936 | 26.611 | 0 | PF019439 202 | PLA2G7 |
| chr6: 31289284-141041329 | rs12211936 | 26.611 | 0 | PF019439 202 | TEAD3 |
| chr11: 88376801-88379332 | rs11020772 | 14.102 | 0 | PF008070 204 | GRM5 |
| chr2: 119984733-120833583 | rs4849816 | 26.273 | 0 | PF019947 212 | SCTR |
| chr2: 70880841-70953745 | rs1030044 | 13.316 | 0 | PF018828 202 | ADD2 |
| chr17: 76173423-76263906 | rs6501186 | 82.909 | 0 | PF004732 211 | TK1 |
| chr21: 37410477-37415603 | rs2835244 | 13.457 | 0 | PF018476 212 | SETD4 |
| chr19: 43474699-55343606 | rs34177062 | 28.815 | 0 | PF004534 211 | CALM3 |
| chr19: 43474699-55343606 | rs34177062 | 28.815 | 0 | PF004534 211 | FPR1 |
| chr19: 43474699-55343606 | rs34177062 | 28.815 | 0 | PF004534 211 | MARK4 |
| chr19: 43474699-55343606 | rs34177062 | 28.815 | 0 | PF004534 211 | PPP2R1A |
| chr19: 43474699-55343606 | rs34177062 | 28.815 | 0 | PF004534 211 | PRMT1 |
| chr19: 43474699-55343606 | rs34177062 | 28.815 | 0 | PF004534 211 | RUVBL2 |
| chr19: 43474699-55343606 | rs34177062 | 28.815 | 0 | PF004534 211 | SHANK1 |
| chr17: 64287309-64288738 | cnvi0008599 | 15.959 | 10188 | PF018770 202 | PRKCA |
| chr5: 110756963-110759537 | rs10052530 | 14.446 | 0 | PF018916 202 | CAMK4 |
| chr6: 88843377-88861698 | rs6928813 | 27.875 | 0 | PF018916 202 | CNR1 |
| chr11: 88376801-88379332 | rs11020772 | 12.682 | 0 | PF016378 203 | GRM5 |
| chr6: 32527079-124471337 | rs2008708 | 42.373 | 0 | PF008788 211 | CNR1 |
| chr6: 32527079-124471337 | rs2008708 | 42.373 | 0 | PF008788 211 | FYN |
| chr6: 32527079-124471337 | rs2008708 | 42.373 | 0 | PF008788 211 | GLP1R |
| chr6: 32527079-124471337 | rs2008708 | 42.373 | 0 | PF008788 211 | GRM4 |
| chr6: 32527079-124471337 | rs2008708 | 42.373 | 0 | PF008788 211 | HSP90AB1 |
| chr6: 32527079-124471337 | rs2008708 | 42.373 | 0 | PF008788 211 | LAMA4 |
| chr6: 32527079-124471337 | rs2008708 | 42.373 | 0 | PF008788 211 | MRPL14 |
| chr6: 32527079-124471337 | rs2008708 | 42.373 | 0 | PF008788 211 | MYO6 |
| chr6: 32527079-124471337 | rs2008708 | 42.373 | 0 | PF008788 211 | PLA2G7 |
| chr6: 32527079-124471337 | rs2008708 | 42.373 | 0 | PF008788 211 | TEAD3 |
| chr6: 88842154-88861698 | rs6928813 | 50.229 | 0 | PF008305 204 | CNR1 |

TABLE 3-continued

| | | | | | |
|---|---|---|---|---|---|
| chr2: 179693712-237821589 | rs7603272 | 32.392 | 0 | PF018908 202 | PSMD1 |
| chr16: 29130999-35279083 | rs649602 | 21.915 | 0 | PF019089 202 | ALDOA |
| chr16: 29130999-35279083 | rs649602 | 21.915 | 0 | PF019089 202 | PHKG2 |
| chr7: 32211433-32399833 | rs10486507 | 103.995 | 0 | PF018913 202 | PDE1C |
| chr18: 58267843-58304032 | rs13382005 | 15.724 | 227842 | PF018939 202 | MC4R |
| chr21: 27194869-27232198 | rs2040273 | 43.862 | 20663 | PF018665 202 | APP |
| chr6: 75923605-76473071 | rs276698 | 195.613 | 0 | PF019692 202 | MYO6 |
| chr11: 88376801-88379332 | rs11020772 | 14.626 | 0 | PF018644 202 | GRM5 |
| chr7: 32220497-32399833 | rs10486507 | 78.211 | 0 | PF018870 202 | PDE1C |
| chr4: 185621249-186622179 | rs1547909 | 451.579 | 0 | PF018998 202 | LRP2BP |
| chr11: 88376801-88379332 | rs11020772 | 15.254 | 0 | PF019037 202 | GRM5 |
| chr19: 43647130-55326739 | rs581623 | 37.188 | 0 | PF016050 203 | CALM3 |
| chr19: 43647130-55326739 | rs581623 | 37.188 | 0 | PF016050 203 | FPR1 |
| chr19: 43647130-55326739 | rs581623 | 37.188 | 0 | PF016050 203 | MARK4 |
| chr19: 43647130-55326739 | rs581623 | 37.188 | 0 | PF016050 203 | PPP2R1A |
| chr19: 43647130-55326739 | rs581623 | 37.188 | 0 | PF016050 203 | PRMT1 |
| chr19: 43647130-55326739 | rs581623 | 37.188 | 0 | PF016050 203 | RUVBL2 |
| chr19: 43647130-55326739 | rs581623 | 37.188 | 0 | PF016050 203 | SHANK1 |
| chr6: 31281438-31795082 | rs5026931 | 54.862 | 0 | PF016411 203 | LTA |
| chr6: 31289284-32514144 | rs34369284 | 29.144 | 0 | PF007954 211 | LTA |
| chr17: 64287309-64288738 | cnvi0008599 | 17.315 | 10188 | PF003694 211 | PRKCA |
| chr19: 18201757-18395537 | rs4254438 | 25.765 | 0 | PF004074 211 | KIAA1683 |
| chr9: 139607966-140266929 | rs9775457 | 30.034 | 0 | PF004074 211 | TRAF2 |
| chr19: 1107035-2141209 | rs3786971 | 41.337 | 0 | PF004074 211 | BTBD2 |
| chr6: 31289284-32499014 | cnvi0006585 | 18.076 | 0 | PF004620 211 | LTA |
| chr20: 8096130-8575671 | rs6039206 | 686.258 | 0 | PF004620 211 | PLCB1 |
| chr6: 3867382-32514144 | rs34369284 | 31.035 | 0 | PF019016 202 | LTA |
| chr6: 3867382-32514144 | rs34369284 | 31.035 | 0 | PF019016 202 | TUBB |
| chr9: 93519280-93529807 | rs1172990 | 14.299 | 34250 | PF019873 203 | SYK |
| chr17: 64287309-64288738 | cnvi0008599 | 17.689 | 10188 | PF016560 203 | PRKCA |
| chr16: 56377045-56381277 | rs7206796 | 14.386 | 0 | PF014850 211 | GNAO1 |
| chr10: 112846298-112859699 | rs7084501 | 15.614 | 5636 | PF003867 211 | ADRA2A |
| chr9: 93557698-93577781 | rs10993698 | 28.286 | 0 | PF018461 212 | SYK |
| chr9: 141026318-141036645 | rs3855758 | 17.636 | 7242 | PF016670 203 | CACNA1B |
| chr17: 64287309-64288738 | cnvi0008599 | 18.455 | 10188 | PF017447 203 | PRKCA |
| chr17: 64287309-64288738 | cnvi0008599 | 17.376 | 10188 | PF020384 221 | PRKCA |
| chr11: 88376801-88379332 | rs11020772 | 16.775 | 0 | PF018897 202 | GRM5 |
| chr6: 19044000-31286381 | rs9265057 | 37.916 | 0 | PF018604 203 | TUBB |
| chr17: 64287309-64288738 | cnvi0008599 | 16.136 | 10188 | PF014893 211 | PRKCA |
| chr7: 45620960-45626376 | rs4720512 | 13.58 | 0 | PF008299 204 | ADCY1 |
| chr9: 139395473-140913833 | cnvi0002661 | 25.969 | 0 | PF008299 204 | CACNA1B |
| chr9: 139395473-140913833 | cnvi0002661 | 25.969 | 0 | PF008299 204 | TRAF2 |
| chr15: 60524025-60551926 | rs10519010 | 23.368 | 87424 | PF016646 203 | ANXA2 |
| chr11: 659906-1611018 | cnvi0004998 | 52.722 | 0 | PF018858 202 | RPLP2 |
| chr9: 140911199-140913833 | cnvi0002661 | 13.206 | 0 | PF008323 204 | CACNA1B |
| chr11: 88533414-88533632 | rs1903841 | 12.69 | 0 | PF008588 204 | GRM5 |
| chr18: 58267843-58310343 | rs1346831 | 29.472 | 227842 | PF017312 203 | MC4R |
| chr17: 64287309-64288738 | cnvi0008599 | 15.947 | 10188 | PF018655 202 | PRKCA |
| chr11: 88557991-88565086 | rs11021512 | 15.042 | 0 | PF008102 204 | GRM5 |
| chr6: 32527079-62189913 | rs6922547 | 16.115 | 0 | PF008511 204 | GLP1R |
| chr6: 32527079-62189913 | rs6922547 | 16.115 | 0 | PF008511 204 | GRM4 |
| chr6: 32527079-62189913 | rs6922547 | 16.115 | 0 | PF008511 204 | HSP90AB1 |
| chr6: 32527079-62189913 | rs6922547 | 16.115 | 0 | PF008511 204 | MRPL14 |
| chr6: 32527079-62189913 | rs6922547 | 16.115 | 0 | PF008511 204 | PLA2G7 |
| chr6: 32527079-62189913 | rs6922547 | 16.115 | 0 | PF008511 204 | TEAD3 |
| chr16: 29130999-34607359 | rs2160315 | 36.497 | 0 | PF004547 211 | ALDOA |
| chr16: 29130999-34607359 | rs2160315 | 36.497 | 0 | PF004547 211 | PHKG2 |
| chr6: 31281438-32514144 | rs34369284 | 56.754 | 0 | PF004531 211 | LTA |
| chr6: 10469826-32519005 | rs28490179 | 115.653 | 0 | PF004451 211 | LTA |
| chr6: 10469826-32519005 | rs28490179 | 115.653 | 0 | PF004451 211 | TUBB |
| chr7: 85686982-85727083 | cnvi0001222 | 24.872 | 546147 | PF003677 211 | GRM3 |
| chr6: 25533534-31286381 | rs9265057 | 33.87 | 0 | PF004584 211 | TUBB |
| chr9: 141017240-141036645 | rs3855758 | 22.906 | 0 | PF019326 203 | CACNA1B |
| chr19: 42012336-55294329 | rs2569676 | 25.419 | 0 | PF008486 204 | CALM3 |
| chr19: 42012336-55294329 | rs2569676 | 25.419 | 0 | PF008486 204 | CIC |
| chr19: 42012336-55294329 | rs2569676 | 25.419 | 0 | PF008486 204 | FPR1 |
| chr19: 42012336-55294329 | rs2569676 | 25.419 | 0 | PF008486 204 | MARK4 |
| chr19: 42012336-55294329 | rs2569676 | 25.419 | 0 | PF008486 204 | PAFAH1B3 |
| chr19: 42012336-55294329 | rs2569676 | 25.419 | 0 | PF008486 204 | PPP2R1A |
| chr19: 42012336-55294329 | rs2569676 | 25.419 | 0 | PF008486 204 | PRMT1 |
| chr19: 42012336-55294329 | rs2569676 | 25.419 | 0 | PF008486 204 | RUVBL2 |
| chr19: 42012336-55294329 | rs2569676 | 25.419 | 0 | PF008486 204 | SHANK1 |
| chr6: 1165092-29899147 | rs2394704 | 58.313 | 0 | PF019474 202 | SERPINB9 |
| chr6: 31289284-32499014 | cnvi0006585 | 28.524 | 0 | PF019853 212 | LTA |
| chr17: 64287309-64288738 | cnvi0008599 | 15.108 | 10188 | PF008029 211 | PRKCA |
| chr6: 31275174-32499014 | cnvi0006585 | 34.737 | 0 | PF004772 211 | LTA |
| chr3: 7110195-7120529 | rs9848973 | 21.088 | 0 | PF006741 211 | GRM7 |
| chr16: 29130999-33908890 | cnvi0022788 | 23.111 | 0 | PF020004 212 | ALDOA |
| chr16: 29130999-33908890 | cnvi0022788 | 23.111 | 0 | PF020004 212 | PHKG2 |
| chr18: 58267843-58310343 | rs1346831 | 30.808 | 227842 | PF008241 204 | MC4R |

TABLE 3-continued

| | | | | | |
|---|---|---|---|---|---|
| chr1: 37532771-37538771 | rs218419 | 17.253 | 32927 | PF008181 204 | GRIK3 |
| chr17: 64287309-64288738 | cnvi0008599 | 16.248 | 10188 | PF008212 204 | PRKCA |
| chr17: 64287309-64288738 | cnvi0008599 | 15.94 | 10188 | PF008275 204 | PRKCA |
| chr6: 31285292-32499014 | cnvi0006585 | 38.035 | 0 | PF008275 204 | LTA |
| chr6: 32519005-124471337 | rs2008708 | 32.455 | 0 | PF003967 211 | CNR1 |
| chr6: 32519005-124471337 | rs2008708 | 32.455 | 0 | PF003967 211 | FYN |
| chr6: 32519005-124471337 | rs2008708 | 32.455 | 0 | PF003967 211 | GLP1R |
| chr6: 32519005-124471337 | rs2008708 | 32.455 | 0 | PF003967 211 | GRM4 |
| chr6: 32519005-124471337 | rs2008708 | 32.455 | 0 | PF003967 211 | HSP90AB1 |
| chr6: 32519005-124471337 | rs2008708 | 32.455 | 0 | PF003967 211 | LAMA4 |
| chr6: 32519005-124471337 | rs2008708 | 32.455 | 0 | PF003967 211 | MRPL14 |
| chr6: 32519005-124471337 | rs2008708 | 32.455 | 0 | PF003967 211 | MYO6 |
| chr6: 32519005-124471337 | rs2008708 | 32.455 | 0 | PF003967 211 | PLA2G7 |
| chr6: 32519005-124471337 | rs2008708 | 32.455 | 0 | PF003967 211 | TEAD3 |
| chr21: 46746161-47590315 | cnvi0010879 | 32.845 | 0 | PF008513 204 | PCBP3 |
| chr19: 649825-55625944 | rs575144 | 37.792 | 0 | PF008513 204 | BTBD2 |
| chr19: 649825-55625944 | rs575144 | 37.792 | 0 | PF008513 204 | CALM3 |
| chr19: 649825-55625944 | rs575144 | 37.792 | 0 | PF008513 204 | CIC |
| chr19: 649825-55625944 | rs575144 | 37.792 | 0 | PF008513 204 | F2RL3 |
| chr19: 649825-55625944 | rs575144 | 37.792 | 0 | PF008513 204 | FPR1 |
| chr19: 649825-55625944 | rs575144 | 37.792 | 0 | PF008513 204 | GNA15 |
| chr19: 649825-55625944 | rs575144 | 37.792 | 0 | PF008513 204 | HOMER3 |
| chr19: 649825-55625944 | rs575144 | 37.792 | 0 | PF008513 204 | KIAA1683 |
| chr19: 649825-55625944 | rs575144 | 37.792 | 0 | PF008513 204 | MARK4 |
| chr19: 649825-55625944 | rs575144 | 37.792 | 0 | PF008513 204 | PAFAH1B3 |
| chr19: 649825-55625944 | rs575144 | 37.792 | 0 | PF008513 204 | PDCD5 |
| chr19: 649825-55625944 | rs575144 | 37.792 | 0 | PF008513 204 | PPP2R1A |
| chr19: 649825-55625944 | rs575144 | 37.792 | 0 | PF008513 204 | PRMT1 |
| chr19: 649825-55625944 | rs575144 | 37.792 | 0 | PF008513 204 | RUVBL2 |
| chr19: 649825-55625944 | rs575144 | 37.792 | 0 | PF008513 204 | RYR1 |
| chr19: 649825-55625944 | rs575144 | 37.792 | 0 | PF008513 204 | SHANK1 |
| chr19: 649825-55625944 | rs575144 | 37.792 | 0 | PF008513 204 | TBXA2R |
| chr22: 19952561-21822059 | cnvi0020983 | 39.556 | 0 | PF008513 204 | RANBP1 |
| chr9: 139403770-140212642 | rs13295516 | 66.879 | 0 | PF008513 204 | TRAF2 |
| chr17: 17400972-81041077 | rs6502043 | 66.933 | 0 | PF008513 204 | ACCN1 |
| chr17: 17400972-81041077 | rs6502043 | 66.933 | 0 | PF008513 204 | ATXN7L3 |
| chr17: 17400972-81041077 | rs6502043 | 66.933 | 0 | PF008513 204 | CNP |
| chr17: 17400972-81041077 | rs6502043 | 66.933 | 0 | PF008513 204 | CRHR1 |
| chr17: 17400972-81041077 | rs6502043 | 66.933 | 0 | PF008513 204 | ERBB2 |
| chr17: 17400972-81041077 | rs6502043 | 66.933 | 0 | PF008513 204 | GRB2 |
| chr17: 17400972-81041077 | rs6502043 | 66.933 | 0 | PF008513 204 | GRB7 |
| chr17: 17400972-81041077 | rs6502043 | 66.933 | 0 | PF008513 204 | LRRC59 |
| chr17: 17400972-81041077 | rs6502043 | 66.933 | 0 | PF008513 204 | MAPT |
| chr17: 17400972-81041077 | rs6502043 | 66.933 | 0 | PF008513 204 | PDE6G |
| chr17: 17400972-81041077 | rs6502043 | 66.933 | 0 | PF008513 204 | PRKCA |
| chr17: 17400972-81041077 | rs6502043 | 66.933 | 0 | PF008513 204 | PRPSAP1 |
| chr17: 17400972-81041077 | rs6502043 | 66.933 | 0 | PF008513 204 | PSMD11 |
| chr17: 17400972-81041077 | rs6502043 | 66.933 | 0 | PF008513 204 | QRICH2 |
| chr17: 17400972-81041077 | rs6502043 | 66.933 | 0 | PF008513 204 | SOCS7 |
| chr17: 17400972-81041077 | rs6502043 | 66.933 | 0 | PF008513 204 | TK1 |
| chr17: 17400972-81041077 | rs6502043 | 66.933 | 0 | PF008513 204 | TUBG1 |
| chr6: 32438542-39590788 | rs2446653 | 17.749 | 0 | PF008632 204 | GLP1R |
| chr6: 32438542-39590788 | rs2446653 | 17.749 | 0 | PF008632 204 | GRM4 |
| chr6: 32438542-39590788 | rs2446653 | 17.749 | 0 | PF008632 204 | TEAD3 |
| chr8: 56757808-56876219 | rs907424 | 75.005 | 0 | PF019466 202 | LYN |
| chr17: 44424726-66163795 | rs8078240 | 71.866 | 0 | PF003876 211 | LRRC59 |
| chr17: 44424726-66163795 | rs8078240 | 71.866 | 0 | PF003876 211 | PRKCA |
| chr15: 30007573-30011918 | rs17671556 | 14.552 | 0 | PF019254 202 | TJP1 |
| chr17: 44458950-66154676 | rs7222649 | 41.043 | 0 | PF003669 211 | LRRC59 |
| chr17: 44458950-66154676 | rs7222649 | 41.043 | 0 | PF003669 211 | PRKCA |
| chr1: 239306319-239410745 | rs16838096 | 126.828 | 139120 | PF018384 221 | CHRM3 |
| chr17: 64287309-64288738 | cnvi0008599 | 15.722 | 10188 | PF020046 202 | PRKCA |
| chr19: 20612645-55326739 | rs581623 | 39.325 | 0 | PF018779 221 | CALM3 |
| chr19: 20612645-55326739 | rs581623 | 39.325 | 0 | PF018779 221 | CIC |
| chr19: 20612645-55326739 | rs581623 | 39.325 | 0 | PF018779 221 | FPR1 |
| chr19: 20612645-55326739 | rs581623 | 39.325 | 0 | PF018779 221 | MARK4 |
| chr19: 20612645-55326739 | rs581623 | 39.325 | 0 | PF018779 221 | PAFAH1B3 |
| chr19: 20612645-55326739 | rs581623 | 39.325 | 0 | PF018779 221 | PDCD5 |
| chr19: 20612645-55326739 | rs581623 | 39.325 | 0 | PF018779 221 | PPP2R1A |
| chr19: 20612645-55326739 | rs581623 | 39.325 | 0 | PF018779 221 | PRMT1 |
| chr19: 20612645-55326739 | rs581623 | 39.325 | 0 | PF018779 221 | RUVBL2 |
| chr19: 20612645-55326739 | rs581623 | 39.325 | 0 | PF018779 221 | RYR1 |
| chr19: 20612645-55326739 | rs581623 | 39.325 | 0 | PF018779 221 | SHANK1 |
| chr19: 1238899-2080051 | rs7256023 | 39.442 | 0 | PF004134 211 | BTBD2 |
| chr19: 43474699-55343606 | rs34177062 | 33.082 | 0 | PF003933 211 | CALM3 |
| chr19: 43474699-55343606 | rs34177062 | 33.082 | 0 | PF003933 211 | FPR1 |
| chr19: 43474699-55343606 | rs34177062 | 33.082 | 0 | PF003933 211 | MARK4 |
| chr19: 43474699-55343606 | rs34177062 | 33.082 | 0 | PF003933 211 | PPP2R1A |
| chr19: 43474699-55343606 | rs34177062 | 33.082 | 0 | PF003933 211 | PRMT1 |
| chr19: 43474699-55343606 | rs34177062 | 33.082 | 0 | PF003933 211 | RUVBL2 |

TABLE 3-continued

| | | | | | | |
|---|---|---|---|---|---|---|
| chr19: 43474699-55343606 | rs34177062 | 33.082 | 0 | PF003933 | 211 | SHANK1 |
| chr18: 58267843-58294706 | rs4588087 | 24.754 | 227842 | PF020043 | 202 | MC4R |
| chr6: 31277740-32525688 | rs28656080 | 32.872 | 0 | PF008074 | 204 | LTA |
| chr7: 125687968-125707685 | rs2079055 | 14.334 | 370967 | PF019246 | 202 | GRM8 |
| chr6: 1171596-29892436 | rs9259806 | 57.331 | 0 | PF008278 | 204 | SERPINB9 |
| chr17: 64287309-64295688 | rs12150089 | 16.812 | 3238 | PF008166 | 204 | PRKCA |
| chr19: 411849-55606101 | rs34972456 | 27.671 | 0 | PF008280 | 206 | BTBD2 |
| chr19: 411849-55606101 | rs34972456 | 27.671 | 0 | PF008280 | 206 | CALM3 |
| chr19: 411849-55606101 | rs34972456 | 27.671 | 0 | PF008280 | 206 | CIC |
| chr19: 411849-55606101 | rs34972456 | 27.671 | 0 | PF008280 | 206 | F2RL3 |
| chr19: 411849-55606101 | rs34972456 | 27.671 | 0 | PF008280 | 206 | FPR1 |
| chr19: 411849-55606101 | rs34972456 | 27.671 | 0 | PF008280 | 206 | GNA15 |
| chr19: 411849-55606101 | rs34972456 | 27.671 | 0 | PF008280 | 206 | HOMER3 |
| chr19: 411849-55606101 | rs34972456 | 27.671 | 0 | PF008280 | 206 | KIAA1683 |
| chr19: 411849-55606101 | rs34972456 | 27.671 | 0 | PF008280 | 206 | MARK4 |
| chr19: 411849-55606101 | rs34972456 | 27.671 | 0 | PF008280 | 206 | PAFAH1B3 |
| chr19: 411849-55606101 | rs34972456 | 27.671 | 0 | PF008280 | 206 | PDCD5 |
| chr19: 411849-55606101 | rs34972456 | 27.671 | 0 | PF008280 | 206 | PPP2R1A |
| chr19: 411849-55606101 | rs34972456 | 27.671 | 0 | PF008280 | 206 | PRMT1 |
| chr19: 411849-55606101 | rs34972456 | 27.671 | 0 | PF008280 | 206 | RUVBL2 |
| chr19: 411849-55606101 | rs34972456 | 27.671 | 0 | PF008280 | 206 | RYR1 |
| chr19: 411849-55606101 | rs34972456 | 27.671 | 0 | PF008280 | 206 | SHANK1 |
| chr19: 411849-55606101 | rs34972456 | 27.671 | 0 | PF008280 | 206 | TBXA2R |
| chr17: 79132759-80758198 | rs868203 | 36.878 | 0 | PF008280 | 206 | PDE6G |
| chr21: 46889666-47591770 | rs2839133 | 44.285 | 0 | PF008280 | 206 | PCBP3 |
| chr9: 138603740-140382705 | rs11137287 | 90.417 | 0 | PF008280 | 206 | TRAF2 |
| chr17: 64287309-64288738 | cnvi0008599 | 15.131 | 10188 | PF019939 | 203 | PRKCA |
| chr18: 58267843-58294706 | rs4588087 | 25.151 | 227842 | PF019226 | 202 | MC4R |
| chr18: 58117428-58120972 | rs2000778 | 21.034 | 77628 | PF019650 | 202 | MC4R |
| chr17: 64287309-64288738 | cnvi0008599 | 15.394 | 10188 | PF019384 | 203 | PRKCA |
| chr9: 139487092-140913833 | cnvi0002661 | 44.554 | 0 | PF008245 | 204 | CACNA1B |
| chr9: 139487092-140913833 | cnvi0002661 | 44.554 | 0 | PF008245 | 204 | TRAF2 |
| chr19: 730235-33902809 | rs754986 | 25.776 | 0 | PF008263 | 204 | BTBD2 |
| chr19: 730235-33902809 | rs754986 | 25.776 | 0 | PF008263 | 204 | F2RL3 |
| chr19: 730235-33902809 | rs754986 | 25.776 | 0 | PF008263 | 204 | GNA15 |
| chr19: 730235-33902809 | rs754986 | 25.776 | 0 | PF008263 | 204 | HOMER3 |
| chr19: 730235-33902809 | rs754986 | 25.776 | 0 | PF008263 | 204 | KIAA1683 |
| chr19: 730235-33902809 | rs754986 | 25.776 | 0 | PF008263 | 204 | PDCD5 |
| chr19: 730235-33902809 | rs754986 | 25.776 | 0 | PF008263 | 204 | TBXA2R |
| chr11: 406483-2050558 | rs7940766 | 34.896 | 0 | PF008263 | 204 | RPLP2 |
| chr21: 46944113-47591770 | rs2839133 | 50.845 | 0 | PF008263 | 204 | PCBP3 |
| chr9: 139492789-140222311 | cnvi0015766 | 64.736 | 0 | PF008263 | 204 | TRAF2 |
| chr17: 79375997-81031768 | rs8072895 | 20.145 | 0 | PF008315 | 204 | PDE6G |
| chr9: 139395473-140671147 | rs7868455 | 26.627 | 0 | PF008535 | 204 | TRAF2 |
| chr19: 581070-2050823 | rs3746101 | 39.268 | 0 | PF008535 | 204 | BTBD2 |
| chr17: 79065650-80758198 | rs868203 | 40.43 | 0 | PF008535 | 204 | PDE6G |
| chr13: 23528685-24897901 | rs9511199 | 1483.004 | 0 | PF019180 | 202 | SACS |
| chr17: 64287309-64288738 | cnvi0008599 | 14.862 | 10188 | PF019125 | 202 | PRKCA |
| chr5: 152821589-152847022 | rs2914621 | 16.033 | 22153 | PF019589 | 202 | GRIA1 |
| chr5: 83030867-150270420 | rs7714584 | 29.083 | 0 | PF019589 | 202 | ADRB2 |
| chr5: 83030867-150270420 | rs7714584 | 29.083 | 0 | PF019589 | 202 | CAMK4 |
| chr5: 83030867-150270420 | rs7714584 | 29.083 | 0 | PF019589 | 202 | RPS14 |
| chr5: 162204206-179888268 | rs7729820 | 42.585 | 0 | PF019589 | 202 | GRM6 |
| chr17: 64287309-64288738 | cnvi0008599 | 15.21 | 10188 | PF019068 | 202 | PRKCA |
| chr13: 23528685-24897901 | rs9511199 | 1257.159 | 0 | PF018564 | 212 | SACS |

TABLE 4

| Chr: Start-Stop(hg19) | NumSNP | Length | State, CN | ChipID | StartSNP |
|---|---|---|---|---|---|
| chr9: 93519280-93529807 | 3 | 10,528 | 3 | 4457235530_R01C02 | rs1172931 |
| chr17: 44458950-66154676 | 3987 | 21,695,727 | 1 | 4461875604_R02C01 | cnvi0016818 |
| chr17: 44458950-66154676 | 3987 | 21,695,727 | 1 | 4461875604_R02C01 | cnvi0016818 |
| chr17: 44458950-66154676 | 3987 | 21,695,727 | 1 | 4461875604_R02C01 | cnvi0016818 |
| chr17: 44458950-66154676 | 3987 | 21,695,727 | 1 | 4461875604_R02C01 | cnvi0016818 |
| chr17: 44458950-66154676 | 3987 | 21,695,727 | 1 | 4461875604_R02C01 | cnvi0016818 |
| chr17: 44458950-66154676 | 3987 | 21,695,727 | 1 | 4461875604_R02C01 | cnvi0016818 |
| chr17: 44458950-66154676 | 3987 | 21,695,727 | 1 | 4461875604_R02C01 | cnvi0016818 |
| chr17: 44458950-66154676 | 3987 | 21,695,727 | 1 | 4461875604_R02C01 | cnvi0016818 |
| chr7: 85686982-85727083 | 6 | 40,102 | 1 | 4459273630_R02C01 | rs2107940 |
| chr7: 64287309-64288738 | 4 | 1,430 | 1 | 4457235441_R02C01 | cnvi0008597 |
| chr13: 34141695-34143447 | 3 | 1,753 | 1 | 4457235441_R02C01 | cnvi0006685 |
| chr5: 1257259-1276121 | 9 | 18,863 | 3 | 4457235382_R01C01 | rs7702814 |
| chr6: 31787630-31795082 | -8886 | 7,453 | 1 | 4457235102_R01C01 | cnvi0006288 |
| chr19: 53514604-55326739 | -9565 | 1,812,136 | 3 | 4432273756_R02C02 | rs10426414 |
| chr4: 72656076-72678078 | 5 | 22,003 | 3 | 4457235025_R01C02 | rs843006 |

TABLE 4-continued

| | | | | | |
|---|---|---|---|---|---|
| chr5: 1272500-1276121 | 5 | 3,622 | 3 | 4457235025_R01C02 | rs10057058 |
| chr2: 227343513-227346034 | 3 | 2,522 | 1 | 4457235025_R01C02 | rs13389027 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr6: 32519005-69913177 | 15343 | 37,394,173 | 3 | 4457235025_R01C02 | rs28490179 |
| chr2: 227343513-227346034 | 3 | 2,522 | 1 | 4432273650_R01C01 | rs13389027 |
| chr6: 31221039-31221914 | 4 | 876 | 1 | 4432265010_R02C01 | rs4416711 |
| chr12: 2245636-2252924 | 7 | 7,289 | 1 | 4457235562_R01C02 | rs12579529 |
| chr10: 112846298-112859699 | 4 | 13,402 | 3 | 4457235530_R01C01 | rs745557 |
| chr17: 44424726-66163795 | 3995 | 21,739,070 | 1 | 4461875494_R02C01 | cnvi0022894 |
| chr17: 44424726-66163795 | 3995 | 21,739,070 | 1 | 4461875494_R02C01 | cnvi0022894 |
| chr17: 44424726-66163795 | 3995 | 21,739,070 | 1 | 4461875494_R02C01 | cnvi0022894 |
| chr17: 44424726-66163795 | 3995 | 21,739,070 | 1 | 4461875494_R02C01 | cnvi0022894 |
| chr17: 44424726-66163795 | 3995 | 21,739,070 | 1 | 4461875494_R02C01 | cnvi0022894 |
| chr17: 44424726-66163795 | 3995 | 21,739,070 | 1 | 4461875494_R02C01 | cnvi0022894 |
| chr17: 44424726-66163795 | 3995 | 21,739,070 | 1 | 4461875494_R02C01 | cnvi0022894 |
| chr17: 44424726-66163795 | 3995 | 21,739,070 | 1 | 4461875494_R02C01 | cnvi0022894 |
| chr4: 72592214-72601331 | 5 | 9,118 | 1 | 4459273642_R01C01 | rs4694105 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr19: 43474699-55343606 | 2759 | 11,868,908 | 3 | 4461875659_R01C02 | rs7256699 |
| chr5: 1272500-1276121 | 5 | 3,622 | 3 | 4457235441_R02C02 | rs10057058 |
| chr5: 1257259-1276121 | 9 | 18,863 | 3 | 4459273628_R01C01 | rs7702814 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr6: 32519005-124471337 | 26247 | 91,952,333 | 3 | 4461875315_R01C02 | rs28490179 |
| chr5: 1272500-1276121 | 5 | 3,622 | 3 | 4461875315_R01C02 | rs10057058 |
| chr11: 60823434-60860889 | 12 | 37,456 | 3 | 4432273650_R02C01 | rs655022 |
| chr12: 2245636-2252924 | 7 | 7,289 | 1 | 4432273758_R01C02 | rs12579529 |
| chr5: 1257259-1276121 | 9 | 18,863 | 3 | 4461875711_R02C01 | rs7702814 |
| chr9: 140911199-140913833 | 4 | 2,635 | 3 | 4432273758_R02C01 | rs10780198 |

TABLE 4-continued

| | | | | | |
|---|---|---|---|---|---|
| chr9: 139607966-140266929 | 89 | 658,964 | 1 | 4457235469_R02C01 | rs11793385 |
| chr9: 139607966-140266929 | 89 | 658,964 | 1 | 4457235469_R02C01 | rs11793385 |
| chr9: 139607966-140266929 | 89 | 658,964 | 1 | 4457235469_R02C01 | rs11793385 |
| chr19: 1107035-2141209 | 166 | 1,034,175 | 1 | 4457235469_R02C01 | rs2074451 |
| chr19: 1107035-2141209 | 166 | 1,034,175 | 1 | 4457235469_R02C01 | rs2074451 |
| chr19: 18201757-18395537 | 42 | 193,781 | 1 | 4457235469_R02C01 | rs7250425 |
| chr3: 196793858-196910082 | 10 | 116,225 | 1 | 4461875659_R01C01 | rs6795358 |
| chr5: 132036252-132043351 | 5 | 7,100 | 1 | 4461875659_R01C01 | rs1468216 |
| chr1: 191772972-191788524 | 5 | 15,553 | 1 | 4461875659_R01C01 | rs9427526 |
| chr19: 1238899-2080051 | 138 | 841,153 | 1 | 4461875659_R01C01 | rs2301759 |
| chr19: 1238899-2080051 | 138 | 841,153 | 1 | 4461875659_R01C01 | rs2301759 |
| chr5: 140227999-140232346 | 3 | 4,348 | 1 | 4457235391_R01C02 | rs4151689 |
| chr13: 31646976-31652085 | 3 | 5,110 | 3 | 4461875693_R01C02 | rs9591486 |
| chr6: 31219869-31221914 | 7 | 2,046 | 1 | 4432265010_R01C02 | rs9264179 |
| chr2: 227343513-227346034 | 3 | 2,522 | 1 | 4432265010_R01C02 | rs13389027 |
| chr17: 1238054-1244992 | 4 | 6,939 | 1 | 4432265010_R01C02 | rs4790152 |
| chr6: 10469826-32519005 | -2924 | 22,049,180 | 1 | 4459273629_R02C02 | rs645297 |
| chr6: 10469826-32519005 | -2924 | 22,049,180 | 1 | 4459273629_R02C02 | rs645297 |
| chr6: 10469826-32519005 | -2924 | 22,049,180 | 1 | 4459273629_R02C02 | rs645297 |
| chr6: 10469826-32519005 | -2924 | 22,049,180 | 1 | 4459273629_R02C02 | rs645297 |
| chr6: 10469826-32519005 | -2924 | 22,049,180 | 1 | 4459273629_R02C02 | rs645297 |
| chr6: 10469826-32519005 | -2924 | 22,049,180 | 1 | 4459273629_R02C02 | rs645297 |
| chr6: 10469826-32519005 | -2924 | 22,049,180 | 1 | 4459273629_R02C02 | rs645297 |
| chr6: 10469826-32519005 | -2924 | 22,049,180 | 1 | 4459273629_R02C02 | rs645297 |
| chr2: 227343513-227346034 | 3 | 2,522 | 1 | 4459273629_R02C02 | rs13389027 |
| chr1: 236290705-238013174 | 526 | 1,722,470 | 3 | 4457235424_R02C02 | rs1468057 |
| chr3: 171220708-171220919 | 3 | 212 | 1 | 4432265249_R01C02 | cnvi0011707 |
| chr6: 31281438-32514144 | -7859 | 1,232,707 | 3 | 4459273629_R01C02 | cnvi0006173 |
| chr6: 31281438-32514144 | -7859 | 1,232,707 | 3 | 4459273629_R01C02 | cnvi0006173 |
| chr6: 31281438-32514144 | -7859 | 1,232,707 | 3 | 4459273629_R01C02 | cnvi0006173 |
| chr6: 31281438-32514144 | -7859 | 1,232,707 | 3 | 4459273629_R01C02 | cnvi0006173 |
| chr21: 37410477-37415603 | 4 | 5,127 | 1 | 4457235102_R01C02 | rs2835239 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr19: 43474699-55343606 | 2759 | 11,868,908 | 3 | 4457235102_R01C02 | rs7256699 |
| chr11: 88376801-88379332 | 4 | 2,532 | 1 | 4432273141_R01C02 | rs1354411 |
| chr10: 46769902-49047366 | 348 | 2,277,465 | 1 | 4432273141_R01C02 | cnvi0015917 |
| chr6: 31785453-31795082 | 8 | 9,630 | 1 | 4432273141_R01C02 | rs508633 |
| chr6: 29130999-34607359 | 690 | 5,476,361 | 3 | 4459273628_R02C01 | rs12922496 |
| chr6: 29130999-34607359 | 690 | 5,476,361 | 3 | 4459273628_R02C01 | rs12922496 |
| chr6: 29130999-34607359 | 690 | 5,476,361 | 3 | 4459273628_R02C01 | rs12922496 |
| chr6: 29130999-34607359 | 690 | 5,476,361 | 3 | 4459273628_R02C01 | rs12922496 |
| chr6: 29130999-34607359 | 690 | 5,476,361 | 3 | 4459273628_R02C01 | rs12922496 |
| chr1: 19947256-20117992 | 47 | 170,737 | 3 | 4457235441_R01C01 | rs10489858 |
| chr10: 46961667-48137589 | 120 | 1,175,923 | 3 | 4461875594_R01C02 | rs506372 |
| chr3: 171220708-171220919 | 3 | 212 | 1 | 4459273630_R02C02 | cnvi0011707 |
| chr6: 25533534-31286381 | -8651 | 5,752,848 | 1 | 4459273630_R02C02 | rs12526480 |
| chr6: 25533534-31286381 | -8651 | 5,752,848 | 1 | 4459273630_R02C02 | rs12526480 |
| chr6: 25533534-31286381 | -8651 | 5,752,848 | 1 | 4459273630_R02C02 | rs12526480 |
| chr19: 18380072-18389135 | 3 | 9,064 | 3 | 4457235383_R01C01 | rs4808776 |
| chr3: 171220708-171220919 | 3 | 212 | 1 | 4457235383_R01C01 | cnvi0011707 |
| chr13: 34141695-34143447 | 3 | 1,753 | 0 | 4457235383_R01C01 | cnvi0006685 |
| chr12: 2245636-2252924 | 7 | 7,289 | 1 | 4459273727_R02C01 | rs12579529 |
| chr13: 34141695-34143447 | 3 | 1,753 | 1 | 4459273748_R02C02 | cnvi0006685 |
| chr10: 45230151-47703613 | 349 | 2,473,463 | 3 | 4457235383_R02C01 | rs960442 |
| chr20: 8096130-8575671 | 180 | 479,542 | 3 | 4457235488_R02C01 | rs6055550 |
| chr6: 31289284-32499014 | 9991 | 1,209,731 | 3 | 4457235488_R02C01 | rs9265170 |
| chr6: 31289284-32499014 | 9991 | 1,209,731 | 3 | 4457235488_R02C01 | rs9265170 |
| chr6: 31289284-32499014 | 9991 | 1,209,731 | 3 | 4457235488_R02C01 | rs9265170 |
| chr6: 31289284-32499014 | 9991 | 1,209,731 | 3 | 4457235488_R02C01 | rs9265170 |
| chr13: 34141695-34143447 | 3 | 1,753 | 1 | 4482537632_R02C02 | cnvi0006685 |
| chr17: 76173423-76263906 | 28 | 90,484 | 3 | 4457235062_R01C02 | rs2854701 |
| chr4: 101754170-101777382 | 5 | 23,213 | 1 | 4459273728_R02C02 | rs7437932 |
| chr13: 34141695-34143447 | 3 | 1,753 | 1 | 4459273709_R01C01 | cnvi0006685 |
| chr6: 31275174-32499014 | 10017 | 1,223,841 | 3 | 4459273709_R01C01 | rs396243 |

TABLE 4-continued

| | | | | | |
|---|---|---|---|---|---|
| chr6: 31275174-32499014 | 10017 | 1,223,841 | 3 | 4459273709_R01C01 | rs396243 |
| chr6: 31275174-32499014 | 10017 | 1,223,841 | 3 | 4459273709_R01C01 | rs396243 |
| chr6: 31275174-32499014 | 10017 | 1,223,841 | 3 | 4459273709_R01C01 | rs396243 |
| chr5: 140227999-140232346 | 3 | 4,348 | 0 | 4459273695_R02C02 | rs4151689 |
| chr13: 34141695-34143447 | 3 | 1,753 | 1 | 4459273748_R01C01 | cnvi0006685 |
| chr12: 2245636-2250396 | 6 | 4,761 | 1 | 4459273748_R01C01 | rs12579529 |
| chr17: 32386209-32392346 | 3 | 6,138 | 3 | 4457235452_R02C02 | rs2214449 |
| chr8: 97219690-97510132 | 61 | 290,443 | 3 | 4461875831_R01C02 | rs11991704 |
| chr6: 31228460-31230701 | 6 | 2,242 | 3 | 4457235421_R02C02 | rs9264368 |
| chr10: 46961667-48137589 | 120 | 1,175,923 | 3 | 4457235343_R01C01 | rs506372 |
| chr5: 140227999-140232346 | 3 | 4,348 | 0 | 4461875494_R01C02 | rs4151689 |
| chr13: 34141695-34143447 | 3 | 1,753 | 1 | 4459273694_R02C02 | cnvi0006685 |
| chr13: 34141695-34143447 | 3 | 1,753 | 1 | 4461875659_R02C01 | cnvi0006685 |
| chr3: 7110195-7120529 | 6 | 10,335 | 1 | 4459273728_R01C01 | rs1353831 |
| chr13: 34141695-34143447 | 3 | 1,753 | 1 | 4482537383_R02C01 | cnvi0006685 |
| chr6: 31785453-31795082 | 8 | 9,630 | 1 | 4432265081_R02C01 | rs508633 |
| chr5: 759485-1276121 | 135 | 516,637 | 3 | 4432265081_R02C01 | rs7710149 |
| chr5: 1257259-1276121 | 9 | 18,863 | 3 | 4457235421_R01C01 | rs7702814 |
| chr12: 2245636-2252924 | 7 | 7,289 | 1 | 4457235391_R02C02 | rs12579529 |
| chr3: 171220708-171220919 | 3 | 212 | 1 | 4432265011_R01C01 | cnvi0011707 |
| chr6: 31289284-32514144 | 1747 | 1,224,861 | 3 | 4457235423_R02C01 | rs9265170 |
| chr6: 31289284-32514144 | 1747 | 1,224,861 | 3 | 4457235423_R02C01 | rs9265170 |
| chr6: 31289284-32514144 | 1747 | 1,224,861 | 3 | 4457235423_R02C01 | rs9265170 |
| chr6: 31289284-32514144 | 1747 | 1,224,861 | 3 | 4457235423_R02C01 | rs9265170 |
| chr5: 140227999-140232346 | 3 | 4,348 | 1 | 4457235045_R01C01 | rs4151689 |
| chr10: 46961667-47703613 | 102 | 741,947 | 3 | 4457235343_R02C01 | rs506372 |
| chr12: 2247179-2252924 | 6 | 5,746 | 1 | 4457235102_R02C01 | rs3794300 |
| chr5: 140227999-140232346 | 3 | 4,348 | 1 | 4432273123_R02C02 | rs4151689 |
| chr16: 82196808-82213799 | 9 | 16,992 | 1 | 4432265012_R01C01 | rs12102917 |
| chr6: 31219869-31221914 | 7 | 2,046 | 0 | 4432265631_R01C01 | rs9264179 |
| chr17: 64287309-64288738 | 4 | 1,430 | 1 | 4459273694_R01C02 | cnvi0008597 |
| chr6: 31787630-31795082 | −8886 | 7,453 | 1 | 4432273318_R01C01 | cnvi0006288 |
| chr4: 113985926-113987369 | 5 | 1,444 | 1 | 4432273318_R01C01 | cnvi0012248 |
| chr11: 88376801-88379332 | 4 | 2,532 | 1 | 4457235045_R02C02 | rs1354411 |
| chr6: 31277740-32525688 | 10024 | 1,247,949 | 3 | 4461875711_R02C02 | rs9264967 |
| chr6: 31277740-32525688 | 10024 | 1,247,949 | 3 | 4461875711_R02C02 | rs9264967 |
| chr6: 31277740-32525688 | 10024 | 1,247,949 | 3 | 4461875711_R02C02 | rs9264967 |
| chr6: 31277740-32525688 | 10024 | 1,247,949 | 3 | 4461875711_R02C02 | rs9264967 |
| chr18: 77948335-77997052 | 13 | 48,718 | 3 | 4461875693_R02C01 | rs8091035 |
| chr3: 171220708-171220919 | 3 | 212 | 3 | 4461875693_R02C01 | cnvi0011707 |
| chr12: 2245636-2252924 | 7 | 7,289 | 1 | 4461875693_R01C02 | rs12579529 |
| chr11: 88557991-88565086 | 4 | 7,096 | 3 | 4459273594_R02C02 | rs10831496 |
| chr17: 64287309-64295688 | 6 | 8,380 | 1 | 4461875763_R01C02 | cnvi0008597 |
| chr6: 31787630-31795082 | −8886 | 7,453 | 1 | 4459273695_R01C02 | cnvi0006288 |
| chr3: 171220708-171220919 | 3 | 212 | 1 | 4461875763_R02C02 | cnvi0011707 |
| chr1: 37532771-37538771 | 5 | 6,001 | 3 | 4461875174_R01C01 | rs12135742 |
| chr10: 46961667-47697026 | 99 | 735,360 | 3 | 4461875833_R01C01 | rs506372 |
| chr17: 64287309-64288738 | 4 | 1,430 | 1 | 4461875174_R01C02 | cnvi0008597 |
| chr5: 1257259-1276121 | 9 | 18,863 | 3 | 4461875174_R01C02 | rs7702814 |
| chr3: 121914706-121918491 | 5 | 3,786 | 1 | 4461875174_R01C02 | rs9832999 |
| chr18: 58267843-58310343 | 9 | 42,501 | 3 | 4459273788_R02C02 | rs7240781 |
| chr12: 124970066-125265636 | 104 | 295,571 | 3 | 4461875832_R01C01 | rs1147289 |
| chr5: 140199039-140232346 | 5 | 33,308 | 1 | 4461875832_R01C01 | rs7732179 |
| chr9: 139487092-140913833 | 197 | 1,426,742 | 1 | 4461875832_R01C01 | rs4880055 |
| chr9: 139487092-140913833 | 197 | 1,426,742 | 1 | 4461875832_R01C01 | rs4880055 |
| chr9: 139487092-140913833 | 197 | 1,426,742 | 1 | 4461875832_R01C01 | rs4880055 |
| chr9: 139487092-140913833 | 197 | 1,426,742 | 1 | 4461875832_R01C01 | rs4880055 |
| chr5: 140227999-140232346 | 3 | 4,348 | 1 | 4459273134_R02C02 | rs4151689 |
| chr19: 17278979-17283942 | 5 | 4,964 | 3 | 4459273134_R01C02 | rs4808583 |
| chr5: 69593713-70636542 | 174 | 1,042,830 | 3 | 4459273134_R01C02 | cnvi0017303 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr19: 730235-33902809 | 5621 | 33,172,575 | 1 | 4461875832_R02C02 | rs1009691 |
| chr5: 140178042-140631925 | 68 | 453,884 | 1 | 4461875832_R02C02 | rs7701203 |

TABLE 4-continued

| | | | | | |
|---|---|---|---|---|---|
| chr21: 46313141-46320283 | 7 | 7,143 | 1 | 4461875832_R02C02 | rs4818740 |
| chr21: 46944113-47591770 | 174 | 647,658 | 1 | 4461875832_R02C02 | cnvi0010857 |
| chr1: 1152631-6456472 | 1260 | 5,303,842 | 1 | 4461875832_R02C02 | rs11721 |
| chr1: 1152631-6456472 | 1260 | 5,303,842 | 1 | 4461875832_R02C02 | rs11721 |
| chr1: 1152631-6456472 | 1260 | 5,303,842 | 1 | 4461875832_R02C02 | rs11721 |
| chr17: 80007887-81047708 | −15718 | 1,039,822 | 1 | 4461875832_R02C02 | rs9915228 |
| chr8: 144550160-145558541 | 149 | 1,008,382 | 1 | 4461875832_R02C02 | rs11786665 |
| chr11: 406483-2050558 | 368 | 1,644,076 | 1 | 4461875832_R02C02 | rs3210908 |
| chr11: 406483-2050558 | 368 | 1,644,076 | 1 | 4461875832_R02C02 | rs3210908 |
| chr9: 139492789-140222311 | 111 | 729,523 | 1 | 4461875832_R02C02 | rs28485548 |
| chr9: 139492789-140222311 | 111 | 729,523 | 1 | 4461875832_R02C02 | rs28485548 |
| chr9: 139492789-140222311 | 111 | 729,523 | 1 | 4461875832_R02C02 | rs28485548 |
| chr17: 64287309-64288738 | 4 | 1,430 | 1 | 4461875174_R02C02 | cnvi0008597 |
| chr5: 1272500-1276121 | 5 | 3,622 | 3 | 4461875174_R02C02 | rs10057058 |
| chr6: 31285292-32499014 | 9998 | 1,213,723 | 3 | 4461875174_R02C02 | rs28367708 |
| chr6: 31285292-32499014 | 9998 | 1,213,723 | 3 | 4461875174_R02C02 | rs28367708 |
| chr6: 31285292-32499014 | 9998 | 1,213,723 | 3 | 4461875174_R02C02 | rs28367708 |
| chr6: 31285292-32499014 | 9998 | 1,213,723 | 3 | 4461875174_R02C02 | rs28367708 |
| chr5: 1257259-1276121 | 9 | 18,863 | 3 | 4457235211_R01C02 | rs7702814 |
| chr6: 31204008-31218984 | 25 | 14,977 | 3 | 4457235211_R01C02 | rs7745906 |
| chr5: 140178042-140261677 | 18 | 83,636 | 1 | 4461875761_R02C01 | rs7701203 |
| chr7: 134436060-134561819 | 56 | 125,760 | 1 | 4461875761_R02C01 | rs6973845 |
| chr6: 1171596-29892436 | 39 | 28,720,841 | 1 | 4461875761_R02C01 | rs3128994 |
| chr6: 1171596-29892436 | 39 | 28,720,841 | 1 | 4461875761_R02C01 | rs3128994 |
| chr6: 1171596-29892436 | 39 | 28,720,841 | 1 | 4461875761_R02C01 | rs3128994 |
| chr6: 1171596-29892436 | 39 | 28,720,841 | 1 | 4461875761_R02C01 | rs3128994 |
| chr1: 1106473-10714911 | 2178 | 9,608,439 | 1 | 4461875782_R02C01 | rs4970420 |
| chr1: 1106473-10714911 | 2178 | 9,608,439 | 1 | 4461875782_R02C01 | rs4970420 |
| chr1: 1106473-10714911 | 2178 | 9,608,439 | 1 | 4461875782_R02C01 | rs4970420 |
| chr16: 88872229-89587871 | 142 | 715,643 | 1 | 4461875782_R02C01 | rs480727 |
| chr9: 138603740-140382705 | 265 | 1,778,966 | 1 | 4461875782_R02C01 | rs487750 |
| chr9: 138603740-140382705 | 265 | 1,778,966 | 1 | 4461875782_R02C01 | rs487750 |
| chr9: 138603740-140382705 | 265 | 1,778,966 | 1 | 4461875782_R02C01 | rs487750 |
| chr21: 46889666-47591770 | 194 | 702,105 | 1 | 4461875782_R02C01 | rs2282117 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |

TABLE 4-continued

| | | | | | |
|---|---|---|---|---|---|
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr19: 411849-55606101 | 10114 | 55,194,253 | 1 | 4461875782_R02C01 | rs753719 |
| chr5: 179264731-179298770 | 18 | 34,040 | 1 | 4461875782_R02C01 | rs10277 |
| chr2: 203300770-203419859 | 10 | 119,090 | 1 | 4461875782_R02C01 | cnvi0010195 |
| chr14: 105170003-105695446 | 92 | 525,444 | 1 | 4461875782_R02C01 | rs7146454 |
| chr22: 30057820-30128380 | 26 | 70,561 | 1 | 4461875782_R02C01 | rs2857642 |
| chr12: 2215448-2227311 | 6 | 11,864 | 1 | 4461875782_R02C01 | rs12813716 |
| chr17: 79132759-80758198 | 237 | 1,625,440 | 1 | 4461875782_R02C01 | rs7209950 |
| chr17: 79132759-80758198 | 237 | 1,625,440 | 1 | 4461875782_R02C01 | rs7209950 |
| chr18: 77336478-77343164 | 4 | 6,687 | 1 | 4461875782_R02C01 | rs645860 |
| chr8: 144508768-145818782 | 207 | 1,310,015 | 1 | 4461875782_R02C01 | rs11783095 |
| chr5: 1257259-1276121 | 9 | 18,863 | 3 | 4459273491_R02C02 | rs7702814 |
| chr7: 45620960-45626376 | 3 | 5,417 | 1 | 4459273491_R02C02 | rs4724420 |
| chr17: 80016452-81047708 | −15719 | 1,031,257 | 1 | 4459273491_R02C02 | rs4280314 |
| chr9: 139395473-140913833 | 210 | 1,518,361 | 1 | 4459273491_R02C02 | rs3124999 |
| chr9: 139395473-140913833 | 210 | 1,518,361 | 1 | 4459273491_R02C02 | rs3124999 |
| chr9: 139395473-140913833 | 210 | 1,518,361 | 1 | 4459273491_R02C02 | rs3124999 |
| chr9: 139395473-140913833 | 210 | 1,518,361 | 1 | 4459273491_R02C02 | rs3124999 |
| chr6: 88842154-88861698 | 10 | 19,545 | 3 | 4457235211_R02C02 | rs11757832 |
| chr6: 31785453-31795082 | 8 | 9,630 | 1 | 4459273550_R02C01 | rs508633 |
| chr17: 79375997-81031768 | 273 | 1,655,772 | 1 | 4475687205_R01C01 | rs1701 |
| chr17: 79375997-81031768 | 273 | 1,655,772 | 1 | 4475687205_R01C01 | rs1701 |
| chr18: 77336478-77343164 | 4 | 6,687 | 1 | 4475687205_R01C01 | rs645860 |
| chr6: 16392159-16400090 | 10 | 7,932 | 3 | 4459273550_R02C02 | rs1476465 |
| chr9: 140911199-140913833 | 4 | 2,635 | 1 | 4459273550_R02C02 | rs10780198 |
| chr10: 46961667-49059803 | 332 | 2,098,137 | 3 | 4459273564_R01C01 | rs506372 |
| chr5: 1272500-1276121 | 5 | 3,622 | 3 | 4457235064_R01C01 | rs10057058 |
| chr3: 171220708-171220919 | 3 | 212 | 1 | 4459273564_R02C01 | cnvi0011707 |
| chr21: 35783219-35904697 | 43 | 121,479 | 3 | 4461875623_R01C01 | rs2834479 |
| chr4: 101754170-101768637 | 4 | 14,468 | 1 | 4459273718_R02C01 | rs7437932 |
| chr12: 2245636-2252924 | 7 | 7,289 | 1 | 4459273718_R02C01 | rs12579529 |
| chr15: 43792097-43924682 | 21 | 132,586 | 1 | 4459273564_R01C01 | rs689781 |
| chr6: 31219869-31221914 | 7 | 2,046 | 1 | 4459273695_R02C02 | rs9264179 |
| chr1: 191749508-191755912 | 3 | 6,405 | 1 | 4459273564_R02C02 | rs844304 |
| chr6: 31787630-31795082 | −8886 | 7,453 | 1 | 4457235303_R02C01 | cnvi0006288 |
| chr6: 31787630-31795082 | −8886 | 7,453 | 1 | 4461875623_R02C01 | cnvi0006288 |
| chr5: 140227999-140232346 | 3 | 4,348 | 1 | 4459273463_R02C01 | rs4151689 |
| chr13: 34141695-34143447 | 3 | 1,753 | 1 | 4459273463_R02C02 | cnvi0006685 |
| chr5: 140227999-140232346 | 3 | 4,348 | 0 | 4461875351_R01C01 | rs4151689 |
| chr4: 176470385-176491850 | 3 | 21,466 | 1 | 4459273653_R02C02 | rs4298092 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr19: 42012336-55294329 | −7189 | 13,281,994 | 3 | 4459273653_R01C02 | rs11540122 |
| chr9: 140039240-140135118 | 9 | 95,879 | 1 | 4457235180_R02C02 | cnvi0002636 |
| chr7: 117229167-117235055 | 8 | 5,889 | 1 | 4457235180_R02C02 | rs213963 |
| chr5: 140097072-140210616 | 20 | 113,545 | 1 | 4457235180_R02C02 | rs2563297 |
| chr6: 31787630-31795082 | −8886 | 7,453 | 1 | 4459273604_R01C02 | cnvi0006288 |
| chr5: 140227999-140232346 | 3 | 4,348 | 1 | 4459273604_R01C02 | rs4151689 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |

TABLE 4-continued

| | | | | | |
|---|---|---|---|---|---|
| chr6: 32527079-62189913 | 13882 | 29,662,835 | 3 | 4459273604_R02C02 | rs28530648 |
| chr6: 32527079-62189913 | 13882 | 29,662,835 | 3 | 4459273604_R02C02 | rs28530648 |
| chr10: 46842850-49059803 | 342 | 2,216,954 | 3 | 4459273604_R02C02 | cnvi0019841 |
| chr21: 46746161-47590315 | 237 | 844,155 | 1 | 4461875351_R02C02 | rs4819063 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr17: 17400972-81041077 | 11745 | 63,640,106 | 1 | 4461875351_R02C02 | rs3760183 |
| chr14: 102979463-106052265 | 512 | 3,072,803 | 1 | 4461875351_R02C02 | rs942024 |
| chr14: 102979463-106052265 | 512 | 3,072,803 | 1 | 4461875351_R02C02 | rs942024 |
| chr12: 132381920-132412260 | 5 | 30,341 | 1 | 4461875351_R02C02 | rs9652059 |
| chr4: 174442919-174447389 | 5 | 4,471 | 1 | 4461875351_R02C02 | rs12644553 |
| chr16: 2015121-2753180 | 95 | 738,060 | 1 | 4461875351_R02C02 | rs1133099 |
| chr16: 88448685-89986634 | 316 | 1,537,950 | 1 | 4461875351_R02C02 | rs4782511 |
| chr9: 139403770-140212642 | 119 | 808,873 | 1 | 4461875351_R02C02 | rs3124599 |
| chr9: 139403770-140212642 | 119 | 808,873 | 1 | 4461875351_R02C02 | rs3124599 |
| chr9: 139403770-140212642 | 119 | 808,873 | 1 | 4461875351_R02C02 | rs3124599 |
| chr5: 140097072-140252615 | 26 | 155,544 | 1 | 4461875351_R02C02 | rs2563297 |
| chr5: 176859848-176940384 | 16 | 80,537 | 1 | 4461875351_R02C02 | rs2731664 |
| chr18: 77336478-77343164 | 4 | 6,687 | 1 | 4461875351_R02C02 | rs645860 |
| chr22: 19952561-21822059 | 391 | 1,869,499 | 1 | 4461875351_R02C02 | rs165774 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |

TABLE 4-continued

| | | | | | |
|---|---|---|---|---|---|
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr19: 649825-55625944 | 10051 | 54,976,120 | 1 | 4461875351_R02C02 | rs12984279 |
| chr8: 144508768-145558541 | 157 | 1,049,774 | 1 | 4461875351_R02C02 | rs11783095 |
| chr5: 1259342-1276121 | 7 | 16,780 | 3 | 4459273637_R01C01 | rs2883171 |
| chr14: 103987140-105672794 | 303 | 1,685,655 | 1 | 4475687205_R02C01 | rs2071407 |
| chr14: 103987140-105672794 | 303 | 1,685,655 | 1 | 4475687205_R02C01 | rs2071407 |
| chr9: 139395473-140671147 | 176 | 1,275,675 | 1 | 4475687205_R02C01 | rs3124999 |
| chr9: 139395473-140671147 | 176 | 1,275,675 | 1 | 4475687205_R02C01 | rs3124999 |
| chr9: 139395473-140671147 | 176 | 1,275,675 | 1 | 4475687205_R02C01 | rs3124999 |
| chr19: 581070-2050823 | 291 | 1,469,754 | 1 | 4475687205_R02C01 | rs10422066 |
| chr19: 581070-2050823 | 291 | 1,469,754 | 1 | 4475687205_R02C01 | rs10422066 |
| chr16: 107275-840769 | 153 | 733,495 | 1 | 4475687205_R02C01 | rs1045001 |
| chr1: 1152631-2379248 | 182 | 1,226,618 | 1 | 4475687205_R02C01 | rs11721 |
| chr1: 1152631-2379248 | 182 | 1,226,618 | 1 | 4475687205_R02C01 | rs11721 |
| chr20: 61585706-62212928 | 137 | 627,223 | 1 | 4475687205_R02C01 | rs2093045 |
| chr17: 79065650-80758198 | 246 | 1,692,549 | 1 | 4475687205_R02C01 | rs4969384 |
| chr17: 79065650-80758198 | 246 | 1,692,549 | 1 | 4475687205_R02C01 | rs4969384 |
| chr10: 46928388-48137589 | 121 | 1,209,202 | 3 | 4459273637_R02C02 | rs7915055 |
| chr11: 88533414-88533632 | 3 | 219 | 3 | 4459273561_R02C01 | rs10501688 |
| chr19: 53514604-55343606 | 524 | 1,829,003 | 3 | 4461875707_R02C02 | rs10426414 |
| chr13: 34141695-34143447 | 3 | 1,753 | 0 | 4461875352_R02C01 | cnvi0006685 |
| chr6: 32438542-39590788 | 9928 | 7,152,247 | 1 | 4461875352_R02C02 | rs9368726 |
| chr6: 32438542-39590788 | 9928 | 7,152,247 | 1 | 4461875352_R02C02 | rs9368726 |
| chr6: 32438542-39590788 | 9928 | 7,152,247 | 1 | 4461875352_R02C02 | rs9368726 |
| chr6: 32438542-39590788 | 9928 | 7,152,247 | 1 | 4461875352_R02C02 | rs9368726 |
| chr6: 32438542-39590788 | 9928 | 7,152,247 | 1 | 4461875352_R02C02 | rs9368726 |
| chr6: 32438542-39590788 | 9928 | 7,152,247 | 1 | 4461875352_R02C02 | rs9368726 |
| chr8: 90773210-90883803 | 27 | 110,594 | 1 | 4461875352_R02C02 | rs390993 |
| chr11: 88533414-88533632 | 3 | 219 | 3 | 4459273718_R02C02 | rs10501688 |
| chr3: 171220708-171220919 | 3 | 212 | 1 | 4457235209_R02C01 | cnvi0011707 |
| chr21: 47091361-47145374 | 8 | 54,014 | 1 | 4457235209_R02C02 | rs2838973 |
| chr10: 46842850-48137589 | 130 | 1,294,740 | 3 | 4457235209_R02C02 | cnvi0019841 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr6: 32527079-124471337 | 26221 | 91,944,259 | 3 | 4457235209_R02C02 | rs28530648 |
| chr5: 1272500-1276121 | 5 | 3,622 | 3 | 4459273594_R01C01 | rs10057058 |
| chr10: 46961667-47121726 | 11 | 160,060 | 3 | 4432273123_R01C02 | rs506372 |

TABLE 4-continued

| | | | | | |
|---|---|---|---|---|---|
| chr2: 203295790-203309066 | 5 | 13,277 | 3 | 4459273491_R01C01 | rs2350807 |
| chr4: 101754170-101768637 | 4 | 14,468 | 1 | 4457235075_R02C02 | rs7437932 |
| chr16: 56377045-56381277 | 6 | 4,233 | 1 | 4457235509_R02C01 | rs4783937 |
| chr13: 34141695-34143447 | 3 | 1,753 | 1 | 4461875713_R02C01 | cnvi0006685 |
| chr6: 31787630-31795082 | −8886 | 7,453 | 1 | 4459273642_R02C01 | cnvi0006288 |
| chr10: 46961667-48137589 | 120 | 1,175,923 | 3 | 4459273463_R02C01 | rs506372 |
| chr17: 64287309-64288738 | 4 | 1,430 | 1 | 4459273463_R02C01 | cnvi0008597 |
| chr5: 140227999-140232346 | 3 | 4,348 | 1 | 4459273463_R02C02 | rs4151689 |
| chr3: 3129349-3148458 | 7 | 19,110 | 3 | 4482537640_R01C01 | rs334807 |
| chr5: 1272500-1276121 | 5 | 3,622 | 3 | 4459273745_R01C01 | rs10057058 |
| chr13: 34141695-34143447 | 3 | 1,753 | 1 | 4482537650_R02C02 | cnvi0006685 |
| chr7: 6036515-7350683 | 282 | 1,314,169 | 3 | 4459273463_R01C02 | rs12112229 |
| chr6: 43238609-43245374 | 4 | 6,766 | 1 | 4457235469_R02C02 | rs2651187 |
| chr13: 34141695-34143447 | 3 | 1,753 | 1 | 4482537600_R02C02 | cnvi0006685 |
| chr4: 72656076-72678078 | 5 | 22,003 | 3 | 4482537600_R02C01 | rs843006 |
| chr2: 223921771-223936738 | 3 | 14,968 | 1 | 4475687204_R02C02 | rs2017069 |
| chr19: 53533161-55326739 | −9567 | 1,793,579 | 3 | 4459273692_R02C02 | rs2870438 |
| chr10: 46961667-48137589 | 120 | 1,175,923 | 3 | 4482537600_R01C02 | rs506372 |
| chr10: 46850713-49059803 | 341 | 2,209,091 | 3 | 4461875594_R02C01 | cnvi0015925 |
| chr5: 1272500-1276121 | 5 | 3,622 | 3 | 4457235208_R01C01 | rs10057058 |
| chr2: 227343513-227346034 | 3 | 2,522 | 1 | 4459273136_R01C01 | rs13389027 |
| chr9: 81038220-81047891 | 4 | 9,672 | 1 | 4432273525_R01C01 | rs7019259 |
| chr11: 2250850-2271323 | 5 | 20,474 | 3 | 4432265400_R01C01 | rs6578247 |
| chr13: 34141695-34143447 | 3 | 1,753 | 1 | 4457235610_R01C01 | cnvi0006685 |
| chr21: 47851753-47868321 | 7 | 16,569 | 3 | 4457235246_R01C01 | rs2073376 |
| chr4: 101754170-101768637 | 4 | 14,468 | 1 | 4432273755_R01C01 | rs7437932 |
| chr6: 31785453-31795082 | 8 | 9,630 | 1 | 4432273430_R01C01 | rs508633 |
| chr13: 34141695-34143447 | 3 | 1,753 | 1 | 4457235246_R02C02 | cnvi0006685 |
| chr5: 140227999-140232346 | 3 | 4,348 | 1 | 4457235401_R02C02 | rs4151689 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr19: 43647130-55326739 | −7353 | 11,679,610 | 1 | 4457235401_R02C01 | rs11083692 |
| chr1: 1220136-1356550 | 16 | 136,415 | 1 | 4457235208_R02C02 | rs2144440 |
| chr3: 171220708-171220919 | 3 | 212 | 1 | 4432273430_R01C02 | cnvi0011707 |
| chr11: 75071783-75080920 | 4 | 9,138 | 1 | 4432273430_R01C02 | rs582477 |
| chr14: 105154105-106516402 | 167 | 1,362,298 | 3 | 4457235026_R01C01 | rs3809456 |
| chr12: 125083696-125097030 | 12 | 13,335 | 3 | 4432273710_R02C01 | rs12230272 |
| chr13: 34141695-34143447 | 3 | 1,753 | 1 | 4457235610_R01C02 | cnvi0006685 |
| chr11: 88376801-88379332 | 4 | 2,532 | 1 | 4457235153_R01C02 | rs1354411 |
| chr10: 46961667-47099529 | 9 | 137,863 | 3 | 4457235401_R01C02 | rs506372 |
| chr6: 31281438-31795082 | −8770 | 513,645 | 1 | 4457235401_R02C01 | cnvi0006173 |
| chr6: 31281438-31795082 | −8770 | 513,645 | 1 | 4457235401_R02C02 | cnvi0006173 |
| chr6: 31281438-31795082 | −8770 | 513,645 | 1 | 4457235401_R02C02 | cnvi0006173 |
| chr6: 31281438-31795082 | −8770 | 513,645 | 1 | 4457235401_R02C02 | cnvi0006173 |
| chr6: 16398959-16400090 | 7 | 1,132 | 3 | 4432273335_R02C02 | rs17591931 |
| chr2: 223921771-223938748 | 4 | 16,978 | 1 | 4432273335_R02C01 | rs2017069 |
| chr17: 64287309-64288738 | 4 | 1,430 | 1 | 4457235506_R02C01 | cnvi0008597 |
| chr19: 53522100-55326739 | −9566 | 1,804,640 | 3 | 4459273573_R02C02 | rs8109866 |
| chr15: 60524025-60551926 | 5 | 27,902 | 3 | 4459273492_R01C02 | rs4775243 |
| chr9: 141026318-141036645 | 4 | 10,328 | 3 | 4459273278_R01C01 | rs17583562 |
| chr5: 140227999-140232346 | 3 | 4,348 | 1 | 4432265617_R01C01 | rs4151689 |
| chr11: 7353097-7369875 | 7 | 16,779 | 3 | 4457235099_R01C01 | rs901755 |
| chr2: 227343513-227346034 | 3 | 2,522 | 1 | 4457235154_R01C01 | rs13389027 |
| chr10: 46928388-47748912 | 105 | 820,525 | 3 | 4457235415_R02C01 | rs7915055 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |

TABLE 4-continued

| | | | | | |
|---|---|---|---|---|---|
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr3: 11714521-90442925 | −97 | 78,728,405 | 1 | 4432273747_R02C02 | rs7627256 |
| chr10: 46928388-47703613 | 103 | 775,226 | 3 | 4459273442_R02C02 | rs7915055 |
| chr12: 2245636-2252924 | 7 | 7,289 | 1 | 4459273476_R02C02 | rs12579529 |
| chr18: 58267843-58310343 | 9 | 42,501 | 3 | 4459273573_R01C02 | rs7240781 |
| chr10: 46928388-47568296 | 54 | 639,909 | 3 | 4459273492_R02C02 | rs7915055 |
| chr10: 46961667-48137589 | 120 | 1,175,923 | 3 | 4459273709_R01C02 | rs506372 |
| chr10: 46928388-49059803 | 333 | 2,131,416 | 3 | 4461875796_R02C01 | rs7915055 |
| chr13: 34141695-34143447 | 3 | 1,753 | 1 | 4457235415_R01C02 | cnvi0006685 |
| chr10: 46961667-47697026 | 99 | 735,360 | 3 | 4432273648_R02C01 | rs506372 |
| chr17: 64287309-64288738 | 4 | 1,430 | 1 | 4459273278_R02C01 | cnvi0008597 |
| chr1: 239306319-239410745 | 34 | 104,427 | 3 | 4461875621_R01C02 | rs1858175 |
| chr6: 151618235-151621611 | 5 | 3,377 | 1 | 4459273748_R01C02 | rs9479007 |
| chr8: 6717107-6725056 | 10 | 7,950 | 1 | 4457235415_R02C02 | rs6989229 |
| chr12: 2245636-2252924 | 7 | 7,289 | 1 | 4457235610_R02C02 | rs12579529 |
| chr6: 31785453-31795082 | 8 | 9,630 | 1 | 4432273039_R01C02 | rs508633 |
| chr18: 58100799-58120972 | 11 | 20,174 | 1 | 4432273039_R01C02 | rs1539984 |
| chr9: 93557698-93577781 | 13 | 20,084 | 3 | 4457235609_R02C01 | rs10993693 |
| chr3: 171220708-171220919 | 3 | 212 | 1 | 4457235609_R02C01 | cnvi0011707 |
| chr13: 31646976-31652085 | 3 | 5,110 | 3 | 4457235504_R01C01 | rs9591486 |
| chr21: 37410477-37415603 | 4 | 5,127 | 1 | 4457235078_R02C02 | rs2835239 |
| chr12: 2245636-2252924 | 7 | 7,289 | 1 | 4432273648_R02C02 | rs12579529 |
| chr5: 140227999-140232346 | 3 | 4,348 | 1 | 4457235046_R01C01 | rs4151689 |
| chr13: 23528685-24897901 | 510 | 1,369,217 | 1 | 4482537640_R02C02 | rs9580476 |
| chr6: 154379152-154393884 | 5 | 14,733 | 1 | 4482537640_R02C02 | rs3823010 |
| chr11: 88533414-88533632 | 3 | 219 | 3 | 4459273634_R02C02 | rs10501688 |
| chr5: 1272500-1276121 | 5 | 3,622 | 3 | 4482537383_R01C01 | rs10057058 |
| chr6: 31787630-31795082 | −8886 | 7,453 | 1 | 4482537650_R02C02 | cnvi0006288 |
| chr13: 31646976-31652085 | 3 | 5,110 | 3 | 4459273574_R01C01 | rs9591486 |
| chr11: 88533414-88533632 | 3 | 219 | 3 | 4461875788_R01C01 | rs10501688 |
| chr13: 34141695-34143447 | 3 | 1,753 | 1 | 4432265060_R02C02 | cnvi0006685 |
| chr6: 19044000-31286381 | −6774 | 12,242,382 | 0 | 4459273423_R01C02 | rs6922929 |
| chr6: 19044000-31286381 | −6774 | 12,242,382 | 0 | 4459273423_R01C02 | rs6922929 |
| chr6: 19044000-31286381 | −6774 | 12,242,382 | 0 | 4459273423_R01C02 | rs6922929 |
| chr6: 19044000-31286381 | −6774 | 12,242,382 | 0 | 4459273423_R01C02 | rs6922929 |
| chr5: 140227999-140232346 | 3 | 4,348 | 1 | 4432273054_R01C01 | rs4151689 |
| chr8: 102696350-102696889 | 3 | 540 | 3 | 4432273054_R02C02 | cnvi0001969 |
| chr13: 34141695-34143447 | 3 | 1,753 | 1 | 4459273278_R02C02 | cnvi0006685 |
| chr5: 711373-1276121 | 137 | 564,749 | 3 | 4457235558_R01C02 | rs373127 |
| chr12: 2245636-2252924 | 7 | 7,289 | 1 | 4432273054_R01C02 | rs12579529 |
| chr4: 101754170-101768637 | 4 | 14,468 | 1 | 4432273286_R01C02 | rs7437932 |
| chr4: 158346878-158424816 | 23 | 77,939 | 1 | 4457235244_R01C01 | rs9992749 |
| chr12: 2247179-2252924 | 6 | 5,746 | 1 | 4457235196_R02C02 | rs3794300 |
| chr12: 2245636-2252924 | 7 | 7,289 | 1 | 4457235346_R01C02 | rs12579529 |
| chr5: 1272500-1276121 | 5 | 3,622 | 3 | 4432273584_R01C02 | rs10057058 |
| chr5: 140227999-140232346 | 3 | 4,348 | 1 | 4457235046_R02C01 | rs4151689 |
| chr13: 34141695-34143447 | 3 | 1,753 | 1 | 4457235345_R01C01 | cnvi0006685 |
| chr11: 88376801-88379332 | 4 | 2,532 | 1 | 4457235345_R01C01 | rs1354411 |
| chr2: 227343513-227346034 | 3 | 2,522 | 1 | 4432273749_R01C02 | rs13389027 |
| chr12: 2245636-2252924 | 7 | 7,289 | 1 | 4459273574_R02C02 | rs12579529 |
| chr17: 64287309-64288738 | 4 | 1,430 | 1 | 4459273574_R02C02 | cnvi0008597 |
| chr13: 34141695-34143447 | 3 | 1,753 | 1 | 4461875644_R01C01 | cnvi0006685 |
| chr21: 27194869-27232198 | 13 | 37,330 | 1 | 4457235244_R01C02 | rs2829916 |
| chr5: 140227999-140232346 | 3 | 4,348 | 1 | 4457235244_R02C02 | rs4151689 |
| chr3: 171220708-171220919 | 3 | 212 | 1 | 4459273424_R01C01 | cnvi0011707 |
| chr10: 46961667-47121726 | 11 | 160,060 | 3 | 4459273424_R01C01 | rs506372 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |

TABLE 4-continued

| | | | | | |
|---|---|---|---|---|---|
| chr19: 43284120-55326739 | −7305 | 12,042,620 | 3 | 4457235010_R02C01 | rs10407540 |
| chr19: 43284120-55326739 | −7305 | 12,042,620 | 3 | 4457235010_R02C01 | rs10407540 |
| chr13: 34141695-34143447 | 3 | 1,753 | 1 | 4457235010_R02C01 | cnvi0006685 |
| chr12: 2245636-2252924 | 7 | 7,289 | 0 | 4461875451_R01C01 | rs12579529 |
| chr13: 34141695-34143447 | 3 | 1,753 | 1 | 4461875451_R01C01 | cnvi0006685 |
| chr4: 101754170-101768637 | 4 | 14,468 | 1 | 4432265249_R01C01 | rs7437932 |
| chr10: 46961667-47703613 | 102 | 741,947 | 3 | 4457235345_R02C01 | rs506372 |
| chr5: 140227999-140232346 | 3 | 4,348 | 1 | 4432273383_R02C02 | rs4151689 |
| chr3: 171220708-171220919 | 3 | 212 | 1 | 4457235234_R01C01 | cnvi0011707 |
| chr8: 103054583-103056517 | 7 | 1,935 | 1 | 4457235046_R02C02 | rs1111909 |
| chr13: 34141695-34143447 | 3 | 1,753 | 0 | 4432273383_R01C01 | cnvi0006685 |
| chr13: 34141695-34143447 | 3 | 1,753 | 1 | 4459273424_R02C01 | cnvi0006685 |
| chr6: 31787630-31795082 | −8886 | 7,453 | 1 | 4459273424_R02C01 | cnvi0006288 |
| chr10: 46961667-47703613 | 102 | 741,947 | 3 | 4459273424_R02C01 | rs506372 |
| chr10: 131474247-131529320 | 23 | 55,074 | 1 | 4457235010_R01C02 | rs7071424 |
| chr6: 21612949-21623715 | 3 | 10,767 | 1 | 4457235010_R01C02 | rs1744849 |
| chr12: 2245636-2252924 | 7 | 7,289 | 1 | 4457235010_R02C02 | rs12579529 |
| chr3: 171220708-171220919 | 3 | 212 | 1 | 4457235010_R02C02 | cnvi0011707 |
| chr13: 31646976-31652085 | 3 | 5,110 | 3 | 4432273383_R02C01 | rs9591486 |
| chr13: 34141695-34143447 | 3 | 1,753 | 0 | 4432273383_R02C01 | cnvi0006685 |
| chr6: 154379152-154393884 | 5 | 14,733 | 1 | 4432273583_R01C01 | rs3823010 |
| chr5: 140227999-140232346 | 3 | 4,348 | 0 | 4459273636_R01C01 | rs4151689 |
| chr9: 140911199-140913833 | 4 | 2,635 | 3 | 4432273583_R02C01 | rs10780198 |
| chr3: 171220708-171220919 | 3 | 212 | 1 | 4457235236_R02C01 | cnvi0011707 |
| chr17: 64287309-64288738 | 4 | 1,430 | 1 | 4457235132_R02C02 | cnvi0008597 |
| chr10: 46961667-47121726 | 11 | 160,060 | 3 | 4457235132_R02C01 | rs506372 |
| chr12: 2245636-2252924 | 7 | 7,289 | 1 | 4457235317_R01C01 | rs12579529 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr19: 20612645-55326739 | −3865 | 34,714,095 | 1 | 4461875644_R02C02 | rs6511105 |
| chr9: 140911199-140913833 | 4 | 2,635 | 3 | 4432273583_R01C02 | rs10780198 |
| chr2: 227334949-227346034 | 4 | 11,086 | 0 | 4432273383_R01C02 | cnvi0010273 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr6: 31277740-44419336 | 12754 | 13,141,597 | 3 | 4432273383_R01C02 | rs9264967 |
| chr13: 31646976-31652085 | 3 | 5,110 | 3 | 4459273547_R01C01 | rs9591486 |
| chr13: 34141695-34143447 | 3 | 1,753 | 1 | 4432273583_R02C02 | cnvi0006685 |
| chr2: 227343513-227346034 | 3 | 2,522 | 1 | 4432273383_R02C02 | rs13389027 |

TABLE 4-continued

| | | | | | |
|---|---|---|---|---|---|
| chr12: 2245636-2252924 | 7 | 7,289 | 1 | 4432273383_R02C02 | rs12579529 |
| chr13: 20220659-20437753 | 37 | 217,095 | 3 | 4457235058_R01C01 | rs1057093 |
| chr3: 148441620-148455199 | 25 | 13,580 | 1 | 4457235058_R02C01 | rs12721241 |
| chr2: 70880841-70953745 | 32 | 72,905 | 1 | 4457235058_R02C01 | rs17697969 |
| chr18: 40640488-40808652 | 40 | 168,165 | 1 | 4457235058_R02C01 | rs4265907 |
| chr10: 46961667-47727297 | 103 | 765,631 | 3 | 4457235132_R02C02 | rs506372 |
| chr9: 140911199-140913833 | 4 | 2,635 | 3 | 4461875645_R01C02 | rs10780198 |
| chr10: 53374729-53375420 | 4 | 692 | 3 | 4459273547_R02C01 | cnvi0004073 |
| chr11: 659906-1611018 | 179 | 951,113 | 3 | 4459273547_R02C02 | rs7940539 |
| chr6: 152095167-152103792 | 5 | 8,626 | 3 | 4482537425_R02C01 | rs2504065 |
| chr7: 32220497-32399833 | 80 | 179,337 | 3 | 4457235356_R01C02 | rs987069 |
| chr4: 101754170-101768637 | 4 | 14,468 | 1 | 4457235356_R01C02 | rs7437932 |
| chr13: 31646976-31652085 | 3 | 5,110 | 3 | 4457235356_R01C02 | rs9591486 |
| chr5: 1272500-1276121 | 5 | 3,622 | 3 | 4457235024_R02C01 | rs10057058 |
| chr5: 140227999-140232346 | 3 | 4,348 | 0 | 4432273292_R02C01 | rs4151689 |
| chr11: 88533414-88533632 | 3 | 219 | 3 | 4457235356_R02C02 | rs10501688 |
| chr3: 171220708-171220919 | 3 | 212 | 1 | 4459273422_R01C02 | cnvi0011707 |
| chr11: 88376801-88379332 | 4 | 2,532 | 1 | 4459273422_R01C01 | rs1354411 |
| chr2: 203285157-203309066 | 7 | 23,910 | 3 | 4457235498_R01C01 | rs6747299 |
| chr16: 29647342-30177807 | 51 | 530,466 | 3 | 4457235024_R02C02 | rs9926100 |
| chr16: 29647342-30177807 | 51 | 530,466 | 3 | 4457235024_R02C02 | rs9926100 |
| chr16: 29647342-30177807 | 51 | 530,466 | 3 | 4457235024_R02C02 | rs9926100 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr2: 179693712-237821589 | 11396 | 58,127,878 | 1 | 4457235234_R02C01 | rs2366912 |
| chr3: 171220708-171220919 | 3 | 212 | 1 | 4457235243_R01C01 | cnvi0011707 |
| chr3: 171220708-171220919 | 3 | 212 | 1 | 4457235243_R02C01 | cnvi0011707 |
| chr13: 34141695-34143447 | 3 | 1,753 | 1 | 4457235243_R02C01 | cnvi0006685 |
| chr5: 1272500-1276121 | 5 | 3,622 | 3 | 4457235243_R01C02 | rs10057058 |
| chr7: 32211433-32399833 | 85 | 188,401 | 3 | 4457235243_R01C02 | rs9648380 |
| chr13: 33822593-33825641 | 5 | 3,049 | 1 | 4457235134_R01C01 | rs2555594 |
| chr6: 88843377-88861698 | 9 | 18,322 | 3 | 4457235134_R01C01 | rs9353525 |
| chr5: 110756963-110759537 | 3 | 2,575 | 1 | 4457235134_R01C01 | rs307533 |
| chr2: 227343513-227346034 | 3 | 2,522 | 1 | 4457235134_R01C01 | rs13389027 |
| chr12: 2245636-2252924 | 7 | 7,289 | 1 | 4457235134_R01C02 | rs12579529 |
| chr4: 101754170-101768637 | 4 | 14,468 | 1 | 4432273640_R02C01 | rs7437932 |
| chr6: 56740504-56792576 | 8 | 52,073 | 1 | 4432273407_R01C02 | rs13191084 |
| chr18: 58267843-58304032 | 7 | 36,190 | 3 | 4457235243_R02C02 | rs7240781 |
| chr6: 31289284-32499014 | 9991 | 1,209,731 | 3 | 4457235234_R02C02 | rs9265170 |
| chr6: 31289284-32499014 | 9991 | 1,209,731 | 3 | 4457235234_R02C02 | rs9265170 |
| chr6: 31289284-32499014 | 9991 | 1,209,731 | 3 | 4457235234_R02C02 | rs9265170 |
| chr6: 31289284-32499014 | 9991 | 1,209,731 | 3 | 4457235234_R02C02 | rs9265170 |
| chr13: 34141695-34143447 | 3 | 1,753 | 1 | 4457235234_R02C02 | cnvi0006685 |
| chr13: 23899627-24336981 | 113 | 437,355 | 3 | 4432273339_R01C02 | rs9510702 |
| chr10: 46961667-47149117 | 12 | 187,451 | 3 | 4432273339_R01C02 | rs506372 |
| chr12: 2245636-2252924 | 7 | 7,289 | 1 | 4457235366_R02C01 | rs12579529 |
| chr1: 144875799-149582448 | 515 | 4,706,650 | 3 | 4432273640_R02C02 | rs764983 |
| chr19: 7124986-7134402 | 6 | 9,417 | 1 | 4432273339_R02C02 | rs2288404 |
| chr4: 185621249-186622179 | 270 | 1,000,931 | 3 | 4457235366_R01C02 | rs877276 |
| chr13: 34141695-34143447 | 3 | 1,753 | 1 | 4457235252_R02C02 | cnvi0006685 |
| chr6: 3867382-32514144 | −112 | 28,646,763 | 3 | 4457235498_R01C02 | rs35779483 |
| chr6: 3867382-32514144 | −112 | 28,646,763 | 3 | 4457235498_R01C02 | rs35779483 |
| chr6: 3867382-32514144 | −112 | 28,646,763 | 3 | 4457235498_R01C02 | rs35779483 |
| chr6: 3867382-32514144 | −112 | 28,646,763 | 3 | 4457235498_R01C02 | rs35779483 |
| chr6: 3867382-32514144 | −112 | 28,646,763 | 3 | 4457235498_R01C02 | rs35779483 |
| chr6: 3867382-32514144 | −112 | 28,646,763 | 3 | 4457235498_R01C02 | rs35779483 |
| chr6: 3867382-32514144 | −112 | 28,646,763 | 3 | 4457235498_R01C02 | rs35779483 |
| chr6: 3867382-32514144 | −112 | 28,646,763 | 3 | 4457235498_R01C02 | rs35779483 |
| chr3: 171220708-171220919 | 3 | 212 | 1 | 4482537425_R02C02 | cnvi0011707 |
| chr11: 88376801-88379332 | 4 | 2,532 | 1 | 4457235366_R02C02 | rs1354411 |
| chr5: 1272500-1276121 | 5 | 3,622 | 3 | 4459273522_R01C02 | rs10057058 |
| chr2: 227343513-227346034 | 3 | 2,522 | 1 | 4459273635_R02C02 | rs13389027 |
| chr6: 31785453-31795082 | 8 | 9,630 | 1 | 4459273627_R01C02 | rs508633 |
| chr13: 31646976-31652085 | 3 | 5,110 | 3 | 4482537427_R01C02 | rs9591486 |
| chr17: 64287309-64288738 | 4 | 1,430 | 1 | 4482537427_R02C02 | cnvi0008597 |
| chr2: 227343513-227346034 | 3 | 2,522 | 1 | 4482537426_R01C01 | rs13389027 |
| chr10: 46961667-48137589 | 120 | 1,175,923 | 3 | 4482537426_R02C01 | rs506372 |

TABLE 4-continued

| | | | | |
|---|---|---|---|---|
| chr16: 29130999-35279083 | 745 | 6,148,085 | 3 | 4457235239_R01C01 | rs12922496 |
| chr16: 29130999-35279083 | 745 | 6,148,085 | 3 | 4457235239_R01C01 | rs12922496 |
| chr16: 29130999-35279083 | 745 | 6,148,085 | 3 | 4457235239_R01C01 | rs12922496 |
| chr16: 29130999-35279083 | 745 | 6,148,085 | 3 | 4457235239_R01C01 | rs12922496 |
| chr16: 29130999-35279083 | 745 | 6,148,085 | 3 | 4457235239_R01C01 | rs12922496 |
| chr6: 31785453-31795082 | 8 | 9,630 | 1 | 4482537374_R02C01 | rs508633 |
| chr5: 1272500-1276121 | 5 | 3,622 | 3 | 4482537374_R02C02 | rs10057058 |
| chr17: 64287309-64288738 | 4 | 1,430 | 1 | 4482537381_R02C01 | cnvi0008597 |
| chr3: 171220708-171220919 | 3 | 212 | 1 | 4482537381_R02C02 | cnvi0011707 |
| chr6: 1175965-29895228 | 39 | 28,719,264 | 0 | 4432273288_R02C02 | rs1611522 |
| chr6: 1175965-29895228 | 39 | 28,719,264 | 0 | 4432273288_R02C02 | rs1611522 |
| chr6: 1175965-29895228 | 39 | 28,719,264 | 0 | 4432273288_R02C02 | rs1611522 |
| chr6: 1175965-29895228 | 39 | 28,719,264 | 0 | 4432273288_R02C02 | rs1611522 |
| chr5: 140227999-140232346 | 3 | 4,348 | 1 | 4432273288_R02C02 | rs4151689 |
| chr8: 48992900-49018790 | 7 | 25,891 | 1 | 4482537405_R01C02 | rs7009048 |
| chr3: 9014942-9019748 | 5 | 4,807 | 1 | 4482537405_R01C02 | rs2728770 |
| chr5: 1259342-1276121 | 7 | 16,780 | 3 | 4482537404_R01C02 | rs2883171 |
| chr6: 64139997-64279571 | 10 | 139,575 | 1 | 4482537404_R01C02 | rs4445042 |
| chr13: 23528685-24897901 | 510 | 1,369,217 | 1 | 4482537037_R01C01 | rs9580476 |
| chr18: 58267843-58294706 | 6 | 26,864 | 3 | 4461875786_R01C02 | rs7240781 |
| chr5: 1272500-1276121 | 5 | 3,622 | 3 | 4461875714_R01C01 | rs10057058 |
| chr7: 125687968-125707685 | 5 | 19,718 | 1 | 4461875714_R02C02 | rs6976605 |
| chr15: 30007573-30011918 | 3 | 4,346 | 1 | 4461875581_R01C01 | rs767514 |
| chr16: 9776728-9784163 | 3 | 7,436 | 1 | 4461875581_R02C01 | rs11646975 |
| chr10: 46961667-47703613 | 102 | 741,947 | 3 | 4461875581_R02C01 | rs506372 |
| chr10: 47041592-49059803 | 328 | 2,018,212 | 3 | 4461875660_R02C02 | rs4593952 |
| chr6: 31219869-31221914 | 7 | 2,046 | 1 | 4461875660_R02C02 | rs9264179 |
| chr19: 1673509-1684137 | 3 | 10,629 | 1 | 4457235258_R02C01 | rs4807948 |
| chr1: 171591189-171592869 | 3 | 1,681 | 1 | 4457235498_R02C02 | rs929115 |
| chr13: 34141695-34143447 | 3 | 1,753 | 1 | 4461875451_R01C01 | cnvi0006685 |
| chr10: 46961667-47748912 | 104 | 787,246 | 3 | 4457235073_R01C02 | rs506372 |
| chr13: 34141695-34143447 | 3 | 1,753 | 1 | 4461875451_R02C02 | cnvi0006685 |
| chr2: 49150192-49230413 | 48 | 80,222 | 1 | 4461875451_R02C02 | rs7602044 |
| chr10: 46961667-47727297 | 103 | 765,631 | 3 | 4461875451_R02C02 | rs506372 |
| chr3: 171220708-171220919 | 3 | 212 | 1 | 4432273753_R02C01 | cnvi0011707 |
| chr13: 34141695-34143447 | 3 | 1,753 | 1 | 4432273753_R02C01 | cnvi0006685 |
| chr12: 2245636-2252924 | 7 | 7,289 | 1 | 4457235238_R02C01 | rs12579529 |
| chr3: 171220708-171220919 | 3 | 212 | 1 | 4459273639_R01C01 | cnvi0011707 |
| chr9: 141017240-141036645 | 6 | 19,406 | 3 | 4459273639_R01C01 | rs3750508 |
| chr17: 64287309-64288738 | 4 | 1,430 | 1 | 4461875802_R02C01 | cnvi0008597 |
| chr13: 34141695-34143447 | 3 | 1,753 | 1 | 4461875801_R01C01 | cnvi0006685 |
| chr2: 227343513-227346034 | 3 | 2,522 | 1 | 4459273749_R01C01 | rs13389027 |
| chr2: 227343513-227346034 | 3 | 2,522 | 1 | 4457235294_R02C01 | rs13389027 |
| chr12: 2245636-2252924 | 7 | 7,289 | 1 | 4457235028_R02C01 | rs12579529 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr6: 31289284-141041329 | 31502 | 109,752,046 | 3 | 4457235028_R02C01 | rs9265170 |
| chr5: 140227999-140232346 | 3 | 4,348 | 0 | 4459273563_R02C01 | rs4151689 |
| chr3: 171220708-171220919 | 3 | 212 | 1 | 4459273749_R01C02 | cnvi0011707 |
| chr13: 31646976-31652085 | 3 | 5,110 | 3 | 4459273749_R01C02 | rs9591486 |
| chr4: 72670191-72678078 | 4 | 7,888 | 3 | 4461875449_R01C01 | rs1565572 |

TABLE 4-continued

| | | | | | |
|---|---|---|---|---|---|
| chr13: 34141695-34143447 | 3 | 1,753 | 1 | 4461875449_R01C01 | cnvi0006685 |
| chr5: 140227999-140232346 | 3 | 4,348 | 1 | 4461875449_R02C01 | rs4151689 |
| chr8: 56757808-56876219 | 38 | 118,412 | 3 | 4461875449_R01C02 | rs12155521 |
| chr3: 171220708-171220919 | 3 | 212 | 1 | 4461875449_R01C02 | cnvi0011707 |
| chr6: 1165092-29899147 | 56 | 28,734,056 | 0 | 4459273656_R02C01 | rs3128864 |
| chr6: 1165092-29899147 | 56 | 28,734,056 | 0 | 4459273656_R02C01 | rs3128864 |
| chr6: 1165092-29899147 | 56 | 28,734,056 | 0 | 4459273656_R02C01 | rs3128864 |
| chr6: 1165092-29899147 | 56 | 28,734,056 | 0 | 4459273656_R02C01 | rs3128864 |
| chr11: 2250850-2271323 | 5 | 20,474 | 3 | 4457235528_R01C01 | rs6578247 |
| chr10: 46961667-47160061 | 13 | 198,395 | 3 | 4461875480_R01C02 | rs506372 |
| chr5: 1272500-1276121 | 5 | 3,622 | 3 | 4459273563_R01C02 | rs10057058 |
| chr6: 2540921-31298743 | 9733 | 28,757,823 | 3 | 4432273639_R02C02 | rs9264651 |
| chr6: 2540921-31298743 | 9733 | 28,757,823 | 3 | 4432273639_R02C02 | rs9264651 |
| chr6: 2540921-31298743 | 9733 | 28,757,823 | 3 | 4432273639_R02C02 | rs9264651 |
| chr6: 2540921-31298743 | 9733 | 28,757,823 | 3 | 4432273639_R02C02 | rs9264651 |
| chr6: 2540921-31298743 | 9733 | 28,757,823 | 3 | 4432273639_R02C02 | rs9264651 |
| chr6: 2540921-31298743 | 9733 | 28,757,823 | 3 | 4432273639_R02C02 | rs9264651 |
| chr5: 140227999-140232346 | 3 | 4,348 | 1 | 4432273639_R02C02 | rs4151689 |
| chr13: 34141695-34143447 | 3 | 1,753 | 1 | 4432265616_R01C01 | cnvi0006685 |
| chr2: 49293369-49321164 | 8 | 27,796 | 3 | 4432265506_R02C02 | rs1882560 |
| chr5: 140227999-140232346 | 3 | 4,348 | 1 | 4432265618_R01C01 | rs4151689 |
| chr4: 114289170-114302266 | 4 | 13,097 | 1 | 4432273182_R02C01 | rs13137710 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 83030867-150270420 | 12963 | 67,239,554 | 3 | 4482537383_R02C02 | rs10058970 |
| chr5: 152821589-152847022 | 5 | 25,434 | 3 | 4482537383_R02C02 | rs4958655 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 162204206-179888268 | 4398 | 17,684,063 | 3 | 4482537383_R02C02 | rs2422269 |
| chr5: 140227999-140232346 | 3 | 4,348 | 0 | 4459273749_R02C02 | rs4151689 |
| chr16: 82165183-82213799 | 21 | 48,617 | 1 | 4459273749_R02C02 | rs12921771 |
| chr6: 31787630-31795082 | −8886 | 7,453 | 1 | 4461875316_R02C01 | cnvi0006288 |
| chr5: 1272500-1276121 | 5 | 3,622 | 3 | 4461875316_R02C01 | rs10057058 |
| chr13: 34141695-34143447 | 3 | 1,753 | 1 | 4457235133_R01C01 | cnvi0006685 |
| chr18: 58117429-58120972 | 4 | 3,544 | 1 | 4461875801_R02C01 | rs1943242 |
| chr13: 34141695-34143447 | 3 | 1,753 | 1 | 4461875801_R02C01 | cnvi0006685 |
| chr1: 16087164-16098866 | 5 | 11,703 | 1 | 4457235183_R02C01 | rs867321 |
| chr6: 75923605-76473071 | 68 | 549,467 | 3 | 4457235337_R01C01 | rs1323070 |
| chr5: 140227999-140232346 | 3 | 4,348 | 0 | 4457235015_R01C02 | rs4151689 |
| chr11: 198510-257030 | 35 | 58,521 | 3 | 4457235015_R01C02 | rs3802985 |
| chr11: 198510-257030 | 35 | 58,521 | 3 | 4457235015_R01C02 | rs3802985 |
| chr6: 73463601-73467087 | 3 | 3,487 | 1 | 4432265059_R02C02 | rs7743377 |
| chr3: 171220708-171220919 | 3 | 212 | 1 | 4457235238_R02C02 | cnvi0011707 |
| chr2: 227343513-227346034 | 3 | 2,522 | 1 | 4432265506_R02C01 | rs13389027 |
| chr4: 101754170-101768637 | 4 | 14,468 | 1 | 4432265506_R02C01 | rs7437932 |
| chr5: 140227999-140232346 | 3 | 4,348 | 0 | 4432265506_R02C01 | rs4151689 |
| chr12: 2245636-2252924 | 7 | 7,289 | 1 | 4432273335_R01C02 | rs12579529 |
| chr12: 2245636-2252924 | 7 | 7,289 | 1 | 4457235072_R02C01 | rs12579529 |
| chr5: 140097072-140232346 | 23 | 135,275 | 1 | 4457235015_R02C02 | rs2563297 |
| chr22: 22315312-25908441 | 1052 | 3,593,130 | 3 | 4457235183_R02C02 | rs2283797 |
| chr22: 22315312-25908441 | 1052 | 3,593,130 | 3 | 4457235183_R02C02 | rs2283797 |
| chr12: 2245636-2252924 | 7 | 7,289 | 1 | 4459273658_R02C02 | rs12579529 |
| chr4: 101798797-101805126 | 3 | 6,330 | 1 | 4432273710_R01C02 | rs11725047 |
| chr10: 46961667-47748912 | 104 | 787,246 | 3 | 4457235392_R01C01 | rs506372 |

TABLE 4-continued

| Chr: Start-Stop(hg19) | | | | | |
|---|---|---|---|---|---|
| chr10: 46961667-47703613 | 102 | 741,947 | 3 | 4432273103_R02C01 | rs506372 |
| chr6: 56740504-56792576 | 8 | 52,073 | 1 | 4457235409_R01C02 | rs13191084 |
| chr10: 111928766-111931752 | 3 | 2,987 | 1 | 4461875802_R02C02 | rs7918659 |
| chr6: 31289284-32499014 | 9991 | 1,209,731 | 3 | 4459273692_R02C01 | rs9265170 |
| chr6: 31289284-32499014 | 9991 | 1,209,731 | 3 | 4459273692_R01C01 | rs9265170 |
| chr6: 31289284-32499014 | 9991 | 1,209,731 | 3 | 4459273692_R01C01 | rs9265170 |
| chr6: 31289284-32499014 | 9991 | 1,209,731 | 3 | 4459273692_R01C01 | rs9265170 |
| chr4: 166469496-166495142 | 13 | 25,647 | 1 | 4457235392_R02C01 | rs17587610 |
| chr10: 46961667-47703613 | 102 | 741,947 | 3 | 4459273638_R01C02 | rs506372 |
| chr21: 37410477-37415603 | 4 | 5,127 | 1 | 4457235072_R02C02 | rs2835239 |
| chr3: 171220708-171220919 | 3 | 212 | 1 | 4432273123_R01C01 | cnvi0011707 |
| chr9: 93519280-93529807 | 3 | 10,528 | 3 | 4457235500_R02C02 | rs1172931 |
| chr12: 2245636-2252924 | 7 | 7,289 | 1 | 4457235212_R02C01 | rs12579529 |
| chr12: 2245636-2252924 | 7 | 7,289 | 1 | 4461875282_R02C02 | rs12579529 |
| chr10: 46961667-47088968 | 8 | 127,302 | 3 | 4459273481_R01C02 | rs506372 |
| chr5: 1257259-1276121 | 9 | 18,863 | 3 | 4457235085_R01C01 | rs7702814 |
| chr18: 39671541-39697934 | 6 | 26,394 | 3 | 4457235085_R02C01 | rs8090403 |
| chr5: 140227999-140232346 | 3 | 4,348 | 0 | 4459273661_R01C02 | rs4151689 |
| chr13: 34141695-34143447 | 3 | 1,753 | 1 | 4459273661_R01C02 | cnvi0006685 |
| chr2: 203292344-203309066 | 6 | 16,723 | 3 | 4457235085_R01C02 | rs16839149 |
| chr12: 2245636-2252924 | 7 | 7,289 | 1 | 4432265321_R02C02 | rs12579529 |
| chr5: 1272500-1276121 | 5 | 3,622 | 3 | 4457235085_R02C02 | rs10057058 |
| chr12: 2245636-2252924 | 7 | 7,289 | 1 | 4461875785_R01C01 | rs12579529 |
| chr17: 64287309-64288738 | 4 | 1,430 | 1 | 4461875785_R01C01 | cnvi0008597 |
| chr2: 119984733-120833583 | 131 | 848,851 | 1 | 4457235057_R02C02 | rs838102 |
| chr13: 34141695-34143447 | 3 | 1,753 | 1 | 4461875801_R02C02 | cnvi0006685 |
| chr1: 169591373-169749154 | 40 | 157,782 | 1 | 4432273126_R01C02 | rs3917683 |
| chr2: 49643063-49654260 | 9 | 11,198 | 1 | 4457235104_R02C01 | rs11125238 |
| chr13: 34141695-34143447 | 3 | 1,753 | 1 | 4459273661_R01C02 | cnvi0006685 |
| chr6: 31787630-31795082 | -8886 | 7,453 | 1 | 4457235408_R02C02 | cnvi0006288 |
| chr4: 102504356-102574367 | 15 | 70,012 | 1 | 4457235408_R01C02 | rs2723048 |
| chr12: 49578661-49586490 | 4 | 7,830 | 3 | 4432273631_R01C02 | rs1062440 |
| chr13: 34141695-34143447 | 3 | 1,753 | 1 | 4459273661_R02C02 | cnvi0006685 |
| chr8: 131968469-132230063 | 60 | 261,595 | 3 | 4432265042_R02C02 | rs6988340 |
| chr6: 56791495-56799262 | 3 | 7,768 | 1 | 4459273747_R01C02 | rs17752435 |
| chr16: 29130999-33908890 | 633 | 4,777,892 | 3 | 4459273747_R01C02 | rs12922496 |
| chr16: 29130999-33908890 | 633 | 4,777,892 | 3 | 4459273747_R01C02 | rs12922496 |
| chr16: 29130999-33908890 | 633 | 4,777,892 | 3 | 4459273747_R01C02 | rs12922496 |
| chr16: 29130999-33908890 | 633 | 4,777,892 | 3 | 4459273747_R01C02 | rs12922496 |
| chr16: 29130999-33908890 | 633 | 4,777,892 | 3 | 4459273747_R01C02 | rs12922496 |
| chr8: 103058601-103060237 | 3 | 1,637 | 1 | 4457235104_R01C02 | rs6991144 |
| chr11: 88533414-88533632 | 3 | 219 | 3 | 4457235487_R02C01 | rs10501688 |
| chr3: 171282951-171286713 | 3 | 3,763 | 1 | 4457235408_R02C02 | rs360418 |
| chr10: 46961667-47748912 | 104 | 787,246 | 3 | 4461875785_R02C01 | rs506372 |
| chr13: 34141695-34143447 | 3 | 1,753 | 0 | 4457235212_R01C02 | cnvi0006685 |
| chr12: 2245636-2252924 | 7 | 7,289 | 1 | 4461875785_R02C02 | rs12579529 |
| chr13: 34141695-34143447 | 3 | 1,753 | 1 | 4461875785_R02C02 | cnvi0006685 |
| chr18: 58267843-58294706 | 6 | 26,864 | 3 | 4461875707_R01C01 | rs7240781 |
| chr13: 34141695-34143447 | 3 | 1,753 | 1 | 4461875707_R02C01 | cnvi0006685 |
| chr17: 64287309-64288738 | 4 | 1,430 | 1 | 4461875621_R01C02 | cnvi0008597 |
| chr13: 34141695-34143447 | 3 | 1,753 | 1 | 4461875801_R02C02 | cnvi0006685 |
| chr5: 140227999-140232346 | 3 | 4,348 | 1 | 4461875801_R02C02 | rs4151689 |
| chr2: 227343513-227346034 | 3 | 2,522 | 1 | 4461875801_R02C02 | rs13389027 |
| chr13: 34141695-34143447 | 3 | 1,753 | 1 | 4459273694_R02C02 | cnvi0006685 |
| chr10: 46961667-47121726 | 11 | 160,060 | 3 | 4432265374_R01C02 | rs506372 |
| chr3: 171220708-171220919 | 3 | 212 | 1 | 4482537179_R02C02 | cnvi0011707 |
| chr12: 124950060-124957153 | 6 | 7,094 | 3 | 4461875732_R01C01 | rs3782281 |
| chr10: 53271054-53295318 | 9 | 24,265 | 1 | 4461875732_R01C01 | rs10762182 |
| chr5: 140227999-140232346 | 3 | 4,348 | 1 | 4461875833_R02C02 | rs4151689 |
| chr6: 31219869-31228460 | 12 | 8,592 | 1 | 4461875783_R02C02 | rs9264179 |
| chr10: 46961667-47748912 | 104 | 787,246 | 3 | 4459273323_R02C01 | rs506372 |
| chr17: 64287309-64288738 | 4 | 1,430 | 1 | 4459273323_R01C02 | cnvi0008597 |
| chr2: 49626781-49646785 | 12 | 20,005 | 1 | 4457235047_R02C02 | rs817038 |

| Chr: Start-Stop(hg19) | EndSNP | Confidence | Distance FromGene | SecondaryID | mGluR gene |
|---|---|---|---|---|---|
| chr9: 93519280-93529807 | rs1172990 | 5.15 | 34205 | PF003657 211 | SYK |
| chr17: 44458950-66154676 | rs7222649 | 41.043 | 0 | PF003669 211 | ABI3 |
| chr17: 44458950-66154676 | rs7222649 | 41.043 | 0 | PF003669 211 | CBX1 |
| chr17: 44458950-66154676 | rs7222649 | 41.043 | 0 | PF003669 211 | COIL |
| chr17: 44458950-66154676 | rs7222649 | 41.043 | 0 | PF003669 211 | DDX5 |
| chr17: 44458950-66154676 | rs7222649 | 41.043 | 0 | PF003669 211 | GH1 |
| chr17: 44458950-66154676 | rs7222649 | 41.043 | 0 | PF003669 211 | LOC400604 |
| chr17: 44458950-66154676 | rs7222649 | 41.043 | 0 | PF003669 211 | LRRC59 |
| chr17: 44458950-66154676 | rs7222649 | 41.043 | 0 | PF003669 211 | MAP3K3 |
| chr17: 44458950-66154676 | rs7222649 | 41.043 | 0 | PF003669 211 | PRKCA |
| chr7: 85686982-85727083 | cnvi0001222 | 24.872 | 546147 | PF003677 211 | GRM3 |
| chr17: 64287309-64288738 | cnvi0008599 | 17.315 | 10188 | PF003694 211 | PRKCA |
| chr13: 34141695-34143447 | rs9285097 | 13.365 | 0 | PF003694 211 | STARD13 |

TABLE 4-continued

| | | | | | |
|---|---|---|---|---|---|
| chr5: 1257259-1276121 | cnvi0012572 | 13.298 | 0 | PF003702 216 | TERT |
| chr6: 31787630-31795082 | rs5026931 | 17.679 | 430 | PF003711 211 | HSPA1B |
| chr19: 53514604-55326739 | rs581623 | 45.845 | 0 | PF003734 211 | PRKCG |
| chr4: 72656076-72678078 | rs7660070 | 13.603 | 0 | PF003738 211 | GC |
| chr5: 1272500-1276121 | cnvi0012572 | 14.792 | 0 | PF003738 211 | TERT |
| chr2: 227343513-227346034 | rs931725 | 13.829 | 249999 | PF003738 211 | IRS1 |
| chr6: 32519005-69913177 | rs3799055 | 55.338 | 0 | PF003738 211 | DST |
| chr6: 32519005-69913177 | rs3799055 | 55.338 | 0 | PF003738 211 | GLP1R |
| chr6: 32519005-69913177 | rs3799055 | 55.338 | 0 | PF003738 211 | GRM4 |
| chr6: 32519005-69913177 | rs3799055 | 55.338 | 0 | PF003738 211 | HLA-DQA2 |
| chr6: 32519005-69913177 | rs3799055 | 55.338 | 0 | PF003738 211 | HSP90AB1 |
| chr6: 32519005-69913177 | rs3799055 | 55.338 | 0 | PF003738 211 | ITPR3 |
| chr6: 32519005-69913177 | rs3799055 | 55.338 | 0 | PF003738 211 | MAD2L1BP |
| chr6: 32519005-69913177 | rs3799055 | 55.338 | 0 | PF003738 211 | MAPK14 |
| chr6: 32519005-69913177 | rs3799055 | 55.338 | 0 | PF003738 211 | MRPL14 |
| chr6: 32519005-69913177 | rs3799055 | 55.338 | 0 | PF003738 211 | NFKBIE |
| chr6: 32519005-69913177 | rs3799055 | 55.338 | 0 | PF003738 211 | PLA2G7 |
| chr6: 32519005-69913177 | rs3799055 | 55.338 | 0 | PF003738 211 | PTP4A1 |
| chr6: 32519005-69913177 | rs3799055 | 55.338 | 0 | PF003738 211 | TEAD3 |
| chr6: 32519005-69913177 | rs3799055 | 55.338 | 0 | PF003738 211 | TTBK1 |
| chr2: 227343513-227346034 | rs931725 | 13.874 | 249999 | PF003755 211 | IRS1 |
| chr6: 31221039-31221914 | rs9264219 | 15.631 | 14612 | PF003795 211 | HLA-C |
| chr12: 2245636-2252924 | rs4765899 | 14.02 | 0 | PF003821 211 | CACNA1C |
| chr10: 112846298-112859699 | rs7084501 | 15.614 | 5636 | PF003867 211 | ADRA2A |
| chr17: 44424726-66163795 | rs8078240 | 71.866 | 0 | PF003876 211 | ABI3 |
| chr17: 44424726-66163795 | rs8078240 | 71.866 | 0 | PF003876 211 | CBX1 |
| chr17: 44424726-66163795 | rs8078240 | 71.866 | 0 | PF003876 211 | COIL |
| chr17: 44424726-66163795 | rs8078240 | 71.866 | 0 | PF003876 211 | DDX5 |
| chr17: 44424726-66163795 | rs8078240 | 71.866 | 0 | PF003876 211 | GH1 |
| chr17: 44424726-66163795 | rs8078240 | 71.866 | 0 | PF003876 211 | LOC400604 |
| chr17: 44424726-66163795 | rs8078240 | 71.866 | 0 | PF003876 211 | LRRC59 |
| chr17: 44424726-66163795 | rs8078240 | 71.866 | 0 | PF003876 211 | MAP3K3 |
| chr17: 44424726-66163795 | rs8078240 | 71.866 | 0 | PF003876 211 | PRKCA |
| chr4: 72592214-72601331 | rs12512631 | 17.222 | 6080 | PF003922 211 | GC |
| chr19: 43474699-55343606 | rs34177062 | 33.082 | 0 | PF003933 211 | CALM3 |
| chr19: 43474699-55343606 | rs34177062 | 33.082 | 0 | PF003933 211 | ETHE1 |
| chr19: 43474699-55343606 | rs34177062 | 33.082 | 0 | PF003933 211 | FPR1 |
| chr19: 43474699-55343606 | rs34177062 | 33.082 | 0 | PF003933 211 | KCNN4 |
| chr19: 43474699-55343606 | rs34177062 | 33.082 | 0 | PF003933 211 | KLK10 |
| chr19: 43474699-55343606 | rs34177062 | 33.082 | 0 | PF003933 211 | MARK4 |
| chr19: 43474699-55343606 | rs34177062 | 33.082 | 0 | PF003933 211 | NUCB1 |
| chr19: 43474699-55343606 | rs34177062 | 33.082 | 0 | PF003933 211 | PLEKHA4 |
| chr19: 43474699-55343606 | rs34177062 | 33.082 | 0 | PF003933 211 | PPP2R1A |
| chr19: 43474699-55343606 | rs34177062 | 33.082 | 0 | PF003933 211 | PRKCG |
| chr19: 43474699-55343606 | rs34177062 | 33.082 | 0 | PF003933 211 | PRMT1 |
| chr19: 43474699-55343606 | rs34177062 | 33.082 | 0 | PF003933 211 | PSG9 |
| chr19: 43474699-55343606 | rs34177062 | 33.082 | 0 | PF003933 211 | PTGIR |
| chr19: 43474699-55343606 | rs34177062 | 33.082 | 0 | PF003933 211 | RELB |
| chr19: 43474699-55343606 | rs34177062 | 33.082 | 0 | PF003933 211 | RUVBL2 |
| chr19: 43474699-55343606 | rs34177062 | 33.082 | 0 | PF003933 211 | SHANK1 |
| chr19: 43474699-55343606 | rs34177062 | 33.082 | 0 | PF003933 211 | STRN4 |
| chr5: 1272500-1276121 | cnvi0012572 | 13.506 | 0 | PF003938 211 | TERT |
| chr5: 1257259-1276121 | cnvi0012572 | 14.763 | 0 | PF003963 211 | TERT |
| chr6: 32519005-124471337 | rs2008708 | 32.455 | 0 | PF003967 211 | CNR1 |
| chr6: 32519005-124471337 | rs2008708 | 32.455 | 0 | PF003967 211 | DST |
| chr6: 32519005-124471337 | rs2008708 | 32.455 | 0 | PF003967 211 | FYN |
| chr6: 32519005-124471337 | rs2008708 | 32.455 | 0 | PF003967 211 | GABRR1 |
| chr6: 32519005-124471337 | rs2008708 | 32.455 | 0 | PF003967 211 | GABRR2 |
| chr6: 32519005-124471337 | rs2008708 | 32.455 | 0 | PF003967 211 | GJA1 |
| chr6: 32519005-124471337 | rs2008708 | 32.455 | 0 | PF003967 211 | GLP1R |
| chr6: 32519005-124471337 | rs2008708 | 32.455 | 0 | PF003967 211 | GRM4 |
| chr6: 32519005-124471337 | rs2008708 | 32.455 | 0 | PF003967 211 | HLA-DQA2 |
| chr6: 32519005-124471337 | rs2008708 | 32.455 | 0 | PF003967 211 | HSP90AB1 |
| chr6: 32519005-124471337 | rs2008708 | 32.455 | 0 | PF003967 211 | ITPR3 |
| chr6: 32519005-124471337 | rs2008708 | 32.455 | 0 | PF003967 211 | KCNQ5 |
| chr6: 32519005-124471337 | rs2008708 | 32.455 | 0 | PF003967 211 | LAMA4 |
| chr6: 32519005-124471337 | rs2008708 | 32.455 | 0 | PF003967 211 | MAD2L1BP |
| chr6: 32519005-124471337 | rs2008708 | 32.455 | 0 | PF003967 211 | MAP3K7 |
| chr6: 32519005-124471337 | rs2008708 | 32.455 | 0 | PF003967 211 | MAPK14 |
| chr6: 32519005-124471337 | rs2008708 | 32.455 | 0 | PF003967 211 | MARCKS |
| chr6: 32519005-124471337 | rs2008708 | 32.455 | 0 | PF003967 211 | MRPL14 |
| chr6: 32519005-124471337 | rs2008708 | 32.455 | 0 | PF003967 211 | MYO6 |
| chr6: 32519005-124471337 | rs2008708 | 32.455 | 0 | PF003967 211 | NFKBIE |
| chr6: 32519005-124471337 | rs2008708 | 32.455 | 0 | PF003967 211 | PLA2G7 |
| chr6: 32519005-124471337 | rs2008708 | 32.455 | 0 | PF003967 211 | PTP4A1 |
| chr6: 32519005-124471337 | rs2008708 | 32.455 | 0 | PF003967 211 | SNAP91 |
| chr6: 32519005-124471337 | rs2008708 | 32.455 | 0 | PF003967 211 | TEAD3 |
| chr6: 32519005-124471337 | rs2008708 | 32.455 | 0 | PF003967 211 | TTBK1 |
| chr6: 32519005-124471337 | rs2008708 | 32.455 | 0 | PF003967 211 | TTK |
| chr5: 1272500-1276121 | cnvi0012572 | 10.89 | 0 | PF003967 211 | TERT |

TABLE 4-continued

| | | | | | | |
|---|---|---|---|---|---|---|
| chr11: 60823434-60860889 | rs440879 | 31.476 | 9041 | PF003998 | 211 | CD5 |
| chr12: 2245636-2252924 | rs4765899 | 11.664 | 0 | PF004005 | 211 | CACNA1C |
| chr5: 1257259-1276121 | cnvi0012572 | 14.953 | 0 | PF004009 | 211 | TERT |
| chr9: 140911199-140913833 | cnvi0002661 | 11.53 | 0 | PF004036 | 211 | CACNA1B |
| chr9: 139607966-140266929 | rs9775457 | 30.034 | 0 | PF004074 | 211 | EDF1 |
| chr9: 139607966-140266929 | rs9775457 | 30.034 | 0 | PF004074 | 211 | GRIN1 |
| chr9: 139607966-140266929 | rs9775457 | 30.034 | 0 | PF004074 | 211 | TRAF2 |
| chr19: 1107035-2141209 | rs3786971 | 41.337 | 0 | PF004074 | 211 | BTBD2 |
| chr19: 1107035-2141209 | rs3786971 | 41.337 | 0 | PF004074 | 211 | TCF3 |
| chr19: 18201757-18395537 | rs4254438 | 25.765 | 0 | PF004074 | 211 | KIAA1683 |
| chr3: 196793858-196910082 | rs9861658 | 18.526 | 0 | PF004134 | 211 | DLG1 |
| chr5: 132036252-132043351 | rs17691077 | 11.478 | 0 | PF004134 | 211 | KIF3A |
| chr1: 191772972-191788524 | rs17402518 | 14.538 | 339068 | PF004134 | 211 | RGS18 |
| chr19: 1238899-2080051 | rs7256023 | 39.442 | 0 | PF004134 | 211 | BTBD2 |
| chr19: 1238899-2080051 | rs7256023 | 39.442 | 0 | PF004134 | 211 | TCF3 |
| chr5: 140227999-140232346 | rs17119246 | 9.075 | 0 | PF004171 | 211 | PCDHA4 |
| chr13: 31646976-31652085 | rs4943078 | 7.623 | 58678 | PF004225 | 211 | HSPH1 |
| chr6: 31219869-31221914 | rs9264219 | 14.638 | 14612 | PF004245 | 211 | HLA-C |
| chr2: 227343513-227346034 | rs931725 | 15.621 | 249999 | PF004245 | 211 | IRS1 |
| chr17: 1238054-1244992 | rs11650689 | 20.012 | 2842 | PF004245 | 211 | YWHAE |
| chr6: 10469826-32519005 | rs28490179 | 115.653 | 0 | PF004451 | 211 | ATXN1 |
| chr6: 10469826-32519005 | rs28490179 | 115.653 | 0 | PF004451 | 211 | CSNK2B |
| chr6: 10469826-32519005 | rs28490179 | 115.653 | 0 | PF004451 | 211 | HLA-A |
| chr6: 10469826-32519005 | rs28490179 | 115.653 | 0 | PF004451 | 211 | HLA-C |
| chr6: 10469826-32519005 | rs28490179 | 115.653 | 0 | PF004451 | 211 | HSPA1A |
| chr6: 10469826-32519005 | rs28490179 | 115.653 | 0 | PF004451 | 211 | HSPA1B |
| chr6: 10469826-32519005 | rs28490179 | 115.653 | 0 | PF004451 | 211 | LTA |
| chr6: 10469826-32519005 | rs28490179 | 115.653 | 0 | PF004451 | 211 | SOX4 |
| chr6: 10469826-32519005 | rs28490179 | 115.653 | 0 | PF004451 | 211 | TUBB |
| chr2: 227343513-227346034 | rs931725 | 14.021 | 249999 | PF004451 | 211 | IRS1 |
| chr1: 236290705-238013174 | rs16835926 | 389.691 | 0 | PF004504 | 211 | ACTN2 |
| chr3: 171220708-171220919 | cnvi0011705 | 11.626 | 42511 | PF004516 | 211 | TNIK |
| chr6: 31281438-32514144 | rs34369284 | 56.754 | 0 | PF004531 | 211 | CSNK2B |
| chr6: 31281438-32514144 | rs34369284 | 56.754 | 0 | PF004531 | 211 | HSPA1A |
| chr6: 31281438-32514144 | rs34369284 | 56.754 | 0 | PF004531 | 211 | HSPA1B |
| chr6: 31281438-32514144 | rs34369284 | 56.754 | 0 | PF004531 | 211 | LTA |
| chr21: 37410477-37415603 | rs2835244 | 10.902 | 0 | PF004534 | 211 | SETD4 |
| chr19: 43474699-55343606 | rs34177062 | 28.815 | 0 | PF004534 | 211 | CALM3 |
| chr19: 43474699-55343606 | rs34177062 | 28.815 | 0 | PF004534 | 211 | ETHE1 |
| chr19: 43474699-55343606 | rs34177062 | 28.815 | 0 | PF004534 | 211 | FPR1 |
| chr19: 43474699-55343606 | rs34177062 | 28.815 | 0 | PF004534 | 211 | KCNN4 |
| chr19: 43474699-55343606 | rs34177062 | 28.815 | 0 | PF004534 | 211 | KLK10 |
| chr19: 43474699-55343606 | rs34177062 | 28.815 | 0 | PF004534 | 211 | MARK4 |
| chr19: 43474699-55343606 | rs34177062 | 28.815 | 0 | PF004534 | 211 | NUCB1 |
| chr19: 43474699-55343606 | rs34177062 | 28.815 | 0 | PF004534 | 211 | PLEKHA4 |
| chr19: 43474699-55343606 | rs34177062 | 28.815 | 0 | PF004534 | 211 | PPP2R1A |
| chr19: 43474699-55343606 | rs34177062 | 28.815 | 0 | PF004534 | 211 | PRKCG |
| chr19: 43474699-55343606 | rs34177062 | 28.815 | 0 | PF004534 | 211 | PRMT1 |
| chr19: 43474699-55343606 | rs34177062 | 28.815 | 0 | PF004534 | 211 | PSG9 |
| chr19: 43474699-55343606 | rs34177062 | 28.815 | 0 | PF004534 | 211 | PTGIR |
| chr19: 43474699-55343606 | rs34177062 | 28.815 | 0 | PF004534 | 211 | RELB |
| chr19: 43474699-55343606 | rs34177062 | 28.815 | 0 | PF004534 | 211 | RUVBL2 |
| chr19: 43474699-55343606 | rs34177062 | 28.815 | 0 | PF004534 | 211 | SHANK1 |
| chr19: 43474699-55343606 | rs34177062 | 28.815 | 0 | PF004534 | 211 | STRN4 |
| chr11: 88376801-88379332 | rs11020772 | 16.464 | 0 | PF004540 | 211 | GRM5 |
| chr10: 46769902-49047366 | cnvi0022253 | 23.58 | 0 | PF004540 | 211 | PPYR1 |
| chr6: 31785453-31795082 | rs5026931 | 40.534 | 0 | PF004540 | 211 | HSPA1A |
| chr16: 29130999-34607359 | rs2160315 | 36.497 | 0 | PF004547 | 211 | ALDOA |
| chr16: 29130999-34607359 | rs2160315 | 36.497 | 0 | PF004547 | 211 | MAPK3 |
| chr16: 29130999-34607359 | rs2160315 | 36.497 | 0 | PF004547 | 211 | PHKG2 |
| chr16: 29130999-34607359 | rs2160315 | 36.497 | 0 | PF004547 | 211 | STX4 |
| chr16: 29130999-34607359 | rs2160315 | 36.497 | 0 | PF004547 | 211 | TAOK2 |
| chr1: 19947256-20117992 | rs11589077 | 51.643 | 0 | PF004567 | 211 | HTR6 |
| chr10: 46961667-48137589 | cnvi0003730 | 32.978 | 0 | PF004569 | 211 | PPYR1 |
| chr3: 171220708-171220919 | cnvi0011705 | 10.836 | 42511 | PF004584 | 211 | TNIK |
| chr6: 25533534-31286381 | rs9265057 | 33.87 | 0 | PF004584 | 211 | HLA-A |
| chr6: 25533534-31286381 | rs9265057 | 33.87 | 0 | PF004584 | 211 | HLA-C |
| chr6: 25533534-31286381 | rs9265057 | 33.87 | 0 | PF004584 | 211 | TUBB |
| chr19: 18380072-18389135 | rs12608504 | 1.875 | 0 | PF004590 | 211 | KIAA1683 |
| chr3: 171220708-171220919 | cnvi0011705 | 8.695 | 42511 | PF004590 | 211 | TNIK |
| chr13: 34141695-34143447 | rs9285097 | 17.642 | 0 | PF004590 | 211 | STARD13 |
| chr12: 2245636-2252924 | rs4765899 | 11.504 | 0 | PF004594 | 211 | CACNA1C |
| chr13: 34141695-34143447 | rs9285097 | 14.76 | 0 | PF004605 | 211 | STARD13 |
| chr10: 45230151-47703613 | rs4128664 | 244.542 | 0 | PF004616 | 211 | PPYR1 |
| chr20: 8096130-8575671 | rs6039206 | 686.258 | 0 | PF004620 | 211 | PLCB1 |
| chr6: 31289284-32499014 | cnvi0006585 | 18.076 | 0 | PF004620 | 211 | CSNK2B |
| chr6: 31289284-32499014 | cnvi0006585 | 18.076 | 0 | PF004620 | 211 | HSPA1A |
| chr6: 31289284-32499014 | cnvi0006585 | 18.076 | 0 | PF004620 | 211 | HSPA1B |
| chr6: 31289284-32499014 | cnvi0006585 | 18.076 | 0 | PF004620 | 211 | LTA |
| chr13: 34141695-34143447 | rs9285097 | 14.594 | 0 | PF004718 | 211 | STARD13 |

TABLE 4-continued

| | | | | | |
|---|---|---|---|---|---|
| chr17: 76173423-76263906 | rs6501186 | 82.909 | 0 | PF004732 211 | TK1 |
| chr4: 101754170-101777382 | rs4698868 | 14.738 | 167205 | PF004742 211 | PPP3CA |
| chr13: 34141695-34143447 | rs9285097 | 13.991 | 0 | PF004772 211 | STARD13 |
| chr6: 31275174-32499014 | cnvi0006585 | 34.737 | 0 | PF004772 211 | CSNK2B |
| chr6: 31275174-32499014 | cnvi0006585 | 34.737 | 0 | PF004772 211 | HSPA1A |
| chr6: 31275174-32499014 | cnvi0006585 | 34.737 | 0 | PF004772 211 | HSPA1B |
| chr6: 31275174-32499014 | cnvi0006585 | 34.737 | 0 | PF004772 211 | LTA |
| chr5: 140227999-140232346 | rs17119246 | 14.236 | 0 | PF004777 211 | PCDHA4 |
| chr13: 34141695-34143447 | rs9285097 | 13.354 | 0 | PF005542 211 | STARD13 |
| chr12: 2245636-2250396 | cnvi0005446 | 13.297 | 0 | PF005542 211 | CACNA1C |
| chr17: 32386209-32392346 | rs12602886 | 0 | 0 | PF005550 211 | ACCN1 |
| chr8: 97219690-97510132 | rs13270556 | 101.44 | 0 | PF005565 211 | SDC2 |
| chr6: 31228460-31230701 | rs2394950 | 10.797 | 5825 | PF005657 211 | HLA-C |
| chr10: 46961667-48137589 | cnvi0003730 | 28.011 | 0 | PF005840 211 | PPYR1 |
| chr5: 140227999-140232346 | rs17119246 | 13.306 | 0 | PF005948 211 | PCDHA4 |
| chr13: 34141695-34143447 | rs9285097 | 14.615 | 0 | PF005964 211 | STARD13 |
| chr13: 34141695-34143447 | rs9285097 | 15.493 | 0 | PF006310 211 | STARD13 |
| chr3: 7110195-7120529 | rs9848973 | 21.088 | 0 | PF006741 211 | GRM7 |
| chr13: 34141695-34143447 | rs9285097 | 16.961 | 0 | PF007444 211 | STARD13 |
| chr6: 31785453-31795082 | rs5026931 | 26.462 | 0 | PF007738 211 | HSPA1A |
| chr5: 759485-1276121 | cnvi0012572 | 158.07 | 0 | PF007738 211 | TERT |
| chr5: 1257259-1276121 | cnvi0012572 | 13.877 | 0 | PF007798 211 | TERT |
| chr12: 2245636-2252924 | rs4765899 | 16.252 | 0 | PF007864 211 | CACNA1C |
| chr3: 171220708-171220919 | cnvi0011705 | 12.855 | 42511 | PF007905 211 | TNIK |
| chr6: 31289284-32514144 | rs34369284 | 29.144 | 0 | PF007954 211 | CSNK2B |
| chr6: 31289284-32514144 | rs34369284 | 29.144 | 0 | PF007954 211 | HSPA1A |
| chr6: 31289284-32514144 | rs34369284 | 29.144 | 0 | PF007954 211 | HSPA1B |
| chr6: 31289284-32514144 | rs34369284 | 29.144 | 0 | PF007954 211 | LTA |
| chr5: 140227999-140232346 | rs17119246 | 14.092 | 0 | PF007963 211 | PCDHA4 |
| chr10: 46961667-47703613 | rs4128664 | 154.459 | 0 | PF008010 211 | PPYR1 |
| chr12: 2247179-2252924 | rs4765899 | 12.541 | 0 | PF008011 211 | CACNA1C |
| chr5: 140227999-140232346 | rs17119246 | 9.436 | 0 | PF008015 211 | PCDHA4 |
| chr16: 82196808-82213799 | rs7205603 | 23.631 | 0 | PF008020 211 | MPHOSPH6 |
| chr6: 31219869-31221914 | rs9264219 | 17.317 | 14612 | PF008022 211 | HLA-C |
| chr17: 64287309-64288738 | cnvi0008599 | 15.108 | 10188 | PF008029 211 | PRKCA |
| chr6: 31787630-31795082 | rs5026931 | 29.099 | 430 | PF008040 211 | HSPA1B |
| chr4: 113985926-113987369 | rs11726017 | 16.116 | 0 | PF008040 211 | ANK2 |
| chr11: 88376801-88379332 | rs11020772 | 14.102 | 0 | PF008070 204 | GRM5 |
| chr6: 31277740-32525688 | rs28656080 | 32.872 | 0 | PF008074 204 | CSNK2B |
| chr6: 31277740-32525688 | rs28656080 | 32.872 | 0 | PF008074 204 | HSPA1A |
| chr6: 31277740-32525688 | rs28656080 | 32.872 | 0 | PF008074 204 | HSPA1B |
| chr6: 31277740-32525688 | rs28656080 | 32.872 | 0 | PF008074 204 | LTA |
| chr18: 77948335-77997052 | rs4398161 | 23.981 | 0 | PF008084 204 | PARD6G |
| chr3: 171220708-171220919 | cnvi0011705 | 6.795 | 42511 | PF008084 204 | TNIK |
| chr12: 2245636-2252924 | rs4765899 | 11.264 | 0 | PF008092 204 | CACNA1C |
| chr11: 88557991-88565086 | rs11021512 | 15.042 | 0 | PF008102 204 | GRM5 |
| chr17: 64287309-64295688 | rs12150089 | 16.812 | 3238 | PF008166 204 | PRKCA |
| chr6: 31787630-31795082 | rs5026931 | 20.914 | 430 | PF008171 204 | HSPA1B |
| chr3: 171220708-171220919 | cnvi0011705 | 13.234 | 42511 | PF008179 204 | TNIK |
| chr1: 37532771-37538771 | rs218419 | 17.253 | 32927 | PF008181 204 | GRIK3 |
| chr10: 46961667-47697026 | rs4466762 | 124.908 | 0 | PF008191 204 | PPYR1 |
| chr17: 64287309-64288738 | cnvi0008599 | 16.248 | 10188 | PF008212 204 | PRKCA |
| chr5: 1257259-1276121 | cnvi0012572 | 16.104 | 0 | PF008212 204 | TERT |
| chr3: 121914706-121918491 | rs1814740 | 12.055 | 0 | PF008212 204 | CASR |
| chr18: 58267843-58310343 | rs1346831 | 30.808 | 227842 | PF008241 204 | MC4R |
| chr12: 124970066-125265636 | rs701106 | 186.188 | 0 | PF008245 204 | NCOR2 |
| chr5: 140199039-140232346 | rs17119246 | 23.559 | 0 | PF008245 204 | PCDHA4 |
| chr9: 139487092-140913833 | cnvi0002661 | 44.554 | 0 | PF008245 204 | CACNA1B |
| chr9: 139487092-140913833 | cnvi0002661 | 44.554 | 0 | PF008245 204 | EDF1 |
| chr9: 139487092-140913833 | cnvi0002661 | 44.554 | 0 | PF008245 204 | GRIN1 |
| chr9: 139487092-140913833 | cnvi0002661 | 44.554 | 0 | PF008245 204 | TRAF2 |
| chr5: 140227999-140232346 | rs17119246 | 11.751 | 0 | PF008245 204 | PCDHA4 |
| chr19: 17278979-17283942 | rs4570995 | 20.866 | 0 | PF008250 204 | MYO9B |
| chr5: 69593713-70636542 | cnvi0017338 | 28.451 | 0 | PF008250 204 | SMN2 |
| chr19: 730235-33902809 | rs754986 | 25.776 | 0 | PF008263 204 | ANKRD24 |
| chr19: 730235-33902809 | rs754986 | 25.776 | 0 | PF008263 204 | BTBD2 |
| chr19: 730235-33902809 | rs754986 | 25.776 | 0 | PF008263 204 | CCNE1 |
| chr19: 730235-33902809 | rs754986 | 25.776 | 0 | PF008263 204 | CNN1 |
| chr19: 730235-33902809 | rs754986 | 25.776 | 0 | PF008263 204 | DAPK3 |
| chr19: 730235-33902809 | rs754986 | 25.776 | 0 | PF008263 204 | EEF2 |
| chr19: 730235-33902809 | rs754986 | 25.776 | 0 | PF008263 204 | F2RL3 |
| chr19: 730235-33902809 | rs754986 | 25.776 | 0 | PF008263 204 | GNA15 |
| chr19: 730235-33902809 | rs754986 | 25.776 | 0 | PF008263 204 | HOMER3 |
| chr19: 730235-33902809 | rs754986 | 25.776 | 0 | PF008263 204 | INSR |
| chr19: 730235-33902809 | rs754986 | 25.776 | 0 | PF008263 204 | KIAA1683 |
| chr19: 730235-33902809 | rs754986 | 25.776 | 0 | PF008263 204 | MYO9B |
| chr19: 730235-33902809 | rs754986 | 25.776 | 0 | PF008263 204 | PDCD5 |
| chr19: 730235-33902809 | rs754986 | 25.776 | 0 | PF008263 204 | PIAS4 |
| chr19: 730235-33902809 | rs754986 | 25.776 | 0 | PF008263 204 | PRKACA |
| chr19: 730235-33902809 | rs754986 | 25.776 | 0 | PF008263 204 | PTPRS |

TABLE 4-continued

| | | | | | | |
|---|---|---|---|---|---|---|
| chr19: 730235-33902809 | rs754986 | 25.776 | 0 | PF008263 | 204 | TBXA2R |
| chr19: 730235-33902809 | rs754986 | 25.776 | 0 | PF008263 | 204 | TCF3 |
| chr19: 730235-33902809 | rs754986 | 25.776 | 0 | PF008263 | 204 | VAV1 |
| chr5: 140178042-140631925 | rs2910337 | 44.436 | 0 | PF008263 | 204 | PCDHA4 |
| chr21: 46313141-46320283 | rs35013643 | 15.67 | 0 | PF008263 | 204 | ITGB2 |
| chr21: 46944113-47591770 | rs2839133 | 50.845 | 0 | PF008263 | 204 | PCBP3 |
| chr1: 1152631-6456472 | rs7524775 | 60.994 | 0 | PF008263 | 204 | DVL1 |
| chr1: 1152631-6456472 | rs7524775 | 60.994 | 0 | PF008263 | 204 | PRKCZ |
| chr1: 1152631-6456472 | rs7524775 | 60.994 | 0 | PF008263 | 204 | TNFRSF14 |
| chr17: 80007887-81047708 | rs35680231 | 25.833 | 0 | PF008263 | 204 | TBCD |
| chr8: 144550160-145558541 | cnvi0002166 | 44.664 | 0 | PF008263 | 204 | EEF1D |
| chr11: 406483-2050558 | rs7940766 | 34.896 | 0 | PF008263 | 204 | RPLP2 |
| chr11: 406483-2050558 | rs7940766 | 34.896 | 0 | PF008263 | 204 | TNNI2 |
| chr9: 139492789-140222311 | cnvi0015766 | 64.736 | 0 | PF008263 | 204 | EDF1 |
| chr9: 139492789-140222311 | cnvi0015766 | 64.736 | 0 | PF008263 | 204 | GRIN1 |
| chr9: 139492789-140222311 | cnvi0015766 | 64.736 | 0 | PF008263 | 204 | TRAF2 |
| chr17: 64287309-64288738 | cnvi0008599 | 15.94 | 10188 | PF008275 | 204 | PRKCA |
| chr5: 1272500-1276121 | cnvi0012572 | 12.973 | 0 | PF008275 | 204 | TERT |
| chr6: 31285292-32499014 | cnvi0006585 | 38.035 | 0 | PF008275 | 204 | CSNK2B |
| chr6: 31285292-32499014 | cnvi0006585 | 38.035 | 0 | PF008275 | 204 | HSPA1A |
| chr6: 31285292-32499014 | cnvi0006585 | 38.035 | 0 | PF008275 | 204 | HSPA1B |
| chr6: 31285292-32499014 | cnvi0006585 | 38.035 | 0 | PF008275 | 204 | LTA |
| chr5: 1257259-1276121 | cnvi0012572 | 6.92 | 0 | PF008276 | 204 | TERT |
| chr6: 31204008-31218984 | rs3130427 | 15.726 | 17542 | PF008276 | 204 | HLA-C |
| chr5: 140178042-140261677 | rs59479 | 23.157 | 0 | PF008278 | 204 | PCDHA4 |
| chr7: 134436060-134561819 | rs10488465 | 113.013 | 0 | PF008278 | 204 | CALD1 |
| chr6: 1171596-29892436 | rs9259806 | 57.331 | 0 | PF008278 | 204 | ATXN1 |
| chr6: 1171596-29892436 | rs9259806 | 57.331 | 0 | PF008278 | 204 | RIPK1 |
| chr6: 1171596-29892436 | rs9259806 | 57.331 | 0 | PF008278 | 204 | SERPINB9 |
| chr6: 1171596-29892436 | rs9259806 | 57.331 | 0 | PF008278 | 204 | SOX4 |
| chr1: 1106473-10714911 | rs2242287 | 81.91 | 0 | PF008280 | 206 | DVL1 |
| chr1: 1106473-10714911 | rs2242287 | 81.91 | 0 | PF008280 | 206 | PRKCZ |
| chr1: 1106473-10714911 | rs2242287 | 81.91 | 0 | PF008280 | 206 | TNFRSF14 |
| chr16: 88872229-89587871 | rs4785686 | 25.539 | 0 | PF008280 | 206 | SPG7 |
| chr9: 138603740-140382705 | rs11137287 | 90.417 | 0 | PF008280 | 206 | EDF1 |
| chr9: 138603740-140382705 | rs11137287 | 90.417 | 0 | PF008280 | 206 | GRIN1 |
| chr9: 138603740-140382705 | rs11137287 | 90.417 | 0 | PF008280 | 206 | TRAF2 |
| chr21: 46889666-47591770 | rs2839133 | 44.285 | 0 | PF008280 | 206 | PCBP3 |
| chr19: 411849-55606101 | rs34972456 | 27.671 | 0 | PF008280 | 206 | ANKRD24 |
| chr19: 411849-55606101 | rs34972456 | 27.671 | 0 | PF008280 | 206 | ARHGEF1 |
| chr19: 411849-55606101 | rs34972456 | 27.671 | 0 | PF008280 | 206 | BTBD2 |
| chr19: 411849-55606101 | rs34972456 | 27.671 | 0 | PF008280 | 206 | CALM3 |
| chr19: 411849-55606101 | rs34972456 | 27.671 | 0 | PF008280 | 206 | CCNE1 |
| chr19: 411849-55606101 | rs34972456 | 27.671 | 0 | PF008280 | 206 | CIC |
| chr19: 411849-55606101 | rs34972456 | 27.671 | 0 | PF008280 | 206 | CNN1 |
| chr19: 411849-55606101 | rs34972456 | 27.671 | 0 | PF008280 | 206 | DAPK3 |
| chr19: 411849-55606101 | rs34972456 | 27.671 | 0 | PF008280 | 206 | EEF2 |
| chr19: 411849-55606101 | rs34972456 | 27.671 | 0 | PF008280 | 206 | ETHE1 |
| chr19: 411849-55606101 | rs34972456 | 27.671 | 0 | PF008280 | 206 | F2RL3 |
| chr19: 411849-55606101 | rs34972456 | 27.671 | 0 | PF008280 | 206 | FFAR1 |
| chr19: 411849-55606101 | rs34972456 | 27.671 | 0 | PF008280 | 206 | FFAR2 |
| chr19: 411849-55606101 | rs34972456 | 27.671 | 0 | PF008280 | 206 | FPR1 |
| chr19: 411849-55606101 | rs34972456 | 27.671 | 0 | PF008280 | 206 | GNA15 |
| chr19: 411849-55606101 | rs34972456 | 27.671 | 0 | PF008280 | 206 | GSK3A |
| chr19: 411849-55606101 | rs34972456 | 27.671 | 0 | PF008280 | 206 | HOMER3 |
| chr19: 411849-55606101 | rs34972456 | 27.671 | 0 | PF008280 | 206 | INSR |
| chr19: 411849-55606101 | rs34972456 | 27.671 | 0 | PF008280 | 206 | KCNN4 |
| chr19: 411849-55606101 | rs34972456 | 27.671 | 0 | PF008280 | 206 | KIAA1683 |
| chr19: 411849-55606101 | rs34972456 | 27.671 | 0 | PF008280 | 206 | KLK10 |
| chr19: 411849-55606101 | rs34972456 | 27.671 | 0 | PF008280 | 206 | MAP3K10 |
| chr19: 411849-55606101 | rs34972456 | 27.671 | 0 | PF008280 | 206 | MARK4 |
| chr19: 411849-55606101 | rs34972456 | 27.671 | 0 | PF008280 | 206 | MRPS12 |
| chr19: 411849-55606101 | rs34972456 | 27.671 | 0 | PF008280 | 206 | MYO9B |
| chr19: 411849-55606101 | rs34972456 | 27.671 | 0 | PF008280 | 206 | NFKBIB |
| chr19: 411849-55606101 | rs34972456 | 27.671 | 0 | PF008280 | 206 | NUCB1 |
| chr19: 411849-55606101 | rs34972456 | 27.671 | 0 | PF008280 | 206 | PAFAH1B3 |
| chr19: 411849-55606101 | rs34972456 | 27.671 | 0 | PF008280 | 206 | PDCD5 |
| chr19: 411849-55606101 | rs34972456 | 27.671 | 0 | PF008280 | 206 | PIAS4 |
| chr19: 411849-55606101 | rs34972456 | 27.671 | 0 | PF008280 | 206 | PLEKHA4 |
| chr19: 411849-55606101 | rs34972456 | 27.671 | 0 | PF008280 | 206 | PPP1R14A |
| chr19: 411849-55606101 | rs34972456 | 27.671 | 0 | PF008280 | 206 | PPP2R1A |
| chr19: 411849-55606101 | rs34972456 | 27.671 | 0 | PF008280 | 206 | PRKACA |
| chr19: 411849-55606101 | rs34972456 | 27.671 | 0 | PF008280 | 206 | PRKCG |
| chr19: 411849-55606101 | rs34972456 | 27.671 | 0 | PF008280 | 206 | PRMT1 |
| chr19: 411849-55606101 | rs34972456 | 27.671 | 0 | PF008280 | 206 | PSG9 |
| chr19: 411849-55606101 | rs34972456 | 27.671 | 0 | PF008280 | 206 | PTGIR |
| chr19: 411849-55606101 | rs34972456 | 27.671 | 0 | PF008280 | 206 | PTPRS |
| chr19: 411849-55606101 | rs34972456 | 27.671 | 0 | PF008280 | 206 | RABAC1 |
| chr19: 411849-55606101 | rs34972456 | 27.671 | 0 | PF008280 | 206 | RELB |
| chr19: 411849-55606101 | rs34972456 | 27.671 | 0 | PF008280 | 206 | RUVBL2 |

TABLE 4-continued

| | | | | | |
|---|---|---|---|---|---|
| chr19: 411849-55606101 | rs34972456 | 27.671 | 0 | PF008280 206 | RYR1 |
| chr19: 411849-55606101 | rs34972456 | 27.671 | 0 | PF008280 206 | SHANK1 |
| chr19: 411849-55606101 | rs34972456 | 27.671 | 0 | PF008280 206 | SIRT2 |
| chr19: 411849-55606101 | rs34972456 | 27.671 | 0 | PF008280 206 | STRN4 |
| chr19: 411849-55606101 | rs34972456 | 27.671 | 0 | PF008280 206 | TBXA2R |
| chr19: 411849-55606101 | rs34972456 | 27.671 | 0 | PF008280 206 | TCF3 |
| chr19: 411849-55606101 | rs34972456 | 27.671 | 0 | PF008280 206 | VAV1 |
| chr19: 411849-55606101 | rs34972456 | 27.671 | 0 | PF008280 206 | WDR62 |
| chr5: 179264731-179298770 | rs3857306 | 15.102 | 0 | PF008280 206 | SQSTM1 |
| chr2: 203300770-203419859 | rs17199235 | 15.385 | 0 | PF008280 206 | BMPR2 |
| chr14: 105170003-105695446 | rs2018404 | 62.926 | 0 | PF008280 206 | AKT1 |
| chr22: 30057820-30128380 | rs140101 | 32.313 | 0 | PF008280 206 | NF2 |
| chr12: 2215448-2227311 | rs4126711 | 8.631 | 0 | PF008280 206 | CACNA1C |
| chr17: 79132759-80758198 | rs868203 | 36.878 | 0 | PF008280 206 | PDE6G |
| chr17: 79132759-80758198 | rs868203 | 36.878 | 0 | PF008280 206 | TBCD |
| chr18: 77336478-77343164 | rs12605781 | 13.843 | 47155 | PF008280 206 | NFATC1 |
| chr8: 144508768-145818782 | rs11988651 | 34.306 | 0 | PF008280 206 | EEF1D |
| chr5: 1257259-1276121 | cnvi0012572 | 15.684 | 0 | PF008299 204 | TERT |
| chr7: 45620960-45626376 | rs4720512 | 13.58 | 0 | PF008299 204 | ADCY1 |
| chr17: 80016452-81047708 | rs35680231 | 27.528 | 0 | PF008299 204 | TBCD |
| chr9: 139395473-140913833 | cnvi0002661 | 25.969 | 0 | PF008299 204 | CACNA1B |
| chr9: 139395473-140913833 | cnvi0002661 | 25.969 | 0 | PF008299 204 | EDF1 |
| chr9: 139395473-140913833 | cnvi0002661 | 25.969 | 0 | PF008299 204 | GRIN1 |
| chr9: 139395473-140913833 | cnvi0002661 | 25.969 | 0 | PF008299 204 | TRAF2 |
| chr6: 88842154-88861698 | rs6928813 | 50.229 | 0 | PF008305 204 | CNR1 |
| chr6: 31785453-31795082 | rs5026931 | 25.66 | 0 | PF008310 204 | HSPA1A |
| chr17: 79375997-81031768 | rs8072895 | 20.145 | 0 | PF008315 204 | PDE6G |
| chr17: 79375997-81031768 | rs8072895 | 20.145 | 0 | PF008315 204 | TBCD |
| chr18: 77336478-77343164 | rs12605781 | 12.341 | 47155 | PF008315 204 | NFATC1 |
| chr6: 16392159-16400090 | rs3819400 | 21.995 | 0 | PF008323 204 | ATXN1 |
| chr9: 140911199-140913833 | cnvi0002661 | 13.206 | 0 | PF008323 204 | CACNA1B |
| chr10: 46961667-49059803 | rs4926101 | 31.638 | 0 | PF008338 204 | PPYR1 |
| chr5: 1272500-1276121 | cnvi0012572 | 13.134 | 0 | PF008345 204 | TERT |
| chr3: 171220708-171220919 | cnvi0011705 | 10.513 | 42511 | PF008351 204 | TNIK |
| chr21: 35783219-35904697 | rs7280739 | 102.338 | 0 | PF008358 204 | KCNE1 |
| chr4: 101754170-101768637 | rs2903222 | 15.021 | 175950 | PF008361 204 | PPP3CA |
| chr12: 2245636-2252924 | rs4765899 | 10.676 | 0 | PF008361 204 | CACNA1C |
| chr15: 43792097-43924682 | rs2920781 | 13.223 | 0 | PF008370 204 | MAP1A |
| chr6: 31219869-31221914 | rs9264219 | 15.394 | 14612 | PF008377 204 | HLA-C |
| chr1: 191749508-191755912 | rs833986 | 10.408 | 371680 | PF008385 204 | RGS18 |
| chr6: 31787630-31795082 | rs5026931 | 24.189 | 430 | PF008389 202 | HSPA1B |
| chr6: 31787630-31795082 | rs5026931 | 28.48 | 430 | PF008419 204 | HSPA1B |
| chr5: 140227999-140232346 | rs17119246 | 8.137 | 0 | PF008421 206 | PCDHA4 |
| chr13: 34141695-34143447 | rs9285097 | 14.572 | 0 | PF008421 206 | STARD13 |
| chr5: 140227999-140232346 | rs17119246 | 10.955 | 0 | PF008432 204 | PCDHA4 |
| chr4: 176470385-176491850 | rs11735559 | 15.417 | 62238 | PF008478 204 | GPM6A |
| chr19: 42012336-55294329 | rs2569676 | 25.419 | 0 | PF008486 204 | ARHGEF1 |
| chr19: 42012336-55294329 | rs2569676 | 25.419 | 0 | PF008486 204 | CALM3 |
| chr19: 42012336-55294329 | rs2569676 | 25.419 | 0 | PF008486 204 | CIC |
| chr19: 42012336-55294329 | rs2569676 | 25.419 | 0 | PF008486 204 | ETHE1 |
| chr19: 42012336-55294329 | rs2569676 | 25.419 | 0 | PF008486 204 | FPR1 |
| chr19: 42012336-55294329 | rs2569676 | 25.419 | 0 | PF008486 204 | GSK3A |
| chr19: 42012336-55294329 | rs2569676 | 25.419 | 0 | PF008486 204 | KCNN4 |
| chr19: 42012336-55294329 | rs2569676 | 25.419 | 0 | PF008486 204 | KLK10 |
| chr19: 42012336-55294329 | rs2569676 | 25.419 | 0 | PF008486 204 | MARK4 |
| chr19: 42012336-55294329 | rs2569676 | 25.419 | 0 | PF008486 204 | NUCB1 |
| chr19: 42012336-55294329 | rs2569676 | 25.419 | 0 | PF008486 204 | PAFAH1B3 |
| chr19: 42012336-55294329 | rs2569676 | 25.419 | 0 | PF008486 204 | PLEKHA4 |
| chr19: 42012336-55294329 | rs2569676 | 25.419 | 0 | PF008486 204 | PPP2R1A |
| chr19: 42012336-55294329 | rs2569676 | 25.419 | 0 | PF008486 204 | PRKCG |
| chr19: 42012336-55294329 | rs2569676 | 25.419 | 0 | PF008486 204 | PRMT1 |
| chr19: 42012336-55294329 | rs2569676 | 25.419 | 0 | PF008486 204 | PSG9 |
| chr19: 42012336-55294329 | rs2569676 | 25.419 | 0 | PF008486 204 | PTGIR |
| chr19: 42012336-55294329 | rs2569676 | 25.419 | 0 | PF008486 204 | RABAC1 |
| chr19: 42012336-55294329 | rs2569676 | 25.419 | 0 | PF008486 204 | RELB |
| chr19: 42012336-55294329 | rs2569676 | 25.419 | 0 | PF008486 204 | RUVBL2 |
| chr19: 42012336-55294329 | rs2569676 | 25.419 | 0 | PF008486 204 | SHANK1 |
| chr19: 42012336-55294329 | rs2569676 | 25.419 | 0 | PF008486 204 | STRN4 |
| chr9: 140039240-140135118 | rs28437704 | 17.986 | 0 | PF008506 204 | GRIN1 |
| chr7: 117229167-117235055 | rs1042077 | 17.113 | 0 | PF008506 204 | CFTR |
| chr5: 140097072-140210616 | rs10038174 | 15.69 | 0 | PF008506 204 | PCDHA4 |
| chr6: 31787630-31795082 | rs5026931 | 24.845 | 430 | PF008508 204 | HSPA1B |
| chr5: 140227999-140232346 | rs17119246 | 12.446 | 0 | PF008508 204 | PCDHA4 |
| chr6: 32527079-62189913 | rs6922547 | 16.115 | 0 | PF008511 204 | DST |
| chr6: 32527079-62189913 | rs6922547 | 16.115 | 0 | PF008511 204 | GLP1R |
| chr6: 32527079-62189913 | rs6922547 | 16.115 | 0 | PF008511 204 | GRM4 |
| chr6: 32527079-62189913 | rs6922547 | 16.115 | 0 | PF008511 204 | HLA-DQA2 |
| chr6: 32527079-62189913 | rs6922547 | 16.115 | 0 | PF008511 204 | HSP90AB1 |
| chr6: 32527079-62189913 | rs6922547 | 16.115 | 0 | PF008511 204 | ITPR3 |
| chr6: 32527079-62189913 | rs6922547 | 16.115 | 0 | PF008511 204 | MAD2L1BP |

TABLE 4-continued

| | | | | | |
|---|---|---|---|---|---|
| chr6: 32527079-62189913 | rs6922547 | 16.115 | 0 | PF008511 204 | MAPK14 |
| chr6: 32527079-62189913 | rs6922547 | 16.115 | 0 | PF008511 204 | MRPL14 |
| chr6: 32527079-62189913 | rs6922547 | 16.115 | 0 | PF008511 204 | NFKBIE |
| chr6: 32527079-62189913 | rs6922547 | 16.115 | 0 | PF008511 204 | PLA2G7 |
| chr6: 32527079-62189913 | rs6922547 | 16.115 | 0 | PF008511 204 | TEAD3 |
| chr6: 32527079-62189913 | rs6922547 | 16.115 | 0 | PF008511 204 | TTBK1 |
| chr10: 46842850-49059803 | rs4926101 | 25.727 | 0 | PF008511 204 | PPYR1 |
| chr21: 46746161-47590315 | cnvi0010879 | 32.845 | 0 | PF008513 204 | PCBP3 |
| chr17: 17400972-81041077 | rs6502043 | 66.933 | 0 | PF008513 204 | ABI3 |
| chr17: 17400972-81041077 | rs6502043 | 66.933 | 0 | PF008513 204 | ACCN1 |
| chr17: 17400972-81041077 | rs6502043 | 66.933 | 0 | PF008513 204 | ATXN7L3 |
| chr17: 17400972-81041077 | rs6502043 | 66.933 | 0 | PF008513 204 | BRCA1 |
| chr17: 17400972-81041077 | rs6502043 | 66.933 | 0 | PF008513 204 | CBX1 |
| chr17: 17400972-81041077 | rs6502043 | 66.933 | 0 | PF008513 204 | CNP |
| chr17: 17400972-81041077 | rs6502043 | 66.933 | 0 | PF008513 204 | COIL |
| chr17: 17400972-81041077 | rs6502043 | 66.933 | 0 | PF008513 204 | CRHR1 |
| chr17: 17400972-81041077 | rs6502043 | 66.933 | 0 | PF008513 204 | DDX5 |
| chr17: 17400972-81041077 | rs6502043 | 66.933 | 0 | PF008513 204 | ERBB2 |
| chr17: 17400972-81041077 | rs6502043 | 66.933 | 0 | PF008513 204 | GALR2 |
| chr17: 17400972-81041077 | rs6502043 | 66.933 | 0 | PF008513 204 | GFAP |
| chr17: 17400972-81041077 | rs6502043 | 66.933 | 0 | PF008513 204 | GH1 |
| chr17: 17400972-81041077 | rs6502043 | 66.933 | 0 | PF008513 204 | GIT1 |
| chr17: 17400972-81041077 | rs6502043 | 66.933 | 0 | PF008513 204 | GRB2 |
| chr17: 17400972-81041077 | rs6502043 | 66.933 | 0 | PF008513 204 | GRB7 |
| chr17: 17400972-81041077 | rs6502043 | 66.933 | 0 | PF008513 204 | ITGB4 |
| chr17: 17400972-81041077 | rs6502043 | 66.933 | 0 | PF008513 204 | KCNJ2 |
| chr17: 17400972-81041077 | rs6502043 | 66.933 | 0 | PF008513 204 | KRT10 |
| chr17: 17400972-81041077 | rs6502043 | 66.933 | 0 | PF008513 204 | LOC400604 |
| chr17: 17400972-81041077 | rs6502043 | 66.933 | 0 | PF008513 204 | LRRC59 |
| chr17: 17400972-81041077 | rs6502043 | 66.933 | 0 | PF008513 204 | MAP3K3 |
| chr17: 17400972-81041077 | rs6502043 | 66.933 | 0 | PF008513 204 | MAPT |
| chr17: 17400972-81041077 | rs6502043 | 66.933 | 0 | PF008513 204 | PDE6G |
| chr17: 17400972-81041077 | rs6502043 | 66.933 | 0 | PF008513 204 | PRKCA |
| chr17: 17400972-81041077 | rs6502043 | 66.933 | 0 | PF008513 204 | PRPSAP1 |
| chr17: 17400972-81041077 | rs6502043 | 66.933 | 0 | PF008513 204 | PSMD11 |
| chr17: 17400972-81041077 | rs6502043 | 66.933 | 0 | PF008513 204 | QRICH2 |
| chr17: 17400972-81041077 | rs6502043 | 66.933 | 0 | PF008513 204 | SLC9A3R1 |
| chr17: 17400972-81041077 | rs6502043 | 66.933 | 0 | PF008513 204 | SOCS7 |
| chr17: 17400972-81041077 | rs6502043 | 66.933 | 0 | PF008513 204 | TBCD |
| chr17: 17400972-81041077 | rs6502043 | 66.933 | 0 | PF008513 204 | TK1 |
| chr17: 17400972-81041077 | rs6502043 | 66.933 | 0 | PF008513 204 | TOP2A |
| chr17: 17400972-81041077 | rs6502043 | 66.933 | 0 | PF008513 204 | TUBG1 |
| chr17: 17400972-81041077 | rs6502043 | 66.933 | 0 | PF008513 204 | VTN |
| chr14: 102979463-106052265 | rs7149006 | 31.684 | 0 | PF008513 204 | AKT1 |
| chr14: 102979463-106052265 | rs7149006 | 31.684 | 0 | PF008513 204 | PPP1R13B |
| chr12: 132381920-132412260 | rs3923716 | 19.541 | 0 | PF008513 204 | ULK1 |
| chr4: 174442919-174447389 | rs2119788 | 14.021 | 263 | PF008513 204 | HAND2 |
| chr16: 2015121-2753180 | rs3094471 | 53.383 | 0 | PF008513 204 | PDPK1 |
| chr16: 88448685-89986634 | rs34020587 | 30.374 | 0 | PF008513 204 | SPG7 |
| chr9: 139403770-140212642 | rs13295516 | 66.879 | 0 | PF008513 204 | EDF1 |
| chr9: 139403770-140212642 | rs13295516 | 66.879 | 0 | PF008513 204 | GRIN1 |
| chr9: 139403770-140212642 | rs13295516 | 66.879 | 0 | PF008513 204 | TRAF2 |
| chr5: 140097072-140252615 | rs251373 | 25.349 | 0 | PF008513 204 | PCDHA4 |
| chr5: 176859848-176940384 | rs335438 | 21.278 | 0 | PF008513 204 | PDLIM7 |
| chr18: 77336478-77343164 | rs12605781 | 12.742 | 47155 | PF008513 204 | NFATC1 |
| chr22: 19952561-21822059 | cnvi0020983 | 39.556 | 0 | PF008513 204 | RANBP1 |
| chr19: 649825-55625944 | rs575144 | 37.792 | 0 | PF008513 204 | ANKRD24 |
| chr19: 649825-55625944 | rs575144 | 37.792 | 0 | PF008513 204 | ARHGEF1 |
| chr19: 649825-55625944 | rs575144 | 37.792 | 0 | PF008513 204 | BTBD2 |
| chr19: 649825-55625944 | rs575144 | 37.792 | 0 | PF008513 204 | CALM3 |
| chr19: 649825-55625944 | rs575144 | 37.792 | 0 | PF008513 204 | CCNE1 |
| chr19: 649825-55625944 | rs575144 | 37.792 | 0 | PF008513 204 | CIC |
| chr19: 649825-55625944 | rs575144 | 37.792 | 0 | PF008513 204 | CNN1 |
| chr19: 649825-55625944 | rs575144 | 37.792 | 0 | PF008513 204 | DAPK3 |
| chr19: 649825-55625944 | rs575144 | 37.792 | 0 | PF008513 204 | EEF2 |
| chr19: 649825-55625944 | rs575144 | 37.792 | 0 | PF008513 204 | ETHE1 |
| chr19: 649825-55625944 | rs575144 | 37.792 | 0 | PF008513 204 | F2RL3 |
| chr19: 649825-55625944 | rs575144 | 37.792 | 0 | PF008513 204 | FFAR1 |
| chr19: 649825-55625944 | rs575144 | 37.792 | 0 | PF008513 204 | FFAR2 |
| chr19: 649825-55625944 | rs575144 | 37.792 | 0 | PF008513 204 | FPR1 |
| chr19: 649825-55625944 | rs575144 | 37.792 | 0 | PF008513 204 | GNA15 |
| chr19: 649825-55625944 | rs575144 | 37.792 | 0 | PF008513 204 | GSK3A |
| chr19: 649825-55625944 | rs575144 | 37.792 | 0 | PF008513 204 | HOMER3 |
| chr19: 649825-55625944 | rs575144 | 37.792 | 0 | PF008513 204 | INSR |
| chr19: 649825-55625944 | rs575144 | 37.792 | 0 | PF008513 204 | KCNN4 |
| chr19: 649825-55625944 | rs575144 | 37.792 | 0 | PF008513 204 | KIAA1683 |
| chr19: 649825-55625944 | rs575144 | 37.792 | 0 | PF008513 204 | KLK10 |
| chr19: 649825-55625944 | rs575144 | 37.792 | 0 | PF008513 204 | MAP3K10 |
| chr19: 649825-55625944 | rs575144 | 37.792 | 0 | PF008513 204 | MARK4 |
| chr19: 649825-55625944 | rs575144 | 37.792 | 0 | PF008513 204 | MRPS12 |

TABLE 4-continued

| | | | | | | |
|---|---|---|---|---|---|---|
| chr19: 649825-55625944 | rs575144 | 37.792 | 0 | PF008513 | 204 | MYO9B |
| chr19: 649825-55625944 | rs575144 | 37.792 | 0 | PF008513 | 204 | NFKBIB |
| chr19: 649825-55625944 | rs575144 | 37.792 | 0 | PF008513 | 204 | NUCB1 |
| chr19: 649825-55625944 | rs575144 | 37.792 | 0 | PF008513 | 204 | PAFAH1B3 |
| chr19: 649825-55625944 | rs575144 | 37.792 | 0 | PF008513 | 204 | PDCD5 |
| chr19: 649825-55625944 | rs575144 | 37.792 | 0 | PF008513 | 204 | PIAS4 |
| chr19: 649825-55625944 | rs575144 | 37.792 | 0 | PF008513 | 204 | PLEKHA4 |
| chr19: 649825-55625944 | rs575144 | 37.792 | 0 | PF008513 | 204 | PPP1R14A |
| chr19: 649825-55625944 | rs575144 | 37.792 | 0 | PF008513 | 204 | PPP2R1A |
| chr19: 649825-55625944 | rs575144 | 37.792 | 0 | PF008513 | 204 | PRKACA |
| chr19: 649825-55625944 | rs575144 | 37.792 | 0 | PF008513 | 204 | PRKCG |
| chr19: 649825-55625944 | rs575144 | 37.792 | 0 | PF008513 | 204 | PRMT1 |
| chr19: 649825-55625944 | rs575144 | 37.792 | 0 | PF008513 | 204 | PSG9 |
| chr19: 649825-55625944 | rs575144 | 37.792 | 0 | PF008513 | 204 | PTGIR |
| chr19: 649825-55625944 | rs575144 | 37.792 | 0 | PF008513 | 204 | PTPRS |
| chr19: 649825-55625944 | rs575144 | 37.792 | 0 | PF008513 | 204 | RABAC1 |
| chr19: 649825-55625944 | rs575144 | 37.792 | 0 | PF008513 | 204 | RELB |
| chr19: 649825-55625944 | rs575144 | 37.792 | 0 | PF008513 | 204 | RUVBL2 |
| chr19: 649825-55625944 | rs575144 | 37.792 | 0 | PF008513 | 204 | RYR1 |
| chr19: 649825-55625944 | rs575144 | 37.792 | 0 | PF008513 | 204 | SHANK1 |
| chr19: 649825-55625944 | rs575144 | 37.792 | 0 | PF008513 | 204 | SIRT2 |
| chr19: 649825-55625944 | rs575144 | 37.792 | 0 | PF008513 | 204 | STRN4 |
| chr19: 649825-55625944 | rs575144 | 37.792 | 0 | PF008513 | 204 | TBXA2R |
| chr19: 649825-55625944 | rs575144 | 37.792 | 0 | PF008513 | 204 | TCF3 |
| chr19: 649825-55625944 | rs575144 | 37.792 | 0 | PF008513 | 204 | VAV1 |
| chr19: 649825-55625944 | rs575144 | 37.792 | 0 | PF008513 | 204 | WDR62 |
| chr8: 144508768-145558541 | cnvi0002166 | 39.919 | 0 | PF008513 | 204 | EEF1D |
| chr5: 1259342-1276121 | cnvi0012572 | 15.55 | 0 | PF008516 | 204 | TERT |
| chr14: 103987140-105672794 | cnvi0019137 | 31.358 | 0 | PF008535 | 204 | AKT1 |
| chr14: 103987140-105672794 | cnvi0019137 | 31.358 | 0 | PF008535 | 204 | PPP1R13B |
| chr9: 139395473-140671147 | rs7868455 | 26.627 | 0 | PF008535 | 204 | EDF1 |
| chr9: 139395473-140671147 | rs7868455 | 26.627 | 0 | PF008535 | 204 | GRIN1 |
| chr9: 139395473-140671147 | rs7868455 | 26.627 | 0 | PF008535 | 204 | TRAF2 |
| chr19: 581070-2050823 | rs3746101 | 39.268 | 0 | PF008535 | 204 | BTBD2 |
| chr19: 581070-2050823 | rs3746101 | 39.268 | 0 | PF008535 | 204 | TCF3 |
| chr16: 107275-840769 | rs3765266 | 36.043 | 0 | PF008535 | 204 | PDIA2 |
| chr1: 1152631-2379248 | rs11581548 | 47.606 | 0 | PF008535 | 204 | DVL1 |
| chr1: 1152631-2379248 | rs11581548 | 47.606 | 0 | PF008535 | 204 | PRKCZ |
| chr20: 61585706-62212928 | rs310672 | 41.964 | 0 | PF008535 | 204 | KCNQ2 |
| chr17: 79065650-80758198 | rs868203 | 40.43 | 0 | PF008535 | 204 | PDE6G |
| chr17: 79065650-80758198 | rs868203 | 40.43 | 0 | PF008535 | 204 | TBCD |
| chr10: 46928388-48137589 | cnvi0003730 | 37.018 | 0 | PF008557 | 204 | PPYR1 |
| chr11: 88533414-88533632 | rs1903841 | 12.69 | 0 | PF008588 | 204 | GRM5 |
| chr19: 53514604-55343606 | rs34177062 | 37.685 | 0 | PF008619 | 206 | PRKCG |
| chr13: 34141695-34143447 | rs9285097 | 14.219 | 0 | PF008628 | 204 | STARD13 |
| chr6: 32438542-39590788 | rs2446653 | 17.749 | 0 | PF008632 | 204 | GLP1R |
| chr6: 32438542-39590788 | rs2446653 | 17.749 | 0 | PF008632 | 204 | GRM4 |
| chr6: 32438542-39590788 | rs2446653 | 17.749 | 0 | PF008632 | 204 | HLA-DQA2 |
| chr6: 32438542-39590788 | rs2446653 | 17.749 | 0 | PF008632 | 204 | ITPR3 |
| chr6: 32438542-39590788 | rs2446653 | 17.749 | 0 | PF008632 | 204 | MAPK14 |
| chr6: 32438542-39590788 | rs2446653 | 17.749 | 0 | PF008632 | 204 | TEAD3 |
| chr8: 90773210-90883803 | rs2091921 | 15.977 | 0 | PF008632 | 204 | RIPK2 |
| chr11: 88533414-88533632 | rs1903841 | 7.273 | 0 | PF008680 | 203 | GRM5 |
| chr3: 171220708-171220919 | cnvi0011705 | 10.548 | 42511 | PF008766 | 211 | TNIK |
| chr21: 47091361-47145374 | rs2838986 | 11.513 | 0 | PF008788 | 211 | PCBP3 |
| chr10: 46842850-48137589 | cnvi0003730 | 29.747 | 0 | PF008788 | 211 | PPYR1 |
| chr6: 32527079-124471337 | rs2008708 | 42.373 | 0 | PF008788 | 211 | CNR1 |
| chr6: 32527079-124471337 | rs2008708 | 42.373 | 0 | PF008788 | 211 | DST |
| chr6: 32527079-124471337 | rs2008708 | 42.373 | 0 | PF008788 | 211 | FYN |
| chr6: 32527079-124471337 | rs2008708 | 42.373 | 0 | PF008788 | 211 | GABRR1 |
| chr6: 32527079-124471337 | rs2008708 | 42.373 | 0 | PF008788 | 211 | GABRR2 |
| chr6: 32527079-124471337 | rs2008708 | 42.373 | 0 | PF008788 | 211 | GJA1 |
| chr6: 32527079-124471337 | rs2008708 | 42.373 | 0 | PF008788 | 211 | GLP1R |
| chr6: 32527079-124471337 | rs2008708 | 42.373 | 0 | PF008788 | 211 | GRM4 |
| chr6: 32527079-124471337 | rs2008708 | 42.373 | 0 | PF008788 | 211 | HLA-DQA2 |
| chr6: 32527079-124471337 | rs2008708 | 42.373 | 0 | PF008788 | 211 | HSP90AB1 |
| chr6: 32527079-124471337 | rs2008708 | 42.373 | 0 | PF008788 | 211 | ITPR3 |
| chr6: 32527079-124471337 | rs2008708 | 42.373 | 0 | PF008788 | 211 | KCNQ5 |
| chr6: 32527079-124471337 | rs2008708 | 42.373 | 0 | PF008788 | 211 | LAMA4 |
| chr6: 32527079-124471337 | rs2008708 | 42.373 | 0 | PF008788 | 211 | MAD2L1BP |
| chr6: 32527079-124471337 | rs2008708 | 42.373 | 0 | PF008788 | 211 | MAP3K7 |
| chr6: 32527079-124471337 | rs2008708 | 42.373 | 0 | PF008788 | 211 | MAPK14 |
| chr6: 32527079-124471337 | rs2008708 | 42.373 | 0 | PF008788 | 211 | MARCKS |
| chr6: 32527079-124471337 | rs2008708 | 42.373 | 0 | PF008788 | 211 | MRPL14 |
| chr6: 32527079-124471337 | rs2008708 | 42.373 | 0 | PF008788 | 211 | MYO6 |
| chr6: 32527079-124471337 | rs2008708 | 42.373 | 0 | PF008788 | 211 | NFKBIE |
| chr6: 32527079-124471337 | rs2008708 | 42.373 | 0 | PF008788 | 211 | PLA2G7 |
| chr6: 32527079-124471337 | rs2008708 | 42.373 | 0 | PF008788 | 211 | PTP4A1 |
| chr6: 32527079-124471337 | rs2008708 | 42.373 | 0 | PF008788 | 211 | SNAP91 |
| chr6: 32527079-124471337 | rs2008708 | 42.373 | 0 | PF008788 | 211 | TEAD3 |

TABLE 4-continued

| | | | | | |
|---|---|---|---|---|---|
| chr6: 32527079-124471337 | rs2008708 | 42.373 | 0 | PF008788 211 | TTBK1 |
| chr6: 32527079-124471337 | rs2008708 | 42.373 | 0 | PF008788 211 | TTK |
| chr5: 1272500-1276121 | cnvi0012572 | 13.466 | 0 | PF008852 211 | TERT |
| chr10: 46961667-47121726 | rs6599598 | 15.156 | 0 | PF008866 211 | PPYR1 |
| chr2: 203295790-203309066 | rs13430786 | 6.234 | 0 | PF008877 211 | BMPR2 |
| chr4: 101754170-101768637 | rs2903222 | 14.058 | 175950 | PF008888 211 | PPP3CA |
| chr16: 56377045-56381277 | rs7206796 | 14.386 | 0 | PF014850 211 | GNAO1 |
| chr13: 34141695-34143447 | rs9285097 | 12.797 | 0 | PF014877 211 | STARD13 |
| chr6: 31787630-31795082 | rs5026931 | 21.403 | 430 | PF014880 211 | HSPA1B |
| chr10: 46961667-48137589 | cnvi0003730 | 40.085 | 0 | PF014893 211 | PPYR1 |
| chr17: 64287309-64288738 | cnvi0008599 | 16.136 | 10188 | PF014893 211 | PRKCA |
| chr5: 140227999-140232346 | rs17119246 | 8.448 | 0 | PF014893 211 | PCDHA4 |
| chr3: 3129349-3148458 | rs334782 | 25.295 | 0 | PF014900 211 | IL5RA |
| chr5: 1272500-1276121 | cnvi0012572 | 11.154 | 0 | PF014901 211 | TERT |
| chr13: 34141695-34143447 | rs9285097 | 14.421 | 0 | PF014915 211 | STARD13 |
| chr7: 6036515-7350683 | rs10486157 | 147.417 | 0 | PF014917 211 | RAC1 |
| chr6: 43238609-43245374 | rs2651189 | 11.512 | 0 | PF014931 211 | TTBK1 |
| chr13: 34141695-34143447 | rs9285097 | 16.161 | 0 | PF014942 211 | STARD13 |
| chr4: 72656076-72678078 | rs7660070 | 14.731 | 0 | PF014942 211 | GC |
| chr2: 223921771-223936738 | rs1440072 | 13.547 | 1416 | PF014943 211 | KCNE4 |
| chr19: 53533161-55326739 | rs581623 | 39.022 | 0 | PF014952 211 | PRKCG |
| chr10: 46961667-48137589 | cnvi0003730 | 23.94 | 0 | PF014960 211 | PPYR1 |
| chr10: 46850713-49059803 | rs4926101 | 45.441 | 0 | PF014963 211 | PPYR1 |
| chr5: 1272500-1276121 | cnvi0012572 | 6.837 | 0 | PF015337 224 | TERT |
| chr2: 227343513-227346034 | rs931725 | 12.143 | 249999 | PF015625 203 | IRS1 |
| chr9: 81038220-81047891 | rs4072157 | 9.881 | 93211 | PF015647 203 | PSAT1 |
| chr11: 2250850-2271323 | rs739545 | 13.785 | 18405 | PF015751 203 | ASCL2 |
| chr13: 34141695-34143447 | rs9285097 | 13.663 | 0 | PF015798 203 | STARD13 |
| chr21: 47851753-47868321 | rs11702704 | 13.191 | 0 | PF015806 203 | PCNT |
| chr4: 101754170-101768637 | rs2903222 | 14.926 | 175950 | PF015858 203 | PPP3CA |
| chr6: 31785453-31795082 | rs5026931 | 33.343 | 0 | PF015965 203 | HSPA1A |
| chr13: 34141695-34143447 | rs9285097 | 15.124 | 0 | PF016024 224 | STARD13 |
| chr5: 140227999-140232346 | rs17119246 | 9.235 | 0 | PF016050 203 | PCDHA4 |
| chr19: 43647130-55326739 | rs581623 | 37.188 | 0 | PF016050 203 | CALM3 |
| chr19: 43647130-55326739 | rs581623 | 37.188 | 0 | PF016050 203 | ETHE1 |
| chr19: 43647130-55326739 | rs581623 | 37.188 | 0 | PF016050 203 | FPR1 |
| chr19: 43647130-55326739 | rs581623 | 37.188 | 0 | PF016050 203 | KCNN4 |
| chr19: 43647130-55326739 | rs581623 | 37.188 | 0 | PF016050 203 | KLK10 |
| chr19: 43647130-55326739 | rs581623 | 37.188 | 0 | PF016050 203 | MARK4 |
| chr19: 43647130-55326739 | rs581623 | 37.188 | 0 | PF016050 203 | NUCB1 |
| chr19: 43647130-55326739 | rs581623 | 37.188 | 0 | PF016050 203 | PLEKHA4 |
| chr19: 43647130-55326739 | rs581623 | 37.188 | 0 | PF016050 203 | PPP2R1A |
| chr19: 43647130-55326739 | rs581623 | 37.188 | 0 | PF016050 203 | PRKCG |
| chr19: 43647130-55326739 | rs581623 | 37.188 | 0 | PF016050 203 | PRMT1 |
| chr19: 43647130-55326739 | rs581623 | 37.188 | 0 | PF016050 203 | PSG9 |
| chr19: 43647130-55326739 | rs581623 | 37.188 | 0 | PF016050 203 | PTGIR |
| chr19: 43647130-55326739 | rs581623 | 37.188 | 0 | PF016050 203 | RELB |
| chr19: 43647130-55326739 | rs581623 | 37.188 | 0 | PF016050 203 | RUVBL2 |
| chr19: 43647130-55326739 | rs581623 | 37.188 | 0 | PF016050 203 | SHANK1 |
| chr19: 43647130-55326739 | rs581623 | 37.188 | 0 | PF016050 203 | STRN4 |
| chr1: 1220136-1356550 | rs12089560 | 9.952 | 0 | PF016082 224 | DVL1 |
| chr3: 171220708-171220919 | cnvi0011705 | 13.571 | 42511 | PF016165 203 | TNIK |
| chr11: 75071783-75080920 | rs11236410 | 15.24 | 8908 | PF016165 203 | ARRB1 |
| chr14: 105154105-106516402 | rs34204778 | 35.917 | 0 | PF016297 203 | AKT1 |
| chr12: 125083696-125097030 | rs837957 | 19.947 | 31686 | PF016344 203 | NCOR2 |
| chr13: 34141695-34143447 | rs9285097 | 13.54 | 0 | PF016346 203 | STARD13 |
| chr11: 88376801-88379332 | rs11020772 | 12.682 | 0 | PF016378 203 | GRM5 |
| chr10: 46961667-47099529 | rs4481963 | 21.688 | 0 | PF016411 203 | PPYR1 |
| chr6: 31281438-31795082 | rs5026931 | 54.862 | 0 | PF016411 203 | CSNK2B |
| chr6: 31281438-31795082 | rs5026931 | 54.862 | 0 | PF016411 203 | HSPA1A |
| chr6: 31281438-31795082 | rs5026931 | 54.862 | 0 | PF016411 203 | HSPA1B |
| chr6: 31281438-31795082 | rs5026931 | 54.862 | 0 | PF016411 203 | LTA |
| chr6: 16398959-16400090 | rs3819400 | 15.72 | 0 | PF016482 203 | ATXN1 |
| chr2: 223921771-223936748 | rs1448299 | 16.254 | 1416 | PF016482 203 | KCNE4 |
| chr17: 64287309-64288738 | cnvi0008599 | 17.689 | 10188 | PF016560 203 | PRKCA |
| chr19: 53522100-55326739 | rs581623 | 37.507 | 0 | PF016609 203 | PRKCG |
| chr15: 60524025-60551926 | rs10519010 | 23.368 | 87424 | PF016646 203 | ANXA2 |
| chr9: 141026318-141036645 | rs3855758 | 17.636 | 7242 | PF016670 203 | CACNA1B |
| chr5: 140227999-140232346 | rs17119246 | 13.192 | 0 | PF016700 203 | PCDHA4 |
| chr11: 7353097-7369875 | rs4525211 | 19.296 | 0 | PF016749 203 | SYT9 |
| chr2: 227343513-227346034 | rs931725 | 15.206 | 249999 | PF016751 203 | IRS1 |
| chr10: 46928388-47748912 | rs3013867 | 214.754 | 0 | PF016882 203 | PPYR1 |
| chr3: 11714521-90442925 | rs2316653 | 36.387 | 0 | PF016986 203 | ATXN7 |
| chr3: 11714521-90442925 | rs2316653 | 36.387 | 0 | PF016986 203 | CCR4 |
| chr3: 11714521-90442925 | rs2316653 | 36.387 | 0 | PF016986 203 | CCR5 |
| chr3: 11714521-90442925 | rs2316653 | 36.387 | 0 | PF016986 203 | CISH |
| chr3: 11714521-90442925 | rs2316653 | 36.387 | 0 | PF016986 203 | CTNNB1 |
| chr3: 11714521-90442925 | rs2316653 | 36.387 | 0 | PF016986 203 | EIF1B |
| chr3: 11714521-90442925 | rs2316653 | 36.387 | 0 | PF016986 203 | FLNB |
| chr3: 11714521-90442925 | rs2316653 | 36.387 | 0 | PF016986 203 | GNAI2 |

TABLE 4-continued

| | | | | | |
|---|---|---|---|---|---|
| chr3: 11714521-90442925 | rs2316653 | 36.387 | 0 | PF016986 203 | GRM2 |
| chr3: 11714521-90442925 | rs2316653 | 36.387 | 0 | PF016986 203 | IMPDH2 |
| chr3: 11714521-90442925 | rs2316653 | 36.387 | 0 | PF016986 203 | LTF |
| chr3: 11714521-90442925 | rs2316653 | 36.387 | 0 | PF016986 203 | MAP4 |
| chr3: 11714521-90442925 | rs2316653 | 36.387 | 0 | PF016986 203 | PLCD1 |
| chr3: 11714521-90442925 | rs2316653 | 36.387 | 0 | PF016986 203 | PRKCD |
| chr3: 11714521-90442925 | rs2316653 | 36.387 | 0 | PF016986 203 | PSMD6 |
| chr3: 11714521-90442925 | rs2316653 | 36.387 | 0 | PF016986 203 | RAB5A |
| chr3: 11714521-90442925 | rs2316653 | 36.387 | 0 | PF016986 203 | RAF1 |
| chr3: 11714521-90442925 | rs2316653 | 36.387 | 0 | PF016986 203 | RASSF1 |
| chr3: 11714521-90442925 | rs2316653 | 36.387 | 0 | PF016986 203 | RBM5 |
| chr3: 11714521-90442925 | rs2316653 | 36.387 | 0 | PF016986 203 | RHOA |
| chr3: 11714521-90442925 | rs2316653 | 36.387 | 0 | PF016986 203 | SGOL1 |
| chr3: 11714521-90442925 | rs2316653 | 36.387 | 0 | PF016986 203 | TDGF1 |
| chr3: 11714521-90442925 | rs2316653 | 36.387 | 0 | PF016986 203 | VIPR1 |
| chr10: 46928388-47703613 | rs4128664 | 163.602 | 0 | PF017088 203 | PPYR1 |
| chr12: 2245636-2252924 | rs4765899 | 13.808 | 0 | PF017227 203 | CACNA1C |
| chr18: 58267843-58310343 | rs1346831 | 29.472 | 227842 | PF017312 203 | MC4R |
| chr10: 46928388-47568296 | rs36104966 | 52.123 | 0 | PF017314 203 | PPYR1 |
| chr10: 46961667-48137589 | cnvi0003730 | 26.403 | 0 | PF017352 221 | PPYR1 |
| chr10: 46928388-49059803 | rs4926101 | 36.124 | 0 | PF017378 203 | PPYR1 |
| chr13: 34141695-34143447 | rs9285097 | 15.12 | 0 | PF017382 203 | STARD13 |
| chr10: 46961667-47697026 | rs4466762 | 170.541 | 0 | PF017439 221 | PPYR1 |
| chr17: 64287309-64288738 | cnvi0008599 | 18.455 | 10188 | PF017447 203 | PRKCA |
| chr1: 239306319-239410745 | rs16838096 | 126.828 | 139120 | PF018384 221 | CHRM3 |
| chr6: 151618235-151621611 | rs2251681 | 15.452 | 0 | PF018397 221 | AKAP12 |
| chr8: 6717107-6725056 | rs2702833 | 26.304 | 3041 | PF018432 212 | DEFB1 |
| chr12: 2245636-2252924 | rs4765899 | 11.191 | 0 | PF018441 212 | CACNA1C |
| chr6: 31785453-31795082 | rs5026931 | 30.325 | 0 | PF018457 212 | HSPA1A |
| chr18: 58100799-58120972 | rs2000778 | 51.574 | 60798 | PF018457 212 | MC4R |
| chr9: 93557698-93577781 | rs10993698 | 28.286 | 0 | PF018461 212 | SYK |
| chr3: 171220708-171220919 | cnvi0011705 | 12.52 | 42511 | PF018461 212 | TNIK |
| chr13: 31646976-31652085 | rs4943078 | 7.743 | 58678 | PF018470 212 | HSPH1 |
| chr21: 37410477-37415603 | rs2835244 | 13.457 | 0 | PF018476 212 | SETD4 |
| chr12: 2245636-2252924 | rs4765899 | 16.68 | 0 | PF018477 212 | CACNA1C |
| chr5: 140227999-140232346 | rs17119246 | 14.999 | 0 | PF018527 212 | PCDHA4 |
| chr13: 23528685-24897901 | rs9511199 | 1257.159 | 0 | PF018564 212 | SACS |
| chr6: 154379152-154393884 | rs3778153 | 17.026 | 0 | PF018564 212 | OPRM1 |
| chr11: 88533414-88533632 | rs1903841 | 10.118 | 0 | PF018576 202 | GRM5 |
| chr5: 1272500-1276121 | cnvi0012572 | 11.192 | 0 | PF018579 202 | TERT |
| chr6: 31787630-31795082 | rs5026931 | 31.541 | 430 | PF018580 202 | HSPA1B |
| chr13: 31646976-31652085 | rs4943078 | 13.168 | 58678 | PF018583 202 | HSPH1 |
| chr11: 88533414-88533632 | rs1903841 | 11.703 | 0 | PF018588 202 | GRM5 |
| chr13: 34141695-34143447 | rs9285097 | 14.07 | 0 | PF018599 202 | STARD13 |
| chr6: 19044000-31286381 | rs9265057 | 37.916 | 0 | PF018604 203 | HLA-A |
| chr6: 19044000-31286381 | rs9265057 | 37.916 | 0 | PF018604 203 | HLA-C |
| chr6: 19044000-31286381 | rs9265057 | 37.916 | 0 | PF018604 203 | SOX4 |
| chr6: 19044000-31286381 | rs9265057 | 37.916 | 0 | PF018604 203 | TUBB |
| chr5: 140227999-140232346 | rs17119246 | 11.039 | 0 | PF018607 202 | PCDHA4 |
| chr8: 102696350-102696889 | cnvi0001968 | 0 | 1881 | PF018608 202 | NCALD |
| chr13: 34141695-34143447 | rs9285097 | 13.323 | 0 | PF018609 202 | STARD13 |
| chr5: 711373-1276121 | cnvi0012572 | 22.854 | 0 | PF018610 203 | TERT |
| chr12: 2245636-2252924 | rs4765899 | 12.502 | 0 | PF018611 202 | CACNA1C |
| chr4: 101754170-101768637 | rs2903222 | 15.75 | 175599 | PF018626 202 | PPP3CA |
| chr4: 158346878-158424816 | rs1025551 | 97.484 | 59652 | PF018630 202 | GRIA2 |
| chr12: 2247179-2252924 | rs4765899 | 14.456 | 0 | PF018631 202 | CACNA1C |
| chr12: 2245636-2252924 | rs4765899 | 15.61 | 0 | PF018636 202 | CACNA1C |
| chr5: 1272500-1276121 | cnvi0012572 | 14.818 | 0 | PF018638 202 | TERT |
| chr5: 140227999-140232346 | rs17119246 | 9.887 | 0 | PF018642 202 | PCDHA4 |
| chr13: 34141695-34143447 | rs9285097 | 13.263 | 0 | PF018644 202 | STARD13 |
| chr11: 88376801-88379332 | rs11020772 | 14.626 | 0 | PF018644 202 | GRM5 |
| chr2: 227343513-227346034 | rs931725 | 12.528 | 249999 | PF018654 202 | IRS1 |
| chr12: 2245636-2252924 | rs4765899 | 15.108 | 0 | PF018655 202 | CACNA1C |
| chr17: 64287309-64288738 | cnvi0008599 | 15.947 | 10188 | PF018655 202 | PRKCA |
| chr13: 34141695-34143447 | rs9285097 | 14.661 | 0 | PF018662 202 | STARD13 |
| chr21: 27194869-27232198 | rs2040273 | 43.862 | 20663 | PF018665 202 | APP |
| chr5: 140227999-140232346 | rs17119246 | 8.247 | 0 | PF018675 202 | PCDHA4 |
| chr3: 171220708-171220919 | cnvi0011705 | 12.619 | 42511 | PF018677 202 | TNIK |
| chr10: 46961667-47121726 | rs6599598 | 17.13 | 0 | PF018677 202 | PPYR1 |
| chr19: 43284120-55326739 | rs581623 | 43.93 | 0 | PF018678 202 | CALM3 |
| chr19: 43284120-55326739 | rs581623 | 43.93 | 0 | PF018678 202 | ETHE1 |
| chr19: 43284120-55326739 | rs581623 | 43.93 | 0 | PF018678 202 | FPR1 |
| chr19: 43284120-55326739 | rs581623 | 43.93 | 0 | PF018678 202 | KCNN4 |
| chr19: 43284120-55326739 | rs581623 | 43.93 | 0 | PF018678 202 | KLK10 |
| chr19: 43284120-55326739 | rs581623 | 43.93 | 0 | PF018678 202 | MARK4 |
| chr19: 43284120-55326739 | rs581623 | 43.93 | 0 | PF018678 202 | NUCB1 |
| chr19: 43284120-55326739 | rs581623 | 43.93 | 0 | PF018678 202 | PLEKHA4 |
| chr19: 43284120-55326739 | rs581623 | 43.93 | 0 | PF018678 202 | PPP2R1A |
| chr19: 43284120-55326739 | rs581623 | 43.93 | 0 | PF018678 202 | PRKCG |
| chr19: 43284120-55326739 | rs581623 | 43.93 | 0 | PF018678 202 | PRMT1 |

TABLE 4-continued

| | | | | | |
|---|---|---|---|---|---|
| chr19: 43284120-55326739 | rs581623 | 43.93 | 0 | PF018678 202 | PSG9 |
| chr19: 43284120-55326739 | rs581623 | 43.93 | 0 | PF018678 202 | PTGIR |
| chr19: 43284120-55326739 | rs581623 | 43.93 | 0 | PF018678 202 | RELB |
| chr19: 43284120-55326739 | rs581623 | 43.93 | 0 | PF018678 202 | RUVBL2 |
| chr19: 43284120-55326739 | rs581623 | 43.93 | 0 | PF018678 202 | SHANK1 |
| chr19: 43284120-55326739 | rs581623 | 43.93 | 0 | PF018678 202 | STRN4 |
| chr13: 34141695-34143447 | rs9285097 | 13.787 | 0 | PF018678 202 | STARD13 |
| chr2: 2245636-2252924 | rs4765899 | 38.703 | 0 | PF018682 202 | CACNA1C |
| chr13: 34141695-34143447 | rs9285097 | 15.236 | 0 | PF018682 202 | STARD13 |
| chr4: 101754170-101768637 | rs2903222 | 14.798 | 175950 | PF018693 202 | PPP3CA |
| chr10: 46961667-47703613 | rs4128664 | 200.337 | 0 | PF018694 202 | PPYR1 |
| chr5: 140227999-140232346 | rs17119246 | 11.636 | 0 | PF018695 203 | PCDHA4 |
| chr3: 171220708-171220919 | cnvi0011705 | 11.987 | 42511 | PF018700 202 | TNIK |
| chr8: 103054583-103056517 | rs11776754 | 23.812 | 0 | PF018704 202 | NCALD |
| chr13: 34141695-34143447 | rs9285097 | 16.226 | 0 | PF018715 202 | STARD13 |
| chr13: 34141695-34143447 | rs9285097 | 13.168 | 0 | PF018716 202 | STARD13 |
| chr6: 31787630-31795082 | rs5026931 | 37.061 | 430 | PF018716 202 | HSPA1B |
| chr10: 46961667-47703613 | rs4128664 | 178.599 | 0 | PF018716 202 | PPYR1 |
| chr10: 131474247-131529320 | rs7898934 | 37.046 | 0 | PF018722 202 | MGMT |
| chr6: 21612949-21623715 | rs1744855 | 13.537 | 14100 | PF018722 202 | SOX4 |
| chr2: 2245636-2252924 | rs4765899 | 12.29 | 0 | PF018753 202 | CACNA1C |
| chr3: 171220708-171220919 | cnvi0011705 | 13.14 | 42511 | PF018753 202 | TNIK |
| chr13: 31646976-31652085 | rs4943078 | 9.249 | 58678 | PF018757 203 | HSPH1 |
| chr13: 34141695-34143447 | rs9285097 | 14.304 | 0 | PF018757 203 | STARD13 |
| chr6: 154379152-154393884 | rs3778153 | 13.286 | 0 | PF018758 202 | OPRM1 |
| chr5: 140227999-140232346 | rs17119246 | 10.989 | 0 | PF018760 202 | PCDHA4 |
| chr9: 140911199-140913833 | cnvi0002661 | 6.514 | 0 | PF018763 202 | CACNA1B |
| chr3: 171220708-171220919 | cnvi0011705 | 9.724 | 42511 | PF018769 202 | TNIK |
| chr17: 64287309-64288738 | cnvi0008599 | 15.959 | 10188 | PF018770 202 | PRKCA |
| chr10: 46961667-47121726 | rs6599598 | 17.992 | 0 | PF018770 202 | PPYR1 |
| chr2: 2245636-2252924 | rs4765899 | 12.583 | 0 | PF018778 221 | CACNA1C |
| chr19: 20612645-55326739 | rs581623 | 39.325 | 0 | PF018779 221 | ARHGEF1 |
| chr19: 20612645-55326739 | rs581623 | 39.325 | 0 | PF018779 221 | CALM3 |
| chr19: 20612645-55326739 | rs581623 | 39.325 | 0 | PF018779 221 | CCNE1 |
| chr19: 20612645-55326739 | rs581623 | 39.325 | 0 | PF018779 221 | CIC |
| chr19: 20612645-55326739 | rs581623 | 39.325 | 0 | PF018779 221 | ETHE1 |
| chr19: 20612645-55326739 | rs581623 | 39.325 | 0 | PF018779 221 | FFAR1 |
| chr19: 20612645-55326739 | rs581623 | 39.325 | 0 | PF018779 221 | FFAR2 |
| chr19: 20612645-55326739 | rs581623 | 39.325 | 0 | PF018779 221 | FPR1 |
| chr19: 20612645-55326739 | rs581623 | 39.325 | 0 | PF018779 221 | GSK3A |
| chr19: 20612645-55326739 | rs581623 | 39.325 | 0 | PF018779 221 | KCNN4 |
| chr19: 20612645-55326739 | rs581623 | 39.325 | 0 | PF018779 221 | KLK10 |
| chr19: 20612645-55326739 | rs581623 | 39.325 | 0 | PF018779 221 | MAP3K10 |
| chr19: 20612645-55326739 | rs581623 | 39.325 | 0 | PF018779 221 | MARK4 |
| chr19: 20612645-55326739 | rs581623 | 39.325 | 0 | PF018779 221 | MRPS12 |
| chr19: 20612645-55326739 | rs581623 | 39.325 | 0 | PF018779 221 | NFKBIB |
| chr19: 20612645-55326739 | rs581623 | 39.325 | 0 | PF018779 221 | NUCB1 |
| chr19: 20612645-55326739 | rs581623 | 39.325 | 0 | PF018779 221 | PAFAH1B3 |
| chr19: 20612645-55326739 | rs581623 | 39.325 | 0 | PF018779 221 | PDCD5 |
| chr19: 20612645-55326739 | rs581623 | 39.325 | 0 | PF018779 221 | PLEKHA4 |
| chr19: 20612645-55326739 | rs581623 | 39.325 | 0 | PF018779 221 | PPP1R14A |
| chr19: 20612645-55326739 | rs581623 | 39.325 | 0 | PF018779 221 | PPP2R1A |
| chr19: 20612645-55326739 | rs581623 | 39.325 | 0 | PF018779 221 | PRKCG |
| chr19: 20612645-55326739 | rs581623 | 39.325 | 0 | PF018779 221 | PRMT1 |
| chr19: 20612645-55326739 | rs581623 | 39.325 | 0 | PF018779 221 | PSG9 |
| chr19: 20612645-55326739 | rs581623 | 39.325 | 0 | PF018779 221 | PTGIR |
| chr19: 20612645-55326739 | rs581623 | 39.325 | 0 | PF018779 221 | RABAC1 |
| chr19: 20612645-55326739 | rs581623 | 39.325 | 0 | PF018779 221 | RELB |
| chr19: 20612645-55326739 | rs581623 | 39.325 | 0 | PF018779 221 | RUVBL2 |
| chr19: 20612645-55326739 | rs581623 | 39.325 | 0 | PF018779 221 | RYR1 |
| chr19: 20612645-55326739 | rs581623 | 39.325 | 0 | PF018779 221 | SHANK1 |
| chr19: 20612645-55326739 | rs581623 | 39.325 | 0 | PF018779 221 | SIRT2 |
| chr19: 20612645-55326739 | rs581623 | 39.325 | 0 | PF018779 221 | STRN4 |
| chr19: 20612645-55326739 | rs581623 | 39.325 | 0 | PF018779 221 | WDR62 |
| chr9: 140911199-140913833 | cnvi0002661 | 8.491 | 0 | PF018791 202 | CACNA1B |
| chr2: 227334949-227346034 | rs931725 | 4.054 | 249999 | PF018793 202 | IRS1 |
| chr6: 31277740-44419336 | rs532492 | 35.835 | 0 | PF018793 202 | CSNK2B |
| chr6: 31277740-44419336 | rs532492 | 35.835 | 0 | PF018793 202 | GLP1R |
| chr6: 31277740-44419336 | rs532492 | 35.835 | 0 | PF018793 202 | GRM4 |
| chr6: 31277740-44419336 | rs532492 | 35.835 | 0 | PF018793 202 | HLA-DQA2 |
| chr6: 31277740-44419336 | rs532492 | 35.835 | 0 | PF018793 202 | HSP90AB1 |
| chr6: 31277740-44419336 | rs532492 | 35.835 | 0 | PF018793 202 | HSPA1A |
| chr6: 31277740-44419336 | rs532492 | 35.835 | 0 | PF018793 202 | HSPA1B |
| chr6: 31277740-44419336 | rs532492 | 35.835 | 0 | PF018793 202 | ITPR3 |
| chr6: 31277740-44419336 | rs532492 | 35.835 | 0 | PF018793 202 | LTA |
| chr6: 31277740-44419336 | rs532492 | 35.835 | 0 | PF018793 202 | MAD2L1BP |
| chr6: 31277740-44419336 | rs532492 | 35.835 | 0 | PF018793 202 | MAPK14 |
| chr6: 31277740-44419336 | rs532492 | 35.835 | 0 | PF018793 202 | MRPL14 |
| chr6: 31277740-44419336 | rs532492 | 35.835 | 0 | PF018793 202 | NFKBIE |
| chr6: 31277740-44419336 | rs532492 | 35.835 | 0 | PF018793 202 | TEAD3 |

TABLE 4-continued

| | | | | | | |
|---|---|---|---|---|---|---|
| chr6: 31277740-44419336 | rs532492 | 35.835 | 0 | PF018793 | 202 | TTBK1 |
| chr13: 31646976-31652085 | rs4943078 | 16.345 | 58678 | PF018794 | 202 | HSPH1 |
| chr13: 34141695-34143447 | rs9285097 | 15.792 | 0 | PF018795 | 202 | STARD13 |
| chr2: 227343513-227346034 | rs931725 | 16.157 | 249999 | PF018803 | 202 | IRS1 |
| chr12: 2245636-2252924 | rs4765899 | 14.634 | 0 | PF018803 | 202 | CACNA1C |
| chr13: 20220659-20437753 | rs9578228 | 39.319 | 0 | PF018827 | 202 | PSPC1 |
| chr3: 148441620-148455199 | rs12721311 | 17.651 | 0 | PF018828 | 202 | AGTR1 |
| chr2: 70880841-70953745 | rs1030044 | 13.316 | 0 | PF018828 | 202 | ADD2 |
| chr18: 40640488-40808652 | rs10502808 | 13.723 | 0 | PF018828 | 202 | RIT2 |
| chr10: 46961667-47727297 | cnvi0015946 | 197.615 | 0 | PF018836 | 202 | PPYR1 |
| chr9: 140911199-140913833 | cnvi0002661 | 0.412 | 0 | PF018857 | 202 | CACNA1B |
| chr10: 53374729-53375420 | rs2339794 | 1.961 | 0 | PF018858 | 202 | PRKG1 |
| chr11: 659906-1611018 | cnvi0004998 | 52.722 | 0 | PF018858 | 202 | RPLP2 |
| chr6: 152095167-152103792 | rs1285057 | 20.368 | 0 | PF018865 | 202 | ESR1 |
| chr7: 32220497-32399833 | rs10486507 | 78.211 | 0 | PF018870 | 202 | PDE1C |
| chr4: 101754170-101768637 | rs2903222 | 15.837 | 175950 | PF018870 | 202 | PPP3CA |
| chr13: 31646976-31652085 | rs4943078 | 12.075 | 58678 | PF018870 | 202 | HSPH1 |
| chr5: 1272500-1276121 | cnvi0012572 | 9.161 | 0 | PF018872 | 202 | TERT |
| chr5: 140227999-140232346 | rs17119246 | 11.993 | 0 | PF018886 | 202 | PCDHA4 |
| chr11: 88533414-88533632 | rs1903841 | 8.511 | 0 | PF018895 | 202 | GRM5 |
| chr3: 171220708-171220919 | cnvi0011705 | 13.087 | 42511 | PF018897 | 202 | TNIK |
| chr11: 88376801-88379332 | rs11020772 | 16.775 | 0 | PF018897 | 202 | GRM5 |
| chr2: 203285157-203309066 | rs13430786 | 6.589 | 0 | PF018906 | 202 | BMPR2 |
| chr16: 29647342-30177807 | rs7202714 | 163.307 | 0 | PF018907 | 202 | ALDOA |
| chr16: 29647342-30177807 | rs7202714 | 163.307 | 0 | PF018907 | 202 | MAPK3 |
| chr16: 29647342-30177807 | rs7202714 | 163.307 | 0 | PF018907 | 202 | TAOK2 |
| chr2: 179693712-237821589 | rs7603272 | 32.392 | 0 | PF018908 | 202 | BMPR2 |
| chr2: 179693712-237821589 | rs7603272 | 32.392 | 0 | PF018908 | 202 | CASP8 |
| chr2: 179693712-237821589 | rs7603272 | 32.392 | 0 | PF018908 | 202 | DGKD |
| chr2: 179693712-237821589 | rs7603272 | 32.392 | 0 | PF018908 | 202 | HSPE1 |
| chr2: 179693712-237821589 | rs7603272 | 32.392 | 0 | PF018908 | 202 | HTR2B |
| chr2: 179693712-237821589 | rs7603272 | 32.392 | 0 | PF018908 | 202 | IRS1 |
| chr2: 179693712-237821589 | rs7603272 | 32.392 | 0 | PF018908 | 202 | KCNE4 |
| chr2: 179693712-237821589 | rs7603272 | 32.392 | 0 | PF018908 | 202 | NCL |
| chr2: 179693712-237821589 | rs7603272 | 32.392 | 0 | PF018908 | 202 | NEUROD1 |
| chr2: 179693712-237821589 | rs7603272 | 32.392 | 0 | PF018908 | 202 | PDE1A |
| chr2: 179693712-237821589 | rs7603272 | 32.392 | 0 | PF018908 | 202 | PDE6D |
| chr2: 179693712-237821589 | rs7603272 | 32.392 | 0 | PF018908 | 202 | PSMD1 |
| chr2: 179693712-237821589 | rs7603272 | 32.392 | 0 | PF018908 | 202 | RPL37A |
| chr2: 179693712-237821589 | rs7603272 | 32.392 | 0 | PF018908 | 202 | SDPR |
| chr2: 179693712-237821589 | rs7603272 | 32.392 | 0 | PF018908 | 202 | SGOL2 |
| chr3: 171220708-171220919 | cnvi0011705 | 12.567 | 42511 | PF018909 | 202 | TNIK |
| chr3: 171220708-171220919 | cnvi0011705 | 12.216 | 42511 | PF018912 | 202 | TNIK |
| chr13: 34141695-34143447 | rs9285097 | 13.569 | 0 | PF018912 | 202 | STARD13 |
| chr5: 1272500-1276121 | cnvi0012572 | 12.247 | 0 | PF018913 | 202 | TERT |
| chr7: 32211433-32399833 | rs10486507 | 103.995 | 0 | PF018913 | 202 | PDE1C |
| chr13: 33822593-33825641 | rs2555595 | 24.604 | 0 | PF018916 | 202 | STARD13 |
| chr6: 88843377-88861698 | rs6928813 | 27.875 | 0 | PF018916 | 202 | CNR1 |
| chr5: 110756963-110759537 | rs10052530 | 14.446 | 0 | PF018916 | 202 | CAMK4 |
| chr2: 227343513-227346034 | rs931725 | 13.534 | 249999 | PF018916 | 202 | IRS1 |
| chr12: 2245636-2252924 | rs4765899 | 13.588 | 0 | PF018918 | 202 | CACNA1C |
| chr4: 101754170-101768637 | rs2903222 | 15.155 | 175950 | PF018919 | 203 | PPP3CA |
| chr6: 56740504-56792576 | rs1599280 | 13.269 | 0 | PF018934 | 202 | DST |
| chr18: 58267843-58304032 | rs13382005 | 15.724 | 227842 | PF018939 | 202 | MC4R |
| chr6: 31289284-32499014 | cnvi0006585 | 11.911 | 0 | PF018951 | 202 | CSNK2B |
| chr6: 31289284-32499014 | cnvi0006585 | 11.911 | 0 | PF018951 | 202 | HSPA1A |
| chr6: 31289284-32499014 | cnvi0006585 | 11.911 | 0 | PF018951 | 202 | HSPA1B |
| chr6: 31289284-32499014 | cnvi0006585 | 11.911 | 0 | PF018951 | 202 | LTA |
| chr13: 34141695-34143447 | rs9285097 | 14.488 | 0 | PF018951 | 202 | STARD13 |
| chr13: 23899627-24336981 | rs1359426 | 233.119 | 0 | PF018955 | 202 | SACS |
| chr10: 46961667-47149117 | rs4979753 | 23.48 | 0 | PF018955 | 202 | PPYR1 |
| chr12: 2245636-2252924 | rs4765899 | 13.366 | 0 | PF018956 | 202 | CACNA1C |
| chr1: 144875799-149582448 | rs2935837 | 22.588 | 0 | PF018957 | 203 | PDE4DIP |
| chr19: 7124986-7134402 | rs6510949 | 15.094 | 0 | PF018987 | 203 | INSR |
| chr4: 185621249-186622179 | rs1547909 | 451.579 | 0 | PF018998 | 202 | LRP2BP |
| chr13: 34141695-34143447 | rs9285097 | 13.324 | 0 | PF019009 | 202 | STARD13 |
| chr6: 3867382-32514144 | rs34369284 | 31.035 | 0 | PF019016 | 202 | ATXN1 |
| chr6: 3867382-32514144 | rs34369284 | 31.035 | 0 | PF019016 | 202 | CSNK2B |
| chr6: 3867382-32514144 | rs34369284 | 31.035 | 0 | PF019016 | 202 | HLA-A |
| chr6: 3867382-32514144 | rs34369284 | 31.035 | 0 | PF019016 | 202 | HLA-C |
| chr6: 3867382-32514144 | rs34369284 | 31.035 | 0 | PF019016 | 202 | HSPA1A |
| chr6: 3867382-32514144 | rs34369284 | 31.035 | 0 | PF019016 | 202 | HSPA1B |
| chr6: 3867382-32514144 | rs34369284 | 31.035 | 0 | PF019016 | 202 | LTA |
| chr6: 3867382-32514144 | rs34369284 | 31.035 | 0 | PF019016 | 202 | SOX4 |
| chr6: 3867382-32514144 | rs34369284 | 31.035 | 0 | PF019016 | 202 | TUBB |
| chr3: 171220708-171220919 | cnvi0011705 | 11.431 | 42511 | PF019021 | 202 | TNIK |
| chr11: 88376801-88379332 | rs11020772 | 15.254 | 0 | PF019037 | 202 | GRM5 |
| chr5: 1272500-1276121 | cnvi0012572 | 15.745 | 0 | PF019040 | 202 | TERT |
| chr2: 227343513-227346034 | rs931725 | 14.572 | 249999 | PF019042 | 202 | IRS1 |
| chr6: 31785453-31795082 | rs5026931 | 20.583 | 0 | PF019043 | 202 | HSPA1A |

TABLE 4-continued

| | | | | | | |
|---|---|---|---|---|---|---|
| chr13: 31646976-31652085 | rs4943078 | 8.233 | 58678 | PF019064 | 202 | HSPH1 |
| chr17: 64287309-64288738 | cnvi0008599 | 15.21 | 10188 | PF019068 | 202 | PRKCA |
| chr2: 227343513-227346034 | rs931725 | 13.534 | 249999 | PF019072 | 202 | IRS1 |
| chr10: 46961667-48137589 | cnvi0003730 | 37.456 | 0 | PF019078 | 202 | PPYR1 |
| chr16: 29130999-35279083 | rs649602 | 21.915 | 0 | PF019089 | 202 | ALDOA |
| chr16: 29130999-35279083 | rs649602 | 21.915 | 0 | PF019089 | 202 | MAPK3 |
| chr16: 29130999-35279083 | rs649602 | 21.915 | 0 | PF019089 | 202 | PHKG2 |
| chr16: 29130999-35279083 | rs649602 | 21.915 | 0 | PF019089 | 202 | STX4 |
| chr16: 29130999-35279083 | rs649602 | 21.915 | 0 | PF019089 | 202 | TAOK2 |
| chr6: 31785453-31795082 | rs5026931 | 28.855 | 0 | PF019105 | 202 | HSPA1A |
| chr5: 1272500-1276121 | cnvi0012572 | 12.898 | 0 | PF019108 | 202 | TERT |
| chr17: 64287309-64288738 | cnvi0008599 | 14.862 | 10188 | PF019125 | 202 | PRKCA |
| chr3: 171220708-171220919 | cnvi0011705 | 11.373 | 42511 | PF019128 | 202 | TNIK |
| chr6: 1175965-29895228 | rs9259831 | 50.146 | 0 | PF019135 | 202 | ATXN1 |
| chr6: 1175965-29895228 | rs9259831 | 50.146 | 0 | PF019135 | 202 | RIPK1 |
| chr6: 1175965-29895228 | rs9259831 | 50.146 | 0 | PF019135 | 202 | SERPINB9 |
| chr6: 1175965-29895228 | rs9259831 | 50.146 | 0 | PF019135 | 202 | SOX4 |
| chr5: 140227999-140232346 | rs17119246 | 11.914 | 0 | PF019135 | 202 | PCDHA4 |
| chr8: 48992900-49018790 | rs4335148 | 12.444 | 18446 | PF019158 | 202 | UBE2V2 |
| chr3: 9014942-9019748 | rs2324710 | 16.78 | 2530 | PF019158 | 202 | SRGAP3 |
| chr5: 1259342-1276121 | cnvi0012572 | 16.116 | 0 | PF019163 | 202 | TERT |
| chr6: 64139997-64279571 | rs2627797 | 25.463 | 0 | PF019175 | 202 | PTP4A1 |
| chr13: 23528685-24897901 | rs9511199 | 1483.004 | 0 | PF019180 | 202 | SACS |
| chr18: 58267843-58294706 | rs4588087 | 25.151 | 227842 | PF019226 | 202 | MC4R |
| chr5: 1272500-1276121 | cnvi0012572 | 13.606 | 0 | PF019235 | 202 | TERT |
| chr7: 125687968-125707685 | rs2079055 | 14.334 | 370967 | PF019246 | 202 | GRM8 |
| chr15: 30007573-30011918 | rs17671556 | 14.552 | 0 | PF019254 | 202 | TJP1 |
| chr16: 9776728-9784163 | rs11644994 | 16.18 | 63102 | PF019261 | 202 | GRIN2A |
| chr10: 46961667-47703613 | rs4128664 | 181.323 | 0 | PF019261 | 202 | PPYR1 |
| chr10: 47041592-49059803 | rs4926101 | 22.008 | 0 | PF019275 | 203 | PPYR1 |
| chr6: 31219869-31221914 | rs9264219 | 20.688 | 14612 | PF019278 | 203 | HLA-C |
| chr19: 1673509-1684137 | rs4392177 | 11.863 | 21181 | PF019282 | 203 | TCF3 |
| chr1: 171591189-171592869 | rs235854 | 12.545 | 11688 | PF019286 | 203 | MYOC |
| chr13: 34141695-34143447 | rs9285097 | 14.103 | 0 | PF019289 | 203 | STARD13 |
| chr10: 46961667-47748912 | rs3013867 | 82.947 | 0 | PF019299 | 203 | PPYR1 |
| chr13: 34141695-34143447 | rs9285097 | 14.925 | 0 | PF019313 | 203 | STARD13 |
| chr2: 49150192-49230413 | rs1922469 | 108.926 | 0 | PF019313 | 203 | FSHR |
| chr10: 46961667-47727297 | cnvi0015946 | 200.145 | 0 | PF019313 | 203 | PPYR1 |
| chr3: 171220708-171220919 | cnvi0011705 | 12.435 | 42511 | PF019321 | 203 | TNIK |
| chr13: 34141695-34143447 | rs9285097 | 15.281 | 0 | PF019321 | 203 | STARD13 |
| chr12: 2245636-2252924 | rs4765899 | 10.499 | 0 | PF019322 | 203 | CACNA1C |
| chr3: 171220708-171220919 | cnvi0011705 | 12.497 | 42511 | PF019326 | 203 | TNIK |
| chr9: 141017240-141036645 | rs3855758 | 22.906 | 0 | PF019326 | 203 | CACNA1B |
| chr17: 64287309-64288738 | cnvi0008599 | 15.394 | 10188 | PF019384 | 203 | PRKCA |
| chr13: 34141695-34143447 | rs9285097 | 15.156 | 0 | PF019409 | 203 | STARD13 |
| chr2: 227343513-227346034 | rs931725 | 13.728 | 249999 | PF019419 | 202 | IRS1 |
| chr2: 227343513-227346034 | rs931725 | 15.154 | 249999 | PF019429 | 202 | IRS1 |
| chr12: 2245636-2252924 | rs4765899 | 11.877 | 0 | PF019439 | 202 | CACNA1C |
| chr6: 31289284-141041329 | rs12211936 | 26.611 | 0 | PF019439 | 202 | CNR1 |
| chr6: 31289284-141041329 | rs12211936 | 26.611 | 0 | PF019439 | 202 | CSNK2B |
| chr6: 31289284-141041329 | rs12211936 | 26.611 | 0 | PF019439 | 202 | DST |
| chr6: 31289284-141041329 | rs12211936 | 26.611 | 0 | PF019439 | 202 | EPB41L2 |
| chr6: 31289284-141041329 | rs12211936 | 26.611 | 0 | PF019439 | 202 | FYN |
| chr6: 31289284-141041329 | rs12211936 | 26.611 | 0 | PF019439 | 202 | GABRR1 |
| chr6: 31289284-141041329 | rs12211936 | 26.611 | 0 | PF019439 | 202 | GABRR2 |
| chr6: 31289284-141041329 | rs12211936 | 26.611 | 0 | PF019439 | 202 | GJA1 |
| chr6: 31289284-141041329 | rs12211936 | 26.611 | 0 | PF019439 | 202 | GLP1R |
| chr6: 31289284-141041329 | rs12211936 | 26.611 | 0 | PF019439 | 202 | GRM4 |
| chr6: 31289284-141041329 | rs12211936 | 26.611 | 0 | PF019439 | 202 | HLA-DQA2 |
| chr6: 31289284-141041329 | rs12211936 | 26.611 | 0 | PF019439 | 202 | HSP90AB1 |
| chr6: 31289284-141041329 | rs12211936 | 26.611 | 0 | PF019439 | 202 | HSPA1A |
| chr6: 31289284-141041329 | rs12211936 | 26.611 | 0 | PF019439 | 202 | HSPA1B |
| chr6: 31289284-141041329 | rs12211936 | 26.611 | 0 | PF019439 | 202 | ITPR3 |
| chr6: 31289284-141041329 | rs12211936 | 26.611 | 0 | PF019439 | 202 | KCNQ5 |
| chr6: 31289284-141041329 | rs12211936 | 26.611 | 0 | PF019439 | 202 | LAMA4 |
| chr6: 31289284-141041329 | rs12211936 | 26.611 | 0 | PF019439 | 202 | LOC154092 |
| chr6: 31289284-141041329 | rs12211936 | 26.611 | 0 | PF019439 | 202 | LTA |
| chr6: 31289284-141041329 | rs12211936 | 26.611 | 0 | PF019439 | 202 | MAD2L1BP |
| chr6: 31289284-141041329 | rs12211936 | 26.611 | 0 | PF019439 | 202 | MAP3K7 |
| chr6: 31289284-141041329 | rs12211936 | 26.611 | 0 | PF019439 | 202 | MAPK14 |
| chr6: 31289284-141041329 | rs12211936 | 26.611 | 0 | PF019439 | 202 | MARCKS |
| chr6: 31289284-141041329 | rs12211936 | 26.611 | 0 | PF019439 | 202 | MRPL14 |
| chr6: 31289284-141041329 | rs12211936 | 26.611 | 0 | PF019439 | 202 | MYO6 |
| chr6: 31289284-141041329 | rs12211936 | 26.611 | 0 | PF019439 | 202 | NFKBIE |
| chr6: 31289284-141041329 | rs12211936 | 26.611 | 0 | PF019439 | 202 | PLA2G7 |
| chr6: 31289284-141041329 | rs12211936 | 26.611 | 0 | PF019439 | 202 | PTP4A1 |
| chr6: 31289284-141041329 | rs12211936 | 26.611 | 0 | PF019439 | 202 | SNAP91 |
| chr6: 31289284-141041329 | rs12211936 | 26.611 | 0 | PF019439 | 202 | TEAD3 |
| chr6: 31289284-141041329 | rs12211936 | 26.611 | 0 | PF019439 | 202 | TTBK1 |
| chr6: 31289284-141041329 | rs12211936 | 26.611 | 0 | PF019439 | 202 | TTK |

TABLE 4-continued

| | | | | | | |
|---|---|---|---|---|---|---|
| chr5: 140227999-140232346 | rs17119246 | 6.755 | 0 | PF019441 | 202 | PCDHA4 |
| chr3: 171220708-171220919 | cnvi0011705 | 10.426 | 42511 | PF019446 | 202 | TNIK |
| chr13: 31646976-31652085 | rs4943078 | 9.513 | 58678 | PF019446 | 202 | HSPH1 |
| chr4: 72670191-72678078 | rs7660070 | 13.148 | 0 | PF019449 | 202 | GC |
| chr13: 34141695-34143447 | rs9285097 | 15.324 | 0 | PF019449 | 202 | STARD13 |
| chr5: 140227999-140232346 | rs17119246 | 11.878 | 0 | PF019465 | 202 | PCDHA4 |
| chr8: 56757808-56876219 | rs907424 | 75.005 | 0 | PF019466 | 202 | LYN |
| chr3: 171220708-171220919 | cnvi0011705 | 12.45 | 42511 | PF019466 | 202 | TNIK |
| chr6: 1165092-29899147 | rs2394704 | 58.313 | 0 | PF019474 | 202 | ATXN1 |
| chr6: 1165092-29899147 | rs2394704 | 58.313 | 0 | PF019474 | 202 | RIPK1 |
| chr6: 1165092-29899147 | rs2394704 | 58.313 | 0 | PF019474 | 202 | SERPINB9 |
| chr6: 1165092-29899147 | rs2394704 | 58.313 | 0 | PF019474 | 202 | SOX4 |
| chr11: 2250850-2271323 | rs739545 | 15.454 | 18405 | PF019475 | 202 | ASCL2 |
| chr10: 46961667-47160061 | rs2489763 | 29.019 | 0 | PF019476 | 202 | PPYR1 |
| chr5: 1272500-1276121 | cnvi0012572 | 13.11 | 0 | PF019479 | 202 | TERT |
| chr6: 2540921-31298743 | rs28752863 | 23.704 | 0 | PF019490 | 202 | ATXN1 |
| chr6: 2540921-31298743 | rs28752863 | 23.704 | 0 | PF019490 | 202 | HLA-A |
| chr6: 2540921-31298743 | rs28752863 | 23.704 | 0 | PF019490 | 202 | HLA-C |
| chr6: 2540921-31298743 | rs28752863 | 23.704 | 0 | PF019490 | 202 | RIPK1 |
| chr6: 2540921-31298743 | rs28752863 | 23.704 | 0 | PF019490 | 202 | SERPINB9 |
| chr6: 2540921-31298743 | rs28752863 | 23.704 | 0 | PF019490 | 202 | SOX4 |
| chr6: 2540921-31298743 | rs28752863 | 23.704 | 0 | PF019490 | 202 | TUBB |
| chr5: 140227999-140232346 | rs17119246 | 13.558 | 0 | PF019490 | 202 | PCDHA4 |
| chr13: 34141695-34143447 | rs9285097 | 14.06 | 0 | PF019528 | 202 | STARD13 |
| chr2: 49293369-49321164 | rs1504185 | 31.495 | 0 | PF019529 | 202 | FSHR |
| chr5: 140227999-140232346 | rs17119246 | 8.574 | 0 | PF019532 | 202 | PCDHA4 |
| chr4: 114289170-114302266 | rs1554667 | 20.47 | 0 | PF019559 | 202 | ANK2 |
| chr5: 83030867-150270420 | rs7714584 | 29.083 | 0 | PF019589 | 202 | ADRB2 |
| chr5: 83030867-150270420 | rs7714584 | 29.083 | 0 | PF019589 | 202 | CAMK2A |
| chr5: 83030867-150270420 | rs7714584 | 29.083 | 0 | PF019589 | 202 | CAMK4 |
| chr5: 83030867-150270420 | rs7714584 | 29.083 | 0 | PF019589 | 202 | CETN3 |
| chr5: 83030867-150270420 | rs7714584 | 29.083 | 0 | PF019589 | 202 | FER |
| chr5: 83030867-150270420 | rs7714584 | 29.083 | 0 | PF019589 | 202 | HARS |
| chr5: 83030867-150270420 | rs7714584 | 29.083 | 0 | PF019589 | 202 | HSPA4 |
| chr5: 83030867-150270420 | rs7714584 | 29.083 | 0 | PF019589 | 202 | KCNN2 |
| chr5: 83030867-150270420 | rs7714584 | 29.083 | 0 | PF019589 | 202 | KIF3A |
| chr5: 83030867-150270420 | rs7714584 | 29.083 | 0 | PF019589 | 202 | KLHL3 |
| chr5: 83030867-150270420 | rs7714584 | 29.083 | 0 | PF019589 | 202 | LMNB1 |
| chr5: 83030867-150270420 | rs7714584 | 29.083 | 0 | PF019589 | 202 | MCC |
| chr5: 83030867-150270420 | rs7714584 | 29.083 | 0 | PF019589 | 202 | MYOT |
| chr5: 83030867-150270420 | rs7714584 | 29.083 | 0 | PF019589 | 202 | PAM |
| chr5: 83030867-150270420 | rs7714584 | 29.083 | 0 | PF019589 | 202 | PCDHA4 |
| chr5: 83030867-150270420 | rs7714584 | 29.083 | 0 | PF019589 | 202 | PFDN1 |
| chr5: 83030867-150270420 | rs7714584 | 29.083 | 0 | PF019589 | 202 | RPS14 |
| chr5: 83030867-150270420 | rs7714584 | 29.083 | 0 | PF019589 | 202 | SMAD5 |
| chr5: 83030867-150270420 | rs7714584 | 29.083 | 0 | PF019589 | 202 | VDAC1 |
| chr5: 152821589-152847022 | rs2914621 | 16.033 | 22153 | PF019589 | 202 | GRIA1 |
| chr5: 162204206-179888268 | rs7729820 | 42.585 | 0 | PF019589 | 202 | C5orf25 |
| chr5: 162204206-179888268 | rs7729820 | 42.585 | 0 | PF019589 | 202 | CLTB |
| chr5: 162204206-179888268 | rs7729820 | 42.585 | 0 | PF019589 | 202 | DBN1 |
| chr5: 162204206-179888268 | rs7729820 | 42.585 | 0 | PF019589 | 202 | DRD1 |
| chr5: 162204206-179888268 | rs7729820 | 42.585 | 0 | PF019589 | 202 | GRM6 |
| chr5: 162204206-179888268 | rs7729820 | 42.585 | 0 | PF019589 | 202 | HMMR |
| chr5: 162204206-179888268 | rs7729820 | 42.585 | 0 | PF019589 | 202 | HMP19 |
| chr5: 162204206-179888268 | rs7729820 | 42.585 | 0 | PF019589 | 202 | PDLIM7 |
| chr5: 162204206-179888268 | rs7729820 | 42.585 | 0 | PF019589 | 202 | RGS14 |
| chr5: 162204206-179888268 | rs7729820 | 42.585 | 0 | PF019589 | 202 | SQSTM1 |
| chr5: 162204206-179888268 | rs7729820 | 42.585 | 0 | PF019589 | 202 | STC2 |
| chr5: 162204206-179888268 | rs7729820 | 42.585 | 0 | PF019589 | 202 | WWC1 |
| chr5: 140227999-140232346 | rs17119246 | 14.177 | 0 | PF019591 | 202 | PCDHA4 |
| chr16: 82165183-82213799 | rs7205603 | 53.666 | 0 | PF019591 | 202 | MPHOSPH6 |
| chr6: 31787630-31795082 | rs5026931 | 23.862 | 430 | PF019604 | 202 | HSPA1B |
| chr5: 1272500-1276121 | cnvi0012572 | 14.59 | 0 | PF019604 | 202 | TERT |
| chr13: 34141695-34143447 | rs9285097 | 13.833 | 0 | PF019626 | 202 | STARD13 |
| chr18: 58117429-58120972 | rs2000778 | 21.034 | 77428 | PF019650 | 202 | MC4R |
| chr13: 34141695-34143447 | rs9285097 | 15.099 | 0 | PF019650 | 202 | STARD13 |
| chr1: 16087164-16098866 | rs10927852 | 25.318 | 0 | PF019687 | 202 | FBLIM1 |
| chr6: 75923605-76473071 | rs276698 | 195.613 | 0 | PF019692 | 202 | MYO6 |
| chr5: 140227999-140232346 | rs17119246 | 19.036 | 0 | PF019701 | 202 | PCDHA4 |
| chr11: 198510-257030 | rs532483 | 70.708 | 0 | PF019701 | 202 | PSMD13 |
| chr11: 198510-257030 | rs532483 | 70.708 | 0 | PF019701 | 202 | RIC8A |
| chr6: 73463601-73467087 | rs7743912 | 14.168 | 0 | PF019702 | 202 | KCNQ5 |
| chr3: 171220708-171220919 | cnvi0011705 | 9.483 | 42511 | PF019718 | 202 | TNIK |
| chr2: 227343513-227346034 | rs931725 | 16.035 | 249999 | PF019720 | 202 | IRS1 |
| chr4: 101754170-101768637 | rs2903222 | 15.315 | 175950 | PF019720 | 202 | PPP3CA |
| chr5: 140227999-140232346 | rs17119246 | 14.484 | 0 | PF019720 | 202 | PCDHA4 |
| chr12: 2245636-2252924 | rs4765899 | 13.179 | 0 | PF019723 | 202 | CACNA1C |
| chr12: 2245636-2252924 | rs4765899 | 10.828 | 0 | PF019733 | 202 | CACNA1C |
| chr5: 140097072-140232346 | rs17119246 | 21.868 | 0 | PF019749 | 202 | PCDHA4 |
| chr22: 22315312-25908441 | rs637629 | 759.909 | 0 | PF019750 | 202 | CABIN1 |

TABLE 4-continued

| | | | | | |
|---|---|---|---|---|---|
| chr22: 22315312-25908441 | rs637629 | 759.909 | 0 | PF019750 202 | GNAZ |
| chr12: 2245636-2252924 | rs4765899 | 13.355 | 0 | PF019756 202 | CACNA1C |
| chr4: 101798797-101805126 | rs13117589 | 12.528 | 139461 | PF019757 202 | PPP3CA |
| chr10: 46961667-47748912 | rs3013867 | 202.161 | 0 | PF019799 203 | PPYR1 |
| chr10: 46961667-47703613 | rs4128664 | 181.431 | 0 | PF019814 202 | PPYR1 |
| chr6: 56740504-56792576 | rs1599280 | 13.633 | 0 | PF019820 202 | DST |
| chr10: 111928766-111931752 | rs7908495 | 10.642 | 33443 | PF019830 202 | ADD3 |
| chr6: 31289284-32499014 | cnvi0006585 | 28.524 | 0 | PF019853 212 | CSNK2B |
| chr6: 31289284-32499014 | cnvi0006585 | 28.524 | 0 | PF019853 212 | HSPA1A |
| chr6: 31289284-32499014 | cnvi0006585 | 28.524 | 0 | PF019853 212 | HSPA1B |
| chr6: 31289284-32499014 | cnvi0006585 | 28.524 | 0 | PF019853 212 | LTA |
| chr4: 166469496-166495142 | rs7662154 | 33.388 | 50014 | PF019860 212 | CPE |
| chr10: 46961667-47703613 | rs4128664 | 179.649 | 0 | PF019860 212 | PPYR1 |
| chr21: 37410477-37415603 | rs2835244 | 11.827 | 0 | PF019865 203 | SETD4 |
| chr3: 171220708-171220919 | cnvi0011705 | 11.981 | 42511 | PF019866 212 | TNIK |
| chr9: 93519280-93529807 | rs1172990 | 14.299 | 34205 | PF019873 203 | SYK |
| chr12: 2245636-2252924 | rs4765899 | 10.404 | 0 | PF019875 212 | CACNA1C |
| chr12: 2245636-2252924 | rs4765899 | 11.01 | 0 | PF019879 212 | CACNA1C |
| chr10: 46961667-47088968 | rs28702886 | 21.062 | 0 | PF019902 212 | PPYR1 |
| chr5: 1257259-1276121 | cnvi0012572 | 12.395 | 0 | PF019905 212 | TERT |
| chr18: 39671541-39697934 | rs1788990 | 14.329 | 10095 | PF019914 203 | PIK3C3 |
| chr5: 140227999-140232346 | rs17119246 | 17.67 | 0 | PF019915 212 | PCDHA4 |
| chr13: 34141695-34143447 | rs9285097 | 11.497 | 0 | PF019915 212 | STARD13 |
| chr2: 203292344-203309066 | rs13430786 | 4.305 | 0 | PF019917 203 | BMPR2 |
| chr12: 2245636-2252924 | rs4765899 | 12.6 | 0 | PF019927 203 | CACNA1C |
| chr5: 1272500-1276121 | cnvi0012572 | 11.978 | 0 | PF019932 203 | TERT |
| chr12: 2245636-2252924 | rs4765899 | 15.006 | 0 | PF019939 203 | CACNA1C |
| chr17: 64287309-64288738 | cnvi0008599 | 15.131 | 10188 | PF019939 203 | PRKCA |
| chr2: 119984733-120833583 | rs4849816 | 26.273 | 0 | PF019947 212 | SCTR |
| chr13: 34141695-34143447 | rs9285097 | 14.919 | 0 | PF019961 212 | STARD13 |
| chr1: 169591373-169749154 | rs12035144 | 102.668 | 0 | PF019974 203 | SELE |
| chr2: 49643063-49654260 | rs1544914 | 31.726 | 261397 | PF019982 203 | FSHR |
| chr13: 34141695-34143447 | rs9285097 | 14.835 | 0 | PF019984 212 | STARD13 |
| chr6: 31787630-31795082 | rs5026931 | 16.422 | 430 | PF019985 212 | HSPA1B |
| chr4: 102504356-102574367 | rs7676236 | 29.638 | 0 | PF019986 203 | BANK1 |
| chr12: 49578661-49586490 | rs11168910 | 8.83 | 0 | PF019994 212 | TUBA1A |
| chr13: 34141695-34143447 | rs9285097 | 15.495 | 0 | PF020001 212 | STARD13 |
| chr8: 131968469-132230063 | rs9643263 | 87.339 | 0 | PF020002 203 | ADCY8 |
| chr6: 56791495-56799262 | rs2599697 | 14.719 | 0 | PF020004 212 | DST |
| chr16: 29130999-33908890 | cnvi0022788 | 23.111 | 0 | PF020004 212 | ALDOA |
| chr16: 29130999-33908890 | cnvi0022788 | 23.111 | 0 | PF020004 212 | MAPK3 |
| chr16: 29130999-33908890 | cnvi0022788 | 23.111 | 0 | PF020004 212 | PHKG2 |
| chr16: 29130999-33908890 | cnvi0022788 | 23.111 | 0 | PF020004 212 | STX4 |
| chr16: 29130999-33908890 | cnvi0022788 | 23.111 | 0 | PF020004 212 | TAOK2 |
| chr8: 103058601-103060237 | rs9656851 | 14.728 | 0 | PF020006 212 | NCALD |
| chr11: 88533414-88533632 | rs1903841 | 8.972 | 0 | PF020010 203 | GRM5 |
| chr3: 171282951-171286713 | rs360414 | 12.768 | 31482 | PF020011 202 | PLD1 |
| chr10: 46961667-47748912 | rs3013867 | 220.446 | 0 | PF020029 202 | PPYR1 |
| chr13: 34141695-34143447 | rs9285097 | 16.394 | 0 | PF020035 202 | STARD13 |
| chr12: 2245636-2252924 | rs4765899 | 14.009 | 0 | PF020042 202 | CACNA1C |
| chr13: 34141695-34143447 | rs9285097 | 13.034 | 0 | PF020042 202 | STARD13 |
| chr18: 58267843-58294706 | rs4588087 | 24.754 | 227842 | PF020043 202 | MC4R |
| chr13: 34141695-34143447 | rs9285097 | 14.19 | 0 | PF020044 202 | STARD13 |
| chr17: 64287309-64288738 | cnvi0008599 | 15.722 | 10188 | PF020046 202 | PRKCA |
| chr13: 34141695-34143447 | rs9285097 | 15.325 | 0 | PF020048 202 | STARD13 |
| chr5: 140227999-140232346 | rs17119246 | 12.553 | 0 | PF020048 202 | PCDHA4 |
| chr2: 227343513-227346034 | rs931725 | 13.533 | 249999 | PF020048 202 | IRS1 |
| chr13: 34141695-34143447 | rs9285097 | 15.608 | 0 | PF020054 202 | STARD13 |
| chr10: 46961667-47121726 | rs6599598 | 12.786 | 0 | PF020292 221 | PPYR1 |
| chr3: 171220708-171220919 | cnvi0011705 | 13.581 | 42511 | PF020352 202 | TNIK |
| chr12: 124950060-124957153 | rs1794942 | 11.122 | 0 | PF020354 221 | NCOR2 |
| chr10: 53271054-53295318 | rs10997954 | 42.729 | 0 | PF020354 221 | PRKG1 |
| chr5: 140227999-140232346 | rs17119246 | 11.872 | 0 | PF020355 221 | PCDHA4 |
| chr6: 31219869-31228460 | rs9264368 | 20.574 | 8066 | PF020358 202 | HLA-C |
| chr10: 46961667-47748912 | rs3013867 | 232.5 | 0 | PF020383 221 | PPYR1 |
| chr17: 64287309-64288738 | cnvi0008599 | 17.376 | 10188 | PF020384 221 | PRKCA |
| chr2: 49626781-49646785 | rs10172488 | 44.261 | 245115 | PF020395 221 | FSHR |

TABLE 6

| BID | SSID | Tier 1 CNV count | Tier 2 CNV count | Tier 3 CNV count | Callrate | LRR_SD |
|---|---|---|---|---|---|---|
| 4457235058_R02C01 | PF018828 202 | 0 | 1 | 3 | 0.969676 | 0.5155 |
| 4457235057_R02C01 | PF019947 212 | 0 | 1 | 1 | 0.985982 | 0.4545 |
| 4461875352_R02C02 | PF008632 204 | 0 | 3 | 7 | 0.986067 | 0.4088 |

TABLE 6-continued

| BID | SSID | Tier 1 CNV count | Tier 2 CNV count | Tier 3 CNV count | Callrate | LRR_SD |
|---|---|---|---|---|---|---|
| 4457235234_R02C01 | PF018908 202 | 0 | 1 | 15 | 0.987138 | 0.4023 |
| 4457235148_R01C01 | PF019065 203 | 0 | 0 | 0 | 0.978736 | 0.3912 |
| 4457235443_R02C01 | PF019851 212 | 0 | 0 | 0 | 0.977574 | 0.3587 |
| 4457235062_R02C01 | PF004515 211 | 0 | 0 | 0 | 0.98636 | 0.3557 |
| 4459273564_R01C02 | PF008370 204 | 0 | 0 | 1 | 0.991379 | 0.334 |
| 4457235469_R02C01 | PF004074 211 | 0 | 3 | 6 | 0.995622 | 0.3314 |
| 4432273525_R01C01 | PF015647 203 | 0 | 1 | 1 | 0.971849 | 0.3093 |
| 4459273561_R01C02 | PF008598 204 | 0 | 0 | 0 | 0.987798 | 0.2813 |
| 4459273653_R02C02 | PF008497 204 | 0 | 0 | 0 | 0.996147 | 0.271 |
| 4461875782_R02C01 | PF008280 206 | 9 | 20 | 67 | 0.997475 | 0.2586 |
| 4457235521_R01C01 | PF018730 202 | 0 | 0 | 0 | 0.998122 | 0.2571 |
| 4459273551_R02C01 | PF018719 202 | 0 | 0 | 0 | 0.992981 | 0.2565 |
| 4457235382_R02C01 | PF008868 211 | 0 | 0 | 0 | 0.997512 | 0.2537 |
| 4457235397_R01C01 | PF019903 212 | 0 | 0 | 0 | 0.993413 | 0.2515 |
| 4432265249_R02C01 | PF008832 211 | 0 | 0 | 0 | 0.995428 | 0.2419 |
| 4457235416_R02C01 | PF014879 211 | 0 | 0 | 0 | 0.996175 | 0.2414 |
| 4475687205_R02C01 | PF008535 204 | 0 | 3 | 13 | 0.996544 | 0.2368 |
| 4457235420_R02C02 | PF018820 202 | 0 | 0 | 0 | 0.997267 | 0.2327 |
| 4461875832_R02C02 | PF008263 204 | 3 | 11 | 32 | 0.996951 | 0.2272 |
| 4432273339_R01C01 | PF018867 203 | 0 | 0 | 0 | 0.998011 | 0.227 |
| 4457235244_R02C01 | PF018637 202 | 0 | 0 | 0 | 0.997525 | 0.2262 |
| 4457235468_R02C01 | PF004542 211 | 0 | 0 | 0 | 0.997343 | 0.2246 |
| 4457235057_R02C02 | PF005816 211 | 0 | 0 | 0 | 0.998177 | 0.2234 |
| 4457235037_R02C02 | PF016457 203 | 0 | 0 | 0 | 0.99688 | 0.2232 |
| 4461875676_R02C02 | PF008423 204 | 0 | 0 | 0 | 0.997926 | 0.2174 |
| 4457235452_R01C01 | PF004551 211 | 0 | 0 | 0 | 0.997742 | 0.2168 |
| 4432273286_R02C01 | PF018620 202 | 0 | 0 | 0 | 0.997384 | 0.2131 |
| 4457235026_R01C01 | PF016297 203 | 0 | 0 | 1 | 0.997307 | 0.2075 |
| 4457235470_R02C02 | PF004600 211 | 0 | 0 | 0 | 0.998293 | 0.206 |
| 4432273710_R02C01 | PF016344 203 | 0 | 0 | 1 | 0.996453 | 0.2037 |
| 4432273339_R01C02 | PF018955 202 | 0 | 1 | 2 | 0.998407 | 0.2035 |
| 4457235208_R01C01 | PF015337 224 | 0 | 0 | 1 | 0.972065 | 0.2015 |
| 4457235469_R01C02 | PF004522 211 | 0 | 0 | 0 | 0.998491 | 0.2014 |
| 4457235073_R01C02 | PF019299 203 | 0 | 0 | 1 | 0.998476 | 0.1995 |
| 4457235423_R02C02 | PF004007 211 | 0 | 0 | 0 | 0.99829 | 0.1979 |
| 4457235509_R01C02 | PF015090 203 | 0 | 0 | 0 | 0.998452 | 0.1971 |
| 4457235431_R01C01 | PF004059 211 | 0 | 0 | 0 | 0.997966 | 0.1964 |
| 4457235562_R02C02 | PF004256 211 | 0 | 0 | 0 | 0.998058 | 0.1963 |
| 4432273339_R02C02 | PF018987 203 | 0 | 0 | 1 | 0.998536 | 0.1958 |
| 4457235558_R01C02 | PF018610 203 | 0 | 0 | 1 | 0.998641 | 0.1927 |
| 4457235209_R01C01 | PF004686 211 | 0 | 0 | 0 | 0.997872 | 0.1921 |
| 4457235211_R02C01 | PF008265 204 | 0 | 0 | 0 | 0.997831 | 0.1919 |
| 4457235441_R01C01 | PF004567 211 | 0 | 0 | 1 | 0.998557 | 0.1918 |
| 4461875351_R02C02 | PF008513 204 | 18 | 38 | 100 | 0.997805 | 0.1908 |
| 4457235210_R01C01 | PF020083 202 | 0 | 0 | 0 | 0.998713 | 0.1897 |
| 4457235562_R01C02 | PF003821 211 | 0 | 0 | 1 | 0.997984 | 0.1896 |
| 4457235509_R02C02 | PF018596 202 | 0 | 0 | 0 | 0.99856 | 0.1889 |
| 4457235390_R01C01 | PF008066 204 | 0 | 0 | 0 | 0.998583 | 0.1889 |
| 4457235259_R01C01 | PF018854 202 | 0 | 0 | 0 | 0.997776 | 0.1888 |
| 4459273636_R02C02 | PF018845 202 | 0 | 0 | 0 | 0.997824 | 0.1886 |
| 4457235469_R02C02 | PF014931 211 | 0 | 0 | 1 | 0.998473 | 0.1885 |
| 4457235468_R02C02 | PF014881 211 | 0 | 0 | 0 | 0.998483 | 0.1883 |
| 4457235530_R02C01 | PF007802 211 | 0 | 0 | 0 | 0.997576 | 0.1874 |
| 4432273126_R02C02 | PF016374 203 | 0 | 0 | 0 | 0.998183 | 0.1873 |
| 4457235085_R01C01 | PF019905 212 | 0 | 0 | 1 | 0.997966 | 0.187 |
| 4457235470_R01C02 | PF004473 211 | 0 | 0 | 0 | 0.998414 | 0.187 |
| 4457235409_R02C01 | PF019928 203 | 0 | 0 | 0 | 0.998889 | 0.1868 |
| 4459273639_R02C02 | PF019468 202 | 0 | 0 | 0 | 0.998711 | 0.1863 |
| 4457235210_R01C02 | PF003917 211 | 0 | 0 | 0 | 0.998599 | 0.1851 |
| 4457235211_R01C02 | PF008276 204 | 0 | 0 | 2 | 0.998658 | 0.185 |
| 4457235382_R01C01 | PF003702 216 | 0 | 0 | 1 | 0.998757 | 0.184 |
| 4457235073_R01C01 | PF018983 202 | 0 | 0 | 0 | 0.998583 | 0.1837 |
| 4459273745_R02C02 | PF018402 221 | 0 | 0 | 0 | 0.998823 | 0.1835 |
| 4457235104_R01C01 | PF019969 203 | 0 | 0 | 0 | 0.998075 | 0.1833 |
| 4475687205_R01C01 | PF008315 204 | 0 | 1 | 3 | 0.99833 | 0.1828 |
| 4457235558_R01C01 | PF018582 202 | 0 | 0 | 0 | 0.998898 | 0.1828 |
| 4457235469_R01C01 | PF003964 211 | 0 | 0 | 0 | 0.998658 | 0.1827 |
| 4457235382_R01C02 | PF007926 211 | 0 | 0 | 0 | 0.998705 | 0.1824 |
| 4457235210_R02C01 | PF003680 211 | 0 | 0 | 0 | 0.998749 | 0.1824 |
| 4457235383_R02C02 | PF008813 211 | 0 | 0 | 0 | 0.998604 | 0.1822 |
| 4457235100_R02C02 | PF018523 212 | 0 | 0 | 0 | 0.998678 | 0.1817 |
| 4457235203_R01C01 | PF018683 202 | 0 | 0 | 0 | 0.998586 | 0.1815 |
| 4457235498_R01C01 | PF018906 202 | 0 | 0 | 1 | 0.99885 | 0.1809 |
| 4461875352_R02C01 | PF008628 204 | 0 | 0 | 1 | 0.99813 | 0.1807 |
| 4457235521_R02C01 | PF018736 202 | 0 | 0 | 0 | 0.998947 | 0.1806 |
| 4457235382_R02C02 | PF018404 221 | 0 | 0 | 0 | 0.998641 | 0.1803 |

TABLE 6-continued

| BID | SSID | Tier 1 CNV count | Tier 2 CNV count | Tier 3 CNV count | Callrate | LRR_SD |
|---|---|---|---|---|---|---|
| 4457235101_R01C01 | PF019746 202 | 0 | 0 | 0 | 0.998151 | 0.1802 |
| 4457235383_R01C01 | PF004590 211 | 1 | 2 | 3 | 0.998443 | 0.1798 |
| 4459273563_R02C02 | PF019628 202 | 0 | 0 | 0 | 0.998166 | 0.1797 |
| 4457235408_R01C02 | PF019986 203 | 0 | 0 | 1 | 0.998897 | 0.1793 |
| 4457235562_R01C01 | PF006018 211 | 0 | 0 | 0 | 0.998038 | 0.1792 |
| 4457235085_R01C02 | PF019917 203 | 0 | 0 | 1 | 0.998175 | 0.1788 |
| 4457235078_R01C01 | PF004409 211 | 0 | 0 | 0 | 0.998006 | 0.1786 |
| 4457235421_R02C01 | PF004057 211 | 0 | 0 | 0 | 0.998339 | 0.1786 |
| 4457235431_R02C02 | PF003704 211 | 0 | 0 | 0 | 0.998111 | 0.1785 |
| 4457235180_R02C02 | PF008506 204 | 0 | 1 | 3 | 0.99876 | 0.1784 |
| 4457235210_R02C02 | PF008821 211 | 0 | 0 | 0 | 0.998773 | 0.1782 |
| 4457235045_R02C02 | PF008850 211 | 0 | 0 | 0 | 0.998501 | 0.1781 |
| 4457235085_R02C01 | PF019914 203 | 0 | 0 | 1 | 0.997853 | 0.1774 |
| 4461875659_R01C01 | PF004134 211 | 0 | 1 | 5 | 0.998848 | 0.1771 |
| 4457235509_R01C01 | PF004637 211 | 0 | 0 | 0 | 0.998554 | 0.1768 |
| 4457235208_R02C01 | PF015989 224 | 0 | 0 | 0 | 0.998528 | 0.1766 |
| 4457235258_R01C02 | PF019301 203 | 0 | 0 | 0 | 0.998431 | 0.1761 |
| 4457235026_R01C02 | PF016590 203 | 0 | 0 | 0 | 0.997721 | 0.1758 |
| 4432273748_R02C02 | PF018929 203 | 0 | 0 | 0 | 0.998423 | 0.1754 |
| 4457235072_R01C01 | PF019688 202 | 0 | 0 | 0 | 0.998439 | 0.1748 |
| 4457235073_R02C01 | PF019293 203 | 0 | 0 | 0 | 0.998789 | 0.1744 |
| 4457235562_R02C01 | PF008854 211 | 0 | 0 | 0 | 0.998149 | 0.174 |
| 4457235208_R02C02 | PF016082 224 | 0 | 0 | 1 | 0.998683 | 0.1739 |
| 4457235279_R01C01 | PF018852 202 | 0 | 0 | 0 | 0.998473 | 0.1739 |
| 4459273626_R01C02 | PF019965 203 | 0 | 0 | 0 | 0.998615 | 0.1735 |
| 4457235209_R02C02 | PF008788 211 | 1 | 11 | 28 | 0.998169 | 0.1733 |
| 4432273103_R02C01 | PF019814 202 | 0 | 0 | 1 | 0.998246 | 0.1726 |
| 4457235236_R02C02 | PF018797 202 | 0 | 0 | 0 | 0.99814 | 0.1726 |
| 4457235470_R02C01 | PF008802 211 | 0 | 0 | 0 | 0.998689 | 0.1724 |
| 4457235558_R02C02 | PF018656 202 | 0 | 0 | 0 | 0.998903 | 0.1724 |
| 4459273641_R02C02 | PF008641 204 | 0 | 0 | 0 | 0.999042 | 0.1722 |
| 4457235383_R01C02 | PF006892 211 | 0 | 0 | 0 | 0.998584 | 0.1719 |
| 4457235509_R02C01 | PF014850 211 | 1 | 1 | 1 | 0.99867 | 0.1718 |
| 4457235209_R01C02 | PF008768 211 | 0 | 0 | 0 | 0.998198 | 0.1718 |
| 4432273631_R01C02 | PF019994 212 | 0 | 1 | 1 | 0.998191 | 0.1717 |
| 4457235452_R02C01 | PF004624 211 | 0 | 0 | 0 | 0.998405 | 0.1713 |
| 4457235470_R01C02 | PF020089 202 | 1 | 0 | 0 | 0.998444 | 0.1713 |
| 4457235421_R01C01 | PF007798 211 | 0 | 0 | 1 | 0.998364 | 0.1712 |
| 4457235431_R02C01 | PF004508 211 | 0 | 0 | 0 | 0.998024 | 0.1712 |
| 4432273407_R01C02 | PF018934 202 | 0 | 0 | 1 | 0.998132 | 0.171 |
| 4457235258_R02C02 | PF019346 203 | 0 | 0 | 0 | 0.998468 | 0.1708 |
| 4459273481_R02C02 | PF019995 212 | 0 | 0 | 0 | 0.998481 | 0.1705 |
| 4457235416_R02C02 | PF004062 211 | 0 | 0 | 0 | 0.998365 | 0.1704 |
| 4432265059_R01C02 | PF019499 202 | 0 | 0 | 0 | 0.998344 | 0.1701 |
| 4457235103_R01C01 | PF014830 211 | 0 | 0 | 0 | 0.998391 | 0.1699 |
| 4457235452_R02C02 | PF005550 211 | 1 | 1 | 1 | 0.998227 | 0.1688 |
| 4457235072_R01C02 | PF019815 202 | 0 | 0 | 0 | 0.998662 | 0.1688 |
| 4457235558_R02C01 | PF018605 202 | 0 | 0 | 0 | 0.998884 | 0.1688 |
| 4432265081_R02C01 | PF007738 211 | 0 | 0 | 2 | 0.99867 | 0.1686 |
| 4457235415_R02C02 | PF018432 212 | 0 | 0 | 1 | 0.998383 | 0.1682 |
| 4457235085_R02C02 | PF019932 203 | 0 | 0 | 1 | 0.997956 | 0.1675 |
| 4457235408_R01C01 | PF019925 212 | 0 | 0 | 0 | 0.998821 | 0.1675 |
| 4457235452_R01C02 | PF008835 211 | 0 | 0 | 0 | 0.998122 | 0.1674 |
| 4457235090_R01C01 | PF019772 202 | 0 | 0 | 0 | 0.998575 | 0.1673 |
| 4432265321_R01C01 | PF019745 202 | 0 | 0 | 0 | 0.99837 | 0.1667 |
| 4459273491_R02C01 | PF014959 211 | 0 | 0 | 0 | 0.998182 | 0.1666 |
| 4432265606_R01C01 | PF019527 202 | 0 | 0 | 0 | 0.998319 | 0.1666 |
| 4457235063_R01C02 | PF008604 204 | 0 | 0 | 0 | 0.998314 | 0.1665 |
| 4457235421_R01C02 | PF004242 211 | 0 | 0 | 0 | 0.998267 | 0.1663 |
| 4457235443_R02C02 | PF019904 212 | 0 | 0 | 0 | 0.998686 | 0.1661 |
| 4457235303_R01C02 | PF008397 202 | 0 | 0 | 0 | 0.997048 | 0.1656 |
| 4457235196_R01C02 | PF018497 212 | 0 | 0 | 0 | 0.998567 | 0.1656 |
| 4459273638_R01C01 | PF019857 212 | 0 | 0 | 0 | 0.998599 | 0.1656 |
| 4457235408_R02C02 | PF020011 202 | 0 | 0 | 1 | 0.998922 | 0.1654 |
| 4432273103_R02C02 | PF019821 202 | 0 | 0 | 0 | 0.998333 | 0.1654 |
| 4457235072_R02C02 | PF019865 203 | 1 | 1 | 1 | 0.998626 | 0.1653 |
| 4432273631_R02C02 | PF020051 202 | 0 | 0 | 0 | 0.998198 | 0.1652 |
| 4432273141_R01C01 | PF003805 211 | 0 | 0 | 0 | 0.997985 | 0.165 |
| 4432273126_R01C02 | PF019974 203 | 1 | 1 | 1 | 0.998911 | 0.1649 |
| 4457235103_R01C02 | PF003895 211 | 0 | 0 | 0 | 0.998354 | 0.1648 |
| 4457235424_R02C02 | PF004504 211 | 0 | 0 | 1 | 0.998642 | 0.1647 |
| 4457235101_R02C02 | PF019887 203 | 0 | 0 | 0 | 0.998164 | 0.1646 |
| 4432265894_R01C02 | PF004024 211 | 0 | 0 | 0 | 0.997404 | 0.1645 |
| 4457235153_R02C01 | PF016265 203 | 0 | 0 | 0 | 0.998153 | 0.1645 |
| 4457235409_R01C01 | PF019748 202 | 0 | 0 | 0 | 0.998819 | 0.1645 |
| 4457235101_R01C02 | PF019786 202 | 0 | 0 | 0 | 0.997955 | 0.1644 |

TABLE 6-continued

| BID | SSID | Tier 1 CNV count | Tier 2 CNV count | Tier 3 CNV count | Callrate | LRR_SD |
|---|---|---|---|---|---|---|
| 4432265616_R01C01 | PF019528 202 | 0 | 0 | 1 | 0.998607 | 0.1642 |
| 4459273522_R01C01 | PF018846 202 | 0 | 0 | 0 | 0.999053 | 0.1642 |
| 4457235431_R01C02 | PF007817 211 | 0 | 0 | 0 | 0.998214 | 0.1641 |
| 4457235258_R01C01 | PF018917 202 | 0 | 0 | 0 | 0.998592 | 0.1639 |
| 4457235238_R01C01 | PF018971 202 | 0 | 0 | 0 | 0.998742 | 0.1637 |
| 4457235049_R02C02 | PF020391 221 | 0 | 0 | 0 | 0.99885 | 0.1637 |
| 4459273655_R01C01 | PF008258 204 | 0 | 0 | 0 | 0.99847 | 0.1636 |
| 4432265042_R02C01 | PF005757 211 | 0 | 0 | 0 | 0.998563 | 0.1635 |
| 4459273564_R01C01 | PF008338 204 | 0 | 0 | 1 | 0.998571 | 0.1633 |
| 4457235390_R01C02 | PF016067 224 | 0 | 0 | 0 | 0.998333 | 0.1633 |
| 4459273424_R02C02 | PF018773 202 | 0 | 0 | 0 | 0.998711 | 0.1631 |
| 4457235102_R01C02 | PF004534 211 | 5 | 8 | 18 | 0.998138 | 0.1627 |
| 4457235317_R02C02 | PF018809 202 | 0 | 0 | 0 | 0.998747 | 0.1625 |
| 4457235420_R01C02 | PF018752 202 | 0 | 0 | 0 | 0.997937 | 0.1624 |
| 4457235238_R01C02 | PF019621 202 | 0 | 0 | 0 | 0.998813 | 0.1624 |
| 4475687204_R01C01 | PF020013 202 | 0 | 0 | 0 | 0.998763 | 0.1622 |
| 4457235101_R02C01 | PF019765 202 | 0 | 0 | 0 | 0.99785 | 0.1621 |
| 4457235424_R01C01 | PF004493 211 | 0 | 0 | 0 | 0.998902 | 0.162 |
| 4457235057_R01C01 | PF019938 212 | 0 | 0 | 0 | 0.99843 | 0.1619 |
| 4457235420_R01C01 | PF018452 212 | 0 | 0 | 0 | 0.998283 | 0.1618 |
| 4457235487_R01C02 | PF020038 202 | 0 | 0 | 0 | 0.998728 | 0.1618 |
| 4482537426_R01C02 | PF019081 202 | 0 | 0 | 0 | 0.998869 | 0.1617 |
| 4482537640_R02C02 | PF018564 212 | 0 | 1 | 2 | 0.998736 | 0.1616 |
| 4457235420_R02C01 | PF018712 202 | 0 | 0 | 0 | 0.998307 | 0.1616 |
| 4457235049_R01C02 | PF008198 206 | 0 | 0 | 0 | 0.991248 | 0.1614 |
| 4461875315_R01C01 | PF020022 203 | 0 | 0 | 0 | 0.998634 | 0.1611 |
| 4457235423_R01C02 | PF008823 211 | 0 | 0 | 0 | 0.998372 | 0.1609 |
| 4457235102_R01C01 | PF003711 211 | 0 | 0 | 1 | 0.998235 | 0.1608 |
| 4457235196_R01C01 | PF016972 203 | 0 | 0 | 0 | 0.998544 | 0.1607 |
| 4457235026_R02C02 | PF017278 203 | 0 | 0 | 0 | 0.997582 | 0.1605 |
| 4459273627_R02C02 | PF019295 203 | 0 | 0 | 0 | 0.998832 | 0.1603 |
| 4457235488_R01C02 | PF005923 211 | 0 | 0 | 0 | 0.998599 | 0.1602 |
| 4459273635_R02C02 | PF019042 202 | 0 | 0 | 1 | 0.997906 | 0.16 |
| 4457235024_R02C01 | PF018872 202 | 0 | 0 | 1 | 0.998703 | 0.1599 |
| 4461875711_R02C02 | PF008074 204 | 0 | 1 | 4 | 0.998296 | 0.1598 |
| 4482537404_R01C02 | PF019175 202 | 0 | 0 | 1 | 0.998792 | 0.1597 |
| 4457235057_R01C02 | PF019956 203 | 0 | 0 | 0 | 0.998492 | 0.1596 |
| 4432265606_R01C02 | PF019829 202 | 0 | 0 | 0 | 0.998001 | 0.1595 |
| 4461875623_R01C02 | PF008532 204 | 0 | 0 | 0 | 0.999013 | 0.1595 |
| 4482537405_R01C02 | PF019158 202 | 0 | 0 | 2 | 0.998769 | 0.1593 |
| 4432265060_R01C02 | PF018581 202 | 0 | 0 | 0 | 0.997744 | 0.1593 |
| 4482537024_R01C02 | PF019038 202 | 0 | 0 | 0 | 0.998426 | 0.1592 |
| 4432273648_R02C02 | PF018477 212 | 0 | 0 | 1 | 0.99819 | 0.1591 |
| 4457235078_R01C01 | PF003900 211 | 0 | 0 | 0 | 0.997917 | 0.1589 |
| 4432273103_R01C02 | PF019819 202 | 0 | 0 | 0 | 0.998269 | 0.1589 |
| 4457235063_R01C01 | PF008548 204 | 0 | 0 | 0 | 0.998215 | 0.1587 |
| 4432265374_R01C02 | PF020292 221 | 0 | 0 | 1 | 0.997584 | 0.1586 |
| 4457235409_R01C02 | PF019820 202 | 0 | 0 | 1 | 0.998705 | 0.1586 |
| 4457235063_R02C02 | PF018741 202 | 0 | 0 | 0 | 0.998428 | 0.1586 |
| 4475687206_R01C01 | PF016715 203 | 0 | 0 | 0 | 0.998583 | 0.1586 |
| 4457235049_R01C01 | PF018727 202 | 0 | 0 | 0 | 0.998831 | 0.1586 |
| 4457235209_R02C01 | PF008766 211 | 1 | 1 | 1 | 0.998338 | 0.1585 |
| 4457235423_R01C01 | PF004682 211 | 0 | 0 | 0 | 0.998328 | 0.1585 |
| 4457235258_R02C01 | PF019282 203 | 0 | 0 | 1 | 0.998544 | 0.1584 |
| 4461875796_R01C02 | PF018423 203 | 0 | 0 | 0 | 0.998697 | 0.1584 |
| 4459273656_R01C01 | PF019469 202 | 0 | 0 | 0 | 0.998723 | 0.1584 |
| 4459273653_R02C01 | PF008478 204 | 0 | 0 | 1 | 0.998415 | 0.1582 |
| 4457235416_R01C01 | PF008831 211 | 1 | 0 | 0 | 0.998534 | 0.1582 |
| 4457235100_R01C01 | PF017383 203 | 0 | 0 | 0 | 0.998596 | 0.1582 |
| 4457235343_R01C01 | PF005840 211 | 0 | 0 | 1 | 0.998491 | 0.1577 |
| 4482537390_R01C02 | PF019095 202 | 0 | 0 | 0 | 0.998658 | 0.1577 |
| 4461875623_R01C01 | PF008358 204 | 0 | 0 | 1 | 0.9989 | 0.1576 |
| 4461875494_R01C01 | PF005917 211 | 0 | 0 | 0 | 0.998879 | 0.1576 |
| 4432273141_R02C01 | PF003849 211 | 0 | 0 | 0 | 0.998035 | 0.1575 |
| 4457235203_R01C01 | PF018653 202 | 0 | 0 | 0 | 0.998496 | 0.1571 |
| 4461875451_R02C02 | PF019313 203 | 0 | 0 | 3 | 0.997798 | 0.157 |
| 4457235259_R01C02 | PF018884 202 | 0 | 0 | 0 | 0.998238 | 0.1569 |
| 4432273639_R01C01 | PF004191 211 | 0 | 0 | 0 | 0.998302 | 0.1568 |
| 4475687204_R01C01 | PF014945 211 | 0 | 0 | 0 | 0.998586 | 0.1568 |
| 4459273653_R01C01 | PF008445 204 | 0 | 0 | 0 | 0.998621 | 0.1567 |
| 4459273638_R01C02 | PF019860 212 | 0 | 0 | 1 | 0.998576 | 0.1566 |
| 4461875832_R01C01 | PF008245 204 | 1 | 3 | 6 | 0.998655 | 0.1564 |
| 4482537199_R01C02 | PF020023 202 | 0 | 0 | 0 | 0.998729 | 0.1563 |
| 4461875644_R02C02 | PF018779 221 | 7 | 11 | 33 | 0.998668 | 0.1562 |
| 4432273648_R02C01 | PF017439 221 | 0 | 0 | 1 | 0.998212 | 0.1562 |
| 4459273628_R01C01 | PF003963 211 | 0 | 0 | 1 | 0.998586 | 0.1562 |

TABLE 6-continued

| BID | SSID | Tier 1 CNV count | Tier 2 CNV count | Tier 3 CNV count | Callrate | LRR_SD |
|---|---|---|---|---|---|---|
| 4457235279_R01C02 | PF018910 202 | 0 | 0 | 0 | 0.998454 | 0.1562 |
| 4461875714_R02C02 | PF019246 202 | 1 | 1 | 1 | 0.998919 | 0.1561 |
| 4457235236_R01C01 | PF018729 202 | 0 | 0 | 0 | 0.998185 | 0.156 |
| 4457235442_R01C02 | PF017014 203 | 0 | 0 | 0 | 0.998499 | 0.156 |
| 4459273728_R02C02 | PF004742 211 | 0 | 0 | 1 | 0.998644 | 0.1559 |
| 4459273492_R01C02 | PF016646 203 | 0 | 1 | 1 | 0.998911 | 0.1559 |
| 4457235346_R02C02 | PF018714 202 | 0 | 0 | 0 | 0.998757 | 0.1559 |
| 4457235317_R02C01 | PF018788 221 | 0 | 0 | 0 | 0.998626 | 0.1556 |
| 4457235279_R02C02 | PF018949 202 | 0 | 0 | 0 | 0.99837 | 0.1554 |
| 4457235024_R01C02 | PF018885 202 | 0 | 0 | 0 | 0.9979 | 0.1552 |
| 4457235026_R02C01 | PF016584 203 | 0 | 0 | 0 | 0.997645 | 0.1549 |
| 4459273628_R01C02 | PF008239 204 | 0 | 0 | 0 | 0.998544 | 0.1547 |
| 4432265042_R01C01 | PF020002 203 | 0 | 0 | 1 | 0.998715 | 0.1546 |
| 4461875658_R02C01 | PF003791 211 | 0 | 0 | 0 | 0.998758 | 0.1546 |
| 4459273748_R02C02 | PF014868 211 | 0 | 0 | 0 | 0.998856 | 0.1545 |
| 4457235103_R02C02 | PF004524 211 | 0 | 0 | 0 | 0.998544 | 0.1544 |
| 4457235390_R02C01 | PF015670 203 | 0 | 0 | 0 | 0.998591 | 0.1541 |
| 4457235243_R01C02 | PF018913 202 | 1 | 1 | 2 | 0.998629 | 0.1539 |
| 4461875480_R01C02 | PF019476 202 | 0 | 0 | 1 | 0.999127 | 0.1539 |
| 4457235028_R01C01 | PF019425 202 | 0 | 0 | 0 | 0.998261 | 0.1539 |
| 4475687206_R01C02 | PF017296 203 | 0 | 0 | 0 | 0.998542 | 0.1538 |
| 4457235062_R01C01 | PF004633 211 | 0 | 0 | 0 | 0.997835 | 0.1537 |
| 4457235366_R01C01 | PF018950 202 | 0 | 0 | 0 | 0.998478 | 0.1537 |
| 4432273279_R02C02 | PF016629 203 | 0 | 0 | 0 | 0.997689 | 0.1536 |
| 4459273636_R01C01 | PF018667 202 | 0 | 0 | 0 | 0.99852 | 0.1536 |
| 4457235062_R01C02 | PF004732 211 | 1 | 1 | 1 | 0.997729 | 0.1535 |
| 4475687205_R02C02 | PF016708 203 | 0 | 0 | 0 | 0.998703 | 0.1534 |
| 4461875832_R01C02 | PF008256 204 | 0 | 0 | 0 | 0.998724 | 0.1534 |
| 4482537600_R01C01 | PF008812 211 | 0 | 0 | 0 | 0.999016 | 0.1534 |
| 4482537404_R01C01 | PF019163 202 | 0 | 0 | 1 | 0.998864 | 0.1533 |
| 4461875381_R01C02 | PF016094 203 | 0 | 0 | 0 | 0.998718 | 0.1533 |
| 4482537426_R01C01 | PF019072 202 | 0 | 0 | 1 | 0.998935 | 0.1531 |
| 4457235423_R02C01 | PF007954 211 | 0 | 1 | 4 | 0.998679 | 0.153 |
| 4457235025_R02C02 | PF004497 211 | 0 | 0 | 0 | 0.99837 | 0.153 |
| 4457235100_R01C02 | PF018474 212 | 0 | 0 | 0 | 0.998657 | 0.153 |
| 4432273181_R01C02 | PF014836 211 | 0 | 0 | 0 | 0.997795 | 0.1528 |
| 4457235416_R01C02 | PF008008 211 | 0 | 0 | 0 | 0.998465 | 0.1527 |
| 4459273635_R01C01 | PF018787 221 | 0 | 0 | 0 | 0.998 | 0.1526 |
| 4457235487_R01C01 | PF019990 212 | 0 | 0 | 0 | 0.998845 | 0.1525 |
| 4457235259_R02C01 | PF018859 202 | 0 | 0 | 0 | 0.998056 | 0.1524 |
| 4461875644_R01C02 | PF018745 202 | 0 | 0 | 0 | 0.998749 | 0.1524 |
| 4457235610_R02C02 | PF018441 212 | 0 | 0 | 1 | 0.997359 | 0.1523 |
| 4432273321_R02C01 | PF018731 202 | 0 | 0 | 0 | 0.998177 | 0.1523 |
| 4457235028_R01C02 | PF019471 202 | 0 | 0 | 0 | 0.998201 | 0.1522 |
| 4482537405_R01C01 | PF019151 202 | 0 | 0 | 0 | 0.998839 | 0.1522 |
| 4457235521_R02C02 | PF018755 202 | 0 | 0 | 0 | 0.998676 | 0.1521 |
| 4457235468_R01C01 | PF003919 211 | 0 | 0 | 0 | 0.99871 | 0.1521 |
| 4461875797_R01C01 | PF018437 203 | 0 | 0 | 0 | 0.998926 | 0.1521 |
| 4475687206_R02C02 | PF017443 203 | 0 | 0 | 0 | 0.99855 | 0.1519 |
| 4432273747_R02C02 | PF016986 203 | 1 | 7 | 23 | 0.998583 | 0.1518 |
| 4432265011_R02C01 | PF007933 211 | 0 | 0 | 0 | 0.998022 | 0.1518 |
| 4459273718_R02C02 | PF008610 204 | 0 | 0 | 0 | 0.998331 | 0.1518 |
| 4482537179_R02C02 | PF018780 202 | 1 | 0 | 0 | 0.998443 | 0.1518 |
| 4432273756_R02C02 | PF003734 211 | 0 | 0 | 1 | 0.998375 | 0.1516 |
| 4457235196_R02C01 | PF016990 203 | 0 | 0 | 0 | 0.998552 | 0.1516 |
| 4457235442_R02C01 | PF016469 203 | 0 | 0 | 0 | 0.9986 | 0.1516 |
| 4461875172_R01C02 | PF018555 212 | 0 | 0 | 0 | 0.998768 | 0.1516 |
| 4461875831_R02C02 | PF005565 211 | 0 | 0 | 1 | 0.998434 | 0.1515 |
| 4457235102_R02C02 | PF005802 211 | 0 | 0 | 0 | 0.998217 | 0.1515 |
| 4432273322_R02C02 | PF018621 202 | 0 | 0 | 0 | 0.998473 | 0.1515 |
| 4457235346_R01C01 | PF018502 212 | 0 | 0 | 0 | 0.998721 | 0.1515 |
| 4457235401_R02C02 | PF016411 203 | 0 | 1 | 5 | 0.998779 | 0.1514 |
| 4459273639_R01C02 | PF019431 202 | 0 | 0 | 0 | 0.998829 | 0.1513 |
| 4461875448_R01C02 | PF020024 202 | 0 | 0 | 0 | 0.998844 | 0.1513 |
| 4459273491_R02C02 | PF008299 204 | 2 | 3 | 7 | 0.998726 | 0.1512 |
| 4457235025_R01C01 | PF004021 211 | 0 | 0 | 0 | 0.998446 | 0.1512 |
| 4457235103_R02C01 | PF003745 211 | 0 | 0 | 0 | 0.998462 | 0.1512 |
| 4459273280_R01C01 | PF007984 211 | 0 | 0 | 0 | 0.998491 | 0.1512 |
| 4457235064_R01C01 | PF008345 204 | 0 | 0 | 1 | 0.998195 | 0.1511 |
| 4459273728_R01C02 | PF004502 211 | 0 | 0 | 0 | 0.998686 | 0.1511 |
| 4461875831_R01C01 | PF020047 202 | 0 | 0 | 0 | 0.99848 | 0.151 |
| 4457235442_R01C01 | PF016459 203 | 0 | 0 | 0 | 0.998641 | 0.151 |
| 4459273641_R01C01 | PF008393 204 | 0 | 0 | 0 | 0.998864 | 0.1509 |
| 4461875494_R01C02 | PF005948 211 | 0 | 1 | 1 | 0.998914 | 0.1508 |
| 4482537600_R01C02 | PF014960 211 | 0 | 0 | 1 | 0.998927 | 0.1508 |
| 4475687205_R01C02 | PF014948 211 | 0 | 0 | 0 | 0.998523 | 0.1508 |

TABLE 6-continued

| BID | SSID | Tier 1 CNV count | Tier 2 CNV count | Tier 3 CNV count | Callrate | LRR_SD |
|---|---|---|---|---|---|---|
| 4457235424_R01C02 | PF007857 211 | 0 | 0 | 0 | 0.998526 | 0.1507 |
| 4457235294_R01C02 | PF019472 202 | 0 | 0 | 0 | 0.998758 | 0.1507 |
| 4457235409_R02C01 | PF019755 202 | 0 | 0 | 0 | 0.998984 | 0.1507 |
| 4457235104_R01C02 | PF020006 212 | 0 | 0 | 1 | 0.998647 | 0.1505 |
| 4457235238_R02C02 | PF019718 202 | 1 | 1 | 1 | 0.998808 | 0.1505 |
| 4459273747_R02C01 | PF019984 212 | 0 | 0 | 1 | 0.998879 | 0.1505 |
| 4457235078_R02C02 | PF018476 212 | 1 | 1 | 1 | 0.998053 | 0.1504 |
| 4457235246_R01C02 | PF015806 203 | 0 | 0 | 1 | 0.998463 | 0.1503 |
| 4432273383_R01C02 | PF018793 202 | 0 | 6 | 16 | 0.998417 | 0.1502 |
| 4432273630_R01C01 | PF019703 202 | 0 | 0 | 0 | 0.998789 | 0.1502 |
| 4459273323_R01C01 | PF008157 204 | 0 | 0 | 0 | 0.998818 | 0.1501 |
| 4459273629_R01C01 | PF003714 211 | 0 | 0 | 0 | 0.99898 | 0.1501 |
| 4459273745_R01C01 | PF014901 211 | 0 | 0 | 1 | 0.998853 | 0.15 |
| 4459273661_R01C02 | PF019915 212 | 0 | 1 | 2 | 0.99832 | 0.1498 |
| 4461875594_R01C02 | PF004569 211 | 0 | 0 | 1 | 0.998758 | 0.1498 |
| 4461875382_R01C01 | PF019930 212 | 0 | 0 | 0 | 0.998943 | 0.1498 |
| 4457235196_R02C02 | PF018631 202 | 0 | 0 | 1 | 0.998641 | 0.1497 |
| 4432265249_R01C01 | PF018693 202 | 0 | 0 | 1 | 0.99898 | 0.1495 |
| 4457235530_R01C01 | PF003867 211 | 0 | 1 | 1 | 0.998323 | 0.1494 |
| 4432273748_R01C01 | PF018874 202 | 0 | 0 | 0 | 0.998449 | 0.1494 |
| 4461875833_R01C01 | PF008191 204 | 0 | 0 | 1 | 0.998831 | 0.1492 |
| 4457235397_R01C02 | PF019918 212 | 1 | 0 | 0 | 0.998861 | 0.1492 |
| 4459273627_R01C01 | PF018988 202 | 0 | 0 | 0 | 0.998911 | 0.1492 |
| 4457235401_R01C01 | PF016044 224 | 0 | 0 | 0 | 0.998829 | 0.1491 |
| 4459273656_R02C01 | PF019474 202 | 1 | 1 | 4 | 0.998381 | 0.149 |
| 4457235521_R01C02 | PF018742 202 | 0 | 0 | 0 | 0.998687 | 0.149 |
| 4482537404_R02C02 | PF019176 202 | 0 | 0 | 0 | 0.998848 | 0.1489 |
| 4432273182_R02C01 | PF019559 202 | 0 | 0 | 1 | 0.998605 | 0.1488 |
| 4457235045_R01C02 | PF008793 211 | 0 | 0 | 0 | 0.99855 | 0.1488 |
| 4459273563_R01C02 | PF019479 202 | 0 | 0 | 1 | 0.998555 | 0.1487 |
| 4457235079_R01C02 | PF019807 202 | 0 | 0 | 0 | 0.998256 | 0.1487 |
| 4482537632_R02C01 | PF018573 202 | 0 | 0 | 0 | 0.998375 | 0.1487 |
| 4459273492_R01C01 | PF008667 204 | 0 | 0 | 0 | 0.999034 | 0.1487 |
| 4457235148_R02C02 | PF019744 202 | 0 | 0 | 0 | 0.997795 | 0.1486 |
| 4457235574_R01C02 | PF020009 203 | 0 | 0 | 0 | 0.99875 | 0.1486 |
| 4457235037_R01C01 | PF016098 203 | 0 | 0 | 0 | 0.998919 | 0.1485 |
| 4459273564_R02C02 | PF008385 204 | 0 | 0 | 1 | 0.998726 | 0.1484 |
| 4459273630_R02C02 | PF004584 211 | 1 | 2 | 4 | 0.9986 | 0.1483 |
| 4457235090_R01C02 | PF019823 202 | 0 | 0 | 0 | 0.99837 | 0.1483 |
| 4459273642_R01C01 | PF003922 211 | 0 | 0 | 1 | 0.998974 | 0.1482 |
| 4457235195_R01C02 | PF018646 202 | 0 | 0 | 0 | 0.998721 | 0.1482 |
| 4461875604_R01C01 | PF008000 211 | 0 | 0 | 0 | 0.998763 | 0.1482 |
| 4459273656_R01C02 | PF019481 202 | 0 | 0 | 0 | 0.998341 | 0.1481 |
| 4457235075_R01C01 | PF019913 212 | 0 | 0 | 0 | 0.998613 | 0.148 |
| 4457235443_R01C02 | PF019889 203 | 0 | 0 | 0 | 0.99867 | 0.148 |
| 4457235366_R01C02 | PF018998 202 | 0 | 1 | 1 | 0.998354 | 0.1479 |
| 4459273491_R01C01 | PF008877 211 | 0 | 0 | 1 | 0.999003 | 0.1479 |
| 4459273280_R01C02 | PF004484 211 | 0 | 0 | 0 | 0.998586 | 0.1479 |
| 4457235107_R01C01 | PF019410 203 | 0 | 0 | 0 | 0.998837 | 0.1478 |
| 4457235075_R01C02 | PF019942 212 | 0 | 0 | 0 | 0.998691 | 0.1476 |
| 4459273727_R01C02 | PF014831 211 | 0 | 0 | 0 | 0.998955 | 0.1476 |
| 4457235238_R02C01 | PF019322 203 | 0 | 0 | 1 | 0.998847 | 0.1474 |
| 4459273491_R01C02 | PF008291 204 | 0 | 0 | 0 | 0.998876 | 0.1474 |
| 4432273755_R01C02 | PF016084 224 | 0 | 0 | 0 | 0.998887 | 0.1474 |
| 4482537024_R01C01 | PF018575 202 | 0 | 0 | 0 | 0.998473 | 0.1473 |
| 4457235303_R01C01 | PF004739 212 | 0 | 0 | 0 | 0.997123 | 0.1472 |
| 4457235078_R02C01 | PF004049 211 | 0 | 0 | 0 | 0.998038 | 0.1472 |
| 4461875645_R01C02 | PF018857 202 | 1 | 1 | 1 | 0.998575 | 0.1471 |
| 4432273429_R02C02 | PF015649 203 | 0 | 0 | 0 | 0.997587 | 0.147 |
| 4457235390_R02C02 | PF016960 203 | 0 | 0 | 0 | 0.998536 | 0.147 |
| 4461875465_R01C02 | PF019451 202 | 0 | 0 | 0 | 0.998671 | 0.147 |
| 4482537404_R02C01 | PF019173 202 | 0 | 0 | 0 | 0.998885 | 0.147 |
| 4457235442_R02C02 | PF017088 203 | 0 | 0 | 1 | 0.998555 | 0.1469 |
| 4432265011_R02C02 | PF008857 211 | 0 | 0 | 0 | 0.998148 | 0.1469 |
| 4459273642_R02C01 | PF014880 211 | 0 | 0 | 1 | 0.999005 | 0.1468 |
| 4457235356_R02C02 | PF018895 202 | 1 | 1 | 1 | 0.9986 | 0.1467 |
| 4457235090_R02C01 | PF019816 202 | 0 | 0 | 0 | 0.998502 | 0.1467 |
| 4459273563_R01C01 | PF019269 203 | 0 | 0 | 0 | 0.99865 | 0.1466 |
| 4459273653_R01C02 | PF008486 204 | 5 | 9 | 22 | 0.998447 | 0.1465 |
| 4432265606_R02C02 | PF015662 203 | 0 | 0 | 0 | 0.997903 | 0.1465 |
| 4457235236_R01C02 | PF019134 202 | 0 | 0 | 0 | 0.998111 | 0.1465 |
| 4432265321_R02C02 | PF019927 203 | 0 | 0 | 1 | 0.998356 | 0.1464 |
| 4459273522_R01C02 | PF019040 202 | 0 | 0 | 1 | 0.998921 | 0.1464 |
| 4459273550_R01C01 | PF008295 204 | 0 | 0 | 0 | 0.998541 | 0.1464 |
| 4482537390_R02C01 | PF019092 202 | 0 | 0 | 0 | 0.998848 | 0.1464 |
| 4432273710_R01C02 | PF019757 202 | 0 | 0 | 1 | 0.997381 | 0.1463 |

TABLE 6-continued

| BID | SSID | Tier 1 CNV count | Tier 2 CNV count | Tier 3 CNV count | Callrate | LRR_SD |
|---|---|---|---|---|---|---|
| 4432265400_R01C01 | PF015751 203 | 0 | 0 | 1 | 0.998681 | 0.1462 |
| 4457235528_R01C01 | PF019475 202 | 0 | 0 | 1 | 0.997914 | 0.1461 |
| 4457235528_R01C02 | PF019542 202 | 0 | 0 | 0 | 0.997843 | 0.1461 |
| 4459273550_R02C02 | PF008323 204 | 1 | 1 | 2 | 0.998119 | 0.146 |
| 4432265249_R01C02 | PF004516 211 | 1 | 1 | 1 | 0.998926 | 0.146 |
| 4461875833_R01C02 | PF020356 221 | 0 | 0 | 0 | 0.998625 | 0.146 |
| 4432273181_R01C01 | PF004065 211 | 0 | 0 | 0 | 0.997584 | 0.1459 |
| 4457235100_R02C01 | PF018442 212 | 0 | 0 | 0 | 0.998755 | 0.1459 |
| 4482537640_R01C01 | PF014900 211 | 0 | 0 | 1 | 0.999035 | 0.1458 |
| 4457235015_R01C01 | PF019686 202 | 0 | 0 | 0 | 0.998734 | 0.1458 |
| 4461875315_R01C02 | PF003967 211 | 0 | 10 | 27 | 0.998526 | 0.1456 |
| 4461875352_R01C01 | PF008616 204 | 0 | 0 | 0 | 0.998589 | 0.1456 |
| 4432265010_R02C01 | PF003795 211 | 0 | 0 | 1 | 0.998877 | 0.1455 |
| 4461875384_R01C01 | PF019864 212 | 0 | 0 | 0 | 0.998309 | 0.1455 |
| 4457235610_R01C01 | PF015798 203 | 0 | 0 | 1 | 0.998154 | 0.1454 |
| 4432273141_R01C02 | PF004540 211 | 1 | 1 | 3 | 0.997966 | 0.1452 |
| 4461875796_R02C01 | PF017378 203 | 0 | 0 | 1 | 0.998742 | 0.1451 |
| 4457235046_R02C02 | PF018704 202 | 0 | 0 | 1 | 0.998146 | 0.145 |
| 4457235317_R01C01 | PF018778 221 | 0 | 0 | 1 | 0.998815 | 0.145 |
| 4457235212_R01C02 | PF020035 202 | 0 | 0 | 1 | 0.998673 | 0.1449 |
| 4461875714_R01C02 | PF019235 202 | 0 | 0 | 1 | 0.998879 | 0.1449 |
| 4457235010_R01C02 | PF018722 202 | 0 | 0 | 2 | 0.998594 | 0.1448 |
| 4457235107_R01C02 | PF019649 202 | 0 | 0 | 0 | 0.998728 | 0.1447 |
| 4459273627_R01C02 | PF019043 202 | 0 | 0 | 1 | 0.998781 | 0.1446 |
| 4459273749_R02C02 | PF019591 202 | 0 | 1 | 2 | 0.998695 | 0.1445 |
| 4461875448_R02C01 | PF019012 202 | 0 | 0 | 0 | 0.99889 | 0.1445 |
| 4457235610_R01C02 | PF016346 203 | 0 | 0 | 1 | 0.998275 | 0.1444 |
| 4459273651_R01C01 | PF008606 204 | 0 | 0 | 0 | 0.998803 | 0.1444 |
| 4461875282_R01C01 | PF019797 203 | 0 | 0 | 0 | 0.998874 | 0.1444 |
| 4459273690_R01C01 | PF018660 202 | 0 | 0 | 0 | 0.998629 | 0.1443 |
| 4457235064_R01C02 | PF008494 204 | 0 | 0 | 0 | 0.997963 | 0.1442 |
| 4457235424_R02C01 | PF007795 211 | 0 | 0 | 0 | 0.99876 | 0.1442 |
| 4457235343_R01C02 | PF008797 211 | 0 | 0 | 0 | 0.998117 | 0.144 |
| 4461875352_R01C02 | PF008631 204 | 0 | 0 | 0 | 0.998552 | 0.1439 |
| 4457235244_R01C01 | PF018630 202 | 0 | 0 | 1 | 0.99879 | 0.1438 |
| 4482537390_R02C02 | PF019098 202 | 0 | 0 | 0 | 0.998744 | 0.1438 |
| 4432265060_R02C02 | PF018599 202 | 0 | 0 | 1 | 0.99789 | 0.1437 |
| 4457235197_R01C01 | PF019533 202 | 0 | 0 | 0 | 0.998665 | 0.1437 |
| 4457235099_R01C01 | PF016749 203 | 0 | 0 | 1 | 0.998657 | 0.1436 |
| 4457235133_R01C01 | PF019626 202 | 0 | 0 | 1 | 0.998797 | 0.1436 |
| 4457235408_R02C01 | PF019985 212 | 0 | 0 | 1 | 0.998935 | 0.1435 |
| 4461875384_R01C02 | PF020015 202 | 0 | 0 | 0 | 0.998204 | 0.1435 |
| 4432273630_R02C02 | PF003742 211 | 0 | 0 | 0 | 0.998826 | 0.1434 |
| 4482537640_R01C02 | PF017223 203 | 0 | 0 | 0 | 0.998937 | 0.1434 |
| 4457235106_R01C02 | PF019138 202 | 0 | 0 | 0 | 0.999061 | 0.1433 |
| 4461875581_R02C01 | PF019261 202 | 0 | 0 | 2 | 0.998238 | 0.1432 |
| 4457235421_R02C02 | PF005657 211 | 0 | 0 | 1 | 0.998066 | 0.1432 |
| 4482537374_R01C02 | PF019108 202 | 0 | 0 | 1 | 0.998555 | 0.1432 |
| 4461875316_R01C02 | PF019652 202 | 0 | 0 | 0 | 0.998694 | 0.1432 |
| 4432273630_R02C02 | PF018600 202 | 0 | 0 | 0 | 0.998737 | 0.1432 |
| 4461875714_R01C01 | PF019231 202 | 0 | 0 | 0 | 0.998968 | 0.1432 |
| 4457235025_R01C02 | PF003738 211 | 0 | 6 | 17 | 0.998265 | 0.1431 |
| 4459273718_R02C02 | PF008680 203 | 1 | 1 | 1 | 0.998117 | 0.1431 |
| 4459273636_R01C02 | PF018760 202 | 0 | 1 | 1 | 0.998481 | 0.1431 |
| 4457235247_R01C01 | PF018777 221 | 0 | 0 | 0 | 0.9987 | 0.1431 |
| 4461875788_R01C01 | PF018588 202 | 1 | 1 | 1 | 0.998195 | 0.143 |
| 4457235401_R01C02 | PF016120 203 | 0 | 0 | 0 | 0.998808 | 0.143 |
| 4459273604_R01C02 | PF008508 204 | 0 | 1 | 2 | 0.999061 | 0.1429 |
| 4461875351_R01C02 | PF008503 204 | 0 | 0 | 0 | 0.998127 | 0.1429 |
| 4457235099_R01C02 | PF018447 212 | 0 | 0 | 0 | 0.998562 | 0.1429 |
| 4461875173_R01C02 | PF017253 203 | 0 | 0 | 0 | 0.998884 | 0.1429 |
| 4459273551_R01C02 | PF019402 203 | 0 | 0 | 0 | 0.998947 | 0.1429 |
| 4459273629_R01C02 | PF004531 211 | 0 | 1 | 4 | 0.998953 | 0.1427 |
| 4459273481_R01C02 | PF019902 212 | 0 | 0 | 1 | 0.998396 | 0.1427 |
| 4457235023_R01C02 | PF018531 212 | 0 | 0 | 0 | 0.998116 | 0.1427 |
| 4457235197_R01C02 | PF019568 202 | 0 | 0 | 0 | 0.998315 | 0.1427 |
| 4459273638_R01C01 | PF019859 212 | 0 | 0 | 0 | 0.998631 | 0.1427 |
| 4461875172_R02C02 | PF018686 202 | 0 | 0 | 0 | 0.998558 | 0.1426 |
| 4482537199_R02C02 | PF014967 211 | 0 | 0 | 0 | 0.998769 | 0.1426 |
| 4461875658_R01C01 | PF004016 211 | 0 | 0 | 0 | 0.998873 | 0.1425 |
| 4461875802_R02C02 | PF019830 202 | 0 | 0 | 0 | 0.998373 | 0.1424 |
| 4461875351_R01C01 | PF008432 204 | 0 | 1 | 1 | 0.998027 | 0.1423 |
| 4457235441_R01C01 | PF003752 211 | 0 | 0 | 0 | 0.998744 | 0.1423 |
| 4457235234_R02C02 | PF018951 202 | 0 | 1 | 5 | 0.997827 | 0.1422 |
| 4461875706_R01C01 | PF019443 202 | 1 | 0 | 0 | 0.998758 | 0.1422 |
| 4432273578_R02C02 | PF018623 202 | 0 | 0 | 0 | 0.998236 | 0.1421 |

TABLE 6-continued

| BID | SSID | Tier 1 CNV count | Tier 2 CNV count | Tier 3 CNV count | Callrate | LRR_SD |
|---|---|---|---|---|---|---|
| 4459273551_R02C02 | PF019972 212 | 0 | 0 | 0 | 0.998811 | 0.1421 |
| 4461875644_R01C01 | PF018662 202 | 0 | 0 | 1 | 0.998691 | 0.142 |
| 4457235343_R02C01 | PF008010 211 | 0 | 0 | 1 | 0.998538 | 0.1419 |
| 4457235356_R01C01 | PF018815 202 | 0 | 0 | 0 | 0.998579 | 0.1419 |
| 4459273547_R02C01 | PF018858 202 | 0 | 1 | 2 | 0.998919 | 0.1418 |
| 4457235500_R01C02 | PF019874 203 | 0 | 0 | 0 | 0.998683 | 0.1418 |
| 4482537640_R02C01 | PF020351 202 | 0 | 0 | 0 | 0.998932 | 0.1418 |
| 4459273136_R01C01 | PF015625 203 | 0 | 0 | 1 | 0.998587 | 0.1417 |
| 4461875711_R01C02 | PF007429 211 | 0 | 0 | 0 | 0.998401 | 0.1417 |
| 4461875382_R01C02 | PF020040 202 | 0 | 0 | 0 | 0.99861 | 0.1417 |
| 4461875465_R01C01 | PF018744 202 | 0 | 0 | 0 | 0.998765 | 0.1417 |
| 4461875383_R01C01 | PF019612 202 | 0 | 0 | 0 | 0.99885 | 0.1417 |
| 4457235063_R02C01 | PF008601 204 | 0 | 0 | 0 | 0.998554 | 0.1416 |
| 4459273476_R01C02 | PF003817 211 | 0 | 0 | 0 | 0.99905 | 0.1416 |
| 4432265400_R02C02 | PF019909 212 | 0 | 0 | 0 | 0.998484 | 0.1415 |
| 4475687204_R02C01 | PF020030 202 | 0 | 0 | 0 | 0.998626 | 0.1415 |
| 4457235392_R01C01 | PF019799 203 | 0 | 0 | 1 | 0.998842 | 0.1414 |
| 4457235079_R01C01 | PF019777 202 | 0 | 0 | 0 | 0.998164 | 0.1414 |
| 4459273635_R01C02 | PF018911 202 | 0 | 0 | 0 | 0.998014 | 0.1413 |
| 4459273634_R01C02 | PF018558 212 | 0 | 0 | 0 | 0.998298 | 0.1413 |
| 4461875659_R01C02 | PF003933 211 | 4 | 7 | 17 | 0.999101 | 0.1412 |
| 4459273481_R01C01 | PF019893 212 | 0 | 0 | 0 | 0.998009 | 0.1412 |
| 4432273757_R02C01 | PF018970 202 | 0 | 0 | 0 | 0.998407 | 0.1412 |
| 4482537374_R01C01 | PF019101 202 | 0 | 0 | 0 | 0.998591 | 0.1412 |
| 4459273641_R01C02 | PF008585 204 | 0 | 0 | 0 | 0.998869 | 0.1412 |
| 4457235294_R01C01 | PF019319 203 | 0 | 0 | 0 | 0.998979 | 0.1412 |
| 4457235247_R01C02 | PF018565 212 | 0 | 0 | 0 | 0.998853 | 0.141 |
| 4461875658_R01C02 | PF006994 211 | 0 | 0 | 0 | 0.998921 | 0.141 |
| 4482537179_R01C02 | PF018641 202 | 0 | 0 | 0 | 0.998169 | 0.1409 |
| 4457235500_R01C01 | PF019813 202 | 0 | 0 | 0 | 0.998678 | 0.1409 |
| 4461875706_R01C02 | PF019444 202 | 0 | 0 | 0 | 0.998834 | 0.1408 |
| 4459273727_R01C01 | PF008849 211 | 0 | 0 | 0 | 0.998861 | 0.1408 |
| 4459273638_R02C02 | PF019888 212 | 0 | 0 | 0 | 0.998631 | 0.1407 |
| 4457235397_R02C01 | PF019912 212 | 0 | 0 | 0 | 0.999034 | 0.1407 |
| 4482537236_R01C01 | PF019200 202 | 0 | 0 | 0 | 0.998881 | 0.1406 |
| 4461875173_R01C01 | PF008661 204 | 0 | 0 | 0 | 0.998974 | 0.1406 |
| 4457235246_R01C01 | PF015009 221 | 0 | 0 | 0 | 0.998241 | 0.1405 |
| 4457235154_R01C02 | PF018436 212 | 0 | 0 | 0 | 0.998819 | 0.1405 |
| 4432265631_R01C01 | PF008022 211 | 0 | 0 | 1 | 0.998264 | 0.1403 |
| 4457235211_R02C02 | PF008305 204 | 0 | 1 | 1 | 0.998798 | 0.1403 |
| 4457235058_R01C01 | PF018827 202 | 0 | 0 | 1 | 0.998807 | 0.1403 |
| 4432273182_R01C02 | PF019560 202 | 0 | 0 | 0 | 0.999053 | 0.1403 |
| 4459273637_R01C01 | PF008516 204 | 0 | 0 | 1 | 0.99827 | 0.1402 |
| 4461875594_R01C01 | PF007953 211 | 0 | 0 | 0 | 0.998663 | 0.1402 |
| 4457235049_R02C01 | PF008233 206 | 0 | 0 | 0 | 0.998847 | 0.1401 |
| 4457235530_R01C02 | PF003657 211 | 0 | 1 | 1 | 0.998256 | 0.14 |
| 4461875451_R01C01 | PF018682 202 | 0 | 0 | 2 | 0.998365 | 0.1399 |
| 4459273476_R02C02 | PF017227 203 | 0 | 0 | 1 | 0.999122 | 0.1399 |
| 4461875782_R01C01 | PF020361 221 | 0 | 0 | 0 | 0.99833 | 0.1399 |
| 4432265010_R02C02 | PF004612 211 | 0 | 0 | 0 | 0.998836 | 0.1399 |
| 4457235383_R02C01 | PF004616 211 | 0 | 0 | 1 | 0.99876 | 0.1398 |
| 4432273322_R02C02 | PF018674 203 | 0 | 0 | 0 | 0.998613 | 0.1397 |
| 4461875315_R02C01 | PF020082 202 | 0 | 0 | 0 | 0.998634 | 0.1397 |
| 4432273181_R02C02 | PF008787 211 | 0 | 0 | 0 | 0.99774 | 0.1395 |
| 4459273573_R01C01 | PF016568 203 | 1 | 0 | 0 | 0.998895 | 0.1395 |
| 4457235045_R01C01 | PF007963 211 | 0 | 1 | 1 | 0.99856 | 0.1394 |
| 4457235046_R01C02 | PF018661 202 | 0 | 0 | 0 | 0.998319 | 0.1394 |
| 4457235391_R01C01 | PF019910 203 | 0 | 0 | 0 | 0.99886 | 0.1394 |
| 4457235401_R02C01 | PF016050 203 | 4 | 8 | 18 | 0.998902 | 0.1393 |
| 4459273628_R02C01 | PF004547 211 | 1 | 2 | 5 | 0.998757 | 0.1393 |
| 4457235154_R01C01 | PF016751 203 | 0 | 0 | 1 | 0.998782 | 0.1393 |
| 4482537383_R01C01 | PF018579 202 | 0 | 0 | 1 | 0.998931 | 0.1393 |
| 4459273695_R01C01 | PF004769 211 | 0 | 0 | 0 | 0.998488 | 0.1393 |
| 4459273424_R01C02 | PF018759 202 | 0 | 0 | 0 | 0.998739 | 0.1391 |
| 4461875660_R01C01 | PF018935 202 | 0 | 0 | 0 | 0.998961 | 0.1391 |
| 4457235356_R01C02 | PF018870 202 | 1 | 1 | 3 | 0.998558 | 0.139 |
| 4461875451_R01C02 | PF019289 203 | 0 | 0 | 1 | 0.998101 | 0.139 |
| 4459273695_R02C02 | PF008171 204 | 0 | 0 | 1 | 0.998375 | 0.139 |
| 4459273709_R01C02 | PF017352 221 | 0 | 0 | 1 | 0.998507 | 0.139 |
| 4457235045_R02C01 | PF008070 204 | 1 | 1 | 1 | 0.998629 | 0.1389 |
| 4482537632_R01C01 | PF019562 202 | 0 | 0 | 0 | 0.997966 | 0.1389 |
| 4461875782_R01C02 | PF008183 204 | 0 | 0 | 0 | 0.998309 | 0.1389 |
| 4457235212_R02C02 | PF014914 211 | 0 | 0 | 0 | 0.998542 | 0.1389 |
| 4461875172_R01C01 | PF014965 211 | 0 | 0 | 0 | 0.998821 | 0.1389 |
| 4482537427_R01C01 | PF019054 202 | 0 | 0 | 0 | 0.998842 | 0.1389 |
| 4461875173_R02C02 | PF017375 203 | 0 | 0 | 0 | 0.998881 | 0.1389 |

TABLE 6-continued

| BID | SSID | Tier 1 CNV count | Tier 2 CNV count | Tier 3 CNV count | Callrate | LRR_SD |
|---|---|---|---|---|---|---|
| 4461875480_R01C01 | PF019461 203 | 0 | 0 | 0 | 0.99904 | 0.1389 |
| 4457235252_R01C02 | PF019005 202 | 0 | 0 | 0 | 0.998808 | 0.1388 |
| 4432273639_R02C01 | PF003780 211 | 0 | 0 | 0 | 0.998584 | 0.1387 |
| 4457235102_R02C01 | PF008011 211 | 0 | 0 | 1 | 0.998275 | 0.1386 |
| 4461875676_R01C01 | PF008356 204 | 0 | 0 | 0 | 0.998657 | 0.1386 |
| 4457235345_R01C01 | PF018644 202 | 1 | 1 | 2 | 0.998373 | 0.1383 |
| 4457235072_R02C01 | PF019733 202 | 0 | 0 | 1 | 0.998605 | 0.1383 |
| 4461875282_R01C02 | PF019852 212 | 0 | 0 | 0 | 0.998753 | 0.1383 |
| 4459273650_R01C01 | PF020362 202 | 0 | 0 | 0 | 0.99903 | 0.1383 |
| 4459273639_R01C01 | PF019326 203 | 2 | 2 | 2 | 0.998816 | 0.1382 |
| 4482537374_R02C02 | PF019116 202 | 0 | 0 | 0 | 0.99853 | 0.1382 |
| 4461875713_R01C02 | PF014852 211 | 0 | 0 | 0 | 0.998676 | 0.1382 |
| 4457235488_R02C01 | PF004620 211 | 0 | 2 | 5 | 0.998729 | 0.1381 |
| 4432265059_R02C02 | PF019702 202 | 0 | 0 | 1 | 0.998269 | 0.1381 |
| 4461875644_R01C01 | PF018771 202 | 0 | 0 | 0 | 0.99879 | 0.1381 |
| 4482537425_R01C01 | PF018861 202 | 0 | 0 | 0 | 0.998963 | 0.1381 |
| 4482537426_R02C02 | PF019082 202 | 0 | 0 | 0 | 0.99899 | 0.1381 |
| 4459273629_R02C01 | PF004455 211 | 0 | 0 | 0 | 0.999038 | 0.1381 |
| 4457235015_R01C02 | PF019701 202 | 1 | 2 | 3 | 0.998769 | 0.138 |
| 4459273594_R01C01 | PF008852 211 | 0 | 0 | 1 | 0.998375 | 0.1379 |
| 4459273728_R01C01 | PF006741 211 | 1 | 1 | 1 | 0.998749 | 0.1379 |
| 4475687204_R02C02 | PF014943 211 | 0 | 0 | 1 | 0.998803 | 0.1379 |
| 4457235498_R01C02 | PF019016 202 | 0 | 2 | 9 | 0.998845 | 0.1378 |
| 4461875316_R02C02 | PF019831 202 | 0 | 0 | 0 | 0.99862 | 0.1378 |
| 4459273651_R01C02 | PF008624 204 | 0 | 0 | 0 | 0.998815 | 0.1378 |
| 4457235392_R02C01 | PF019858 212 | 0 | 0 | 1 | 0.998945 | 0.1377 |
| 4457235079_R02C01 | PF019785 212 | 0 | 0 | 0 | 0.998132 | 0.1377 |
| 4459273594_R01C02 | PF008108 204 | 0 | 0 | 0 | 0.998261 | 0.1377 |
| 4461875581_R01C02 | PF019279 202 | 0 | 0 | 0 | 0.998533 | 0.1377 |
| 4461875174_R01C02 | PF008212 204 | 0 | 1 | 3 | 0.998695 | 0.1376 |
| 4457235236_R02C01 | PF018769 202 | 1 | 1 | 1 | 0.998291 | 0.1376 |
| 4461875711_R02C01 | PF004009 211 | 0 | 0 | 1 | 0.998636 | 0.1376 |
| 4459273788_R01C01 | PF008133 204 | 0 | 0 | 0 | 0.998855 | 0.1376 |
| 4461875316_R02C01 | PF019604 202 | 0 | 0 | 2 | 0.998571 | 0.1375 |
| 4457235609_R01C02 | PF018469 212 | 1 | 0 | 0 | 0.998101 | 0.1375 |
| 4482537383_R01C02 | PF020377 202 | 1 | 0 | 0 | 0.99884 | 0.1374 |
| 4459273658_R01C01 | PF019635 202 | 0 | 0 | 0 | 0.998902 | 0.1374 |
| 4432273584_R01C02 | PF018638 202 | 0 | 0 | 1 | 0.998233 | 0.1373 |
| 4459273550_R01C02 | PF008319 204 | 0 | 0 | 0 | 0.998227 | 0.1373 |
| 4457235203_R02C01 | PF018657 202 | 0 | 0 | 0 | 0.99841 | 0.1373 |
| 4482537199_R02C02 | PF018664 202 | 0 | 0 | 0 | 0.998711 | 0.1373 |
| 4432273318_R01C02 | PF003948 211 | 0 | 0 | 0 | 0.998763 | 0.1373 |
| 4457235488_R02C02 | PF003804 211 | 0 | 0 | 0 | 0.998773 | 0.1373 |
| 4457235392_R02C01 | PF019935 212 | 0 | 0 | 0 | 0.998811 | 0.1373 |
| 4459273709_R01C01 | PF004772 211 | 0 | 1 | 5 | 0.998581 | 0.1372 |
| 4432265617_R01C01 | PF016700 203 | 0 | 1 | 1 | 0.999103 | 0.1372 |
| 4457235259_R02C02 | PF018915 202 | 0 | 0 | 0 | 0.998314 | 0.1372 |
| 4461875604_R01C02 | PF003828 211 | 0 | 0 | 0 | 0.998433 | 0.1372 |
| 4457235010_R01C01 | PF018676 202 | 0 | 0 | 0 | 0.998644 | 0.1372 |
| 4482537381_R01C01 | PF019126 202 | 0 | 0 | 0 | 0.999016 | 0.1372 |
| 4457235246_R02C02 | PF016024 224 | 0 | 0 | 1 | 0.998484 | 0.1371 |
| 4459273745_R01C02 | PF004144 211 | 0 | 0 | 0 | 0.998737 | 0.1371 |
| 4457235046_R02C01 | PF018642 202 | 0 | 1 | 1 | 0.998576 | 0.137 |
| 4457235212_R01C01 | PF019414 202 | 0 | 0 | 0 | 0.998605 | 0.137 |
| 4459273574_R01C01 | PF017449 203 | 0 | 0 | 0 | 0.998736 | 0.137 |
| 4457235133_R01C02 | PF019660 202 | 0 | 0 | 0 | 0.998823 | 0.1369 |
| 4459273278_R01C01 | PF016670 203 | 1 | 1 | 1 | 0.99855 | 0.1368 |
| 4459273628_R02C02 | PF008269 204 | 0 | 0 | 0 | 0.998499 | 0.1368 |
| 4457235154_R02C01 | PF016753 203 | 0 | 0 | 0 | 0.998616 | 0.1368 |
| 4461875655_R02C02 | PF019442 202 | 0 | 0 | 0 | 0.998861 | 0.1368 |
| 4459273423_R01C01 | PF018567 212 | 0 | 0 | 0 | 0.998985 | 0.1368 |
| 4482537178_R01C01 | PF019047 202 | 0 | 0 | 0 | 0.998098 | 0.1367 |
| 4461875676_R01C02 | PF008382 204 | 0 | 0 | 0 | 0.998753 | 0.1367 |
| 4457235090_R02C02 | PF019901 212 | 0 | 0 | 0 | 0.998191 | 0.1366 |
| 4432265010_R01C01 | PF006326 211 | 0 | 0 | 0 | 0.998853 | 0.1366 |
| 4457235345_R02C01 | PF018694 202 | 0 | 0 | 1 | 0.998354 | 0.1365 |
| 4457235046_R01C01 | PF018527 212 | 0 | 1 | 1 | 0.998583 | 0.1365 |
| 4457235346_R01C01 | PF018636 202 | 0 | 0 | 1 | 0.998615 | 0.1364 |
| 4461875796_R02C02 | PF018431 212 | 0 | 0 | 0 | 0.998386 | 0.1364 |
| 4461875494_R02C01 | PF003876 211 | 0 | 2 | 9 | 0.998861 | 0.1362 |
| 4432273749_R01C01 | PF017390 203 | 0 | 0 | 0 | 0.998133 | 0.1362 |
| 4457235064_R02C01 | PF008366 204 | 0 | 0 | 0 | 0.998093 | 0.1361 |
| 4457235079_R02C02 | PF019846 202 | 0 | 0 | 0 | 0.998254 | 0.1361 |
| 4459273651_R02C01 | PF008615 204 | 0 | 0 | 0 | 0.998963 | 0.1361 |
| 4461875383_R01C02 | PF019725 202 | 0 | 0 | 0 | 0.998902 | 0.136 |
| 4459273642_R01C02 | PF003886 211 | 0 | 0 | 0 | 0.999056 | 0.136 |

TABLE 6-continued

| BID | SSID | Tier 1 CNV count | Tier 2 CNV count | Tier 3 CNV count | Callrate | LRR_SD |
|---|---|---|---|---|---|---|
| 4432273123_R01C02 | PF008866 211 | 0 | 0 | 1 | 0.99798 | 0.1359 |
| 4457235104_R02C01 | PF019982 203 | 0 | 0 | 1 | 0.998341 | 0.1359 |
| 4432273640_R02C02 | PF018957 203 | 0 | 0 | 1 | 0.997845 | 0.1358 |
| 4457235153_R01C02 | PF016378 203 | 1 | 1 | 1 | 0.998763 | 0.1358 |
| 4461875763_R01C02 | PF008166 204 | 0 | 1 | 1 | 0.998757 | 0.1357 |
| 4457235345_R02C02 | PF018698 202 | 0 | 0 | 0 | 0.998307 | 0.1357 |
| 4457235441_R02C01 | PF003694 211 | 0 | 1 | 2 | 0.998839 | 0.1356 |
| 4457235028_R02C02 | PF019473 202 | 0 | 0 | 0 | 0.99827 | 0.1356 |
| 4457235347_R01C01 | PF008679 202 | 0 | 0 | 0 | 0.998233 | 0.1355 |
| 4457235366_R02C01 | PF018956 202 | 0 | 0 | 1 | 0.998399 | 0.1354 |
| 4482537374_R02C01 | PF019105 202 | 0 | 0 | 1 | 0.998676 | 0.1353 |
| 4459273574_R01C02 | PF018583 202 | 0 | 0 | 1 | 0.998794 | 0.1352 |
| 4457235246_R02C01 | PF015046 221 | 0 | 0 | 0 | 0.998151 | 0.1352 |
| 4457235337_R01C01 | PF019622 202 | 0 | 0 | 0 | 0.998573 | 0.1352 |
| 4457235391_R02C02 | PF007864 211 | 0 | 0 | 1 | 0.998844 | 0.1351 |
| 4459273718_R02C01 | PF008361 204 | 0 | 0 | 2 | 0.998351 | 0.1349 |
| 4457235528_R02C02 | PF019611 202 | 0 | 0 | 0 | 0.99781 | 0.1349 |
| 4457235345_R01C02 | PF018697 202 | 0 | 0 | 0 | 0.998304 | 0.1349 |
| 4457235279_R02C01 | PF018860 202 | 0 | 0 | 0 | 0.99867 | 0.1349 |
| 4432273123_R01C01 | PF019866 212 | 1 | 1 | 1 | 0.997969 | 0.1348 |
| 4457235504_R01C01 | PF018470 212 | 0 | 0 | 1 | 0.998972 | 0.1348 |
| 4457235487_R02C02 | PF020041 202 | 0 | 0 | 0 | 0.998831 | 0.1348 |
| 4461875381_R01C01 | PF016065 224 | 0 | 0 | 0 | 0.998911 | 0.1348 |
| 4457235441_R02C02 | PF003938 211 | 0 | 0 | 1 | 0.998876 | 0.1347 |
| 4457235443_R01C01 | PF019788 202 | 0 | 0 | 0 | 0.998626 | 0.1347 |
| 4459273748_R01C02 | PF018397 221 | 0 | 0 | 1 | 0.998882 | 0.1346 |
| 4457235148_R02C01 | PF019323 203 | 0 | 0 | 0 | 0.99833 | 0.1346 |
| 4482537632_R02C02 | PF004718 211 | 0 | 0 | 1 | 0.998157 | 0.1345 |
| 4459273635_R02C01 | PF018789 221 | 0 | 0 | 0 | 0.997711 | 0.1345 |
| 4459273651_R02C02 | PF008652 204 | 0 | 0 | 0 | 0.998803 | 0.1345 |
| 4459273604_R01C01 | PF008459 204 | 0 | 0 | 0 | 0.999058 | 0.1345 |
| 4482537381_R01C01 | PF019124 202 | 0 | 0 | 0 | 0.999096 | 0.1345 |
| 4457235487_R02C01 | PF020010 203 | 1 | 1 | 1 | 0.998958 | 0.1343 |
| 4432273429_R01C02 | PF015559 203 | 0 | 0 | 0 | 0.997471 | 0.1343 |
| 4457235294_R02C02 | PF019610 202 | 0 | 0 | 0 | 0.998753 | 0.1343 |
| 4461875713_R01C01 | PF014869 211 | 0 | 0 | 0 | 0.998798 | 0.1343 |
| 4461875448_R02C02 | PF018385 221 | 0 | 0 | 0 | 0.998811 | 0.1343 |
| 4457235574_R01C01 | PF019924 203 | 0 | 0 | 0 | 0.998813 | 0.1343 |
| 4461875707_R01C01 | PF020043 202 | 0 | 1 | 1 | 0.998989 | 0.1342 |
| 4475687206_R02C01 | PF017207 203 | 0 | 0 | 0 | 0.998533 | 0.1342 |
| 4461875831_R02C02 | PF004226 211 | 0 | 0 | 0 | 0.998538 | 0.1341 |
| 4461875832_R02C01 | PF019383 202 | 1 | 0 | 0 | 0.998757 | 0.1341 |
| 4459273658_R02C01 | PF019636 202 | 0 | 0 | 0 | 0.998831 | 0.1341 |
| 4461875581_R01C01 | PF019254 202 | 0 | 1 | 1 | 0.998414 | 0.134 |
| 4457235415_R01C02 | PF017382 203 | 0 | 0 | 1 | 0.998449 | 0.134 |
| 4482537427_R01C02 | PF019064 202 | 0 | 0 | 1 | 0.998813 | 0.134 |
| 4459273573_R02C01 | PF016609 203 | 0 | 0 | 1 | 0.998911 | 0.134 |
| 4482537024_R02C02 | PF019645 202 | 0 | 0 | 0 | 0.998141 | 0.134 |
| 4461875660_R01C02 | PF019276 203 | 0 | 0 | 0 | 0.998889 | 0.134 |
| 4461875693_R01C02 | PF008092 204 | 0 | 0 | 1 | 0.998694 | 0.1339 |
| 4457235303_R02C01 | PF008389 202 | 0 | 0 | 1 | 0.997093 | 0.1338 |
| 4457235234_R01C02 | PF018930 202 | 0 | 0 | 0 | 0.997871 | 0.1338 |
| 4457235530_R02C02 | PF016711 203 | 0 | 0 | 0 | 0.998222 | 0.1338 |
| 4457235234_R01C01 | PF018700 202 | 1 | 1 | 1 | 0.997818 | 0.1337 |
| 4459273594_R02C02 | PF008120 204 | 0 | 0 | 0 | 0.998381 | 0.1337 |
| 4461875833_R02C01 | PF020348 221 | 0 | 0 | 0 | 0.998789 | 0.1337 |
| 4482537632_R01C01 | PF004554 211 | 0 | 0 | 0 | 0.998389 | 0.1336 |
| 4457235244_R01C02 | PF018665 202 | 1 | 1 | 1 | 0.998739 | 0.1335 |
| 4457235609_R02C02 | PF018487 212 | 0 | 0 | 0 | 0.997686 | 0.1335 |
| 4432265374_R02C01 | PF020291 221 | 0 | 0 | 0 | 0.998046 | 0.1335 |
| 4459273749_R01C02 | PF019446 202 | 1 | 1 | 2 | 0.998636 | 0.1334 |
| 4459273630_R02C01 | PF003677 211 | 1 | 1 | 1 | 0.99915 | 0.1334 |
| 4457235195_R01C01 | PF018569 212 | 0 | 0 | 0 | 0.998856 | 0.1332 |
| 4457235609_R02C01 | PF018461 212 | 1 | 2 | 2 | 0.997537 | 0.1331 |
| 4457235047_R01C01 | PF008195 206 | 0 | 0 | 0 | 0.998769 | 0.1331 |
| 4457235015_R02C02 | PF019749 202 | 0 | 1 | 1 | 0.998861 | 0.1329 |
| 4459273136_R01C02 | PF017354 203 | 0 | 0 | 0 | 0.998599 | 0.1328 |
| 4457235252_R01C01 | PF018979 202 | 0 | 0 | 0 | 0.998836 | 0.1328 |
| 4461875797_R02C02 | PF018622 203 | 0 | 0 | 0 | 0.998884 | 0.1328 |
| 4461875761_R02C02 | PF008289 204 | 0 | 0 | 0 | 0.998449 | 0.1327 |
| 4432273287_R01C01 | PF018640 202 | 0 | 0 | 0 | 0.998711 | 0.1327 |
| 4461875494_R02C02 | PF006822 211 | 0 | 0 | 0 | 0.998861 | 0.1327 |
| 4461875621_R01C01 | PF020036 202 | 0 | 0 | 0 | 0.99898 | 0.1327 |
| 4461875711_R01C01 | PF018410 221 | 0 | 0 | 0 | 0.998683 | 0.1326 |
| 4461875833_R02C02 | PF020355 221 | 0 | 1 | 1 | 0.998654 | 0.1325 |
| 4432265618_R02C02 | PF004443 211 | 0 | 0 | 0 | 0.998947 | 0.1325 |

TABLE 6-continued

| BID | SSID | Tier 1 CNV count | Tier 2 CNV count | Tier 3 CNV count | Callrate | LRR_SD |
|---|---|---|---|---|---|---|
| 4461875623_R02C01 | PF008419 204 | 0 | 0 | 1 | 0.998784 | 0.1324 |
| 4432265011_R01C02 | PF008028 211 | 0 | 0 | 0 | 0.998526 | 0.1323 |
| 4432273749_R01C02 | PF018654 202 | 0 | 0 | 1 | 0.998333 | 0.1322 |
| 4432265894_R02C02 | PF008049 211 | 0 | 0 | 0 | 0.997563 | 0.1322 |
| 4461875604_R02C02 | PF003899 211 | 0 | 0 | 0 | 0.998312 | 0.1322 |
| 4461875761_R02C01 | PF008278 204 | 1 | 2 | 6 | 0.998645 | 0.1321 |
| 4457235037_R02C01 | PF016273 203 | 0 | 0 | 0 | 0.998771 | 0.1321 |
| 4459273522_R02C01 | PF019032 202 | 0 | 0 | 0 | 0.99905 | 0.1321 |
| 4457235212_R02C01 | PF019875 212 | 0 | 0 | 1 | 0.998402 | 0.132 |
| 4457235574_R02C02 | PF020012 202 | 0 | 0 | 0 | 0.998484 | 0.132 |
| 4459273492_R02C01 | PF008668 204 | 0 | 0 | 0 | 0.998943 | 0.132 |
| 4457235198_R01C01 | PF003760 211 | 0 | 0 | 0 | 0.998976 | 0.132 |
| 4459273727_R02C02 | PF008129 204 | 0 | 0 | 0 | 0.998842 | 0.1319 |
| 4459273749_R01C01 | PF019419 202 | 0 | 0 | 1 | 0.998763 | 0.1318 |
| 4461875621_R01C02 | PF018384 221 | 1 | 1 | 1 | 0.998977 | 0.1318 |
| 4461875797_R02C01 | PF018591 203 | 0 | 0 | 0 | 0.998934 | 0.1318 |
| 4461875801_R01C01 | PF019409 203 | 0 | 0 | 1 | 0.99819 | 0.1317 |
| 4482537383_R02C01 | PF007444 211 | 0 | 0 | 1 | 0.998753 | 0.1317 |
| 4475687179_R01C01 | PF018556 212 | 0 | 0 | 0 | 0.99875 | 0.1317 |
| 4459273658_R01C02 | PF019641 202 | 0 | 0 | 0 | 0.998824 | 0.1317 |
| 4461875449_R01C01 | PF019449 202 | 0 | 0 | 2 | 0.998808 | 0.1316 |
| 4457235099_R02C01 | PF018561 212 | 0 | 0 | 0 | 0.998587 | 0.1316 |
| 4459273627_R02C01 | PF018991 202 | 0 | 0 | 0 | 0.998898 | 0.1316 |
| 4432273754_R01C02 | PF019892 212 | 0 | 0 | 0 | 0.999051 | 0.1316 |
| 4432265011_R01C01 | PF007905 211 | 1 | 1 | 1 | 0.99836 | 0.1315 |
| 4459273547_R01C01 | PF018794 202 | 0 | 0 | 1 | 0.998823 | 0.1315 |
| 4457235294_R02C01 | PF019429 202 | 0 | 0 | 1 | 0.998953 | 0.1315 |
| 4457235180_R01C02 | PF020287 221 | 1 | 0 | 0 | 0.99874 | 0.1315 |
| 4459273551_R01C01 | PF018666 202 | 0 | 0 | 0 | 0.998989 | 0.1315 |
| 4459273476_R01C01 | PF007983 211 | 0 | 0 | 0 | 0.999074 | 0.1315 |
| 4482537426_R02C01 | PF019078 202 | 0 | 0 | 1 | 0.999053 | 0.1314 |
| 4457235153_R01C01 | PF016241 203 | 0 | 0 | 0 | 0.998544 | 0.1314 |
| 4459273630_R01C02 | PF004202 211 | 0 | 0 | 0 | 0.999072 | 0.1314 |
| 4482537024_R02C01 | PF018603 202 | 0 | 0 | 0 | 0.998304 | 0.1313 |
| 4432273757_R02C02 | PF019771 202 | 0 | 0 | 0 | 0.998378 | 0.1313 |
| 4457235024_R01C01 | PF018831 202 | 0 | 0 | 0 | 0.998692 | 0.1313 |
| 4457235047_R02C01 | PF008534 204 | 0 | 0 | 0 | 0.998823 | 0.1312 |
| 4459273476_R02C01 | PF006148 211 | 0 | 0 | 0 | 0.99909 | 0.1312 |
| 4432273640_R02C01 | PF018919 203 | 0 | 0 | 1 | 0.998161 | 0.1311 |
| 4432273430_R01C01 | PF015965 203 | 0 | 0 | 1 | 0.998193 | 0.1311 |
| 4457235391_R01C02 | PF004171 211 | 0 | 1 | 1 | 0.998774 | 0.1311 |
| 4482537425_R02C01 | PF018865 202 | 0 | 0 | 1 | 0.999014 | 0.1311 |
| 4459273637_R01C02 | PF019202 202 | 0 | 0 | 0 | 0.998364 | 0.1311 |
| 4482537600_R02C02 | PF018557 212 | 0 | 0 | 0 | 0.998964 | 0.1311 |
| 4482537425_R01C02 | PF019018 202 | 0 | 0 | 0 | 0.999001 | 0.1311 |
| 4459273561_R01C01 | PF008528 204 | 0 | 0 | 0 | 0.99928 | 0.1311 |
| 4457235243_R01C01 | PF018909 202 | 1 | 1 | 1 | 0.998484 | 0.131 |
| 4457235506_R01C01 | PF016435 203 | 0 | 0 | 0 | 0.998781 | 0.131 |
| 4459273639_R02C01 | PF019426 202 | 0 | 0 | 0 | 0.998832 | 0.131 |
| 4432273054_R01C02 | PF018611 202 | 0 | 0 | 1 | 0.998091 | 0.1309 |
| 4432273039_R01C02 | PF018457 212 | 0 | 1 | 2 | 0.999051 | 0.1308 |
| 4459273692_R02C01 | PF020057 202 | 0 | 0 | 0 | 0.997774 | 0.1308 |
| 4461875384_R02C01 | PF020014 202 | 0 | 0 | 0 | 0.998404 | 0.1308 |
| 4459273488_R01C02 | PF008112 206 | 1 | 0 | 0 | 0.998662 | 0.1308 |
| 4459273661_R01C01 | PF019845 202 | 0 | 0 | 0 | 0.998523 | 0.1307 |
| 4457235247_R02C02 | PF018814 202 | 0 | 0 | 0 | 0.998819 | 0.1307 |
| 4457235134_R01C02 | PF018918 202 | 0 | 0 | 1 | 0.998781 | 0.1306 |
| 4461875783_R01C01 | PF014846 211 | 0 | 0 | 0 | 0.998201 | 0.1306 |
| 4432273755_R01C01 | PF015858 203 | 0 | 0 | 1 | 0.998438 | 0.1305 |
| 4457235104_R02C02 | PF020087 202 | 0 | 0 | 0 | 0.998662 | 0.1305 |
| 4461875658_R02C02 | PF008881 211 | 0 | 0 | 0 | 0.998744 | 0.1305 |
| 4461875763_R01C01 | PF008117 204 | 0 | 0 | 0 | 0.998948 | 0.1305 |
| 4461875655_R01C01 | PF019362 202 | 0 | 0 | 0 | 0.998953 | 0.1305 |
| 4432265012_R01C01 | PF008020 211 | 0 | 0 | 1 | 0.998354 | 0.1304 |
| 4432273394_R01C01 | PF018798 203 | 0 | 0 | 0 | 0.998275 | 0.1304 |
| 4432273753_R01C01 | PF018972 202 | 0 | 0 | 2 | 0.998861 | 0.1304 |
| 4461875449_R01C02 | PF019466 202 | 1 | 2 | 2 | 0.998439 | 0.1303 |
| 4457235337_R01C02 | PF019692 202 | 0 | 1 | 1 | 0.998552 | 0.1303 |
| 4432265618_R01C01 | PF019532 202 | 0 | 1 | 1 | 0.998969 | 0.1303 |
| 4457235064_R02C02 | PF008545 204 | 0 | 0 | 0 | 0.998019 | 0.1303 |
| 4459273573_R02C02 | PF017312 203 | 0 | 1 | 1 | 0.998864 | 0.1302 |
| 4461875786_R01C02 | PF019226 202 | 0 | 1 | 1 | 0.999146 | 0.1302 |
| 4459273547_R01C02 | PF018893 202 | 0 | 0 | 0 | 0.998858 | 0.1301 |
| 4457235099_R02C02 | PF018506 212 | 0 | 0 | 0 | 0.998612 | 0.13 |
| 4459273424_R02C01 | PF018716 202 | 0 | 0 | 3 | 0.998768 | 0.1299 |
| 4432273286_R01C02 | PF018626 202 | 0 | 0 | 1 | 0.9986 | 0.1299 |

TABLE 6-continued

| BID | SSID | Tier 1 CNV count | Tier 2 CNV count | Tier 3 CNV count | Callrate | LRR_SD |
|---|---|---|---|---|---|---|
| 4432265631_R01C02 | PF003873 211 | 0 | 0 | 0 | 0.997868 | 0.1298 |
| 4432273639_R02C02 | PF019490 202 | 1 | 3 | 8 | 0.998455 | 0.1297 |
| 4457235303_R02C02 | PF008273 202 | 0 | 0 | 0 | 0.997545 | 0.1297 |
| 4457235347_R01C02 | PF020007 213 | 0 | 0 | 0 | 0.998323 | 0.1297 |
| 4461875315_R02C02 | PF004180 211 | 0 | 0 | 0 | 0.998541 | 0.1297 |
| 4457235180_R01C01 | PF020079 202 | 0 | 0 | 0 | 0.998931 | 0.1297 |
| 4432273297_R01C02 | PF018969 203 | 0 | 0 | 0 | 0.998945 | 0.1297 |
| 4482537037_R01C02 | PF019186 202 | 0 | 0 | 0 | 0.998691 | 0.1296 |
| 4457235239_R01C01 | PF019089 202 | 1 | 2 | 5 | 0.999003 | 0.1295 |
| 4461875761_R01C02 | PF008286 204 | 0 | 0 | 0 | 0.998765 | 0.1295 |
| 4432273753_R01C02 | PF016003 224 | 0 | 0 | 0 | 0.998789 | 0.1295 |
| 4459273630_R01C01 | PF003665 211 | 0 | 0 | 0 | 0.999195 | 0.1295 |
| 4461875604_R02C01 | PF003669 211 | 0 | 2 | 9 | 0.998657 | 0.1294 |
| 4459273424_R01C01 | PF018677 202 | 1 | 1 | 2 | 0.9987 | 0.1294 |
| 4432265506_R02C02 | PF019529 202 | 0 | 0 | 1 | 0.998354 | 0.1294 |
| 4457235397_R02C02 | PF019923 203 | 0 | 0 | 0 | 0.998976 | 0.1294 |
| 4457235028_R02C01 | PF019439 202 | 0 | 11 | 33 | 0.998249 | 0.1293 |
| 4432265012_R02C01 | PF015546 224 | 0 | 0 | 0 | 0.998219 | 0.1293 |
| 4461875623_R02C02 | PF008563 204 | 0 | 0 | 0 | 0.998884 | 0.1293 |
| 4461875174_R01C01 | PF008181 204 | 1 | 1 | 1 | 0.998816 | 0.1292 |
| 4432273321_R01C01 | PF018717 202 | 0 | 0 | 0 | 0.998278 | 0.1292 |
| 4482537037_R02C01 | PF019184 202 | 0 | 0 | 0 | 0.99876 | 0.1292 |
| 4432265618_R01C02 | PF019557 202 | 0 | 0 | 0 | 0.998881 | 0.1292 |
| 4457235391_R02C01 | PF019926 203 | 0 | 0 | 0 | 0.998924 | 0.1292 |
| 4457235356_R02C01 | PF018829 202 | 0 | 0 | 0 | 0.998665 | 0.1291 |
| 4457235528_R02C01 | PF019526 202 | 0 | 0 | 0 | 0.997837 | 0.129 |
| 4459273626_R02C02 | PF019997 212 | 0 | 0 | 0 | 0.998658 | 0.129 |
| 4459273574_R02C01 | PF018480 212 | 0 | 0 | 0 | 0.998774 | 0.129 |
| 4459273561_R02C02 | PF008612 204 | 0 | 0 | 0 | 0.999124 | 0.129 |
| 4457235415_R02C01 | PF016882 203 | 0 | 0 | 1 | 0.998597 | 0.1289 |
| 4461875282_R02C02 | PF019879 212 | 0 | 0 | 1 | 0.998832 | 0.1289 |
| 4457235347_R02C01 | PF008582 203 | 0 | 0 | 0 | 0.998346 | 0.1289 |
| 4459273695_R02C01 | PF004777 211 | 0 | 1 | 1 | 0.998544 | 0.1288 |
| 4457235075_R02C02 | PF008888 211 | 0 | 0 | 1 | 0.998658 | 0.1288 |
| 4459273423_R01C02 | PF018604 203 | 0 | 1 | 4 | 0.998976 | 0.1287 |
| 4432265010_R01C02 | PF004245 211 | 0 | 0 | 3 | 0.99898 | 0.1287 |
| 4461875732_R02C01 | PF014841 211 | 0 | 0 | 0 | 0.999096 | 0.1287 |
| 4457235366_R02C02 | PF019037 202 | 1 | 1 | 1 | 0.998283 | 0.1286 |
| 4459273278_R02C02 | PF018609 202 | 0 | 0 | 1 | 0.998468 | 0.1286 |
| 4482537037_R01C01 | PF019180 202 | 0 | 1 | 1 | 0.998765 | 0.1286 |
| 4457235075_R02C01 | PF019919 212 | 0 | 0 | 0 | 0.998736 | 0.1286 |
| 4432273318_R01C01 | PF008040 211 | 0 | 0 | 2 | 0.998803 | 0.1285 |
| 4432265631_R02C01 | PF008804 211 | 0 | 0 | 0 | 0.998462 | 0.1285 |
| 4457235195_R02C02 | PF018648 202 | 0 | 0 | 0 | 0.998705 | 0.1285 |
| 4457235010_R02C02 | PF018753 202 | 1 | 1 | 2 | 0.998544 | 0.1284 |
| 4459273695_R02C02 | PF008377 204 | 0 | 0 | 1 | 0.998351 | 0.1284 |
| 4459273573_R02C02 | PF017372 203 | 0 | 0 | 0 | 0.998964 | 0.1284 |
| 4432273335_R02C01 | PF016482 203 | 1 | 0 | 2 | 0.998405 | 0.1283 |
| 4461875801_R01C02 | PF019961 212 | 0 | 0 | 1 | 0.997908 | 0.1283 |
| 4461875449_R02C02 | PF019491 202 | 0 | 0 | 0 | 0.998322 | 0.1283 |
| 4432273650_R01C01 | PF003755 211 | 0 | 0 | 1 | 0.9988 | 0.1282 |
| 4475687179_R02C02 | PF019345 203 | 0 | 0 | 0 | 0.998668 | 0.1282 |
| 4482537650_R02C02 | PF014915 211 | 0 | 0 | 1 | 0.998926 | 0.1281 |
| 4461875659_R02C02 | PF004041 211 | 0 | 0 | 0 | 0.999024 | 0.128 |
| 4461875173_R02C01 | PF016682 203 | 1 | 0 | 0 | 0.999034 | 0.1277 |
| 4432273383_R01C01 | PF018715 202 | 0 | 0 | 1 | 0.998475 | 0.1276 |
| 4457235025_R02C01 | PF006744 211 | 0 | 0 | 0 | 0.998599 | 0.1276 |
| 4461875382_R02C01 | PF020034 202 | 0 | 0 | 0 | 0.998842 | 0.1276 |
| 4459273694_R01C02 | PF008029 211 | 0 | 1 | 1 | 0.998447 | 0.1275 |
| 4457235243_R02C02 | PF018939 202 | 0 | 1 | 1 | 0.99879 | 0.1275 |
| 4432273292_R01C01 | PF018882 202 | 0 | 0 | 0 | 0.997752 | 0.1275 |
| 4459273522_R02C02 | PF014924 211 | 0 | 0 | 0 | 0.999037 | 0.1275 |
| 4461875801_R02C02 | PF020048 202 | 0 | 1 | 3 | 0.997864 | 0.1274 |
| 4432273430_R02C01 | PF015977 203 | 0 | 0 | 0 | 0.99793 | 0.1274 |
| 4457235239_R01C02 | PF019659 202 | 0 | 0 | 0 | 0.998797 | 0.1274 |
| 4461875714_R02C01 | PF019234 202 | 0 | 0 | 0 | 0.998939 | 0.1274 |
| 4459273788_R02C02 | PF008241 204 | 0 | 1 | 1 | 0.998354 | 0.1273 |
| 4461875383_R02C02 | PF019770 202 | 0 | 0 | 0 | 0.999185 | 0.1273 |
| 4432265506_R02C01 | PF019720 202 | 0 | 1 | 3 | 0.998396 | 0.1272 |
| 4432273383_R02C01 | PF018757 203 | 0 | 0 | 2 | 0.998547 | 0.1272 |
| 4457235343_R02C02 | PF003775 211 | 0 | 0 | 0 | 0.998146 | 0.1272 |
| 4432265081_R01C01 | PF007903 211 | 0 | 0 | 0 | 0.998787 | 0.1272 |
| 4459273604_R02C01 | PF008476 204 | 0 | 0 | 0 | 0.998876 | 0.1272 |
| 4457235133_R02C02 | PF019661 202 | 0 | 0 | 0 | 0.998884 | 0.1272 |
| 4457235134_R01C01 | PF018916 202 | 0 | 2 | 4 | 0.998871 | 0.1271 |
| 4457235243_R02C01 | PF018912 202 | 1 | 1 | 2 | 0.998758 | 0.1271 |

TABLE 6-continued

| BID | SSID | Tier 1 CNV count | Tier 2 CNV count | Tier 3 CNV count | Callrate | LRR_SD |
|---|---|---|---|---|---|---|
| 4459273655_R02C02 | PF008327 204 | 0 | 0 | 0 | 0.998697 | 0.1271 |
| 4457235107_R02C01 | PF019586 202 | 0 | 0 | 0 | 0.998771 | 0.1271 |
| 4432273384_R01C02 | PF016755 203 | 0 | 0 | 0 | 0.998558 | 0.127 |
| 4482537381_R02C02 | PF019128 202 | 1 | 1 | 1 | 0.999084 | 0.1269 |
| 4432273038_R01C01 | PF016769 203 | 0 | 0 | 0 | 0.998536 | 0.1269 |
| 4461875381_R02C02 | PF016112 203 | 0 | 0 | 0 | 0.998494 | 0.1268 |
| 4457235247_R02C01 | PF018786 221 | 0 | 0 | 0 | 0.998713 | 0.1268 |
| 4482537427_R02C01 | PF019058 202 | 0 | 0 | 0 | 0.998931 | 0.1268 |
| 4432273383_R02C02 | PF018803 202 | 0 | 0 | 2 | 0.998454 | 0.1267 |
| 4432273753_R02C02 | PF019321 203 | 1 | 1 | 2 | 0.998731 | 0.1267 |
| 4457235183_R02C02 | PF019750 202 | 0 | 0 | 2 | 0.999022 | 0.1267 |
| 4459273481_R02C02 | PF019894 212 | 0 | 0 | 0 | 0.998257 | 0.1267 |
| 4459273745_R02C01 | PF004588 211 | 0 | 0 | 0 | 0.998861 | 0.1267 |
| 4461875480_R02C01 | PF019467 202 | 0 | 0 | 0 | 0.999001 | 0.1267 |
| 4459273629_R02C02 | PF004451 211 | 0 | 2 | 10 | 0.998977 | 0.1266 |
| 4459273550_R02C01 | PF008310 204 | 0 | 0 | 1 | 0.99862 | 0.1266 |
| 4461875786_R02C01 | PF019212 202 | 0 | 0 | 0 | 0.999093 | 0.1266 |
| 4461875786_R02C02 | PF019227 202 | 0 | 0 | 0 | 0.999095 | 0.1266 |
| 4461875713_R02C01 | PF014877 211 | 0 | 0 | 1 | 0.99836 | 0.1264 |
| 4459273564_R02C01 | PF008351 204 | 1 | 1 | 1 | 0.998784 | 0.1264 |
| 4457235574_R02C01 | PF019940 203 | 0 | 0 | 0 | 0.99862 | 0.1264 |
| 4432273286_R02C02 | PF018639 202 | 0 | 0 | 0 | 0.998587 | 0.1263 |
| 4461875465_R02C01 | PF018837 202 | 0 | 0 | 0 | 0.998794 | 0.1263 |
| 4461875381_R02C01 | PF016086 224 | 0 | 0 | 0 | 0.998943 | 0.1263 |
| 4432265173_R01C01 | PF019031 202 | 0 | 0 | 0 | 0.998953 | 0.1263 |
| 4459273634_R02C02 | PF018576 202 | 1 | 1 | 1 | 0.998061 | 0.1262 |
| 4432273054_R01C01 | PF018607 202 | 0 | 1 | 1 | 0.99824 | 0.1262 |
| 4461875465_R02C02 | PF020008 212 | 0 | 0 | 0 | 0.998655 | 0.1261 |
| 4432273755_R02C01 | PF015955 203 | 0 | 0 | 0 | 0.998691 | 0.1261 |
| 4432273336_R01C01 | PF018997 203 | 0 | 0 | 0 | 0.998536 | 0.126 |
| 4457235252_R02C01 | PF018996 203 | 0 | 0 | 0 | 0.998821 | 0.126 |
| 4459273728_R02C01 | PF015567 221 | 0 | 0 | 0 | 0.998903 | 0.126 |
| 4482537425_R02C02 | PF019021 202 | 1 | 1 | 1 | 0.999014 | 0.1259 |
| 4457235023_R02C01 | PF007877 211 | 0 | 0 | 0 | 0.997946 | 0.1259 |
| 4482537179_R02C01 | PF020352 202 | 1 | 1 | 1 | 0.998486 | 0.1258 |
| 4461875384_R02C02 | PF004223 211 | 0 | 0 | 0 | 0.998338 | 0.1256 |
| 4457235337_R02C02 | PF019798 202 | 0 | 0 | 0 | 0.99862 | 0.1256 |
| 4459273134_R01C01 | PF008243 204 | 0 | 0 | 0 | 0.999029 | 0.1256 |
| 4457235132_R01C01 | PF018761 202 | 0 | 0 | 0 | 0.99919 | 0.1256 |
| 4459273563_R02C01 | PF019441 202 | 0 | 1 | 1 | 0.998674 | 0.1255 |
| 4461875707_R01C02 | PF020074 202 | 0 | 0 | 0 | 0.998768 | 0.1255 |
| 4459273642_R02C02 | PF004051 211 | 0 | 0 | 0 | 0.999169 | 0.1254 |
| 4459273694_R02C02 | PF005964 211 | 0 | 0 | 1 | 0.998541 | 0.1253 |
| 4457235047_R02C02 | PF020395 221 | 0 | 0 | 1 | 0.998868 | 0.1253 |
| 4482537381_R02C01 | PF019125 202 | 0 | 1 | 1 | 0.99913 | 0.1253 |
| 4459273280_R02C01 | PF008873 211 | 0 | 0 | 0 | 0.997995 | 0.1253 |
| 4459273641_R02C01 | PF008470 204 | 0 | 0 | 0 | 0.998815 | 0.1253 |
| 4457235015_R02C01 | PF019693 202 | 0 | 0 | 0 | 0.998871 | 0.1253 |
| 4432273584_R02C02 | PF018701 202 | 0 | 0 | 0 | 0.998193 | 0.1252 |
| 4432273430_R01C02 | PF016165 203 | 1 | 2 | 2 | 0.997834 | 0.1251 |
| 4432273292_R02C02 | PF018894 202 | 0 | 0 | 0 | 0.997842 | 0.1249 |
| 4461875783_R01C02 | PF020359 221 | 0 | 0 | 0 | 0.998153 | 0.1249 |
| 4457235010_R02C01 | PF018678 202 | 4 | 7 | 18 | 0.998628 | 0.1248 |
| 4432273749_R02C02 | PF018695 203 | 0 | 1 | 1 | 0.998193 | 0.1248 |
| 4459273788_R01C02 | PF008230 204 | 0 | 0 | 0 | 0.998905 | 0.1248 |
| 4432273123_R02C02 | PF008015 211 | 0 | 1 | 1 | 0.998029 | 0.1247 |
| 4432273335_R01C01 | PF019723 202 | 0 | 0 | 1 | 0.998459 | 0.1247 |
| 4459273694_R02C01 | PF020054 202 | 0 | 0 | 1 | 0.998707 | 0.1247 |
| 4459273636_R02C01 | PF018687 202 | 0 | 0 | 0 | 0.998462 | 0.1247 |
| 4457235133_R02C01 | PF018566 212 | 0 | 0 | 0 | 0.998852 | 0.1246 |
| 4461875594_R02C02 | PF004766 211 | 0 | 0 | 0 | 0.998629 | 0.1245 |
| 4457235023_R01C01 | PF014939 211 | 0 | 0 | 0 | 0.998162 | 0.1244 |
| 4461875713_R02C02 | PF014936 211 | 0 | 0 | 0 | 0.998401 | 0.1244 |
| 4457235106_R02C02 | PF019148 202 | 0 | 0 | 0 | 0.998963 | 0.1244 |
| 4459273626_R02C01 | PF019946 212 | 0 | 0 | 0 | 0.998906 | 0.1243 |
| 4482537383_R02C02 | PF019589 202 | 0 | 6 | 32 | 0.998671 | 0.1242 |
| 4459273656_R02C02 | PF019482 202 | 0 | 0 | 0 | 0.998372 | 0.1242 |
| 4461875783_R02C01 | PF020358 202 | 0 | 0 | 1 | 0.997705 | 0.1241 |
| 4459273278_R02C01 | PF017447 203 | 0 | 1 | 1 | 0.99872 | 0.1241 |
| 4461875655_R02C01 | PF019367 202 | 0 | 0 | 0 | 0.998932 | 0.124 |
| 4461875786_R01C01 | PF019207 202 | 0 | 0 | 0 | 0.999098 | 0.124 |
| 4482537650_R02C01 | PF018580 202 | 0 | 0 | 1 | 0.998989 | 0.1239 |
| 4432273758_R01C02 | PF004005 211 | 0 | 0 | 1 | 0.997776 | 0.1238 |
| 4461875801_R02C01 | PF019650 202 | 0 | 1 | 2 | 0.998481 | 0.1237 |
| 4457235132_R02C01 | PF018770 202 | 0 | 1 | 2 | 0.998958 | 0.1237 |
| 4459273658_R02C02 | PF019756 202 | 0 | 0 | 1 | 0.998787 | 0.1237 |

TABLE 6-continued

| BID | SSID | Tier 1 CNV count | Tier 2 CNV count | Tier 3 CNV count | Callrate | LRR_SD |
|---|---|---|---|---|---|---|
| 4459273692_R01C01 | PF019853 212 | 0 | 1 | 4 | 0.998438 | 0.1235 |
| 4432273451_R01C01 | PF018796 202 | 0 | 0 | 0 | 0.99813 | 0.1235 |
| 4457235180_R02C01 | PF020286 221 | 0 | 0 | 0 | 0.998977 | 0.1235 |
| 4459273136_R02C01 | PF016572 203 | 0 | 0 | 0 | 0.998439 | 0.1234 |
| 4459273661_R02C01 | PF019850 212 | 0 | 0 | 0 | 0.998333 | 0.1233 |
| 4482537405_R02C01 | PF019157 202 | 0 | 0 | 0 | 0.998842 | 0.1233 |
| 4459273422_R01C01 | PF018897 202 | 2 | 2 | 2 | 0.998914 | 0.1232 |
| 4461875351_R02C01 | PF008468 204 | 0 | 0 | 0 | 0.998095 | 0.1232 |
| 4457235197_R02C01 | PF019558 202 | 0 | 0 | 0 | 0.998608 | 0.1232 |
| 4461875282_R02C01 | PF019803 202 | 0 | 0 | 0 | 0.998803 | 0.1231 |
| 4457235183_R01C02 | PF019732 202 | 0 | 0 | 0 | 0.99898 | 0.1231 |
| 4457235132_R01C02 | PF018772 202 | 0 | 0 | 0 | 0.99898 | 0.1231 |
| 4459273492_R02C02 | PF017314 203 | 0 | 0 | 1 | 0.998931 | 0.123 |
| 4459273661_R02C02 | PF020001 212 | 0 | 0 | 1 | 0.998338 | 0.1229 |
| 4457235023_R02C02 | PF003769 211 | 0 | 0 | 0 | 0.997879 | 0.1229 |
| 4457235024_R02C02 | PF018907 202 | 1 | 1 | 3 | 0.998375 | 0.1228 |
| 4482537600_R02C01 | PF014942 211 | 0 | 0 | 2 | 0.999003 | 0.1228 |
| 4461875782_R02C02 | PF020365 221 | 0 | 0 | 0 | 0.99819 | 0.1227 |
| 4457235197_R02C02 | PF019577 202 | 0 | 0 | 0 | 0.99838 | 0.1227 |
| 4457235195_R02C01 | PF018597 202 | 0 | 0 | 0 | 0.999072 | 0.1227 |
| 4459273709_R02C02 | PF003910 211 | 0 | 0 | 0 | 0.998281 | 0.1226 |
| 4461875763_R02C01 | PF008161 204 | 0 | 0 | 0 | 0.998893 | 0.1226 |
| 4432273288_R02C02 | PF019135 202 | 1 | 2 | 5 | 0.998586 | 0.1222 |
| 4482537427_R02C02 | PF019068 202 | 0 | 1 | 1 | 0.99881 | 0.1222 |
| 4432265631_R02C02 | PF004488 211 | 0 | 0 | 0 | 0.998083 | 0.1222 |
| 4482537179_R01C01 | PF020357 221 | 0 | 0 | 0 | 0.998418 | 0.1222 |
| 4457235198_R01C02 | PF004597 211 | 0 | 0 | 0 | 0.998953 | 0.1222 |
| 4461875660_R02C02 | PF019278 203 | 0 | 0 | 1 | 0.998953 | 0.1221 |
| 4459273323_R02C01 | PF020383 221 | 0 | 0 | 1 | 0.998834 | 0.122 |
| 4461875732_R01C01 | PF020354 221 | 0 | 0 | 2 | 0.999148 | 0.1219 |
| 4461875707_R02C01 | PF020044 202 | 0 | 0 | 1 | 0.998943 | 0.1219 |
| 4459273422_R02C02 | PF018921 202 | 0 | 0 | 0 | 0.998732 | 0.1219 |
| 4459273594_R02C01 | PF008102 204 | 1 | 1 | 1 | 0.998454 | 0.1218 |
| 4461875449_R02C01 | PF019465 202 | 0 | 1 | 1 | 0.998831 | 0.1218 |
| 4461875660_R02C01 | PF019275 203 | 0 | 0 | 1 | 0.998995 | 0.1218 |
| 4461875785_R02C01 | PF020029 202 | 0 | 0 | 1 | 0.999098 | 0.1218 |
| 4459273136_R02C02 | PF018589 202 | 0 | 0 | 0 | 0.99857 | 0.1217 |
| 4432273748_R02C01 | PF018754 202 | 0 | 0 | 0 | 0.998414 | 0.1216 |
| 4461875802_R01C02 | PF019445 202 | 0 | 0 | 0 | 0.998455 | 0.1214 |
| 4432273650_R02C01 | PF003998 211 | 1 | 0 | 1 | 0.998757 | 0.1213 |
| 4457235239_R02C01 | PF019606 202 | 0 | 0 | 0 | 0.998815 | 0.1213 |
| 4459273488_R01C01 | PF020368 202 | 0 | 0 | 0 | 0.99865 | 0.121 |
| 4461875676_R02C01 | PF008374 204 | 0 | 0 | 0 | 0.998749 | 0.121 |
| 4459273423_R02C02 | PF018663 202 | 0 | 0 | 0 | 0.998911 | 0.1209 |
| 4457235239_R02C02 | PF019662 202 | 0 | 0 | 0 | 0.998947 | 0.1208 |
| 4459273604_R02C02 | PF008511 204 | 0 | 6 | 14 | 0.999095 | 0.1207 |
| 4432273600_R02C01 | PF018464 212 | 0 | 0 | 0 | 0.998615 | 0.1206 |
| 4459273323_R02C02 | PF014856 211 | 0 | 0 | 0 | 0.99884 | 0.1206 |
| 4461875732_R01C02 | PF014834 211 | 0 | 0 | 0 | 0.999154 | 0.1205 |
| 4432273451_R02C02 | PF018864 203 | 0 | 0 | 0 | 0.99827 | 0.1204 |
| 4459273547_R02C02 | PF018896 202 | 0 | 0 | 0 | 0.998797 | 0.1204 |
| 4459273788_R02C01 | PF008154 204 | 0 | 0 | 0 | 0.998927 | 0.1202 |
| 4461875693_R01C01 | PF004225 211 | 0 | 0 | 1 | 0.998647 | 0.1201 |
| 4459273463_R01C01 | PF020376 221 | 0 | 0 | 0 | 0.998483 | 0.1201 |
| 4457235244_R02C02 | PF018675 202 | 0 | 1 | 1 | 0.998839 | 0.1199 |
| 4459273574_R02C02 | PF018655 202 | 0 | 1 | 2 | 0.998742 | 0.1198 |
| 4459273748_R02C02 | PF004605 211 | 0 | 0 | 1 | 0.9989 | 0.1197 |
| 4461875706_R02C02 | PF019834 203 | 0 | 0 | 0 | 0.998716 | 0.1197 |
| 4461875594_R02C01 | PF014963 211 | 0 | 0 | 1 | 0.998045 | 0.1195 |
| 4461875621_R02C01 | PF020046 202 | 0 | 1 | 1 | 0.999038 | 0.1194 |
| 4459273134_R01C02 | PF008250 204 | 0 | 0 | 2 | 0.998956 | 0.1193 |
| 4461875645_R02C02 | PF018862 202 | 0 | 0 | 0 | 0.99861 | 0.1193 |
| 4457235500_R02C01 | PF019873 203 | 0 | 1 | 1 | 0.998457 | 0.1192 |
| 4459273747_R01C02 | PF020004 212 | 1 | 2 | 6 | 0.998971 | 0.1191 |
| 4457235498_R02C02 | PF019286 203 | 0 | 0 | 1 | 0.998752 | 0.1191 |
| 4459273323_R01C02 | PF020384 221 | 0 | 1 | 1 | 0.998827 | 0.119 |
| 4432273583_R02C01 | PF018763 202 | 1 | 1 | 1 | 0.999093 | 0.119 |
| 4432273384_R02C02 | PF016984 203 | 0 | 0 | 0 | 0.998452 | 0.119 |
| 4461875645_R01C01 | PF018790 221 | 0 | 0 | 0 | 0.998463 | 0.119 |
| 4457235198_R02C01 | PF007969 211 | 0 | 0 | 0 | 0.998866 | 0.1189 |
| 4457235337_R02C01 | PF019625 202 | 0 | 0 | 0 | 0.99855 | 0.1187 |
| 4432273451_R02C01 | PF018808 202 | 0 | 0 | 0 | 0.997763 | 0.1186 |
| 4457235506_R02C01 | PF016560 203 | 0 | 1 | 1 | 0.998645 | 0.1185 |
| 4457235500_R02C02 | PF019882 203 | 0 | 0 | 0 | 0.998473 | 0.1185 |
| 4459273727_R02C01 | PF004594 211 | 0 | 0 | 1 | 0.998826 | 0.1184 |
| 4457235252_R02C02 | PF019009 202 | 0 | 0 | 1 | 0.998858 | 0.1184 |

TABLE 6-continued

| BID | SSID | Tier 1 CNV count | Tier 2 CNV count | Tier 3 CNV count | Callrate | LRR_SD |
|---|---|---|---|---|---|---|
| 4461875659_R02C01 | PF006310 211 | 0 | 0 | 1 | 0.998856 | 0.1182 |
| 4432273318_R02C02 | PF004199 211 | 0 | 0 | 0 | 0.998697 | 0.1182 |
| 4461875785_R02C02 | PF020042 202 | 0 | 0 | 2 | 0.998884 | 0.1181 |
| 4457235134_R02C02 | PF018928 202 | 0 | 0 | 0 | 0.998961 | 0.118 |
| 4461875785_R01C02 | PF020033 202 | 0 | 0 | 0 | 0.998987 | 0.118 |
| 4461875785_R01C01 | PF019939 203 | 0 | 1 | 2 | 0.999137 | 0.1178 |
| 4457235132_R02C02 | PF018836 202 | 0 | 0 | 1 | 0.998977 | 0.1178 |
| 4459273749_R02C01 | PF019440 202 | 0 | 0 | 0 | 0.998781 | 0.1178 |
| 4432273292_R02C01 | PF018886 202 | 0 | 1 | 1 | 0.997901 | 0.1176 |
| 4461875645_R02C01 | PF018835 202 | 0 | 0 | 0 | 0.998497 | 0.1169 |
| 4461875707_R02C02 | PF008619 206 | 0 | 0 | 1 | 0.998778 | 0.1167 |
| 4459273488_R02C02 | PF020373 202 | 0 | 0 | 0 | 0.998575 | 0.1167 |
| 4459273423_R02C01 | PF018587 202 | 0 | 0 | 0 | 0.998803 | 0.1167 |
| 4461875783_R02C02 | PF020360 221 | 0 | 0 | 0 | 0.998046 | 0.1164 |
| 4432265173_R02C02 | PF019571 202 | 0 | 0 | 0 | 0.998874 | 0.1164 |
| 4461875383_R02C01 | PF019724 202 | 0 | 0 | 0 | 0.998956 | 0.1162 |
| 4459273748_R01C01 | PF005542 211 | 0 | 0 | 2 | 0.998966 | 0.116 |
| 4459273637_R02C01 | PF008542 204 | 0 | 0 | 0 | 0.998186 | 0.116 |
| 4432273583_R01C01 | PF018758 202 | 0 | 0 | 1 | 0.999198 | 0.1154 |
| 4457235498_R02C01 | PF018927 202 | 0 | 0 | 0 | 0.998679 | 0.1154 |
| 4459273692_R02C02 | PF014952 211 | 0 | 0 | 1 | 0.997576 | 0.1151 |
| 4432273287_R02C02 | PF018718 202 | 0 | 0 | 0 | 0.998821 | 0.115 |
| 4459273488_R02C01 | PF020369 202 | 0 | 0 | 0 | 0.998668 | 0.1147 |
| 4432273758_R02C01 | PF004036 211 | 1 | 1 | 1 | 0.998217 | 0.1146 |
| 4459273422_R02C01 | PF018898 202 | 0 | 0 | 0 | 0.998893 | 0.1146 |
| 4432273583_R01C02 | PF018791 202 | 1 | 1 | 1 | 0.999109 | 0.1145 |
| 4461875174_R02C01 | PF008206 204 | 0 | 0 | 0 | 0.998839 | 0.1142 |
| 4457235183_R02C01 | PF019687 202 | 0 | 0 | 1 | 0.999042 | 0.1141 |
| 4461875172_R02C01 | PF014947 211 | 0 | 0 | 0 | 0.99879 | 0.1141 |
| 4457235506_R02C02 | PF016747 203 | 0 | 0 | 0 | 0.998744 | 0.1139 |
| 4459273634_R02C01 | PF019422 202 | 0 | 0 | 0 | 0.998109 | 0.1135 |
| 4461875174_R02C02 | PF008275 204 | 0 | 2 | 6 | 0.998681 | 0.1131 |
| 4432265081_R01C02 | PF003688 211 | 0 | 0 | 0 | 0.998813 | 0.113 |
| 4457235153_R02C02 | PF016427 203 | 0 | 0 | 0 | 0.99847 | 0.1129 |
| 4459273561_R02C01 | PF008588 204 | 1 | 1 | 1 | 0.999043 | 0.1124 |
| 4459273637_R02C02 | PF008557 204 | 0 | 0 | 1 | 0.998203 | 0.1118 |
| 4459273747_R02C02 | PF020049 202 | 0 | 0 | 0 | 0.998971 | 0.1116 |
| 4432273054_R02C01 | PF018608 202 | 0 | 0 | 1 | 0.998378 | 0.1113 |
| 4482537037_R02C02 | PF019190 202 | 0 | 0 | 0 | 0.998521 | 0.1113 |
| 4459273463_R02C02 | PF008421 206 | 0 | 1 | 2 | 0.998462 | 0.1108 |
| 4459273463_R02C01 | PF014893 211 | 0 | 2 | 3 | 0.99808 | 0.1106 |
| 4459273134_R02C01 | PF008249 204 | 0 | 1 | 1 | 0.998989 | 0.1106 |
| 4457235198_R02C02 | PF005745 211 | 0 | 0 | 0 | 0.998826 | 0.11 |
| 4432273583_R02C02 | PF018795 202 | 0 | 0 | 1 | 0.999121 | 0.1088 |
| 4461875621_R02C02 | PF014961 211 | 0 | 0 | 0 | 0.998919 | 0.1086 |
| 4461875802_R02C01 | PF019384 203 | 0 | 1 | 1 | 0.998489 | 0.1077 |
| 4459273463_R01C02 | PF014917 211 | 0 | 0 | 1 | 0.99856 | 0.1075 |
| 4461875693_R02C01 | PF008084 204 | 1 | 1 | 2 | 0.998441 | 0.1068 |
| 4461875763_R02C02 | PF008179 204 | 1 | 1 | 1 | 0.998658 | 0.1056 |

What is claimed is:

1. A method of treating anorexia nervosa (AN) in a subject with attention deficit hyperactivity disorder (ADHD), the method comprising administering fasoracetam to the subject.

2. The method of claim 1, wherein the fasoracetam is fasoracetam monohydrate.

3. The method of claim 1, wherein the fasoracetam is administered at a dose of 50-400 mg and wherein the dose is administered once, twice, or three times daily.

4. The method of claim 1, wherein the fasoracetam is administered at a dose of 100 mg, 200 mg, 300 mg, or 400 mg twice daily.

5. The method of claim 1, wherein the subject has at least one genetic alteration in a metabotropic glutamate receptor (mGluR) network gene.

6. The method of claim 5, wherein the genetic alteration is a copy number variation (CNV).

7. The method of claim 6, wherein the CNV is a deletion.

8. The method of claim 6, wherein the CNV is a duplication.

9. The method of claim 5, wherein at least one of the following applies:
(i) the genetic alteration is in at least 2, 3, 4, 5, 6, 7, 8, 9, 10, 15, 20, 30, 40, 50, 60, 70, or all Tier 1 mGluR network genes;
(ii) the genetic alteration is in at least 2, 3, 4, 5, 6, 7, 8, 9, 10, 15, 20, 30, 40, 50, 60, 70, or all Tier 2 mGluR network genes; or
(iii) the genetic alteration is in at least 2, 3, 4, 5, 6, 7, 8, 9, 10, 15, 20, 30, 40, 50, 60, 70, or all Tier 3 mGluR network genes.

10. The method of claim 5, wherein the genetic alteration is not in one or more of GRM1, GRM2, GRM3, GRM4, GRM5, GRM6, GRM7 or GRM8.

11. The method of claim 1, wherein the subject has the bingeing and/or purging subtype of AN.

12. The method of claim 1, wherein the subject has the restricting subtype of AN.

13. The method of claim 1, wherein the subject is a pediatric or adolescent subject.

14. The method of claim 1, wherein the subject is an adult subject.

15. The method of claim 1, wherein the subject is already taking or is administered one or more of an antidepressant, an anxiolytic or an anti-psychotic.

16. The method of claim 15, wherein the antidepressant is fluoxetine, escitalopram, bupropion, mirtazapine, amitriptyline, imipramine, venlafaxine, sertraline, paroxetine, a tricyclic antidepressant, a selective serotonin reuptake inhibitor, a serotonin and norepinephrine reuptake inhibitor, a norepinephrine and dopamine reuptake inhibitor, or a monoamine oxidase inhibitor.

17. The method of claim 15, wherein the anxiolytic is a barbiturate, pregabalin, or a benzodiazepine.

18. The method of claim 15, wherein the anti-psychotic is olanzapine, quetiapine, aripiprazole or risperidone.

19. The method of claim 1, wherein the fasoracetam is administered in combination with non-pharmaceutical therapy selected from vagus nerve stimulation, repetitive transcranial magnetic stimulation, magnetic seizure therapy, and deep brain stimulation.

\* \* \* \* \*